US012807981B2

(12) United States Patent
Handique et al.

(10) Patent No.: US 12,807,981 B2
(45) **Date of Patent: *Nov. 24, 2026**

(54) MICROFLUIDIC SYSTEM FOR AMPLIFYING AND DETECTING POLYNUCLEOTIDES IN PARALLEL

(71) Applicant: Handylab, Inc., Franklin Lakes, NJ (US)

(72) Inventors: Kalyan Handique, Ypsilanti, MI (US); Sundaresh N. Brahmasandra, Ann Arbor, MI (US); Karthik Ganesan, Ann Arbor, MI (US); Jeff Williams, Chelsea, MI (US)

(73) Assignee: HANDYLAB, INC., Milford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/631,561

(22) Filed: Apr. 10, 2024

(65) Prior Publication Data

US 2025/0075250 A1 Mar. 6, 2025

Related U.S. Application Data

(63) Continuation of application No. 17/496,160, filed on Oct. 7, 2021, now Pat. No. 11,959,126, which is a (Continued)

(51) Int. Cl.

*C12Q 1/6806* (2018.01)
*B01L 3/00* (2006.01)

(Continued)

(52) U.S. Cl.

CPC ...... *C12Q 1/6806* (2013.01); *B01L 3/502715* (2013.01); *B01L 3/502723* (2013.01);

(Continued)

(58) Field of Classification Search

CPC ........ B01L 7/52; B01L 9/527; B01L 2300/18; C12Q 1/686; C12Q 1/6806; C12Q 1/6844; C12Q 2565/629

See application file for complete search history.

(56) References Cited

U.S. PATENT DOCUMENTS

| | | | |
|---|---|---|---|
| D189,404 | S | 12/1960 | Nicolle |
| 3,050,239 | A | 8/1962 | Williams |

(Continued)

FOREIGN PATENT DOCUMENTS

| | | |
|---|---|---|
| AU | 1357102 | 3/2002 |
| AU | 3557502 | 7/2002 |

(Continued)

OTHER PUBLICATIONS

Allemand et al., "pH-Dependent Specific Binding and Combing of DNA", Biophys J. (1997) 73(4):2064-2070.

(Continued)

*Primary Examiner* — Young J Kim

(74) *Attorney, Agent, or Firm* — Knobbe, Martens, Olson & Bear, LLP

(57) ABSTRACT

The present technology provides for an apparatus for detecting polynucleotides in samples, particularly from biological samples. The technology more particularly relates to microfluidic systems that carry out PCR on nucleotides of interest within microfluidic channels, and detect those nucleotides. The apparatus includes a microfluidic cartridge that is configured to accept a plurality of samples, and which can carry out PCR on each sample individually, or a group of, or all of the plurality of samples simultaneously.

20 Claims, 61 Drawing Sheets

Related U.S. Application Data continuation of application No. 16/787,977, filed on Feb. 11, 2020, now Pat. No. 11,142,785, which is a continuation of application No. 14/796,239, filed on Jul. 10, 2015, now abandoned, which is a continuation of application No. 13/692,929, filed on Dec. 3, 2012, now Pat. No. 9,080,207, which is a continuation of application No. 13/035,725, filed on Feb. 25, 2011, now Pat. No. 8,323,900, which is a continuation of application No. 11/985,577, filed on Nov. 14, 2007, now Pat. No. 7,998,708, which is a continuation-in-part of application No. 11/728,964, filed on Mar. 26, 2007, now Pat. No. 9,040,288.

(60) Provisional application No. 60/959,437, filed on Jul. 13, 2007, provisional application No. 60/859,284, filed on Nov. 14, 2006, provisional application No. 60/786,007, filed on Mar. 24, 2006.

(51) Int. Cl.

| | |
|---|---|
| ***B01L 7/00*** | (2006.01) |
| ***B01L 9/00*** | (2006.01) |
| ***C12Q 1/686*** | (2018.01) |
| ***F16K 99/00*** | (2006.01) |
| ***G01N 21/64*** | (2006.01) |
| *G01N 35/00* | (2006.01) |

(52) U.S. Cl.

CPC ........... *B01L 3/502738* (2013.01); *B01L 7/52* (2013.01); *B01L 9/527* (2013.01); *C12Q 1/686* (2013.01); *F16K 99/0001* (2013.01); *F16K 99/003* (2013.01); *F16K 99/0032* (2013.01); *F16K 99/0044* (2013.01); *F16K 99/0061* (2013.01); *G01N 21/6428* (2013.01); *B01L 2200/027* (2013.01); *B01L 2200/10* (2013.01); *B01L 2200/147* (2013.01); *B01L 2200/148* (2013.01); *B01L 2200/16* (2013.01); *B01L 2300/021* (2013.01); *B01L 2300/045* (2013.01); *B01L 2300/0681* (2013.01); *B01L 2300/0816* (2013.01); *B01L 2300/0867* (2013.01); *B01L 2300/087* (2013.01); *B01L 2300/0887* (2013.01); *B01L 2300/1822* (2013.01); *B01L 2300/1827* (2013.01); *B01L 2300/1861* (2013.01); *B01L 2400/0442* (2013.01); *B01L 2400/0481* (2013.01); *B01L 2400/0487* (2013.01); *B01L 2400/0611* (2013.01); *B01L 2400/0677* (2013.01); *B01L 2400/0683* (2013.01); *F16K 2099/0084* (2013.01); *G01N 2021/6419* (2013.01); *G01N 2021/6421* (2013.01); *G01N 2021/6441* (2013.01); *G01N 2035/00881* (2013.01)

(56) References Cited

U.S. PATENT DOCUMENTS 3,444,742 A 5/1969 Ellis et al.
3,905,772 A 9/1975 Hartnett et al.
3,985,649 A 10/1976 Eddelman
4,018,089 A 4/1977 Dzula et al.
4,018,652 A 4/1977 Lanham et al.
4,038,192 A 7/1977 Serur
4,055,395 A 10/1977 Honkawa et al.
D249,706 S 9/1978 Adamski
4,139,005 A 2/1979 Dickey
D252,157 S 6/1979 Kronish et al.
D252,341 S 7/1979 Thomas
D254,687 S 4/1980 Fadler et al.
4,212,744 A 7/1980 Oota
D261,033 S 9/1981 Armbruster
D261,173 S 10/1981 Armbruster
4,301,412 A 11/1981 Hill et al.
4,439,526 A 3/1984 Columbus
4,457,329 A 7/1984 Werley et al.
4,466,740 A 8/1984 Kano et al.
4,472,357 A 9/1984 Levy et al.
4,504,582 A 3/1985 Swann
4,522,786 A 6/1985 Ebersole
D279,817 S 7/1985 Chen et al.
D282,208 S 1/1986 Lowry
4,599,315 A 7/1986 Terasaki et al.
4,612,873 A 9/1986 Eberle
4,612,959 A 9/1986 Costello
D288,478 S 2/1987 Carlson et al.
4,647,432 A 3/1987 Wakatake
4,654,127 A 3/1987 Baker et al.
4,673,657 A 6/1987 Christian
4,678,752 A 7/1987 Thorne et al.
4,683,195 A 7/1987 Mullis et al.
4,683,202 A 7/1987 Mullis
4,698,302 A 10/1987 Whitehead et al.
D292,735 S 11/1987 Lovborg
4,720,374 A 1/1988 Ramachandran
4,724,207 A 2/1988 Hou et al.
4,795,698 A 1/1989 Owen et al.
4,798,693 A 1/1989 Mase et al.
4,800,022 A 1/1989 Leonard
4,827,944 A 5/1989 Nugent
4,841,786 A 6/1989 Schulz
D302,294 S 7/1989 Hillman
4,855,110 A 8/1989 Marker et al.
4,871,779 A 10/1989 Killat et al.
4,889,818 A 12/1989 Gelfand et al.
4,895,650 A 1/1990 Wang
4,902,624 A 2/1990 Columbus et al.
4,914,710 A 4/1990 Ward et al.
4,919,829 A 4/1990 Gates et al.
4,921,809 A 5/1990 Schiff et al.
4,935,342 A 6/1990 Seligson et al.
4,946,562 A 8/1990 Guruswamy
4,948,561 A 8/1990 Hinckley et al.
4,949,742 A 8/1990 Rando et al.
D310,413 S 9/1990 Bigler et al.
4,963,498 A 10/1990 Hillman
4,965,188 A 10/1990 Mullis et al.
4,967,950 A 11/1990 Legg et al.
D312,692 S 12/1990 Bradley
4,978,502 A 12/1990 Dole et al.
4,978,622 A 12/1990 Mishell et al.
4,989,626 A 2/1991 Takagi et al.
4,994,373 A 2/1991 Stavrianopoulos et al.
4,997,772 A 3/1991 Sutton et al.
5,001,417 A 3/1991 Pumphrey et al.
5,004,583 A 4/1991 Guruswamy et al.
5,048,554 A 9/1991 Kremer
5,053,199 A 10/1991 Keiser et al.
5,060,823 A 10/1991 Perlman
5,061,336 A 10/1991 Soane
5,064,618 A 11/1991 Baker et al.
5,071,531 A 12/1991 Soane
5,089,233 A 2/1992 DeVaney, Jr. et al.
5,091,328 A 2/1992 Miller
D324,426 S 3/1992 Fan et al.
5,096,669 A 3/1992 Lauks et al.
5,098,663 A 3/1992 Berthold et al.
D325,638 S 4/1992 Sloat et al.
5,126,002 A 6/1992 Iwata et al.
5,126,022 A 6/1992 Soane et al.
D328,135 S 7/1992 Fan et al.
D328,794 S 8/1992 Frenkel et al.
5,135,627 A 8/1992 Soane
5,135,872 A 8/1992 Pouletty et al.
5,147,606 A 9/1992 Charlton et al.
5,147,777 A 9/1992 Sutton et al.
5,155,166 A 10/1992 Danielson et al.
5,169,512 A 12/1992 Wiedenmann et al.
5,173,269 A 12/1992 Mon et al.
D333,522 S 2/1993 Gianino

(56) References Cited

U.S. PATENT DOCUMENTS

| | | | |
|---|---|---|---|
| 5,186,339 | A | 2/1993 | Heissler |
| 5,192,507 | A | 3/1993 | Taylor et al. |
| 5,208,163 | A | 5/1993 | Charlton et al. |
| 5,217,694 | A | 6/1993 | Gibler et al. |
| 5,223,226 | A | 6/1993 | Wittmer et al. |
| 5,229,297 | A | 7/1993 | Schnipelsky et al. |
| 5,231,015 | A | 7/1993 | Cummins et al. |
| D338,275 | S | 8/1993 | Fischer et al. |
| 5,234,809 | A | 8/1993 | Boom et al. |
| 5,250,263 | A | 10/1993 | Manz |
| 5,252,743 | A | 10/1993 | Barrett et al. |
| 5,256,376 | A | 10/1993 | Callan et al. |
| 5,273,716 | A | 12/1993 | Northrup et al. |
| 5,275,787 | A | 1/1994 | Yuguchi et al. |
| 5,282,950 | A | 2/1994 | Dietze et al. |
| 5,296,375 | A | 3/1994 | Kricka et al. |
| 5,304,477 | A | 4/1994 | Nagoh et al. |
| 5,304,487 | A | 4/1994 | Wilding et al. |
| D347,478 | S | 5/1994 | Pinkney |
| 5,311,896 | A | 5/1994 | Kaartinen et al. |
| 5,311,996 | A | 5/1994 | Duffy et al. |
| 5,316,727 | A | 5/1994 | Suzuki et al. |
| 5,327,038 | A | 7/1994 | Culp |
| 5,334,499 | A | 8/1994 | Burdick et al. |
| 5,338,671 | A | 8/1994 | Scalice et al. |
| 5,339,486 | A | 8/1994 | Persic, Jr. |
| D351,475 | S | 10/1994 | Gerber |
| D351,913 | S | 10/1994 | Hieb et al. |
| 5,364,591 | A | 11/1994 | Green et al. |
| 5,372,946 | A | 12/1994 | Cusak et al. |
| 5,374,395 | A | 12/1994 | Robinson |
| 5,384,499 | A | 1/1995 | Pedersen et al. |
| 5,389,339 | A | 2/1995 | Petschek et al. |
| D356,232 | S | 3/1995 | Armstrong et al. |
| 5,397,709 | A | 3/1995 | Berndt |
| 5,401,465 | A | 3/1995 | Smethers et al. |
| 5,411,708 | A | 5/1995 | Moscetta et al. |
| 5,414,245 | A | 5/1995 | Hackleman |
| 5,415,839 | A | 5/1995 | Zaun et al. |
| 5,416,000 | A | 5/1995 | Allen et al. |
| 5,422,271 | A | 6/1995 | Chen et al. |
| 5,422,284 | A | 6/1995 | Lau |
| 5,427,946 | A | 6/1995 | Kricka et al. |
| 5,443,791 | A | 8/1995 | Cathcart et al. |
| 5,466,574 | A | 11/1995 | Liberti et al. |
| 5,474,796 | A | 12/1995 | Brennan |
| 5,475,487 | A | 12/1995 | Mariella, Jr. et al. |
| D366,116 | S | 1/1996 | Biskupski |
| 5,486,335 | A | 1/1996 | Wilding et al. |
| 5,494,639 | A | 2/1996 | Grzegorzewski |
| 5,498,392 | A | 3/1996 | Wilding et al. |
| 5,503,803 | A | 4/1996 | Brown |
| 5,516,410 | A | 5/1996 | Schneider et al. |
| 5,519,635 | A | 5/1996 | Miyake et al. |
| 5,529,677 | A | 6/1996 | Schneider et al. |
| 5,559,432 | A | 9/1996 | Logue |
| 5,565,171 | A | 10/1996 | Dovichi et al. |
| 5,569,364 | A | 10/1996 | Hooper et al. |
| 5,576,218 | A | 11/1996 | Zurek et al. |
| 5,578,270 | A | 11/1996 | Reichler et al. |
| 5,578,818 | A | 11/1996 | Kain et al. |
| 5,579,928 | A | 12/1996 | Anukwuem |
| 5,580,523 | A | 12/1996 | Bard |
| 5,582,884 | A | 12/1996 | Ball et al. |
| 5,582,988 | A | 12/1996 | Backus et al. |
| 5,585,069 | A | 12/1996 | Zanucchi et al. |
| 5,585,089 | A | 12/1996 | Queen et al. |
| 5,585,242 | A | 12/1996 | Bouma et al. |
| 5,587,128 | A | 12/1996 | Wilding et al. |
| 5,589,136 | A | 12/1996 | Northrup et al. |
| 5,593,838 | A | 1/1997 | Zanzucchi et al. |
| 5,595,708 | A | 1/1997 | Berndt |
| 5,599,432 | A | 2/1997 | Manz et al. |
| 5,599,503 | A | 2/1997 | Manz et al. |
| 5,599,667 | A | 2/1997 | Arnold, Jr. et al. |
| 5,601,727 | A | 2/1997 | Bormann et al. |
| 5,603,351 | A | 2/1997 | Cherukuri et al. |
| 5,605,662 | A | 2/1997 | Heller et al. |
| 5,609,910 | A | 3/1997 | Hackleman |
| D378,782 | S | 4/1997 | LaBarbera et al. |
| 5,628,890 | A | 5/1997 | Carter et al. |
| 5,630,920 | A | 5/1997 | Friese et al. |
| 5,631,337 | A | 5/1997 | Sassi et al. |
| 5,632,876 | A | 5/1997 | Zanzucchi et al. |
| 5,632,957 | A | 5/1997 | Heller et al. |
| 5,635,358 | A | 6/1997 | Wilding et al. |
| 5,637,469 | A | 6/1997 | Wilding et al. |
| 5,639,423 | A | 6/1997 | Northrup et al. |
| 5,639,428 | A | 6/1997 | Cottingham |
| 5,643,738 | A | 7/1997 | Zanzucchi et al. |
| 5,645,801 | A | 7/1997 | Bouma et al. |
| 5,646,039 | A | 7/1997 | Northrup et al. |
| 5,646,049 | A | 7/1997 | Tayi |
| 5,647,994 | A | 7/1997 | Tuunanen et al. |
| 5,651,839 | A | 7/1997 | Rauf |
| 5,652,141 | A | 7/1997 | Henco et al. |
| 5,652,149 | A | 7/1997 | Mileaf et al. |
| D382,346 | S | 8/1997 | Buhler et al. |
| D382,647 | S | 8/1997 | Staples et al. |
| 5,654,141 | A | 8/1997 | Mariani et al. |
| 5,658,515 | A | 8/1997 | Lee et al. |
| 5,667,976 | A | 9/1997 | Van Ness et al. |
| 5,671,303 | A | 9/1997 | Shieh et al. |
| 5,674,394 | A | 10/1997 | Whitmore |
| 5,674,742 | A | 10/1997 | Northrup et al. |
| 5,681,484 | A | 10/1997 | Zanzucchi et al. |
| 5,681,529 | A | 10/1997 | Taguchi et al. |
| 5,683,657 | A | 11/1997 | Mian |
| 5,683,659 | A | 11/1997 | Hovatter |
| 5,699,157 | A | 12/1997 | Parce et al. |
| 5,700,429 | A | 12/1997 | Bühler et al. |
| 5,700,637 | A | 12/1997 | Southern |
| 5,705,610 | A | 1/1998 | Zuckermann et al. |
| 5,705,813 | A | 1/1998 | Apffel et al. |
| 5,720,923 | A | 2/1998 | Haff et al. |
| 5,721,136 | A | 2/1998 | Finney et al. |
| 5,725,831 | A | 3/1998 | Reichler et al. |
| 5,726,026 | A | 3/1998 | Wilding et al. |
| 5,726,404 | A | 3/1998 | Brody |
| 5,726,944 | A | 3/1998 | Pelley et al. |
| 5,731,212 | A | 3/1998 | Gavin et al. |
| 5,744,366 | A | 4/1998 | Kricka et al. |
| 5,746,978 | A | 5/1998 | Bienhaus et al. |
| 5,747,666 | A | 5/1998 | Willis |
| 5,750,015 | A | 5/1998 | Soane et al. |
| 5,755,942 | A | 5/1998 | Zanzucchi et al. |
| 5,762,874 | A | 6/1998 | Seaton et al. |
| 5,763,262 | A | 6/1998 | Wong et al. |
| 5,770,029 | A | 6/1998 | Nelson et al. |
| 5,770,388 | A | 6/1998 | Vorpahl |
| 5,772,966 | A | 6/1998 | Maracas et al. |
| 5,779,868 | A | 7/1998 | Parce et al. |
| 5,783,148 | A | 7/1998 | Cottingham et al. |
| 5,787,032 | A | 7/1998 | Heller et al. |
| 5,788,814 | A | 8/1998 | Sun et al. |
| 5,800,600 | A | 9/1998 | Lima-Marques et al. |
| 5,800,690 | A | 9/1998 | Chow et al. |
| 5,804,436 | A | 9/1998 | Okun et al. |
| D399,959 | S | 10/1998 | Prokop et al. |
| 5,819,749 | A | 10/1998 | Lee et al. |
| 5,827,481 | A | 10/1998 | Bente et al. |
| 5,842,106 | A | 11/1998 | Thaler et al. |
| 5,842,787 | A | 12/1998 | Kopf-Sill et al. |
| 5,846,396 | A | 12/1998 | Zanzucchi et al. |
| 5,846,493 | A | 12/1998 | Bankier et al. |
| 5,849,208 | A | 12/1998 | Hayes et al. |
| 5,849,486 | A | 12/1998 | Heller et al. |
| 5,849,489 | A | 12/1998 | Heller |
| 5,849,598 | A | 12/1998 | Wilson et al. |
| 5,851,492 | A | 12/1998 | Blattner |
| 5,852,495 | A | 12/1998 | Parce |
| 5,856,174 | A | 1/1999 | Lipshutz et al. |
| 5,858,187 | A | 1/1999 | Ramsey et al. |
| 5,858,188 | A | 1/1999 | Soane et al. |

(56) References Cited

U.S. PATENT DOCUMENTS 5,863,502 A 1/1999 Southgate et al.
5,863,708 A 1/1999 Zanzucchi et al.
5,863,801 A 1/1999 Southgate et al.
5,866,345 A 2/1999 Wilding et al.
5,869,004 A 2/1999 Parce et al.
5,869,244 A 2/1999 Martin et al.
5,872,010 A 2/1999 Karger et al.
5,872,623 A 2/1999 Stabile et al.
5,874,046 A 2/1999 Megerle
5,876,675 A 3/1999 Kennedy
5,880,071 A 3/1999 Parce et al.
5,882,465 A 3/1999 McReynolds
5,883,211 A 3/1999 Sassi et al.
5,885,432 A 3/1999 Hooper et al.
5,885,470 A 3/1999 Parce et al.
5,895,762 A 4/1999 Greenfield et al.
5,900,130 A 5/1999 Benvegnu et al.
5,911,737 A 6/1999 Lee et al.
5,912,124 A 6/1999 Kumar
5,912,134 A 6/1999 Shartle
5,914,229 A 6/1999 Loewy
5,916,522 A 6/1999 Boyd et al.
5,916,776 A 6/1999 Kumar
5,919,646 A 7/1999 Okun et al.
5,919,711 A 7/1999 Boyd et al.
5,922,289 A 7/1999 Wong
5,922,591 A 7/1999 Anderson et al.
5,927,547 A 7/1999 Papen et al.
5,928,161 A 7/1999 Krulevitch et al.
5,928,880 A 7/1999 Wilding et al.
5,929,208 A 7/1999 Heller et al.
D413,391 S 8/1999 Lapeus et al.
5,932,799 A 8/1999 Moles
5,935,401 A 8/1999 Amigo
5,935,522 A 8/1999 Swerdlow et al.
5,939,291 A 8/1999 Loewy et al.
5,939,312 A 8/1999 Baier et al.
5,942,443 A 8/1999 Parce et al.
5,944,717 A 8/1999 Lee et al.
D413,677 S 9/1999 Dumitrescu et al.
D414,271 S 9/1999 Mendoza
5,948,227 A 9/1999 Dubrow
5,948,363 A 9/1999 Gaillard
5,948,673 A 9/1999 Cottingham
5,955,028 A 9/1999 Chow
5,955,029 A 9/1999 Wilding et al.
5,957,579 A 9/1999 Kopf-Sill et al.
5,958,203 A 9/1999 Parce et al.
5,958,349 A 9/1999 Petersen et al.
5,958,694 A 9/1999 Nikiforov
5,959,221 A 9/1999 Boyd et al.
5,959,291 A 9/1999 Jensen
5,964,995 A 10/1999 Nikiforov et al.
5,964,997 A 10/1999 McBride
5,965,001 A 10/1999 Chow et al.
5,965,410 A 10/1999 Chow et al.
5,965,886 A 10/1999 Sauer et al.
5,968,745 A 10/1999 Thorp et al.
5,972,187 A 10/1999 Parce et al.
5,973,138 A 10/1999 Collis
D417,009 S 11/1999 Boyd
5,976,336 A 11/1999 Dubrow et al.
5,980,704 A 11/1999 Cherukuri et al.
5,980,719 A 11/1999 Cherukuri et al.
5,981,735 A 11/1999 Thatcher et al.
5,985,651 A 11/1999 Hunicke-Smith
5,989,402 A 11/1999 Chow et al.
5,992,820 A 11/1999 Fare et al.
5,993,611 A 11/1999 Moroney, III et al.
5,993,750 A 11/1999 Ghosh et al.
5,997,708 A 12/1999 Craig
6,001,229 A 12/1999 Ramsey
6,001,231 A 12/1999 Kopf-Sill
6,001,307 A 12/1999 Naka et al.
6,004,450 A 12/1999 Northrup et al.
6,004,515 A 12/1999 Parce et al.
6,007,690 A 12/1999 Nelson et al.
6,010,607 A 1/2000 Ramsey
6,010,608 A 1/2000 Ramsey
6,010,627 A 1/2000 Hood, III
6,012,902 A 1/2000 Parce
D420,747 S 2/2000 Dumitrescu et al.
D421,130 S 2/2000 Cohen et al.
6,024,920 A 2/2000 Cunanan
D421,653 S 3/2000 Purcell
6,033,546 A 3/2000 Ramsey
6,033,880 A 3/2000 Haff et al.
6,043,080 A 3/2000 Lipshutz et al.
6,043,880 A 3/2000 Andrews et al.
6,046,056 A 4/2000 Parce et al.
6,048,734 A 4/2000 Burns et al.
6,054,034 A 4/2000 Soane et al.
6,054,277 A 4/2000 Furcht et al.
6,056,860 A 5/2000 Amigo et al.
6,057,149 A 5/2000 Burns et al.
6,062,261 A 5/2000 Jacobson et al.
6,063,341 A 5/2000 Fassbind et al.
6,063,589 A 5/2000 Kellogg et al.
6,066,300 A 5/2000 Carey et al.
6,068,751 A 5/2000 Neukermans
6,068,752 A 5/2000 Dubrow et al.
6,071,478 A 6/2000 Chow
6,074,725 A 6/2000 Kennedy
6,074,827 A 6/2000 Nelson et al.
D428,497 S 7/2000 Lapeus et al.
6,086,740 A 7/2000 Kennedy
6,096,509 A 8/2000 Okun et al.
6,100,541 A 8/2000 Nagle et al.
6,102,897 A 8/2000 Lang
6,103,537 A 8/2000 Ullman et al.
6,106,685 A 8/2000 McBride et al.
6,110,343 A 8/2000 Ramsey et al.
6,117,398 A 9/2000 Bienhaus et al.
6,123,205 A 9/2000 Dumitrescu et al.
6,123,798 A 9/2000 Gandhi et al.
6,130,098 A 10/2000 Handique et al.
6,132,580 A 10/2000 Mathies et al.
6,132,684 A 10/2000 Marino
6,133,436 A 10/2000 Koster et al.
D433,759 S 11/2000 Mathis et al.
6,143,250 A 11/2000 Tajima
6,143,547 A 11/2000 Hsu
6,149,787 A 11/2000 Chow et al.
6,149,872 A 11/2000 Mack et al.
6,156,199 A 12/2000 Zuk, Jr.
6,158,269 A 12/2000 Dorenkott et al.
6,167,910 B1 1/2001 Chow
6,168,948 B1 1/2001 Anderson et al.
6,171,850 B1 1/2001 Nagle et al.
6,174,675 B1 1/2001 Chow et al.
6,180,950 B1 1/2001 Olsen
D438,311 S 2/2001 Yamanishi et al.
6,190,619 B1 2/2001 Kilcoin et al.
6,194,563 B1 2/2001 Cruickshank
D438,632 S 3/2001 Miller
D438,633 S 3/2001 Miller
D439,673 S 3/2001 Brophy et al.
6,197,595 B1 3/2001 Anderson et al.
6,203,759 B1 3/2001 Pelc et al.
6,211,989 B1 4/2001 Wulf et al.
6,213,151 B1 4/2001 Jacobson et al.
6,221,600 B1 4/2001 MacLeod et al.
6,228,635 B1 5/2001 Armstrong et al.
6,232,072 B1 5/2001 Fisher
6,235,175 B1 5/2001 Dubrow et al.
6,235,313 B1 5/2001 Mathiowitz et al.
6,235,471 B1 5/2001 Knapp et al.
6,236,456 B1 5/2001 Giebeler et al.
6,236,581 B1 5/2001 Foss et al.
6,238,626 B1 5/2001 Higuchi et al.
6,251,343 B1 6/2001 Dubrow et al.
6,254,826 B1 7/2001 Acosta et al.
6,259,635 B1 7/2001 Khouri et al.
6,261,431 B1 7/2001 Mathies et al.

(56) References Cited

U.S. PATENT DOCUMENTS 6,267,858 B1 7/2001 Parce et al.
D446,306 S 8/2001 Ochi et al.
6,271,021 B1 8/2001 Burns et al.
6,274,089 B1 8/2001 Chow et al.
6,280,967 B1 8/2001 Ransom et al.
6,281,008 B1 8/2001 Komai et al.
6,284,113 B1 9/2001 Bjornson et al.
6,284,470 B1 9/2001 Bitner et al.
6,287,254 B1 9/2001 Dodds
6,287,774 B1 9/2001 Nikiforov
6,291,248 B1 9/2001 Haj-Ahmad
6,294,063 B1 9/2001 Becker et al.
6,300,124 B1 10/2001 Blumenfeld et al.
6,302,134 B1 10/2001 Kellogg et al.
6,302,304 B1 10/2001 Spencer
6,303,343 B1 10/2001 Kopf-sill
6,306,273 B1 10/2001 Wainright et al.
6,306,590 B1 10/2001 Mehta et al.
6,310,199 B1 10/2001 Smith et al.
6,316,774 B1 11/2001 Giebeler et al.
6,319,469 B1 11/2001 Mian et al.
6,319,474 B1 11/2001 Krulevitch et al.
6,322,683 B1 11/2001 Wolk et al.
6,326,083 B1 12/2001 Yang et al.
6,326,147 B1 12/2001 Oldham et al.
6,326,211 B1 12/2001 Anderson et al.
6,334,980 B1 1/2002 Hayes et al.
6,337,435 B1 1/2002 Chu et al.
6,352,673 B1 3/2002 Rainin et al.
6,353,475 B1 3/2002 Jensen et al.
6,358,387 B1 3/2002 Kopf-sill et al.
6,366,924 B1 4/2002 Parce
6,368,561 B1 4/2002 Rutishauser et al.
6,368,871 B1 4/2002 Christel et al.
6,370,206 B1 4/2002 Schenk
6,375,185 B1 4/2002 Lin
6,375,901 B1 4/2002 Robotti et al.
6,379,884 B2 4/2002 Wada et al.
6,379,929 B1 4/2002 Burns et al.
6,379,974 B1 4/2002 Parce et al.
6,382,254 B1 5/2002 Yang et al.
6,391,541 B1 5/2002 Petersen et al.
6,391,623 B1 5/2002 Besemer et al.
6,395,161 B1 5/2002 Schneider et al.
6,398,956 B1 6/2002 Coville et al.
6,399,025 B1 6/2002 Chow
6,399,389 B1 6/2002 Parce et al.
6,399,952 B1 6/2002 Maher et al.
6,401,552 B1 6/2002 Elkins
6,403,338 B1 6/2002 Knapp et al.
6,408,878 B2 6/2002 Unger et al.
6,413,401 B1 7/2002 Chow et al.
6,416,642 B1 7/2002 Alajoki et al.
6,420,143 B1 7/2002 Kopf-sill
6,425,972 B1 7/2002 McReynolds
D461,906 S 8/2002 Pham
6,428,987 B2 8/2002 Franzen
6,430,512 B1 8/2002 Gallagher
6,432,366 B2 8/2002 Ruediger et al.
6,440,725 B1 8/2002 Pourahmadi et al.
D463,031 S 9/2002 Slomski et al.
6,444,461 B1 9/2002 Knapp et al.
6,447,661 B1 9/2002 Chow et al.
6,447,727 B1 9/2002 Parce et al.
6,448,047 B2 9/2002 Dattagupta et al.
6,448,064 B1 9/2002 Vo-Dinh et al.
6,453,928 B1 9/2002 Kaplan et al.
6,458,259 B1 10/2002 Parce et al.
6,461,570 B2 10/2002 Ishihara et al.
6,465,257 B1 10/2002 Parce et al.
6,468,761 B2 10/2002 Yang et al.
6,472,141 B2 10/2002 Nikiforov
D466,219 S 11/2002 Wynschenk et al.
6,475,364 B1 11/2002 Dubrow et al.
D467,348 S 12/2002 McMichael et al.
D467,349 S 12/2002 Niedbala et al.
6,488,897 B2 12/2002 Dubrow et al.
6,495,104 B1 12/2002 Unno et al.
6,498,497 B1 12/2002 Chow et al.
6,500,323 B1 12/2002 Chow et al.
6,500,390 B1 12/2002 Boulton et al.
D468,437 S 1/2003 McMenamy et al.
6,506,609 B1 1/2003 Wada et al.
6,509,186 B1 1/2003 Zou et al.
6,509,193 B1 1/2003 Tajima
6,511,853 B1 1/2003 Kopf-Sill et al.
D470,595 S 2/2003 Crisanti et al.
6,515,753 B2 2/2003 Maher
6,517,783 B2 2/2003 Horner et al.
6,520,197 B2 2/2003 Deshmukh et al.
6,521,181 B1 2/2003 Northrup et al.
6,521,188 B1 2/2003 Webster
6,524,456 B1 2/2003 Ramsey et al.
6,524,532 B1 2/2003 Northrup
6,524,790 B1 2/2003 Kopf-sill et al.
D472,324 S 3/2003 Rumore et al.
6,534,295 B2 3/2003 Tai et al.
6,537,432 B1 3/2003 Schneider et al.
6,537,771 B1 3/2003 Farinas et al.
6,540,896 B1 4/2003 Manz et al.
6,544,734 B1 4/2003 Briscoe et al.
6,547,942 B1 4/2003 Parce et al.
6,555,389 B1 4/2003 Ullman et al.
6,556,923 B2 4/2003 Gallagher et al.
D474,279 S 5/2003 Mayer et al.
D474,280 S 5/2003 Niedbala et al.
6,558,916 B2 5/2003 Veerapandian et al.
6,558,945 B1 5/2003 Kao
6,565,815 B1 5/2003 Chang et al.
6,569,607 B2 5/2003 McReynolds
6,572,830 B1 6/2003 Burdon et al.
6,575,188 B2 6/2003 Parunak
6,576,459 B2 6/2003 Miles et al.
6,579,453 B1 6/2003 Bächler et al.
6,589,729 B2 7/2003 Chan et al.
6,592,821 B1 7/2003 Wada et al.
6,597,450 B1 7/2003 Andrews et al.
6,602,474 B1 8/2003 Tajima
6,605,475 B1 8/2003 Taylor et al.
6,613,211 B1 9/2003 Mccormick et al.
6,613,512 B1 9/2003 Kopf-sill et al.
6,613,580 B1 9/2003 Chow et al.
6,613,581 B1 9/2003 Wada et al.
6,614,030 B2 9/2003 Maher et al.
6,620,625 B2 9/2003 Wolk et al.
6,623,860 B2 9/2003 Hu et al.
6,627,406 B1 9/2003 Singh et al.
D480,814 S 10/2003 Lafferty et al.
6,632,655 B1 10/2003 Mehta et al.
6,633,785 B1 10/2003 Kasahara et al.
D482,796 S 11/2003 Oyama et al.
6,640,981 B2 11/2003 Lafond et al.
6,649,358 B1 11/2003 Parce et al.
6,664,104 B2 12/2003 Pourahmadi et al.
6,669,831 B2 12/2003 Chow et al.
6,670,133 B2 12/2003 Knapp et al.
6,670,153 B2 12/2003 Stern
D484,989 S 1/2004 Gebrian
6,672,458 B2 1/2004 Hansen et al.
6,679,279 B1 1/2004 Lui et al.
6,681,616 B2 1/2004 Spaid et al.
6,681,788 B2 1/2004 Parce et al.
6,685,813 B2 2/2004 Williams et al.
6,692,700 B2 2/2004 Handique
6,695,009 B2 2/2004 Chien et al.
6,699,713 B2 3/2004 Benett et al.
6,706,519 B1 3/2004 Kellogg et al.
6,720,148 B1 4/2004 Nikiforov
6,730,206 B2 5/2004 Ricco et al.
6,733,645 B1 5/2004 Chow
6,734,401 B2 5/2004 Bedingham et al.
6,737,026 B1 5/2004 Bergh et al.
6,740,518 B1 5/2004 Duong et al.
D491,272 S 6/2004 Alden et al.

(56) References Cited

U.S. PATENT DOCUMENTS

D491,273 S 6/2004 Biegler et al.
D491,276 S 6/2004 Langille
6,750,661 B2 6/2004 Brooks et al.
6,752,966 B1 6/2004 Chazan
6,756,019 B1 6/2004 Dubrow et al.
6,762,049 B2 7/2004 Zou et al.
6,764,859 B1 7/2004 Kreuwel et al.
6,766,817 B2 7/2004 Dias da Silva
6,773,567 B1 8/2004 Wolk
6,777,184 B2 8/2004 Nikiforov et al.
6,783,962 B1 8/2004 Olander et al.
D495,805 S 9/2004 Lea et al.
6,787,015 B2 9/2004 Lackritz et al.
6,787,016 B2 9/2004 Tan et al.
6,787,111 B2 9/2004 Roach et al.
6,790,328 B2 9/2004 Jacobson et al.
6,790,330 B2 9/2004 Gascoyne et al.
6,811,668 B1 11/2004 Berndt et al.
6,818,113 B2 11/2004 Williams et al.
6,819,027 B2 11/2004 Saraf
6,824,663 B1 11/2004 Boone
D499,813 S 12/2004 Wu
D500,142 S 12/2004 Crisanti et al.
D500,363 S 12/2004 Fanning et al.
6,827,831 B1 12/2004 Chow et al.
6,827,906 B1 12/2004 Björnson et al.
6,838,156 B1 1/2005 Neyer et al.
6,838,680 B2 1/2005 Maher et al.
6,852,287 B2 2/2005 Ganesan
6,858,185 B1 2/2005 Kopf-sill et al.
6,859,698 B2 2/2005 Schmeisser
6,861,035 B2 3/2005 Pham et al.
6,878,540 B2 4/2005 Pourahmadi et al.
6,878,755 B2 4/2005 Singh et al.
6,884,628 B2 4/2005 Hubbell et al.
6,887,693 B2 5/2005 McMillan et al.
6,893,879 B2 5/2005 Petersen et al.
6,900,889 B2 5/2005 Bjornson et al.
6,905,583 B2 6/2005 Wainright et al.
6,905,612 B2 6/2005 Dorian et al.
6,906,797 B1 6/2005 Kao et al.
6,908,594 B1 6/2005 Schaevitz et al.
6,911,183 B1 6/2005 Handique et al.
6,914,137 B2 7/2005 Baker
6,915,679 B2 7/2005 Chien et al.
6,918,404 B2 7/2005 Dias da Silva
D508,999 S 8/2005 Fanning et al.
6,939,451 B2 9/2005 Zhao et al.
6,940,598 B2 9/2005 Christel et al.
6,942,771 B1 9/2005 Kayyem
6,951,632 B2 10/2005 Unger et al.
6,958,392 B2 10/2005 Fomovskaia et al.
D512,155 S 11/2005 Matsumoto
6,964,747 B2 11/2005 Banerjee et al.
6,969,835 B1 11/2005 Rushbrooke et al.
6,977,163 B1 12/2005 Mehta
6,979,424 B2 12/2005 Northrup et al.
6,984,516 B2 1/2006 Briscoe et al.
D515,707 S 2/2006 Sinohara et al.
D516,221 S 2/2006 Wohlstadter et al.
7,001,853 B1 2/2006 Brown et al.
7,004,184 B2 2/2006 Handique et al.
D517,554 S 3/2006 Yanagisawa et al.
7,010,391 B2 3/2006 Handique et al.
7,023,007 B2 4/2006 Gallagher
7,024,281 B1 4/2006 Unno
7,036,667 B2 5/2006 Greenstein et al.
7,037,416 B2 5/2006 Parce et al.
7,038,472 B1 5/2006 Chien
7,039,527 B2 5/2006 Tripathi et al.
7,040,144 B2 5/2006 Spaid et al.
7,041,258 B2 5/2006 Desmond et al.
7,049,558 B2 5/2006 Baer et al.
D523,153 S 6/2006 Akashi et al.
7,055,695 B2 6/2006 Greenstein et al.
7,060,171 B1 6/2006 Nikiforov et al.
7,066,586 B2 6/2006 Dias da Silva
7,069,952 B1 7/2006 McReynolds et al.
7,072,036 B2 7/2006 Jones et al.
7,099,778 B2 8/2006 Chien
D528,215 S 9/2006 Malmsater
7,101,467 B2 9/2006 Spaid
7,105,304 B1 9/2006 Nikiforov et al.
D531,321 S 10/2006 Godfrey et al.
7,118,892 B2 10/2006 Ammann et al.
7,118,910 B2 10/2006 Unger et al.
7,122,799 B2 10/2006 Hsieh et al.
7,135,144 B2 11/2006 Christel et al.
7,138,032 B2 11/2006 Gandhi et al.
D534,280 S 12/2006 Gomm et al.
7,150,814 B1 12/2006 Parce et al.
7,150,999 B1 12/2006 Shuck
D535,403 S 1/2007 Isozaki et al.
7,160,423 B2 1/2007 Chien et al.
7,161,356 B1 1/2007 Chien
7,169,277 B2 1/2007 Ausserer et al.
7,169,601 B1 1/2007 Northrup et al.
7,169,618 B2 1/2007 Skold
D537,951 S 3/2007 Okamoto et al.
D538,436 S 3/2007 Patadia et al.
7,188,001 B2 3/2007 Young et al.
7,192,557 B2 3/2007 Wu et al.
7,195,986 B1 3/2007 Bousse et al.
7,205,154 B2 4/2007 Corson
7,208,125 B1 4/2007 Dong
7,235,406 B1 6/2007 Woudenberg et al.
7,247,274 B1 7/2007 Chow
D548,841 S 8/2007 Brownell et al.
D549,827 S 8/2007 Maeno et al.
7,252,928 B1 8/2007 Hafeman et al.
7,255,833 B2 8/2007 Chang et al.
7,270,786 B2 9/2007 Parunak et al.
D554,069 S 10/2007 Bolotin et al.
D554,070 S 10/2007 Bolotin et al.
7,276,208 B2 10/2007 Sevigny et al.
7,276,330 B2 10/2007 Chow et al.
7,288,228 B2 10/2007 Lefebvre
7,297,313 B1 11/2007 Northrup et al.
D556,914 S 12/2007 Okamoto et al.
7,303,727 B1 12/2007 Dubrow et al.
D559,995 S 1/2008 Handique et al.
7,315,376 B2 1/2008 Bickmore et al.
7,323,140 B2 1/2008 Handique et al.
7,332,130 B2 2/2008 Handique
7,338,760 B2 3/2008 Gong et al.
D566,291 S 4/2008 Parunak et al.
7,351,377 B2 4/2008 Chazan et al.
D569,526 S 5/2008 Duffy et al.
7,374,949 B2 5/2008 Kuriger
7,390,460 B2 6/2008 Osawa et al.
7,419,784 B2 9/2008 Dubrow et al.
7,422,669 B2 9/2008 Jacobson et al.
7,440,684 B2 10/2008 Spaid et al.
7,476,313 B2 1/2009 Siddiqi
7,480,042 B1 1/2009 Phillips et al.
7,494,577 B2 2/2009 Williams et al.
7,494,770 B2 2/2009 Wilding et al.
7,514,046 B2 4/2009 Kechagia et al.
7,518,726 B2 4/2009 Rulison et al.
7,521,186 B2 4/2009 Burd Mehta
7,527,769 B2 5/2009 Bunch et al.
D595,423 S 6/2009 Johansson et al.
7,553,671 B2 6/2009 Sinclair et al.
D596,312 S 7/2009 Giraud et al.
D598,566 S 8/2009 Allaer
7,578,976 B1 8/2009 Northrup et al.
D599,234 S 9/2009 Ito
7,595,197 B2 9/2009 Brasseur
7,604,938 B2 10/2009 Takahashi et al.
7,622,296 B2 11/2009 Joseph et al.
7,628,902 B2 12/2009 Knowlton et al.
7,633,606 B2 12/2009 Northrup et al.
7,635,588 B2 12/2009 King et al.
7,645,581 B2 1/2010 Knapp et al.

(56) References Cited

U.S. PATENT DOCUMENTS 7,670,559 B2 3/2010 Chien et al.
7,674,431 B2 3/2010 Ganesan
7,689,022 B2 3/2010 Weiner et al.
7,704,735 B2 4/2010 Facer et al.
7,705,739 B2 4/2010 Northrup et al.
7,723,123 B1 5/2010 Murphy et al.
D618,820 S 6/2010 Wilson et al.
7,727,371 B2 6/2010 Kennedy et al.
7,727,477 B2 6/2010 Boronkay et al.
7,744,817 B2 6/2010 Bui
D621,060 S 8/2010 Handique
7,785,868 B2 8/2010 Yuan et al.
D628,305 S 11/2010 Gorrec et al.
7,829,025 B2 11/2010 Ganesan et al.
7,858,366 B2 12/2010 Northrup et al.
7,867,776 B2 1/2011 Kennedy et al.
7,892,819 B2 2/2011 Wilding et al.
D637,737 S 5/2011 Wilson et al.
7,955,864 B2 6/2011 Cox et al.
7,987,022 B2 7/2011 Handique et al.
7,998,708 B2 * 8/2011 Handique ........... F16K 99/0044 435/6.1
8,053,214 B2 11/2011 Northrup
8,071,056 B2 12/2011 Burns et al.
8,088,616 B2 1/2012 Handique
8,105,783 B2 1/2012 Handique
8,110,158 B2 2/2012 Handique
8,133,671 B2 3/2012 Williams et al.
8,182,763 B2 5/2012 Duffy et al.
8,232,900 B2 7/2012 Takeda
8,246,919 B2 8/2012 Herchenbach et al.
8,273,308 B2 9/2012 Handique et al.
D669,597 S 10/2012 Cavada et al.
8,287,820 B2 10/2012 Williams et al.
8,323,584 B2 12/2012 Ganesan
8,323,900 B2 * 12/2012 Handique ........... F16K 99/0061 435/6.12
8,324,372 B2 12/2012 Brahmasandra et al.
8,415,103 B2 4/2013 Handique
8,420,015 B2 4/2013 Ganesan et al.
8,440,149 B2 5/2013 Handique
8,470,586 B2 6/2013 Wu et al.
8,473,104 B2 6/2013 Handique et al.
D686,749 S 7/2013 Trump
D687,567 S 8/2013 Jungheim et al.
D692,162 S 10/2013 Lentz et al.
8,592,157 B2 11/2013 Petersen et al.
8,679,831 B2 3/2014 Handique et al.
D702,854 S 4/2014 Nakahana et al.
8,685,341 B2 4/2014 Ganesan
8,703,069 B2 4/2014 Handique et al.
8,709,787 B2 4/2014 Handique
8,710,211 B2 4/2014 Brahmasandra et al.
8,734,733 B2 5/2014 Handique
D710,024 S 7/2014 Guo
8,765,076 B2 7/2014 Handique et al.
8,765,454 B2 7/2014 Zhou et al.
8,768,517 B2 7/2014 Handique et al.
8,852,862 B2 10/2014 Wu et al.
8,883,490 B2 11/2014 Handique et al.
8,894,947 B2 11/2014 Ganesan et al.
8,895,311 B1 11/2014 Handique et al.
D729,404 S 5/2015 Teich et al.
9,028,773 B2 5/2015 Ganesan
9,040,288 B2 * 5/2015 Handique ............... B01L 9/527 435/303.1
9,051,604 B2 6/2015 Handique
9,080,207 B2 * 7/2015 Handique ........... F16K 99/0061
D742,027 S 10/2015 Lentz et al.
9,186,677 B2 11/2015 Williams et al.
9,217,143 B2 12/2015 Brahmasandra et al.
9,222,954 B2 12/2015 Lentz et al.
9,234,236 B2 1/2016 Thomas et al.
9,238,223 B2 1/2016 Handique
9,259,734 B2 2/2016 Williams et al.
9,259,735 B2 2/2016 Handique et al.
9,347,586 B2 5/2016 Williams et al.
9,382,532 B2 7/2016 Brahmasandra et al.
9,480,983 B2 11/2016 Lentz et al.
9,528,142 B2 12/2016 Handique
9,618,139 B2 4/2017 Handique
D787,087 S 5/2017 Duffy et al.
9,670,528 B2 6/2017 Handique et al.
9,677,121 B2 6/2017 Ganesan et al.
9,701,957 B2 7/2017 Wilson et al.
9,745,623 B2 8/2017 Steel
9,765,389 B2 9/2017 Gubatayao et al.
9,789,481 B2 10/2017 Petersen et al.
9,802,199 B2 10/2017 Handique et al.
9,815,057 B2 11/2017 Handique
9,958,466 B2 5/2018 Dalbert et al.
10,065,185 B2 9/2018 Handique
10,071,376 B2 9/2018 Williams et al.
10,076,754 B2 9/2018 Lentz et al.
10,100,302 B2 10/2018 Brahmasandra et al.
10,139,012 B2 11/2018 Handique
10,179,910 B2 1/2019 Duffy et al.
10,234,474 B2 3/2019 Williams et al.
10,351,901 B2 7/2019 Ganesan et al.
10,364,456 B2 7/2019 Wu et al.
10,443,088 B1 10/2019 Wu et al.
10,494,663 B1 12/2019 Wu et al.
10,571,935 B2 2/2020 Handique et al.
10,590,410 B2 3/2020 Brahmasandra et al.
10,604,788 B2 3/2020 Wu et al.
10,619,191 B2 4/2020 Ganesan et al.
10,625,261 B2 4/2020 Williams et al.
10,625,262 B2 4/2020 Williams et al.
10,632,466 B1 4/2020 Williams et al.
10,695,764 B2 6/2020 Handique et al.
10,710,069 B2 7/2020 Handique et al.
10,717,085 B2 7/2020 Williams et al.
10,731,201 B2 8/2020 Handique et al.
10,781,482 B2 9/2020 Gubatayao et al.
10,799,862 B2 10/2020 Handique et al.
10,821,436 B2 11/2020 Handique et al.
10,821,446 B1 11/2020 Handique et al.
10,822,644 B2 11/2020 Steel et al.
10,843,188 B2 11/2020 Handique et al.
10,844,368 B2 11/2020 Duffy et al.
10,857,535 B2 12/2020 Handique et al.
10,865,437 B2 12/2020 Handique et al.
10,875,022 B2 12/2020 Williams et al.
10,900,066 B2 1/2021 Handique et al.
10,913,061 B2 2/2021 Handique et al.
11,060,082 B2 7/2021 Brahmasandra et al.
11,078,523 B2 8/2021 Handique et al.
11,085,069 B2 8/2021 Handique et al.
11,141,734 B2 10/2021 Handique et al.
11,142,785 B2 10/2021 Handique et al.
11,254,927 B2 2/2022 Brahmasandra et al.
11,266,987 B2 3/2022 Handique
11,441,171 B2 9/2022 Wu et al.
11,453,906 B2 9/2022 Handique
11,466,263 B2 10/2022 Duffy et al.
11,549,959 B2 1/2023 Williams et al.
11,666,903 B2 6/2023 Handique et al.
11,788,127 B2 10/2023 Gubatayao et al.
11,806,718 B2 11/2023 Handique et al.
11,845,081 B2 12/2023 Williams et al.
11,959,126 B2 4/2024 Handique et al.
12,030,050 B2 7/2024 Handique
12,128,402 B2 10/2024 Handique
12,128,405 B2 10/2024 Handique et al.
12,139,745 B2 11/2024 Handique et al.
12,162,007 B2 12/2024 Handique et al.
2001/0005489 A1 6/2001 Roach et al.
2001/0012492 A1 8/2001 Acosta et al.
2001/0016358 A1 8/2001 Osawa et al.
2001/0018513 A1 8/2001 Baker
2001/0021355 A1 9/2001 Baugh et al.
2001/0023848 A1 9/2001 Gjerde et al.
2001/0038450 A1 11/2001 McCaffrey et al.
2001/0045358 A1 11/2001 Kopf-Sill et al.

(56) References Cited

U.S. PATENT DOCUMENTS

| | | | |
|---|---|---|---|
| 2001/0046702 A1 | 11/2001 | Schembri | |
| 2001/0048899 A1 | 12/2001 | Marouiss et al. | |
| 2001/0051340 A1 | 12/2001 | Singh et al. | |
| 2001/0055765 A1 | 12/2001 | O'Keefe et al. | |
| 2002/0001848 A1 | 1/2002 | Bedingham et al. | |
| 2002/0008053 A1 | 1/2002 | Hansen et al. | |
| 2002/0009015 A1 | 1/2002 | Laugharn, Jr. et al. | |
| 2002/0014443 A1 | 2/2002 | Hansen et al. | |
| 2002/0015667 A1 | 2/2002 | Chow | |
| 2002/0021983 A1 | 2/2002 | Comte et al. | |
| 2002/0022261 A1 | 2/2002 | Anderson et al. | |
| 2002/0037499 A1 | 3/2002 | Quake et al. | |
| 2002/0039783 A1 | 4/2002 | McMillan et al. | |
| 2002/0047003 A1 | 4/2002 | Bedingham et al. | |
| 2002/0053399 A1 | 5/2002 | Soane et al. | |
| 2002/0054835 A1 | 5/2002 | Robotti et al. | |
| 2002/0055167 A1 | 5/2002 | Pourahmadi et al. | |
| 2002/0058332 A1 | 5/2002 | Quake et al. | |
| 2002/0060156 A1 | 5/2002 | Mathies et al. | |
| 2002/0068357 A1 | 6/2002 | Mathies et al. | |
| 2002/0068821 A1 | 6/2002 | Gundling | |
| 2002/0081669 A1 | 6/2002 | Festoc | |
| 2002/0086417 A1 | 7/2002 | Chen | |
| 2002/0086443 A1 | 7/2002 | Bamdad | |
| 2002/0090320 A1 | 7/2002 | Burow et al. | |
| 2002/0092767 A1 | 7/2002 | Bjornson et al. | |
| 2002/0094303 A1 | 7/2002 | Yamamoto et al. | |
| 2002/0131903 A1 | 9/2002 | Ingenhoven et al. | |
| 2002/0141903 A1 | 10/2002 | Parunak et al. | |
| 2002/0143297 A1 | 10/2002 | Francavilla et al. | |
| 2002/0155010 A1 | 10/2002 | Karp et al. | |
| 2002/0155477 A1 | 10/2002 | Ito | |
| 2002/0169518 A1 | 11/2002 | Luoma et al. | |
| 2002/0173032 A1 | 11/2002 | Zou et al. | |
| 2002/0176804 A1 | 11/2002 | Strand et al. | |
| 2002/0187557 A1 | 12/2002 | Hobbs et al. | |
| 2002/0192808 A1 | 12/2002 | Gambini et al. | |
| 2003/0008308 A1 | 1/2003 | Enzelberger et al. | |
| 2003/0008320 A1 | 1/2003 | Baker | |
| 2003/0019522 A1 | 1/2003 | Parunak | |
| 2003/0022392 A1 | 1/2003 | Hudak | |
| 2003/0036067 A1 | 2/2003 | Schwartz | |
| 2003/0049833 A1 | 3/2003 | Chen et al. | |
| 2003/0059823 A1 | 3/2003 | Matsunaga et al. | |
| 2003/0064507 A1 | 4/2003 | Gallagher et al. | |
| 2003/0072683 A1 | 4/2003 | Stewart et al. | |
| 2003/0073106 A1 | 4/2003 | Johansen et al. | |
| 2003/0073110 A1 | 4/2003 | Aritomi et al. | |
| 2003/0083686 A1 | 5/2003 | Freeman et al. | |
| 2003/0087300 A1 | 5/2003 | Knapp et al. | |
| 2003/0088657 A1 | 5/2003 | Eggers | |
| 2003/0096310 A1 | 5/2003 | Hansen et al. | |
| 2003/0099954 A1 | 5/2003 | Miltenyi et al. | |
| 2003/0124611 A1 | 7/2003 | Schwartz | |
| 2003/0127327 A1 | 7/2003 | Kurnik | |
| 2003/0129094 A1 | 7/2003 | Schubert et al. | |
| 2003/0134333 A1 | 7/2003 | Dehlinger et al. | |
| 2003/0136679 A1 | 7/2003 | Bohn et al. | |
| 2003/0156991 A1 | 8/2003 | Halas et al. | |
| 2003/0180192 A1 | 9/2003 | Seippel | |
| 2003/0186295 A1 | 10/2003 | Colin et al. | |
| 2003/0190608 A1 | 10/2003 | Blackburn et al. | |
| 2003/0199081 A1 | 10/2003 | Wilding et al. | |
| 2003/0211517 A1 | 11/2003 | Carulli et al. | |
| 2004/0014202 A1 | 1/2004 | King et al. | |
| 2004/0014238 A1 | 1/2004 | Krug et al. | |
| 2004/0018119 A1 | 1/2004 | Massaro | |
| 2004/0022689 A1 | 2/2004 | Wulf et al. | |
| 2004/0029258 A1 | 2/2004 | Heaney et al. | |
| 2004/0029260 A1 | 2/2004 | Hansen et al. | |
| 2004/0037739 A1 | 2/2004 | McNeely et al. | |
| 2004/0043479 A1 | 3/2004 | Briscoe et al. | |
| 2004/0053290 A1 | 3/2004 | Terbrueggen et al. | |
| 2004/0063217 A1 | 4/2004 | Webster et al. | |
| 2004/0065655 A1 | 4/2004 | Brown | |
| 2004/0072278 A1 | 4/2004 | Chou et al. | |
| 2004/0072375 A1 | 4/2004 | Gjerde et al. | |
| 2004/0076996 A1 | 4/2004 | Kondo et al. | |
| 2004/0086427 A1 | 5/2004 | Childers et al. | |
| 2004/0086870 A1 | 5/2004 | Tyvoll et al. | |
| 2004/0086956 A1 | 5/2004 | Bachur | |
| 2004/0132059 A1 | 7/2004 | Scurati et al. | |
| 2004/0141887 A1 | 7/2004 | Mainquist et al. | |
| 2004/0151629 A1 | 8/2004 | Pease et al. | |
| 2004/0157220 A1 | 8/2004 | Kurnool et al. | |
| 2004/0161788 A1 | 8/2004 | Chen et al. | |
| 2004/0171515 A1 | 9/2004 | Hamers et al. | |
| 2004/0189311 A1 | 9/2004 | Glezer et al. | |
| 2004/0197810 A1 | 10/2004 | Takenaka et al. | |
| 2004/0200909 A1 | 10/2004 | McMillan et al. | |
| 2004/0203173 A1 | 10/2004 | Peck et al. | |
| 2004/0209331 A1 | 10/2004 | Ririe | |
| 2004/0209354 A1 | 10/2004 | Mathies et al. | |
| 2004/0224317 A1 | 11/2004 | Kordunsky et al. | |
| 2004/0235154 A1 | 11/2004 | Oh et al. | |
| 2004/0240097 A1 | 12/2004 | Evans | |
| 2004/0258565 A1 | 12/2004 | Watari | |
| 2005/0009174 A1 | 1/2005 | Nikiforov et al. | |
| 2005/0013737 A1 | 1/2005 | Chow et al. | |
| 2005/0019902 A1 | 1/2005 | Mathies et al. | |
| 2005/0037471 A1 | 2/2005 | Liu et al. | |
| 2005/0041525 A1 | 2/2005 | Pugia et al. | |
| 2005/0042639 A1 | 2/2005 | Knapp et al. | |
| 2005/0048540 A1 | 3/2005 | Inami et al. | |
| 2005/0058574 A1 | 3/2005 | Bysouth et al. | |
| 2005/0058577 A1 | 3/2005 | Micklash et al. | |
| 2005/0064535 A1 | 3/2005 | Favuzzi et al. | |
| 2005/0069898 A1 | 3/2005 | Moon et al. | |
| 2005/0106066 A1 | 5/2005 | Saltsman et al. | |
| 2005/0112754 A1 | 5/2005 | Yoon et al. | |
| 2005/0121324 A1 | 6/2005 | Park et al. | |
| 2005/0129580 A1 | 6/2005 | Swinehart et al. | |
| 2005/0130198 A1 | 6/2005 | Ammann et al. | |
| 2005/0133370 A1 | 6/2005 | Park et al. | |
| 2005/0135655 A1 | 6/2005 | Kopf-sill et al. | |
| 2005/0142036 A1 | 6/2005 | Kim et al. | |
| 2005/0158781 A1 | 7/2005 | Woudenberg et al. | |
| 2005/0170362 A1 | 8/2005 | Wada et al. | |
| 2005/0186585 A1 | 8/2005 | Juncosa et al. | |
| 2005/0196321 A1 | 9/2005 | Huang | |
| 2005/0202470 A1 | 9/2005 | Sundberg et al. | |
| 2005/0202489 A1 | 9/2005 | Cho et al. | |
| 2005/0202504 A1 | 9/2005 | Anderson et al. | |
| 2005/0205788 A1 | 9/2005 | Itoh | |
| 2005/0208676 A1 | 9/2005 | Kahatt | |
| 2005/0214172 A1 | 9/2005 | Burgisser | |
| 2005/0220675 A1 | 10/2005 | Reed et al. | |
| 2005/0226779 A1 | 10/2005 | Oldham et al. | |
| 2005/0227269 A1 | 10/2005 | Lloyd et al. | |
| 2005/0233370 A1 | 10/2005 | Ammann et al. | |
| 2005/0238545 A1 | 10/2005 | Parce et al. | |
| 2005/0239127 A1 | 10/2005 | Ammann et al. | |
| 2005/0266489 A1 | 12/2005 | Ammann et al. | |
| 2005/0276728 A1 | 12/2005 | Muller-Cohn et al. | |
| 2006/0002817 A1 | 1/2006 | Bohm et al. | |
| 2006/0003373 A1 | 1/2006 | Ammann et al. | |
| 2006/0041058 A1 | 2/2006 | Yin et al. | |
| 2006/0057039 A1 | 3/2006 | Morse et al. | |
| 2006/0057629 A1 | 3/2006 | Kim | |
| 2006/0058519 A1 | 3/2006 | Deggerdal et al. | |
| 2006/0062696 A1 | 3/2006 | Chow et al. | |
| 2006/0081539 A1 | 4/2006 | Safar et al. | |
| 2006/0094004 A1 | 5/2006 | Nakajima et al. | |
| 2006/0094108 A1* | 5/2006 | Yoder | B01L 3/508<br>435/293.1 |
| 2006/0113190 A1 | 6/2006 | Kurnik | |
| 2006/0133965 A1 | 6/2006 | Tajima et al. | |
| 2006/0134790 A1 | 6/2006 | Tanaka et al. | |
| 2006/0148063 A1 | 7/2006 | Fauzzi et al. | |
| 2006/0154341 A1 | 7/2006 | Chen | |
| 2006/0165558 A1 | 7/2006 | Witty et al. | |
| 2006/0165559 A1 | 7/2006 | Greenstein et al. | |
| 2006/0177376 A1 | 8/2006 | Tomalia et al. | |
| 2006/0177855 A1 | 8/2006 | Utermohlen et al. | |

(56) References Cited

U.S. PATENT DOCUMENTS

| | | | |
|---|---|---|---|
| 2006/0183216 | A1 | 8/2006 | Handique |
| 2006/0201887 | A1 | 9/2006 | Siddiqi |
| 2006/0205085 | A1 | 9/2006 | Handique |
| 2006/0207944 | A1 | 9/2006 | Siddiqi |
| 2006/0210435 | A1 | 9/2006 | Alavie et al. |
| 2006/0223169 | A1 | 10/2006 | Bedingham et al. |
| 2006/0228268 | A1 | 10/2006 | Heimberg et al. |
| 2006/0228734 | A1 | 10/2006 | Vann et al. |
| 2006/0246493 | A1 | 11/2006 | Jensen et al. |
| 2006/0246533 | A1 | 11/2006 | Fathollahi et al. |
| 2006/0269641 | A1 | 11/2006 | Atwood et al. |
| 2006/0269961 | A1 | 11/2006 | Fukushima et al. |
| 2007/0004028 | A1 | 1/2007 | Lair et al. |
| 2007/0009386 | A1 | 1/2007 | Padmanabhan et al. |
| 2007/0014695 | A1 | 1/2007 | Yue et al. |
| 2007/0020699 | A1 | 1/2007 | Carpenter et al. |
| 2007/0020764 | A1 | 1/2007 | Miller |
| 2007/0026421 | A1 | 2/2007 | Sundberg et al. |
| 2007/0042441 | A1 | 2/2007 | Masters et al. |
| 2007/0048188 | A1 | 3/2007 | Bigus |
| 2007/0054413 | A1 | 3/2007 | Aviles et al. |
| 2007/0077643 | A1 | 4/2007 | Nakamura et al. |
| 2007/0077648 | A1 | 4/2007 | Okamoto et al. |
| 2007/0092901 | A1 | 4/2007 | Ligler et al. |
| 2007/0098600 | A1 | 5/2007 | Kayyem et al. |
| 2007/0099200 | A1 | 5/2007 | Chow et al. |
| 2007/0104617 | A1 | 5/2007 | Coulling et al. |
| 2007/0116613 | A1 | 5/2007 | Elsener |
| 2007/0134808 | A1 | 6/2007 | Sullivan |
| 2007/0154895 | A1 | 7/2007 | Spaid et al. |
| 2007/0177147 | A1 | 8/2007 | Parce |
| 2007/0178603 | A1 | 8/2007 | Takii et al. |
| 2007/0178607 | A1 | 8/2007 | Prober et al. |
| 2007/0184463 | A1 | 8/2007 | Molho et al. |
| 2007/0184547 | A1 | 8/2007 | Handique et al. |
| 2007/0196237 | A1 | 8/2007 | Neuzil et al. |
| 2007/0196238 | A1 | 8/2007 | Kennedy et al. |
| 2007/0199821 | A1 | 8/2007 | Chow |
| 2007/0215554 | A1 | 9/2007 | Kreuwel et al. |
| 2007/0218459 | A1 | 9/2007 | Miller et al. |
| 2007/0231213 | A1 | 10/2007 | Prabhu et al. |
| 2007/0238161 | A1 | 10/2007 | Cerrone et al. |
| 2007/0243626 | A1 | 10/2007 | Windeyer et al. |
| 2007/0248958 | A1 | 10/2007 | Jovanovich et al. |
| 2007/0261479 | A1 | 11/2007 | Spaid et al. |
| 2007/0269861 | A1 | 11/2007 | Williams et al. |
| 2007/0292941 | A1 | 12/2007 | Handique et al. |
| 2008/0000774 | A1 | 1/2008 | Park et al. |
| 2008/0003649 | A1 | 1/2008 | Maltezos et al. |
| 2008/0017306 | A1 | 1/2008 | Liu et al. |
| 2008/0056948 | A1 | 3/2008 | Dale et al. |
| 2008/0069729 | A1 | 3/2008 | McNeely |
| 2008/0090244 | A1 | 4/2008 | Knapp et al. |
| 2008/0095673 | A1 | 4/2008 | Xu |
| 2008/0118987 | A1 | 5/2008 | Eastwood et al. |
| 2008/0124723 | A1 | 5/2008 | Dale et al. |
| 2008/0153152 | A1 | 6/2008 | Wakabayashi et al. |
| 2008/0166793 | A1 | 7/2008 | Beer et al. |
| 2008/0176230 | A1 | 7/2008 | Owen et al. |
| 2008/0192254 | A1 | 8/2008 | Kim et al. |
| 2008/0220509 | A1 | 9/2008 | Segawa et al. |
| 2008/0226502 | A1 | 9/2008 | Jonsmann et al. |
| 2008/0240898 | A1 | 10/2008 | Manz et al. |
| 2008/0247914 | A1 | 10/2008 | Edens et al. |
| 2008/0257882 | A1 | 10/2008 | Turner |
| 2008/0280285 | A1 | 11/2008 | Chen et al. |
| 2008/0308500 | A1 | 12/2008 | Brassard |
| 2009/0047180 | A1 | 2/2009 | Kawahara |
| 2009/0066339 | A1 | 3/2009 | Glezer et al. |
| 2009/0136385 | A1 | 5/2009 | Handique et al. |
| 2009/0148933 | A1 | 6/2009 | Battrell et al. |
| 2009/0189089 | A1 | 7/2009 | Bedingham et al. |
| 2009/0223925 | A1 | 9/2009 | Morse et al. |
| 2009/0325164 | A1 | 12/2009 | Vossenaar et al. |
| 2009/0325276 | A1 | 12/2009 | Battrell et al. |
| 2010/0009343 | A1 | 1/2010 | Fischer et al. |
| 2010/0009351 | A1 | 1/2010 | Brahmasandra et al. |
| 2010/0120129 | A1 | 5/2010 | Amshey et al. |
| 2010/0233763 | A1 | 9/2010 | Shigeura et al. |
| 2010/0284864 | A1 | 11/2010 | Holenstein et al. |
| 2011/0008825 | A1 | 1/2011 | Ingber et al. |
| 2011/0027151 | A1 | 2/2011 | Handique et al. |
| 2011/0060136 | A1 | 3/2011 | Matsunaga et al. |
| 2011/0097493 | A1 | 4/2011 | Kerr et al. |
| 2011/0127292 | A1 | 6/2011 | Sarofim et al. |
| 2011/0158865 | A1 | 6/2011 | Miller et al. |
| 2011/0245061 | A1 | 10/2011 | Haechler |
| 2011/0287447 | A1 | 11/2011 | Norderhaug |
| 2011/0300033 | A1 | 12/2011 | Battisti |
| 2012/0122231 | A1 | 5/2012 | Tajima |
| 2012/0160826 | A1 | 6/2012 | Handique |
| 2012/0171678 | A1 | 7/2012 | Maltezos et al. |
| 2012/0258463 | A1 | 10/2012 | Duffy et al. |
| 2013/0183769 | A1 | 7/2013 | Tajima |
| 2013/0210127 | A1 | 8/2013 | Williams et al. |
| 2013/0315800 | A1 | 11/2013 | Yin et al. |
| 2014/0030798 | A1 | 1/2014 | Wu et al. |
| 2014/0120544 | A1 | 5/2014 | Brahmasandra et al. |
| 2014/0227710 | A1 | 8/2014 | Handique et al. |
| 2015/0045234 | A1 | 2/2015 | Stone et al. |
| 2015/0174579 | A1 | 6/2015 | Iten et al. |
| 2015/0315631 | A1 | 11/2015 | Handique et al. |
| 2016/0038942 | A1 | 2/2016 | Roberts |
| 2017/0275702 | A1 | 9/2017 | Dahiya et al. |
| 2018/0333722 | A1 | 11/2018 | Handique |
| 2019/0144849 | A1 | 5/2019 | Duffy et al. |
| 2019/0145546 | A1 | 5/2019 | Handique |
| 2019/0151854 | A1 | 5/2019 | Baum et al. |
| 2019/0154719 | A1 | 5/2019 | LaChance et al. |
| 2019/0284606 | A1 | 9/2019 | Wu et al. |
| 2019/0324050 | A1 | 10/2019 | Williams et al. |
| 2020/0139363 | A1 | 5/2020 | Handique et al. |
| 2021/0121887 | A1 | 4/2021 | Handique et al. |
| 2021/0123090 | A1 | 4/2021 | Handique et al. |
| 2021/0147923 | A1 | 5/2021 | Steel et al. |
| 2022/0010364 | A1 | 1/2022 | Handique et al. |
| 2022/0170008 | A1 | 6/2022 | Brahmasandra et al. |
| 2023/0023741 | A1 | 1/2023 | Handique |
| 2023/0041595 | A1 | 2/2023 | Wu et al. |
| 2024/0110236 | A1 | 4/2024 | Gubatayao et al. |
| 2024/0326057 | A1 | 10/2024 | Handique et al. |
| 2024/0359179 | A1 | 10/2024 | Williams et al. |
| 2025/0010295 | A1 | 1/2025 | Handique |

FOREIGN PATENT DOCUMENTS

| | | | |
|---|---|---|---|
| AU | 4437602 | | 7/2002 |
| AU | 4437702 | | 7/2002 |
| AU | 764319 | B2 | 8/2003 |
| CA | 2574107 | | 9/1998 |
| CA | 2294819 | | 1/1999 |
| CN | 1934451 | | 3/2007 |
| CN | 1312287 | C | 4/2007 |
| CN | 1942590 | A | 4/2007 |
| CN | 1968754 | A | 5/2007 |
| CN | 101466848 | | 6/2009 |
| CN | 101522909 | | 9/2009 |
| CN | 103540518 | | 1/2014 |
| DE | 19755479 | A1 | 6/1999 |
| DE | 19929734 | | 12/1999 |
| DE | 19833293 | C1 | 1/2000 |
| EP | 0136126 | A2 | 4/1985 |
| EP | 0365828 | A2 | 5/1990 |
| EP | 0483620 | A2 | 5/1992 |
| EP | 0402994 | B1 | 11/1994 |
| EP | 0393744 | B1 | 1/1995 |
| EP | 0688602 | A2 | 12/1995 |
| EP | 0707077 | A2 | 4/1996 |
| EP | 0698046 | B1 | 3/1997 |
| EP | 0766256 | | 4/1997 |
| EP | 0772494 | B1 | 5/1997 |
| EP | 0810030 | A1 | 12/1997 |
| EP | 1059458 | A2 | 12/2000 |
| EP | 1064090 | A1 | 1/2001 |

(56) References Cited

FOREIGN PATENT DOCUMENTS

| | | | |
|---|---|---|---|
| EP | 1077086 | A2 | 2/2001 |
| EP | 1346772 | A2 | 9/2003 |
| EP | 1541237 | A2 | 6/2005 |
| EP | 1574586 | A2 | 9/2005 |
| EP | 1621890 | A1 | 2/2006 |
| EP | 1780290 | A2 | 5/2007 |
| EP | 1792656 | A1 | 6/2007 |
| EP | 2372367 | A1 | 10/2011 |
| FR | 2672301 | | 8/1992 |
| FR | 2795426 | | 12/2000 |
| GB | 2453432 | A | 4/2009 |
| JP | S50-100881 | | 8/1975 |
| JP | 58212921 | A | 12/1983 |
| JP | S62-119460 | | 5/1987 |
| JP | H01-502319 | | 8/1989 |
| JP | H03181853 | | 8/1991 |
| JP | 04-053555 | U | 5/1992 |
| JP | 06-064156 | U | 9/1994 |
| JP | 07-020010 | | 1/1995 |
| JP | H07-290706 | | 11/1995 |
| JP | H08-122336 | | 5/1996 |
| JP | H08-173194 | | 7/1996 |
| JP | H08-211071 | | 8/1996 |
| JP | H08-285859 | | 11/1996 |
| JP | H08-337116 | | 12/1996 |
| JP | H09-304385 | | 11/1997 |
| JP | H09-325151 | | 12/1997 |
| JP | 2001-502790 | | 1/1998 |
| JP | H01-219669 | | 9/1998 |
| JP | H10-327515 | | 12/1998 |
| JP | H11-009258 | | 1/1999 |
| JP | H11-501504 | | 2/1999 |
| JP | H11-503315 | | 3/1999 |
| JP | H11-156231 | | 6/1999 |
| JP | H11-316226 | | 11/1999 |
| JP | H11-515106 | | 12/1999 |
| JP | 2000-180455 | | 6/2000 |
| JP | 2000-266760 | | 9/2000 |
| JP | 2000-275255 | | 10/2000 |
| JP | 2000-514928 | | 11/2000 |
| JP | 2001-502319 | | 2/2001 |
| JP | 2001-204462 | | 7/2001 |
| JP | 2001-509437 | | 7/2001 |
| JP | 3191150 | B2 | 7/2001 |
| JP | 2001-515216 | | 9/2001 |
| JP | 2001-523812 | | 11/2001 |
| JP | 2001-527220 | | 12/2001 |
| JP | 2002-503331 | | 1/2002 |
| JP | 2002-085961 | | 3/2002 |
| JP | 2002-517735 | | 6/2002 |
| JP | 2002-215241 | | 7/2002 |
| JP | 2002-540382 | | 11/2002 |
| JP | 2002-544476 | | 12/2002 |
| JP | 2003-500169 | | 1/2003 |
| JP | 2003-500674 | | 1/2003 |
| JP | 2003-047839 | A | 2/2003 |
| JP | 2003-047840 | A | 2/2003 |
| JP | 2003-516125 | | 5/2003 |
| JP | 2003-164279 | | 6/2003 |
| JP | 2003-185584 | | 7/2003 |
| JP | 2003-299485 | | 10/2003 |
| JP | 2003-329693 | | 11/2003 |
| JP | 2003-329696 | | 11/2003 |
| JP | 2003-532382 | A | 11/2003 |
| JP | 2004-003989 | | 1/2004 |
| JP | 2004-506179 | A | 2/2004 |
| JP | 2004-150797 | A | 5/2004 |
| JP | 2004-283728 | A | 10/2004 |
| JP | 2004-531360 | A | 10/2004 |
| JP | 2004-533838 | | 11/2004 |
| JP | 2004-534157 | | 11/2004 |
| JP | 2004-361421 | | 12/2004 |
| JP | 2004-536291 | | 12/2004 |
| JP | 2004-536689 | A | 12/2004 |
| JP | 2005-009870 | | 1/2005 |
| JP | 2005-010179 | | 1/2005 |
| JP | 2005-511264 | | 4/2005 |
| JP | 2005-514718 | | 5/2005 |
| JP | 2005-518825 | | 6/2005 |
| JP | 2005-176613 | A | 7/2005 |
| JP | 2005-192439 | | 7/2005 |
| JP | 2005-192554 | | 7/2005 |
| JP | 2005-519751 | | 7/2005 |
| JP | 2005-204661 | | 8/2005 |
| JP | 2005-525816 | | 9/2005 |
| JP | 2005-291954 | A | 10/2005 |
| JP | 2005-532043 | | 10/2005 |
| JP | 2005-323519 | | 11/2005 |
| JP | 2005-533652 | | 11/2005 |
| JP | 2005-535904 | | 11/2005 |
| JP | 2006-021156 | A | 1/2006 |
| JP | 2006-055837 | A | 3/2006 |
| JP | 2006-094866 | A | 4/2006 |
| JP | 2006-145458 | | 6/2006 |
| JP | 2006-167569 | | 6/2006 |
| JP | 2006-284409 | | 10/2006 |
| JP | 2007-024742 | A | 2/2007 |
| JP | 2007-074960 | | 3/2007 |
| JP | 2007-097477 | | 4/2007 |
| JP | 2007-101364 | | 4/2007 |
| JP | 2007-510518 | | 4/2007 |
| JP | 2007-514405 | A | 6/2007 |
| JP | 2007-178328 | | 7/2007 |
| JP | 2007-535933 | | 12/2007 |
| JP | 2009-515140 | | 4/2009 |
| JP | 2009-542207 | | 12/2009 |
| JP | 3193848 | U | 10/2014 |
| KR | 1020060044489 | A | 5/2006 |
| RU | 2418633 | C2 | 5/2011 |
| WO | WO 1988/006633 | | 9/1988 |
| WO | WO 1990/012350 | | 10/1990 |
| WO | WO 1992/005443 | | 4/1992 |
| WO | WO 1994/005414 | | 3/1994 |
| WO | WO 1994/011103 | | 5/1994 |
| WO | WO 1995/033846 | | 12/1995 |
| WO | WO 1996/000228 | | 1/1996 |
| WO | WO 1996/004547 | | 2/1996 |
| WO | WO 1996/018731 | | 6/1996 |
| WO | WO 1996/039547 | | 12/1996 |
| WO | WO 1997/005492 | | 2/1997 |
| WO | WO 1997/016835 | | 5/1997 |
| WO | WO 1997/021090 | | 6/1997 |
| WO | WO 1997/022825 | | 6/1997 |
| WO | WO 1997/027324 | | 7/1997 |
| WO | WO 1998/000231 | | 1/1998 |
| WO | WO 1998/007019 | | 2/1998 |
| WO | WO 1998/022625 | | 5/1998 |
| WO | WO 1998/035013 | | 8/1998 |
| WO | WO 1998/038487 | | 9/1998 |
| WO | WO 1998/049548 | | 11/1998 |
| WO | WO 1998/050147 | | 11/1998 |
| WO | WO 1998/053311 | | 11/1998 |
| WO | WO 1999/001688 | | 1/1999 |
| WO | WO 1999/009042 | | 2/1999 |
| WO | WO 1999/012016 | | 3/1999 |
| WO | WO 1999/016549 | | 4/1999 |
| WO | WO 1999/017093 | | 4/1999 |
| WO | WO 1999/029703 | | 6/1999 |
| WO | WO 1999/033559 | | 7/1999 |
| WO | WO 1999/060397 | | 11/1999 |
| WO | WO 2000/022436 | | 4/2000 |
| WO | WO 2000/066783 | | 11/2000 |
| WO | WO 2000/073412 | | 12/2000 |
| WO | WO 2000/075623 | | 12/2000 |
| WO | WO 2000/078455 | | 12/2000 |
| WO | WO 2001/005510 | | 1/2001 |
| WO | WO 2001/014931 | | 3/2001 |
| WO | WO 2001/027614 | | 4/2001 |
| WO | WO 2001/028684 | | 4/2001 |
| WO | WO 2001/030995 | | 5/2001 |
| WO | WO 2001/041931 | | 6/2001 |
| WO | WO 2001/046474 | | 6/2001 |
| WO | WO 2001/054813 | | 8/2001 |
| WO | WO 2001/089681 | | 11/2001 |

(56) References Cited

FOREIGN PATENT DOCUMENTS

| | | | |
|---|---|---|---|
| WO | WO 2001/089705 | 11/2001 | |
| WO | WO 2001/092569 | 12/2001 | |
| WO | WO 2002/043864 | 6/2002 | |
| WO | WO 2002/048164 | 6/2002 | |
| WO | WO 2002/052002 | 7/2002 | |
| WO | WO 2002/072264 | 9/2002 | |
| WO | WO 2002/078845 | 10/2002 | |
| WO | WO 2002/086454 | 10/2002 | |
| WO | WO 2002/094185 | 11/2002 | |
| WO | WO 2003/007677 | 1/2003 | |
| WO | WO 2003/012325 | 2/2003 | |
| WO | WO 2003/012406 | 2/2003 | |
| WO | WO 2003/048295 | 6/2003 | |
| WO | WO 2003/055605 | 7/2003 | |
| WO | WO 2003/076661 | 9/2003 | |
| WO | WO 2003/078065 | 9/2003 | |
| WO | WO 2003/080868 | 10/2003 | |
| WO | WO 2003/087410 | 10/2003 | |
| WO | WO 2004/007081 | 1/2004 | |
| WO | WO 2004/010760 | 2/2004 | |
| WO | WO 2004/048545 | 6/2004 | |
| WO | WO 2004/055522 | 7/2004 | |
| WO | WO 2004/056485 | 7/2004 | |
| WO | WO 2004/074848 | 9/2004 | |
| WO | WO 2004/094986 | 11/2004 | |
| WO | WO 2005/008255 | 1/2005 | |
| WO | WO 2005/011867 | 2/2005 | |
| WO | WO 2005/030984 | 4/2005 | |
| WO | WO 2005/072353 | 8/2005 | |
| WO | WO-2005075081 A1 * | 8/2005 | ............. B01L 9/527 |
| WO | WO 2005/094981 | 10/2005 | |
| WO | WO 2005/100538 | 10/2005 | |
| WO | WO 2005/107947 | 11/2005 | |
| WO | WO 2005/108571 | 11/2005 | |
| WO | WO 2005/108620 | 11/2005 | |
| WO | WO 2005/116202 | 12/2005 | |
| WO | WO 2005/118867 | 12/2005 | |
| WO | WO 2005/120710 | 12/2005 | |
| WO | WO 2006/010584 | 2/2006 | |
| WO | WO 2006/032044 | 3/2006 | |
| WO | WO 2006/035800 | 4/2006 | |
| WO | WO 2006/043642 | 4/2006 | |
| WO | WO 2006/066001 | 6/2006 | |
| WO | WO 2006/079082 | 7/2006 | |
| WO | WO 2006/081324 | 8/2006 | |
| WO | WO 2006/081995 | 8/2006 | |
| WO | WO 2006/113198 | 10/2006 | |
| WO | WO 2006/118420 | 11/2006 | |
| WO | WO 2006/119280 | 11/2006 | |
| WO | WO 2007/044917 | 4/2007 | |
| WO | WO 2007/050327 | 5/2007 | |
| WO | WO 2007/064117 | 6/2007 | |
| WO | WO 2007/075919 | 7/2007 | |
| WO | WO 2007/091530 | 8/2007 | |
| WO | WO 2007/112114 | 10/2007 | |
| WO | WO 2007/120240 | 10/2007 | |
| WO | WO 2007/120241 | 10/2007 | |
| WO | WO 2008/005321 | 1/2008 | |
| WO | WO 2008/030914 | 3/2008 | |
| WO | WO 2008/044387 | 4/2008 | |
| WO | WO 2008/060604 | 5/2008 | |
| WO | WO 2008/118566 | 10/2008 | |
| WO | WO 2008/134470 | 11/2008 | |
| WO | WO 2008/149282 | 12/2008 | |
| WO | WO 2009/012185 | 1/2009 | |
| WO | WO 2009/054870 | 4/2009 | |
| WO | WO 2010/118541 | 10/2010 | |
| WO | WO 2010/130310 | 11/2010 | |
| WO | WO 2010/140680 | 12/2010 | |
| WO | WO 2011/009073 | 1/2011 | |
| WO | WO 2011/101467 | 8/2011 | |

OTHER PUBLICATIONS

Altet et al., [Eds.] “Thermal Transfer and Thermal Coupling in IC’s”, Thermal Testing of Integrated Circuits; Chapter 2 (2002) Springer Science pp. 23-51.
Anderson et al., “Microfluidic biochemical analysis system” Proc. 1997 IEEE Int. Conf. Solid-State Sens. Actuat. (1997) pp. 477-480.
Anderson et al., “Advances in Integrated Genetic Analysis” Micro Total Analysis Systems ’98 Conference Proceedings, D. Kluwer Academic Publishers (1998) in 6 pages.
Anderson et al., “A Miniature Integrated Device for Automated Multistep Genetic Assays” Nucleic Acids Research (2000) 28(12), i-vi.
Ateya et al., “The good, the bad, and the tiny: a review of microflow cytometry”, Anal Bioanal Chem. (2008) 391(5):1485-1498.
Auroux et al., “Miniaturised nucleic acid analysis”, Lab Chip. (2004) 4(6):534-546.
Baechi et al., “High-density microvalve arrays for sample processing in PCR chips”, Biomed Microdevices. (2001) 3(3):183-190.
Baker M., “Clever PCR: more genotyping, smaller volumes.” Nature Methods (May 2010) 70(5):351-356.
BDProbeTec™ ET Neisseria gonorrhoeae Amplified DNA Assay Package Insert, Jul. 2010 (13 pages).
BDProbeTec™ ET System Brochure, Aug. 2010 (9 pages).
Becker H. “Fabrication of Polymer Microfluidic Devices”, in Biochip Technology (2001), Chapter 4, pp. 63-96.
Becker H., “Microfluidic Devices Fabricated by Polymer Hot Embossing,” in Integrated Microfabricated Biodevices: Advanced Technologies for Genomics, Drug Discovery, Bioanalysis, and Clinical Diagnostics (2002), Chapter 13, 32 pages.
Becker H., “Microfluidics: A Technology Coming of Age”, Med Device Technol. (2008) 19(3):21-24.
Becker et al., “Portable CE system with contactless conductivity detection in an injection molded polymer chip for on-site food analysis”, SPIE Proceedings MOEMS-MEMS 2008 Micro and Nanofabrication (2008) vol. 6886 in 8 pages.
Becker H., “Hype, hope and hubris: the quest for the killer application in microfluidics”, Lab on a Chip, The Royal Society of Chemistry (2009) 9:2119-2122.
Becker H., “Collective Wisdom”, Lab on a Chip, The Royal Society of Chemistry (2010) 10:1351-1354.
Belgrader et al., “ Rapid PCR for Identity Testing Using a Battery-Powered Miniature Thermal Cycler”, J Forensic Sci. (1998) 43(2):315-319.
Belgrader et al., “A minisonicator to rapidly disrupt bacterial spores for DNA analysis.”, Anal Chem. (1999) 71(19):4232-4236.
Belgrader et al., “Real-time PCR Analysis on Nucleic Acids Purified from Plasma Using a Silicon Chip”, Micro Total Analysis Systems 2000 (pp. 525-528). Springer, Dordrecht.
Belgrader et al., “A microfluidic cartridge to prepare spores for PCR analysis”, Biosens Bioelectron. (2000) 14(10-11):849-852.
Belgrader et al., “A Battery-Powered Notebook Thermal Cycler for Rapid Multiplex Real-Time PCR Analysis”, Anal Chem. (2001) 73(2):286-289.
Belgrader et al., “Rapid and Automated Cartridge-based Extraction of Leukocytes from Whole Blood for Microsatellite DNA Analysis by Capillary Electrophoresis”, Clin Chem. (2001) 47(10):1917-1933.
Belgrader et al., “A Rapid, Flow-through, DNA Extraction Module for Integration into Microfluidic Systems”, Micro Total Analysis Systems (2002) pp. 697-699). Springer, Dordrecht.
Belgrader et al., “Development of a Battery-Powered Portable Instrumentation for Rapid PCR Analysis”, in Integrated Microfabricated Devices, (2002) Ch. 8, pp. 183-206, CRC Press.
Bell M., “Integrated Microsystems in Clinical Chemistry”, in Integrated Microfabricated Devices, (2002) Ch. 16, pp. 415-435, CRC Press.
Benters et al., “Dendrimer-Activated Solid Supports for Nucleic Acid and Protein Microarrays”, ChemBioChem (2001) 2(9): 686-694.
Berthier et al., “Managing evaporation for more robust microscale assays Part 1. Volume loss in high throughput assays”, Lab Chip (2008) 8(6):852-859.

(56) References Cited

OTHER PUBLICATIONS

Berthier et al., "Managing evaporation for more robust microscale assays Part 2. Characterization of convection and diffusion for cell biology", Lab Chip (2008) 8(6):860-864.
Berthier et al., "Microdrops," in Microfluidics for Biotechnology (2006), Chapter 2, pp. 51-88.
BioMerieux Press Release: "bioMérieux—2018 Financial Results," dated Feb. 27, 2019, accessed at www.biomerieux.com, pp. 13.
Blanchard et al., "Micro structure mechanical failure characterization using rotating Couette flow in a small gap", J Micromech Microengin. (2005) 15(4):792-801.
Blanchard et al., "Single-disk and double-disk viscous micropumps", Sensors and Actuators A (2005) 122:149-158.
Blanchard et al., "Performance and Development of a Miniature Rotary Shaft Pump", J Fluids Eng. (2005) 127(4):752-760.
Blanchard et al., "Single-disk and double-disk viscous micropump", ASME 2004 Inter'l Mechanical Engineering Congress & Exposition, Nov. 13-20, 2004, Anaheim, CA, IMECE2004-61705:411-417.
Blanchard et al., "Miniature Single-Disk Viscous Pump (Single-DVP), Performance Characterization", J Fluids Eng. (2006) 128(3):602-610.
Bollet, C. et al., "A simple method for the isolation of chromosomal DNA from Gram positive or acid-fast bacteria", Nucleic Acids Research, vol. 19, No. 8 (1991), p. 1955.
Brahmasandra et al., On-chip DNA detection in microfabricated separation systems, SPIE Conference on Microfluidic Devices and Systems, 1998, vol. 3515, pp. 242-251, Santa Clara, CA.
Brahmasandra et al., "Microfabricated Devices for Integrated DNA Analysis", in Biochip Technology by Cheng et al., [Eds.] (2001) pp. 229-250.
Breadmore, M.C. et al., "Microchip-Based Purification of DNA from Biological Samples", Anal. Chem., vol. 75 (2003), pp. 1880-1886.
Brody, et al., Diffusion-Based Extraction in a Microfabricated Device, Sensors and Actuators Elsevier, 1997, vol. A58, No. 1, pp. 13-18.
Broyles et al., "Sample Filtration, Concentration, and Separation Integrated on Microfluidic Devices" Analytical Chemistry (American Chemical Society), (2003) 75(11): 2761-2767.
Bu et al., "Design and theoretical evaluation of a novel microfluidic device to be used for PCR", J Micromech Microengin. (2003) 13(4):S125-S130.
Burns et al., "Microfabricated Structures for Integrated DNA Analysis" Proc. Natl. Acad. Sci. USA (May 1996) 93: 5556-5561.
Burns et al., "An Integrated Nanoliter DNA Analysis Device", Science 282:484-487 (1998).
Cady et al., "Real-time PCR detection of Listeria monocytogenes using an integrated microfluidics platform", Sensors Actuat B. (2005) 107:332-341.
Carlen et al., "Paraffin Actuated Surface Micromachined Valve," in IEEE MEMS 2000 Conference, Miyazaki, Japan, (Jan. 2000) pp. 381-385.
Carles et al., "Polymerase Chain Reaction on Microchips" in Methods in Molecular Biolog—Microfluidic Techniques, Reviews & Protocols by Minteer S.D. [Ed.] Humana Press (2006), vol. 321; Chapter 11, pp. 131-140.
Chang-Yen et al., "A novel integrated optical dissolved oxygen sensor for cell culture and micro total analysis systems", IEEE Technical Digest MEMS International Conference Jan. 24, 2002, 4 pages.
Chang-Yen et al., "A PDMS microfluidic spotter for fabrication of lipid microarrays", IEEE 3rd EMBS Special Topic Conference May 12-15, 2005; 2 pages.
Chang-Yen et al., "Design and fabrication of a multianalyte-capable optical biosensor using a multiphysics approach", IEEE 3rd EMBS Special Topic Conference May 12-15, 2005; 2 pages.
Chang-Yen et al., "A Novel PDMS Microfluidic Spotter for Fabrication of Protein Chips and Microarrays", IEEE J of Microelectromech Sys. (2006) 15(5): 1145-1151.
Chang-Yen et al., "Design, fabrication, and packaging of a practical multianalyte-capable optical biosensor," J Microlith Microfab Microsyst. (2006) 5(2):021105 in 8 pages.
Chang-Yen et al., "Spin-assembled nanofilms for gaseous oxygen sensing." Sens Actuators B: Chemical (2007), 120(2):426-433.
Chaudhari et al., "Transient Liquid Crystal Thermometry of Microfabricated PCR Vessel Arrays", J Microelectro Sys., (1998) 7(4):345-355.
Chen P-C., "Accelerating micro-scale PCR (polymerase chain reactor) for modular lab-on-a-chip system", LSU Master's Theses—Digital Commons, (2006) 111 pages.
Chen et al., "Total nucleic acid analysis integrated on microfluidic devices," Lab on a Chip. (2007) 7:1413-1423.
Cheng et al., "Biochip-Based Portable Laboratory", Biochip Tech. (2001):269-289.
Cho et al., "A facility for characterizing the steady-state and dynamic thermal performance of microelectromechanical system thermal switches", Rev Sci Instrum. (2008) 79(3):034901-1 to -8.
Chong et al., "Disposable Polydimethylsiloxane Package for 'Bio-Microfluidic System'", IEEE Proceedings Electronic Components and Technology (2005); 5 pages.
Chou et al., "A miniaturized cyclic PCR device—modeling and experiments", Microelec Eng. (2002) 61-62:921-925.
Christel et al., "Nucleic Acid Concentration and PCR for Diagnostic Applications", in Micro Total Analysis Systems. (1998) D.J. Harrison et al. [Eds.] pp. 277-280.
Christel et al., "Rapid, Automated Nucleic Acid Probe Assays Using Silicon Microstructures for Nucleic Acid Concentration", J Biomech Eng. (1999) 121(1):22-27.
Christensen et al., "Characterization of interconnects used in PDMS microfluidic systems", J Micromech Microeng. (2005) 15:928 in 8 pages.
Chung, Y. et al., "Microfluidic chip for high efficiency DNA extraction", Miniaturisation for Chemistry, Biology & Bioengineering, vol. 4, No. 2 (Apr. 2004), pp. 141-147.
Cooley et al., "Applications of Ink-Jet Printing Technology to BioMEMS and Microfluidic Systems", Proceedings, SPIE Conference on Microfluids and BioMEMS, (Oct. 2001), 12 pages.
Crews et al., "Rapid Prototyping of a Continuous-Flow PCR Microchip", Proceedings of the AiChE Annual Meeting(Nov. 15, 2006) (335a) 3 pages.
Crews et al., Thermal gradient PCR in a continuous-flow microchip. In Microfluidics, BioMEMS, and Medical Microsystems V; Jan. 2007; vol. 6465, p. 646504; 12 pages.
Crews et al., "Continuous-flow thermal gradient PCR", Biomed Microdevices. (2008) 10(2):187-195.
Cui et al., "Electrothermal modeling of silicon PCR chips", In MEMS Design, Fabrication, Characterization, and Packaging, (Apr. 2001) (vol. 4407, pp. 275-280.
Cui et al., "Design and Experiment of Silicon PCR Chips," Proc. SPIE 4755, Design, Test, Integration, and Packaging of MEMS/MOEMS 2002, (Apr. 19, 2002) pp. 71-76.
Danaher Press Release: "Danaher to Acquire Cepheid for $53.00 per share, or approximately $4 Billion," dated Sep. 6, 2016, accessed at www.danaher.com, pp. 3.
Davis et al., "Surface vibrational sum frequency and Raman studies of PAMAM G0, G1 and acylated PAMAM G0 dendrimers". Anal Chimica Acta. Oct. 3, 20031;496(1-2): 117-131.
Demchenko A.P., "The problem of self-calibration of fluorescence signal in microscale sensor systems", Lab Chip. (2005) 5(11):1210-1223.
Devarakonda et al., "The effect of PAMAM dendrimer generation size and surface functional group on the aqueous solubility of nifedipine", Int J Pharma. (2004) 284(1-2): 133-140.
Dineva et al., "Sample preparation: a challenge in the development of point-of-care nucleic acid-based assays for resource-limited settings", Analyst. (2007) 132(12):1193-1199.
Dishinger et al., "Multiplexed Detection and Applications for Separations on Parallel Microchips", Electrophoresis. (2008) 29(16):3296-3305.
Dittrich et al., "Single-molecule fluorescence detection in microfluidic channels—the Holy Grail in muTAS?", Anal Bioanal Chem. (2005) 382(8):1771-1782.

(56) References Cited

OTHER PUBLICATIONS

Dittrich et al., "Lab-on-a-chip: microfluidics in drug discovery", Nat Rev Drug Discov. (2006) 5(3):210-218.
Dunnington et al., "Approaches to Miniaturized High-Throughput Screening of Chemical Libraries", in Integrated Microfabricated Devices, (2002) Ch. 15, pp. 371-414, CRC Press.
Eddings et al., "A PDMS-based gas permeation pump for on-chip fluid handling in microfluidic devices", J Micromech Microengin. (2006) 16(11):2396-2402.
Edwards, "Silicon (Si)," in "Handbook of Optical Constants of Solids" (Ghosh & Palik eds., 1997) in 24 pages.
Edwards et al., "Micro Scale Purification Systems for Biological Sample Preparation", Biomed Microdevices (2001) 3(3):211-218.
Edwards et al., "A microfabricated thermal field-flow fractionation system", Anal Chem. (2002) 74(6):1211-1216.
Ehrlich et al., "Microfluidic devices for DNA analysis", Trends Biotechnol. (1999) 17(8):315-319.
El-Ali et al., "Simulation and experimental validation of a SU-8 based PCR thermocycler chip with integrated heaters and temperature sensor", Sens Actuators A: Physical (2004) 110(1-3):3-10.
Erickson et al., "Joule heating and heat transfer in poly(dimethylsiloxane) microfluidic systems", Lab Chip (2003) 3(3):141-149.
Erickson et al., "Integrated Microfluidic Devices", Analytica Chim Acta. (2004) 507:11-26.
Erill et al., "Development of a CMOS-compatible PCR chip: comparison of design and system strategies", J Micromech Microengin. (2004) 14(11):1-11.
European Supplemental Search Report dated Aug. 5, 2010 for Application No. EP 08826342.1, filed Jul. 11, 2008.
European Supplemental Search Report dated Jul. 13, 2012 for Application No. EP 08843060.8, filed Jul. 14, 2008.
European Extended Search Report dated Feb. 16, 2017 for Application No. EP 16191793.5, filed Sep. 30, 2016.
European Extended Search Report dated May 11, 2017 for Application No. EP 16191787.7, filed Sep. 30, 2016.
Fair R.B., Digital microfluidics: is a true lab-on-a-chip possible? Microfluidics Nanofluid. (2007) 3:245-281.
Fan et al., "Integrated Plastic Microfluidic Devices for Bacterial Detection", in Integrated Biochips for DNA Analysis by Liu et al. [Eds], (2007) Chapter 6, pp. 78-89.
Fiorini et al., "Disposable microfluidic devices: fabrication, function, and application", Biotechniques (2005) 38(3):429-446.
Frazier et al., "Integrated micromachined components for biological analysis systems", J Micromech. (2000) 1(1):67-83.
Gale et al., "Micromachined electrical field-flow fractionation (mu-EFFF) system", IEEE Trans Biomed Eng. (1998) 45(12):1459-1469.
Gale et al., "Geometric scaling effects in electrical field flow fractionation. 1. Theoretical analysis", Anal Chem. (2001) 73(10):2345-2352.
Gale et al., "BioMEMS Education at Louisiana Tech University", Biomed Microdevices, (2002) 4:223-230.
Gale et al., "Geometric scaling effects in electrical field flow fractionation. 2. Experimental results", Anal Chem. (2002) 74(5):1024-1030.
Gale et al., "Cyclical electrical field flow fractionation", Electrophoresis. (2005) 26(9):1623-1632.
Gale et al., "Low-Cost MEMS Technologies", Elsevier B.V. (2008), Chapter 1.12; pp. 342-372.
Garst et al., "Fabrication of Multilayered Microfluidic 3D Polymer Packages", IEEE Proceedings Electronic Components & Tech, Conference May/Jun. 2005, pp. 603-610.
Gärtner et al., "Methods and instruments for continuous-flow PCR on a chip", Proc. SPIE 6465, Microfluidics, BioMEMS, and Medical Microsystems V, (2007) 646502; 8 pages.
Gill et al., "Nucleic Acid Isothermal Amplification Technologies—A Review", Nucleosides Nucleotides Nucleic Acids, (2008) 27(3): 224-243.
Giordano et al., "Toward an Integrated Electrophoretic Microdevice for Clinical Diagnostics", in Integrated Microfabricated Biodevices: Advanced Technologies for Genomics, Drug Discovery, Bioanalysis, and Clinical Diagnostics (2002) Chapter 1; pp. 1-34.
Goldmeyer et al., "Identification of *Staphylococcus aureus* and Determination of Methicillin Resistance Directly from Positive Blood Cultures by Isothermal Amplification and a Disposable Detection Device", J Clin Microbiol. (Apr. 2008) 46(4): 1534-1536.
Graff et al., "Nanoparticle Separations Using Miniaturized Field-flow Fractionation Systems", Proc. Nanotechnology Conference and Trade Show (NSTI) (2005); pp. 8-12.
Greer et al., "Comparison of glass etching to xurography prototyping of microfluidic channels for DNA melting analysis", J Micromech Microengin. (2007) 17(12):2407-2413.
Grunenwald H., "Optimization of Polymerase Chain Reactions," in Methods in Molecular Biology, PCR Protocols., Second Edition by Bartlett et al. [Eds.] Humana Press (2003) vol. 226, pp. 89-99.
Guijt et al., "Chemical and physical processes for integrated temperature control in microfluidic devices", Lab Chip. (2003) 3(1):1-4.
Gulliksen A., "Microchips for Isothermal Amplification of RNA", Doctoral Thesis (2007); Department of Mol. Biosciences—University of Oslo; 94 pages.
Guttenberg et al., "Planar chip device for PCR and hybridization with surface acoustic wave pump", Lab Chip. (2005) 5(3):308-317.
Haeberle et al., "Microfluidic platforms for lab-on-a-chip applications", Lab Chip. (2007) 7(9):1094-1110.
Hale et al., "Optical constants of Water in the 200-nm to 200-μm Wavelength Region", Applied Optics, 12(3): 555-563 (1973).
Handal et al., "DNA mutation detection and analysis using miniaturized microfluidic systems", Expert Rev Mol Diagn. (2006) 6(1):29-38.
Handique et al, "Microfluidic flow control using selective hydrophobic patterning", SPIE, (1997) 3224: 185-194.
Handique et al., "On-Chip Thermopneumatic Pressure for Discrete Drop Pumping", Anal. Chem., (2001) 73(8):1831-1838.
Handique et al., "Nanoliter-volume discrete drop injection and pumping in microfabricated chemical analysis systems", Solid-State Sensor and Actuator Workshop (Hilton Head, South Carolina, Jun. 8-11, 1998) pp. 346-349.
Handique et al., "Mathematical Modeling of Drop Mixing in a Slit-Type Microchannel", J. Micromech. Microeng., 11:548-554 (2001).
Handique et al., "Nanoliter Liquid Metering in Microchannels Using Hydrophobic Patterns", Anal. Chem., 72(17):4100-4109 (2000).
Hansen et al., "Microfluidics in structural biology: smaller, faster . . . better", Curr Opin Struct Biol. (2003) 13(5):538-544.
Harding et al., "DNA isolation using Methidium-Spermine-Sepharose", Meth Enzymol. (1992) 216: 29-39.
Harding et al., "Rapid isolation of DNA from complex biological samples using a novel capture reagent—methidium-spermine-sepharose", Nucl Acids Res. (1989) 17(17): 6947-6958.
Harrison et al., "Capillary Electrophoresis and Sample Injection Systems Integrated on a Planar Glass Chip", Anal. Chem., (1992) 64: 1926-1932.
He et al., Microfabricated Filters for Microfluidic Analytical Systems, Analytical Chemistry, American Chemical Society, 1999, vol. 71, No. 7, pp. 1464-1468.
Heid et al., "Genome Methods—Real Time Quantitative PCR", Genome Res. (1996) 6(10):986-994.
Henry C.S. [Ed], "Microchip Capillary electrophoresis", Methods in Molecular Biology, Humana Press 339 (2006) Parts I-IV in 250 pages.
Herr et al., "Investigation of a miniaturized capillary isoelectric focusing (cIEF) system using a full-field detection approach", Solid State Sensor and Actuator Workshop, Hilton Head Island (2000), pp. 4-8.
Herr et al., "Miniaturized Isoelectric Focusing (μIEF) as a Component of a Multi-Dimensional Microfluidic System", Micro Total Analysis Systems (2001) pp. 51-53.
Herr et al., Miniaturized Capillary Isoelectric Focusing (cIEF): Towards a Portable High-Speed Separation Method. In Micro Total Analysis Systems (2000) Springer, Dordrecht; pp. 367-370.
Holland et al., "Point-of-care molecular diagnostic systems—past, present and future", Curr Opin Microbiol. (2005) 8(5):504-509.

(56) References Cited

OTHER PUBLICATIONS

Hong et al., "Integrated nanoliter systems", Nat Biotechnol. (2003) 21(10):1179-1183.
Hong et al., "Molecular biology on a microfluidic chip", J Phys.: Condensed Matter (2006) 18(18):S691-S701.
Hong et al., "Integrated Nucleic Acid Analysis in Parallel Matrix Architecture", in Integrated Biochips for DNA Analysis by Liu et al. [Eds], (2007) Chapter 8, pp. 107-116.
Horsman et al., "Forensic DNA Analysis on Microfluidic Devices: A Review", J Forensic Sci. (2007) 52(4):784-799.
Hsieh et al., "Enhancement of thermal uniformity for a microthermal cycler and its application for polymerase chain reaction", Sens Actuators B: Chemical. (2008) 130(2):848-856.
Hsueh et al., "A microfabricated, electrochemiluminescence cell for the detection of amplified DNA" Proc. 1995 IEEE Int. Conf. Solid-State Sens. Actuators (1995) pp. 768-771.
Hsueh et al., "DNA quantification with an electrochemiluminescence microcell" Proc. 1997 IEEE Int. Conf. Solid-State Sens. Actuators (1997) pp. 175-178.
Huang et al., "Temperature Uniformity and DNA Amplification Efficiency in Micromachined GlassPCR Chip", TechConnect Briefs; Tech Proc. of the 2005 NSTI Nanotechnology Conference and Trade Show. (2005) vol. 1:452-455.
Huebner et al., "Microdroplets: A sea of applications?", Lab Chip. (2008) 8(8):1244-1254.
Ibrahim, et al., Real-Time Microchip PCR for Detecting Single-Base Differences in Viral and Human DNA, Analytical Chemistry, American Chemical Society, 1998, 70(9): 2013-2017.
International Search Report and Written Opinion dated Apr. 4, 2008 for PCT/US2007/007513, filed Mar. 26, 2007.
International Search Report and Written Opinion dated Jan. 5, 2009 for PCT/US2007/024022, filed Nov. 14, 2007.
International Search Report and Written Opinion, dated Oct. 3, 2008, issued in International Application No. PCT/US2008/069897, filed Jul. 11, 2008.
International Search Report and Written Opinion dated Jun. 17, 2009 for Application No. PCT/US2008/008640, filed Jul. 14, 2008.
Iordanov et al., "PCR Array on Chip—Thermal Characterization", IEEE Sensors (2003) Conference Oct. 22-24, 2003; pp. 1045-1048.
Irawan et al., "Cross-Talk Problem on a Fluorescence Multi-Channel Microfluidic Chip System," Biomed Micro. (2005) 7(3):205-211.
Ji et al., "DNA Purification Silicon Chip", Sensors and Actuators A: Physical (2007) 139(1-2):139-144.
Jia et al., "A low-cost, disposable card for rapid polymerase chain reaction", Colloids Surfaces B: Biointerfaces (2007) 58:52-60.
Jiang et al., "Directing cell migration with asymmetric micropatterns" Proc. Natl. Acad. Sci. USA (2005) 102, 975-978.
Kaigala et al., "An inexpensive and portable microchip-based platform for integrated RT-PCR and capillary electrophoresis", The Analyst (2008) 133(3):331-338.
Kajiyama et al., "Genotyping on a Thermal Gradient DNA Chip", Genome Res. (2003) 13(3):467-475.
Kang et al., "Simulation and Optimization of a Flow-Through Micro PCR Chip", NSTI-Nanotech (2006) vol. 2, pp. 585-588.
Kantak et al., "Microfluidic platelet function analyzer for shear-induced platelet activation studies", 2nd Annual International IEEE-EMBS Special Topic Conference on Microtechnologies in Med and Biol. (May 2002) 5 pages.
Kantak et al., "Microfabricated cyclical electrical field flow fractionation", 7th International Conference on Miniaturized Chomical and Biochem Analysis Sys. (2003) pp. 1199-1202.
Kantak et al., "Platelet function analyzer: Shear activation of platelets in microchannels", Biomedical Microdevices (2003) 5(3):207-215.
Kantak et al., "Characterization of a microscale cyclical electrical field flow fractionation system", Lab Chip. (2006) 6(5):645-654.
Kantak et al., "Effect of carrier ionic strength in microscale cyclical electrical field-flow fractionation", Anal Chem. (2006) 78(8):2557-2564.
Kantak et al., "Improved theory of cyclical electrical field flow fractions", Electrophoresis (2006) 27(14):2833-2843.
Karunasiri et al.,"Extraction of thermal parameters of microbolometer infrared detectors using electrical measurement", SPIE's Inter'l Symposium on Optical Science, Engineering, and Instrumentation; Proceedings (1998) vol. 3436, Infrared Technology and Applications XXIV; (1998) 8 pages.
Kelly et al., "Microfluidic Systems for Integrated, High-Throughput DNA Analysis," Analytical Chemistry, (2005), 97A-102A, Mar. 1, 2005, in 7 pages.
Khandurina et al., Microfabricated Porous Membrane Structure for Sample Concentration and Electrophoretic Analysis, Analytical Chemistry American Chemical Society, 1999, 71(9): 1815-1819.
Khandurina et al., "Bioanalysis in microfluidic devices," J Chromatography A, (2002) 943:159-183.
Kim et al., "Reduction of Microfluidic End Effects In Micro-Field Flow Fractionation Channels", Proc. MicroTAS 2003, pp. 5-9.
Kim et al., "Multi-DNA extraction chip based on an aluminum oxide membrane integrated into a PDMS microfluidic structure", 3rd IEEE/EMBS Special Topic Conference on Microtechnology in Med and Biol. (May 2005).
Kim et al., "Electrohydrodynamic Generation and Delivery of Monodisperse Picoliter Droplets Using a Poly(dimethylsiloxane) Microchip", Anal Chem. (2006) 78: 8011-8019.
Kim et al., "Geometric optimization of a thin film ITO heater to generate a uniform temperature distribution", (2006), Tokyo, Japan; pp. 293-295; Abstract.
Kim et al., "Micro-Raman thermometry for measuring the temperature distribution inside the microchannel of a polymerase chain reaction chip", J Micromech Microeng. (2006) 16(3):526-530.
Kim et al., "Patterning of a Nanoporous Membrane for Multi-sample DNA Extraction", J Micromech Microeng. (2006) 16:33-39.
Kim et al., "Performance evaluation of thermal cyclers for PCR in a rapid cycling condition", Biotechniques. (2008) 44(4):495-505.
Kim et al., "Quantitative and qualitative analysis of a microfluidic DNA extraction system using a nanoporous AlO(x) membrane", Lab Chip. (2008) 8(9):1516-1523.
Kogi et al., "Microinjection-microspectroscopy of single oil droplets in water: an application to liquid/liquid extraction under solution-flow conditions", Anal Chim Acta. (2000) 418(2):129-135.
Kopf-Sill et al., "Creating a Lab-on-a-Chip with Microfluidic Technologies", in IntegratedMicrofabricated Biodevices: Advanced Technologies for Genomics, Drug Discovery, Bioanalysis, and Clinical Diagnostics (2002) Chapter 2; pp. 35-54.
Kopp et al., Chemical Amplification: Continuous-Flow PCR on a Chip, www.sciencemag.org, 1998, vol. 280, pp. 1046-1048.
Kricka L.J., "Microchips, Bioelectronic Chips, and Gene Chips—Microanalyzers for the Next Century", in Biochip Technology by Cheng et al. [Eds]; (2006) Chapter 1, pp. 1-16.
Krishnan et al., "Polymerase chain reaction in high surface-to-volume ratio SiO2 microstructures", Anal Chem. (2004) 76(22):6588-6593.
Kuo et al., "Remnant cationic dendrimers block RNA migration in electrophoresis after monophasic lysis", J Biotech. (2007) 129: 383-390.
Kuswandi et al., "Optical sensing systems for microfluidic devices: a review", Anal Chim Acta. (2007) 601(2):141-155.
Kutter et al., Solid Phase Extraction on Microfluidic Devices, J. Microcolumn Separations, John Wiley & Sons, Inc., 2000, 12(2): 93-97.
Labchem; Sodium Hydroxide, 0.5N (0.5M); Safety Data Sheet, 2015; 8 pages.
Lagally et al., "Monolithic integrated microfluidic DNA amplification and capillary electrophoresis analysis system" Sensors and Actuators B (2000) 63:138-146.
Lagally et al., Single-Molecule DNA Amplification and Analysis in an Integrated Microfluidic Device, Analytical Chemistry, American Chemical Society, 2001, 73(3): 565-570.
Lagally et al., "Genetic Analysis Using Portable PCR-CE Microsystem", Proceedings 7th International Conference on Miniaturized Chemical and Biochemical Analysis Systems (2003) pp. 1283-1286.

(56) References Cited

OTHER PUBLICATIONS

Lagally et al., "Integrated portable genetic analysis microsystem for pathogen/infectious disease detection", Anal Chem. (2004) 76(11):3152-3170.
Lauerman L.H., "Advances in PCR technology", Anim Health Res Rev. (2004) 5(2):247-248.
Lawyer et al., "High-level Expression, Purification, and Enzymatic Characterization of Full-length Thermus aquaticus DNA Polymerase and a Truncated Form Deficient in 5' to 3'Exonuclease Activity." Genome research (1993) 2(4):275-287.
Lee et al., "Submicroliter-volume PCR chip with fast thermal response and very power consumption", 7th International Conference on Miniaturized Chemical and Biochemical Analysis Systems, (2003) pp. 187-190.
Lee et al., "Bulk-micromachined submicroliter-volume PCR chip with very rapid thermal response and low power consumption", Lab Chip. (2004) 4(4):401-407.
Lewin et al., "Use of Real-Time PCR and Molecular Beacons to Detect Virus Replication in HumanImmunodeficiency Virus Type 1-infected Individuals on Prolonged Effective Antiretroviral Therapy". J Virol. (1999) 73(7), 6099-6103.
Li et al., "Effect of high-aspect-ratio microstructures on cell growth and attachment", 1st Annual Inter'l IEEE-EMBS Special Topic Conference on Microtechnologies in Med and Biol. Proceedings Cat. No. 00EX451; (Oct. 2000) Poster 66, pp. 531-536.
Li PCH., "Micromachining Methods et al." in Microfluidic Lab-on-a-Chip for Chemical and Biological Analysis and Discovery, CRC Press (2005), Chapter 2-3 to 2-5; pp. 10-49.
Li PCH., "Microfluidic Flow" in Microfluidic Lab-on-a-Chip for Chemical and Biological Analysis and Discovery, CRC Press (2005), Chapter 3, pp. 55-99.
Li PCH., "Detection Methods" in Microfluidic Lab-on-a-Chip for Chemical and Biological Analysis and Discovery, CRC Press (2005), Chapter 7, pp. 187-249.
Li PCH., "Applications to Nucleic Acids Analysis" in Microfluidic Lab-on-a-Chip for Chemical and Biological Analysis and Discovery, CRC Press (2005), Chapter 9; pp. 293-325.
Li et al., "A Continuous-Flow Polymerase Chain Reaction Microchip With Regional Velocity Control", J Microelectromech Syst. (2006) 15(1):223-236.
Liao et al., "Miniature RT-PCR system for diagnosis of RNA-based viruses," Nucl Acids Res. (2005) 33(18):e156 in 7 pages.
Lien et al., "Integrated reverse transcription polymerase chain reaction systems for virus detection", Biosens Bioelectron. (2007) 22(8):1739-1748.
Lien et al., "Microfluidic Systems Integrated with a Sample Pretreatment Device for Fast Nucleic-Acid Amplification", J Microelectro Sys. (2008) 17(2):288-301.
Lifesciences et al., "Microfluidics in commercial applications; an industry perspective." Lab Chip (2006) 6:1118-1121.
Lin et al., "Thermal Uniformity of 12-in Silicon Wafer During Rapid Thermal Processing by Inverse Heat Transfer Method," IEEE Transactions on Semiconductor Manufacturing, (2000) 13(4):448-456.
Lin et al., "Simulation and experimental validation of micro polymerase chain reaction chips", Sens Actuators B: Chemical. (2000) 71(1-2):127-133.
Linder et al., "Microfluidics at the Crossroad with Point-of-care Diagnostics", Analyst (2007) 132:1186-1192.
Liu et al., "Integrated portable polymerase chain reaction-capillary electrophoresis microsystem for rapid forensic short tandem repeat typing", Anal Chem. (2007) 79(5):1881-1889.
Liu et al. [Eds], Integrated Biochips for DNA Analysis—Biotechnology Intelligence Unit; Springer/Landes Bioscience (2007) ISBN:978-0-387-76758-1; 216 pages.
Livache et al., "Polypyrrole DNA chip on a Silicon Device: Example of Hepatitis C Virus Genotyping", Analytical Biochemistry, (1998) 255: 188-194.
Locascio et al., "ANYL 67 Award Address—Microfluidics as a tool to enable research and discovery in the life sciences", Abstract; The 236th ACS National Meeting (Aug. 2008); 2 pages.
Mahjoob et al., "Rapid microfluidic thermal cycler for polymerase chain reaction nucleic acid amplification", Inter'I J Heat Mass Transfer. (2008) 51(9-10):2109-2122.
Malitson, "Interspecimen Comparison of the Refractive Index of Fused Silica," J Optical Society of America, 55:1205-1209 (1965).
Manz et al., "Miniaturized Total Chemical Analysis Systems: a Novel Concept for Chemical Sensing," Sensors and Actuators B1, (1990) 244-248.
Manz et al., "Design of an open-tubular column liquid chromatograph using silicon chip technology" Sensors and Actuators B (1990) 1:249-255.
Manz et al., "Planar chips technology for miniaturization and integration of separation techniques intomonitoring systems: Capillary electrophoresis on a chip" Journal of Chromatography A (1992) 593:253-258.
Marcus et al., "Parallel picoliter rt-PCR assays using microfluidics", Anal Chem. (2006) 78(3):956-958.
Mariella R.P. Jr., "Microtechnology", Thrust Area Report FY 96 UCRL-ID-125472; Lawrence Livermore National Lab., CA (Feb. 1997) Chapter 3 in 44 pages.
Mariella R., "Sample preparation: the weak link in microfluidics-based biodetection", Biomed Microdevices. (2008) 10(6):777-784.
Mastrangelo et al., Microfabricated Devices for Genetic Diagnostics. Proceedings of the IEEE (1998) 86(8):1769-1787.
Mascini et al., "DNA electrochemical biosensors", Fresenius J. Anal. Chem., 369: 15-22, (2001).
McMillan et al., "Application of advanced microfluidics and rapid PCR to analysis of microbial targets", In Proceedings of the 8th international symposium on microbial ecology (1999), in 13 pages.
Melin et al., "Microfluidic large-scale integration: the evolution of design rules for biological automation", Annu Rev Biophys Biomol Struct. (2007) 36:213-231.
Merugu et al., "High Throughput Separations Using a Microfabricated Serial Electric Split System" (2003), Proceedings of μTAS 2003, 7th International Conference on Miniaturized Chemical and Biochemical Analysis Systems, Oct. 5-9, 2003, Squaw Valley, California; 1191-1194, in 3 pages.
Meyers, R.A., Molecular Biology and Biotechnology: A Comprehensive Desk Reference; VCH Publishers, Inc. New York, NY; (1995) pp. 418-419.
Miao et al., "Low cost micro-PCR array and micro-fluidic integration on single silicon chip", Int'l J Comput Eng Science (2003) 4(2):231-234.
Miao et al., "Flip-Chip packaged micro-plate for low cost thermal multiplexing", Int'l J Comput Eng Science. (2003) 4(2):235-238.
Micheletti et al., "Microscale Bioprocess Optimisation", Curr Opin Biotech. (2006) 17:611-618.
MicroTAS 2005., "Micro Total Analysis Systems", Proceedings 9th Int. Conference on Miniaturized Systems for Chemistry and Life Sciences; Presentations/Posters/Articles for Conference; Boston, MA in Oct. 10-12, 2005 in 1667 pages.
MicroTAS 2007., "Micro Total Analysis Systems", Proceedings 11th Int. Conference on Miniaturized Systems for Chemistry and Life Sciences; Presentations/Posters/Articles for Conference; Paris, France in Oct. 7-11, 2007 in 1948 pages.
MicroTAS 2007., "Micro Total Analysis Systems", Advance Program for the Proceedings 11th Int. Conference on Miniaturized Systems for Chemistry and Life Sciences; Presentations/Posters/Articles for Conference; Paris, France in Oct. 7-11, 2007 in 42 pages.
Minco, "Conductive Heating Technologies for Medical Diagnostic Equipment," (2006) in 13 pages.
Mitchell et al., "Modeling and validation of a molded polycarbonate continuous-flow polymerase chain reaction device," Microfluidics, BioMEMS, and Medical Microsystems, Proc. SPIE (2003) 4982:83-98.
Myers et al., "Innovations in optical microfluidic technologies for point-of-care diagnostics", Lab Chip (2008) 8:2015-2031.

(56) References Cited

OTHER PUBLICATIONS

Nakagawa et al., Fabrication of amino silane-coated microchip for DNA extraction from whole blood, J of Biotechnology, Mar. 2, 2005, 116: 105-111.
Namasivayam et al., "Advances in on-chip photodetection for applications in miniaturized genetic analysis systems", J Micromech Microeng. (2004) 14:81-90.
Narayanan et al., "A microfabricated electrical SPLITT system," Lab Chip, (2006) 6:105-114.
Neuzil et al., "Disposable real-time microPCR device: lab-on-a-chip at a low cost, " Mol. Biosyst., (2006) 2:292-298.
Neuzil et al., "Ultra fast miniaturized real-time PCR: 40 cycles in less than six minutes," Nucleic Acids Research, (2006) 34(11)e77, in 9 pages.
Nguyen et al. [Eds], "Microfluidics for Internal Flow Control: Microfluidics" in Fundamentals and Applications of Microfluidics; 2nd Edition (2006) Introduction Chapter 1, pp. 1-9.
Nguyen et al. [Eds], "Microfluidics for Internal Flow Control: Microvalves" in Fundamentals and Applications of Microfluidics; (2006) 2nd Edition, Chapter 6, pp. 211-254.
Nguyen et al. [Eds], "Microfluidics for Internal Flow Control: Micropumps" in Fundamentals and Applications of Microfluidics; (2006) 2nd Edition, Chapter 7, pp. 255-309.
Nguyen et al. [Eds], "Microfluidics for Life Sciences and Chemistry: Microdispensers" in Fundamentals and Applications of Microfluidics; (2006) , Chapter 11, pp. 395-418.
Nguyen et al. [Eds], "Microfluidics for Life Sciences and Chemistry: Microreactors" in Fundamentals and Applications of Microfluidics; (2006) 2nd Edition, Chapter 13, pp. 443-477.
Ning et al., "Microfabrication Processes for Silicon and Glass Chips", in Biochip Technology, CRC-Press (2006) Chapter 2, pp. 17-38.
Northrup et al., "A MEMS-based Miniature DNA Analysis System," Lawrence Livermore National Laboratory, (1995), submitted to Transducers '95, Stockholm, Sweden, Jun. 25-29, 1995, in 7 pages (Prepublication).
Northrup et al., "A MEMS-based Miniature DNA Analysis System." Transducers '95—Eurosensors in Proc. 1995 (8th) IEEE Int. Conf. Solid-State Sens. Actuators, pp. 764-767.
Northrup et al., "Advantages Afforded by Miniaturization and Integration of DNA Analysis Instrumentation," Microreaction Technology, (1998) 278-288.
Northrup et al., A Miniature Analytical Instrument for Nucleic Acids Based on Micromachined Silicon Reaction Chambers, Analytical Chemistry, American Chemical Society, 1998, 70(5): 918-922.
Northrup et al., "A New Generation of PCR Instruments and Nucleic Acid Concentration Systems," in PCR Applications: Protocols for Functional Genomics, (1999), Chapter 8, pp. 105-125.
Northrup, "Microfluidics, A few good tricks," Nature materials (2004), 3:282-283.
Northrup et al., "Microfluidics-based integrated airborne pathogen detection systems," Abstract, Proceedings of the SPIE, (2006), vol. 6398, Abstract in 2 pages.
Oh et al., "World-to-chip microfluidic interface with built-in valves for multichamber chip-based PCR assays," Lab Chip, (2005), 5:845-850.
Oh K.W et al., "A Review of Microvalves", J Micromech Microeng. (2006) 16:R13-R39.
Ohno et al., "Microfluidics: Applications for analytical purposes in chemistry and biochemistry," Electrophoresis (2008), 29:4443-4453.
Oleschuk et al., Trapping of Bead-Based Reagents within Microfluidic Systems: On-Chip Solid-Phase Extraction and Electrochromatography, Analytical Chemistry, American Chemical Society, 2000, 72(3): 585-590.
Pal et al., "Phase Change Microvalve for Integrated Devices", Anal Chem. (2004) 76: 3740-3748.
Pal et al., "An integrated microfluidic for influenza and other genetic analyses," Lab Chip, (2005), 5:1024-1032.
Palina et al., "Laser Assisted Boron Doping of Silicon Wafer Solar Cells Using Nanosecond and Picosecond Laser Pulses," 2011 37th IEEE Photovoltaic Specialists Conference, pp. 002193-002197, IEEE (2011).
Pamme, "Continuous flow separations in microfluidic devices," Lab Chip, (2007), 7:1644-1659.
Pang et al., "A novel single-chip fabrication technique for three-dimensional MEMS structures," Institute of Microelectronics, Tsinghua University, Beijing, P.R. China, (1998), IEEE, 936-938.
Pang et al., "The Study of Single-Chip Integrated Microfluidic System," Tsinghua University, Beijing, P.R. China, (1998), IEEE, 895-898.
Papautsky et al., "Effects of rectangular microchannel aspect ratio on laminar friction constant", in Microfluidic Devices and Systems II (1999) 3877:147-158.
Paulson et al., "Optical dispersion control in surfactant-free DNA thin films by vitamin B2 doping," Nature, Scientific Reports 8:9358 (2018) published at www.nature.com/scientificreports, Jun. 19, 2018.
Petersen, Kurt E., "Silicon as a Mechanical Material." Proceedings of the IEEE, (May 1982) 70(5):420-457.
Petersen et al., "Toward Next Generation Clinical Diagnostic Instruments: Scaling and New Processing Paradigms," Biomedical Microdevices (1998) 1(1):71-79.
Picard et al., Laboratory Detection of Group B Streptococcus for Prevention of Perinatal Disease, Eur. J. Clin. Microbiol. Infect. Dis., Jul. 16, 2004, 23: 665-671.
Plambeck et al., "Electrochemical Studies of Antitumor Antibiotics", J. Electrochem Soc.: Electrochemical Science and Technology (1984), 131(11): 2556-2563.
Poser et al., "Chip elements for fast thermocycling," Sensors and Actuators A, (1997), 62:672-675.
Pourahmadi et al., "Toward a Rapid, Integrated, and Fully Automated DNA Diagnostic Assay for Chlamydia trachomatis and Neisseria gonorrhea," Clinical Chemistry, (2000), 46(9):1511-1513.
Pourahmadi et al., "Versatile, Adaptable and Programmable Microfluidic Platforms for DNA Diagnostics and Drug Discovery Assays," Micro Total Analysis Systems, (2000), 243-248.
Raisi et al., "Microchip isoelectric focusing using a miniature scanning detection system," Electrophoresis, (2001), 22:2291-2295.
Raja et al., "Technology for Automated, Rapid, and Quantitative PCR or Reverse Transcription—PCR Clinical Testing," Clinical Chemistry, (2005), 51(5):882-890.
Reyes et al., "Micro Total Analysis Systems. 1. Introduction, Theory, and Technology", Anal Chem (2002) 74:2623-2636.
Rhee et al., "Drop Mixing in a Microchannel for Lab-on-a-Chip Applications" Langmuir (2008) 24 (2):590-601.
Roche et al. "Ectodermal commitment of insulin-producing cells derived from mouse embryonic stem cells" Faseb J (2005) 19: 1341-1343.
Rodriguez et al., "Practical integration of polymerase chain reaction amplification and electrophoretic analysis in microfluidic devices for genetic analysis," Electrophoresis, (2003), 24:172-178.
Rohsenow et al. [Eds.], Handbook of Heat Transfer, 3rd Edition McGraw-Hill Publishers (1998) Chapters 1 & 3; pp. 108.
Roper et al., "Advances in Polymer Chain Reaction on Microfluidic Chips," Anal. Chem., (2005), 77:3887-3894.
Ross et al., Analysis of DNA Fragments from Conventional and Microfabricated PCR Devices Using Delayed Extraction MALDI-TOF Mass Spectrometry, Analytical Chemistry, American Chemical Society, 1998, 70(10): 2067-2073.
Ross et al., "Scanning Temperature Gradient Focusing for Simultaneous Concentration and Separation of Complex Samples," Micro Total Analysis Systems 2005, vol. 2, (2005), Proceedings of µTAS 2005, Ninth International Conference on Miniaturized Systems for Chemistry and Life Sciences, Oct. 9-13, 2005, Boston, Massachusetts; 1022-1024.
Ross et al., "Simple Device for Multiplexed Electrophoretic Separations Using Gradient Elution Moving Boundary Electrophoresis with Channel Current Detection," Anal. Chem., (2008), 80(24):9467-9474.
Rush et al., "Dispersion by Pressure-Driven Flow in Serpentine Microfluidic Channels", Ind Eng Chem Res., (2002) 41: 4652-4662.

(56) References Cited

OTHER PUBLICATIONS

Sadler et al., "Thermal Management of BioMEMS: Temperature Control for Ceramic-Based PCR and DNA Detection Devices," IEEE Transactions on Components and Packaging Technologies, (2003) 26(2):309-316.
Sammarco et al., "Thermocapillary Pumping of Discrete Drops in Microfabricated Analysis Devices" AIChE Journal (1999) 45(2): 350-366.
Sanchez et al., "Linear-After-The-Exponential (LATE)-PCR: An advanced method of asymmetric PCR and its uses in quantitative real-time analysis", PNAS (2004) 101(7): 1933-1938.
Sant et al., "An Integrated Optical Detector for Microfabricated Electrical Field Flow Fractionation System," Proceedings of µTAS 2003, 7th International Conference on Miniaturized Chemical and Biochemical Analysis Systems, Oct. 5-9, 2003, Squaw Valley, California; pp. 1259-1262.
Sant et al., "Geometric scaling effects on instrumental plate height in field flow fractionation", J Chromatography A (2006) 1104:282-290.
Sant H.J., "Reduction of End Effect-Induced Zone Broadening in Field-Flow Fractionation Channels", Anal Chem. (2006) 78:7978-7985.
Sant et al., "Microscale Field-Flow Fractionation: Theory and Practice", in Microfluidic Technologies for Miniaturized Analysis Systems. (2007) Chapter 12, pp. 471-521.
Schäferling et al., "Optical technologies for the read out and quality control of DNA and protein microarrays," Anal Bioanal Chem, (2006), 385: 500-517.
Serpengüzel et al., "Microdroplet identification and size measurement in sprays with lasing images", Optics express (2002) 10(20):1118-1132.
Shackman et al., "Gradient Elution Moving Boundary Electrophoresis for High-Throughput Multiplexed Microfluidic Devices," Anal. Chem. (2007), 79(2), 565-571.
Shackman et al., "Temperature gradient focusing for microchannel separations," Anal Bioanal Chem, (2007), 387:155-158.
Shadpour et al., "Multichannel Microchip Electrophoresis Device Fabricated in Polycarbonate with an Integrated Contact Conductivity Sensor Array," Anal Chem., (2007), 79(3), 870-878.
Shen et al., "A microchip-based PCR device using flexible printed circuit technology," Sensors and Actuators B (2005), 105:251-258.
Shoffner et al., Chip PCR.I. Surface Passivation of Microfabricated Silicon-Glass Chips for PCR, Nucleic Acids Research, Oxford University Press, (1996) 24(2): 375-379.
Sia et al., "Microfluidic devices fabricated in poly(dimethylsiloxane) for biological studies," Electrophoresis, (2003), 24:3563-3576.
Sigurdson M., "AC Electrokinetic Enhancement for Assay Enhancement", ProQuest LLC (2008) Doctoral Thesis UMI Microform 3319791 in 24 pages.
Singh et al., "PCR thermal management in an integrated Lab on Chip," Journal of Physics: Conference Series, (2006), 34:222-227.
Situma et al., "Merging microfluidics with microarray-based bioassays", Biomol Engin. (2006) 23:213-231.
Smith, K. et al., "Comparison of Commercial DNA Extraction Kits for Extraction of Bacterial Genomic DNA from Whole-Blood Samples", Journal of Clinical Microbiology, vol. 41, No. 6 (Jun. 2003), pp. 2440-2443.
Smith et al., "(576d) Micropatterned fluid lipid bilayers created using a continuous flow microspotter for multi-analyte assays," (2007), Biosensors II, 2007 AIChE Annual Meeting, Nov. 8, 2007, Abstract in 2 pages.
Sommer et al., "Introduction to Microfluidics", in Microfluidics for Biological Applications by Tian et al. [Eds] (2008) Chapter 1, pp. 1-34.
Spitzack et al., "Polymerase Chain Reaction in Miniaturized Systems: Big Progress in Little Devices", in Methods in Molecular Biology—Microfluidic Techniques, Minteer S.D. [Ed.] Humana Press (2006), Chapter 10, pp. 97-129.
Squires et al., "Microfluidics: Fluid physics at the nanoliter scale", Rev Modern Phys. (2005) 77(3):977-1026.
Sundberg et al., "Solution-phase DNA mutation scanning and SNP genotyping by nanoliter melting analysis," Biomed Microdevices, (2007), 9:159-166, in 8 pages.
Tabeling, P. [Ed.], "Physics at the micrometric scale," in Introduction to Microfluidics (2005) Chapter 1, pp. 24-69.
Tabeling, P. [Ed.], "Hydrodynamics of Microfluidic Systems", in Introduction to Microfluidics; (2005) Chapter 2, pp. 70-129.
Tabeling, P. [Ed.], Introduction to Microfluidics; (2005) Chapters 5-7, pp. 216-297.
Tanaka et al., "Improved Method of DNA Extraction from Seeds Using Amine-Dendrimer Modified Magnetic Particles", Proceedings of the 74th Annual Meeting of the Electrochemical Society of Japan; Abstract #2E09 on p. 149, Mar. 29, 2007; Faculty of Engineering, Science University of Tokyo; 4 pages.
Taylor et al., "Optimization of the performance of the polymerase chain reaction in silicon-based microstructures" Nucleic Acids Res. (1997) vol. 25, pp. 3164-3168.
Taylor et al., Fully Automated Sample Preparation for Pathogen Detection Performed in a Microfluidic Cassette, in Micro Total Analysis Systems, Springer (2001), pp. 670-672.
Taylor et al., "Lysing Bacterial Spores by Sonication through a Flexible Interface in a Microfluidic System," Anal. Chem., (2001), 73(3):492-496.
Taylor et al., "Microfluidic Bioanalysis Cartridge with Interchangeable Microchannel Separation Components," (2001), The 11th International Conference on Solid-State Sensors and Actuators, Jun. 10-14, 2001, Munich, Germany; 1214-1247.
Taylor et al., "Disrupting Bacterial Spores and Cells using Ultrasound Applied through a Solid Interface," (2002), 2nd Annual International IEEE-EMBS Special Topic Conference on Microtechnologies in Medicine & Biology, May 2-4, 2002, Madison, Wisconsin; 551-555.
Terry et al., "A Gas Chromatographic Air Analyzer Fabricated on a Silicon Wafer" IEEE T Electron Dev (1979) 26:1880-1886.
Thorsen et al., "Microfluidic Large-scale integration," Science, (2002), 298:580-584.
Toriello et al., "Multichannel Reverse Transcription-Polymerase Chain Reaction Microdevice for Rapid Gene Expression and Biomarker Analysis," Anal. Chem., (2006) 78(23):7997-8003.
Ugaz et al., "Microfabricated electrophoresis systems for DNA sequencing and genotyping applications," Phil. Trans. R. Soc. Lond. A, (2004), 362:1105-1129.
Ugaz et al., "PCR in Integrated Microfluidic Systems", in Integrated Biochips for DNA Analysis by Liu et al. [Eds]; (2007) Chapter 7, pp. 90-106.
Ullman et al., "Luminescent oxygen channeling assay (LOCI™): sensitive, broadly applicable homogeneous immunoassay method". Clin Chem. (1996) 42(9), 1518-1526.
U.S. Appl. No. 60/491,264, filed Jul. 31, 2003 (41 pages).
U.S. Appl. No. 60/491,269, filed Jul. 31, 2003 (52 pages).
U.S. Appl. No. 60/491,539, filed Aug. 1, 2003 (45 pages).
U.S. Appl. No. 60/553,553, filed Mar. 17, 2004 (49 pages).
U.S. Appl. No. 60/726,066, filed Oct. 11, 2005 (54 pages).
U.S. Appl. No. 60/786,007, filed Mar. 24, 2006 (223 pages).
U.S. Appl. No. 60/859,284, filed Nov. 14, 2006 (114 pages).
Velten et al., "Packaging of Bio-MEMS: Strategies, Technologies, and Applications," IEEE Transactions on Advanced Packaging, (2005) 28(4):533-546.
Vinet et al., "Microarrays and microfluidic devices: miniaturized systems for biological analysis," Microelectronic Engineering, (2002), 61-62:41-47.
Walker et al., "Strand displacement amplification—an isothermal, in vitro DNA amplification technique", Nucleic Acids Res. (1992) 20(7): 1691-1696.
Wang, "Survey and Summary, from DNA Biosensors to Gene Chips", Nucleic Acids Research, 28(16):3011-3016, (2000).
Wang et al., "From biochips to laboratory-on-a-chip system", in Genomic Signal Processing and Statistics by Dougherty et al. [Eds]; (2005) Chapter 5, pp. 163-200.
Wang et al., "A disposable microfluidic cassette for DNA amplification and detection", Lab on a Chip (2006) 6(1):46-53.

(56) References Cited

OTHER PUBLICATIONS

Wang et al., "Micromachined Flow-through Polymerase Chain Reaction Chip Utilizing Multiple Membrane-activated Micropumps," (2006), MEMS 2006, Jan. 22-26, 2006, Istanbul, Turkey; 374-377.
Waters et al., Microchip Device for Cell Lysis, Multiplex PCR Amplification, and Electrophoretic Sizing, Analytical Chemistry, American Chemical Society, 1998, 70(1): 158-162.
Weigl, et al., Microfluidic Diffusion-Based Separation and Detection, www.sciencemag.org, 1999, vol. 283, pp. 346-347.
Whitesides G.M., "The origins and the future of microfluidics" Nature (2006) 442(7101):368-373.
Woias P., "Micropumps—past, progress and future prospects" Sensors and Actuators B (2005) 105, 28-38.
Woolley et al., "Functional integration of PCR amplification and capillary electrophoresis in a microfabricated DNA analysis device" Anal. Chem. (1996) vol. 68, pp. 4081-4086.
Woolley A.T., "Integrating Sample Processing and Detection with Microchip Capillary Electrophoresis of DNA", in Integrated Biochips for DNA Analysis by Liu et al. [Eds]; (2007) Chapter 5, pp. 68-77.
Wu et al., "Fabrication of Complex Three-dimensional Microchannel Systems in Pdms" J. Am. Chem. Soc. (2003) 125, 554-559.
Wu et al., "Polycationic dendrimers interact with RNA molecules: polyamine dendrimers inhibit the catalytic activity of Candida ribozymes", Chem Commun. (2005) 3: 313-315.
Xiang et al., "Real Time PCR on Disposable PDMS Chip with a Miniaturized Thermal Cycler," Biomedical Microdevices, (2005), 7(4):273-279.
Xuan, "Joule heating in electrokinetic flow," Electrophoresis, (2008), 298:33-43.
Yang et al., "High sensitivity PCR assay in plastic micro reactors," Lab Chip, (2002), 2:179-187.
Yang et al., "An independent, temperature controllable-microelectrode array," Anal. Chem., (2004), 76(5):1537-1543.
Yang et al., "Cost-effective thermal isolation techniques for use on microfabricated DNA amplification and analysis devices," J Micromech Microeng, (2005), 15:221-230.
Yobas et al., "Microfluidic Chips for Viral RNA Extraction & Detection", (2005), 2005 IEEE, 49-52.
Yobas et al., "Nucleic Acid Extraction, Amplification, and Detection on Si-Based Microfluidic Platforms," IEEE Journal of Solid-State Circuits, (2007), 42(8):1803-1813.
Yoon et al., "Precise temperature control and rapid thermal cycling in a micromachined DNA polymer chain reaction chip," J. Micromech. Microeng., (2002), 12:813-823.
Yoza et al., "Fully Automated DNA Extraction from Blood Using Magnetic Particles Modified with a Hyperbranched Polyamidoamine Dendrimer", J Biosci Bioeng, 2003, 95(1): 21-26.
Yoza et al., DNA extraction using bacterial magnetic particles modified with hyperbranched polyamidoamine dendrimer, J Biotechnol., Mar. 20, 2003, 101(3): 219-228.
Zhang et al, "Temperature analysis of continuous-flow micro-PCR based on FEA," Sensors and Actuators B, (2002), 82:75-81.
Zhang et al., "PCR Microfluidic Devices for DNA Amplification," Biotechnology Advances, 24:243-284 (2006).
Zhang et al, "Continuous-flow PCR Microfluidics for Rapid DNA Amplification Using Thin Film Heater with Low Thermal Mass," Analytical Letters, (2007), 40:1672-1685, in 15 pages.
Zhang et al, "Direct Adsorption and Detection of Proteins, Including Ferritin, onto Microlens Array Patterned Bioarrays," J Am Chem Soc., (2007), 129:9252-9253.
Zhang et al, "Micropumps, microvalves, and micromixers within PCR microfluidic chips: Advances and trends," Biotechnology Advances, (2007), 25:483-514.
Zhang et al., "Miniaturized PCR chips for nucleic acid amplification and analysis: latest advances and future trends," Nucl Acids Res., (2007) 35(13):4223-4237.
Zhang et al., "Parallel DNA amplification by convective polymerase chain reaction with various annealing temperatures on a thermal gradient device," Analytical Biochemistry, (2009) 387:102-112.
Zhao et al, "Heat properties of an integrated micro PCR vessel," Proceedings of SPIE, (2001), International Conference on Sensor Technology, 4414:31-34.
Zhou et al., "Cooperative binding and self-assembling behavior of cationic low molecular-weight dendrons with RNA molecules", Org Biomol Chem. (2006) 4(3): 581-585.
Zhou et al., "PAMAM dendrimers for efficient siRNA delivery and potent gene silencing", Chem Comm.(Camb.) (2006) 22: 2362-2364.
Zou et al., "A Micromachined Integratable Thermal Reactor," technical digest from International Electron Devices Meeting, IEEE, Washington, D.C., Dec. 2-5, 2001 (6 pages).
Zou et al., "Micro-assembled multi-chamber thermal cycler for low-cost reaction chip thermal multiplexing," Sensors and Actuators A, (2002), 102:114-121.
Zou et al., "Miniaturized Independently Controllable Multichamber Thermal Cycler," IEEE Sensors Journal, (2003), 3(6):774-780.
Petition for Inter Partes Review of U.S. Pat. No. 7,998,708 (Paper 1 in IPR2019-00488) dated Dec. 20, 2018 (94 pages).
Declaration of Bruce K. Gale, Ph.D. (Exhibit 1001 in IPR2019-00488 and IPR2019-00490) dated Dec. 20, 2018 (235 pages).
Patent Owner Preliminary Response to Petition for Inter Partes Review of U.S. Pat. No. 7,998,708 and Exhibit List (Papers 5 and 6 in IPR2019-00488) dated Apr. 18, 2019 (79 pages).
Decision instituting Inter Partes Review of U.S. Pat. No. 7,998,708 (Paper 8 in IPR2019-00488) dated Jul. 16, 2019 (20 pages).
Petition for Inter Partes Review of U.S. Pat. No. 8,323,900 (Paper 1 in IPR2019-00490) dated Dec. 20, 2018 (85 pages).
Declaration of Michael G. Mauk, Ph.D. in Support of Patent Owner Preliminary Responses in IPR2019-00488 and IPR2019-00490 dated Apr. 18, 2019 (43 pages).
Patent Owner Preliminary Response to Petition for Inter Partes Review of U.S. Pat. No. 8,323,900 and Exhibit List (Papers 5 and 6 in IPR2019-00490) dated Apr. 18, 2019 (73 pages).
Decision instituting Inter Partes Review of U.S. Pat. No. 8,323,900 (Paper 8 in IPR2019-00490) dated Jul. 16, 2019 (23 pages).
Patent Owner's Response in Inter Partes Review of U.S. Pat. No. 8,323,900 and Exhibit List (Paper 25 in IPR2019-00490) dated Oct. 16, 2019 (80 pages).
Patent Owner's Response in Inter Partes Review of U.S. Pat. No. 7,998,708 and Exhibit List (Paper 25 in IPR 2019-00488) dated Oct. 16, 2019 (93 pages).
Transcript of Deposition of Bruce K. Gale, Ph.D., in Support of Patent Owner's Responses (Exhibit 2012 in IPR2019-00488 and IPR2019-00490), taken Sep. 24, 2019 (124 pages).
Declaration of M. Allen Northrup, Ph.D. in Support of Patent Owner's Responses (Exhibit 2036 in IPR2019-00488 and IPR2019-00490) dated Oct. 16, 2019 (365 pages).
Petitioner's Reply to Patent Owner's Response to Petition in Inter Partes Review of U.S. Pat. No. 7,998,708 and Exhibit List (Paper 32 in IPR 2019-00488) dated Jan. 31, 2020 (34 pages).
Petitioner's Reply to Patent Owner's Response to Petition in Inter Partes Review of U.S. Pat. No. 8,323,900 and Exhibit List (Paper 32 in IPR 2019-00490) dated Jan. 31, 2020 (35 pages).
Second Declaration of Bruce K. Gale, Ph.D. (Exhibit 1026 in IPR2019-00488 and IPR2019-00490) dated Jan. 31, 2020 (91 pages).
Transcript of Deposition of M. Allen Northrup, Ph.D., (Exhibit 1027 in IPR2019-00488 and IPR2019-00490), taken Dec. 19, 2019 (109 pages).
Patent Owner's Sur-Reply in Inter Partes Review of U.S. Pat. No. 8,323,900 (Paper 42 in IPR2019-00490) dated Mar. 12, 2020 (39 pages).
Patent Owner's Sur-Reply in Inter Partes Review of U.S. Pat. No. 7,998,708 (Paper 43 in IPR 2019-00488) dated Mar. 12, 2020 (41 pages).
Transcript of Second Deposition of Bruce K. Gale, Ph.D., (Exhibit 2068 in IPR2019-00488 and IPR2019-00490), taken Feb. 19, 2020 (352 pages).
Record of Oral Hearing in IPR2019 00488 and IPR2019 00490 held Apr. 21, 2020 (80 pages); Petitioner's Demonstratives for Oral Hearing in IPR2019 00488 and IPR2019 00490 held Apr. 21, 2020 (72 pages); Patent Owner's Demonstratives for Oral Hearing in

(56) References Cited

OTHER PUBLICATIONS

IPR2019 00488 and IPR2019 00490 held Apr. 21, 2020 (88 pages); Patent Owner's Objections to Petitioner's Oral Hearing Demonstratives in IPR2019 00488 and IPR2019 00490 dated Apr. 16, 2020 (4 pages).
Judgment/Final Written Decision Determining No Challenged Claims Unpatentable in Inter Partes Review of U.S. Pat. No. 7,998,708 (Paper No. 52 in IPR2019-00488) dated Jul. 14, 2020 (43 pages).
Judgment/Final Written Decision Determining No Challenged Claims Unpatentable in Inter Partes Review of U.S. Pat. No. 8,323,900 (Paper No. 51 in IPR2019-00490) dated Jul. 14, 2020 (43 pages).
Petitioner's Notice of Appeal in Inter Partes Review of U.S. Pat. No. 7,998,708 (Paper No. 54 in IPR2019-00488) dated Sep. 9, 2020 (48 pages).
Petitioner's Notice of Appeal in Inter Partes Review of U.S. Pat. No. 8,323,900 (Paper No. 53 in IPR2019-00490) dated Sep. 9, 2020 (48 pages).
Petition for Inter Partes Review of U.S. Pat. No. 8,273,308 (Paper 2 in IPR2020 01083) dated Jun. 12, 2020 (104 pages).
Petition for Inter Partes Review of U.S. Pat. No. 8,273,308 (Paper 2 in IPR2020 01091) dated Jun. 12, 2020 (105 pages).
Petition for Inter Partes Review of U.S. Pat. No. 8,803,069 (Paper 2 in IPR2020 01095) dated Jun. 12, 2020 (84 pages).
Petition for Inter Partes Review of U.S. Pat. No. 8,803,069 (Paper 3 in IPR2020-01100) dated Jun. 12, 2020 (83 pages).
Petition for Inter Partes Review of U.S. Pat. No. 8,709,787 (Paper 2 in IPR2020-01132) dated Jun. 18, 2020 (96 pages).
Petition for Inter Partes Review of U.S. Pat. No. 8,415,103 (Paper 2 in IPR2020-01133) dated Jun. 18, 2020 (96 pages).
Petition for Inter Partes Review of U.S. Pat. No. 8,709,787 (Paper 2 in IPR2020-01137) dated Jun. 19, 2020 (86 pages).
Petition for Inter Partes Review of U.S. Pat. No. 8,415,103 (Paper 2 in IPR2020-01136) dated Jun. 19, 2020 (85 pages).
Declaration of Mark A. Burns, Ph.D. (Exhibit N1001 in IPR2020-01083, IPR2020-01091, IPR2020-01095 and IPR2020-01100) dated Jun. 12, 2020 (378 pages).
Declaration of Mark A. Burns, Ph.D. (Exhibit N1101 in IPR2020-01132 and IPR2020-01133) dated Jun. 17, 2020 (253 pages).
Declaration of Mark A. Burns, Ph.D. (Exhibit N1201 in IPR2020-01136 and IPR2020-01137) dated Jun. 19, 2020 (205 pages).
Patent Owner's Preliminary Response to Petition for Inter Partes Review of U.S. Pat. No. 8,703,069 (Paper 13 in IPR2020-01095) dated Sep. 17, 2020 (77 pages).
Patent Owner's Preliminary Response to Petition for Inter Partes Review of U.S. Pat. No. 8,273,308 (Paper 13 in IPR2020-01091) dated Sep. 17, 2020 (70 pages).
Patent Owner's Preliminary Response to Petition for Inter Partes Review of U.S. Pat. No. 8,703,069 (Paper 14 in IPR2020-01100) dated Sep. 17, 2020 (59 pages).
Declaration of M. Allen Northrup, Ph.D. in Support of Patent Owner Preliminary Responses in IPR2020-01091, IPR2020-01095 and IPR2020-01100 (Exhibit H2003) dated Sep. 16, 2020 (137 pages).
Patent Owner's Preliminary Response to Petition for Inter Partes Review of U.S. Pat. No. 8,273,308 (Paper 13 in IPR2020-01083) dated Oct. 22, 2020 (88 pages).
Declaration of M. Allen Northrup, Ph.D. in support of Patent Owner Preliminary Responses in IPR2020-01083, IPR2020-01091, IPR2020-01095 and IPR2020-01100 (Exhibit H2003) dated Oct. 21, 2020 (171 pages).
Petition for Inter Partes Review of U.S. Pat. No. 10,625,262 (Paper 2 in IPR2021-00250) dated Nov. 25, 2020 (107 pages).
Petition for Inter Partes Review of U.S. Pat. No. 10,625,261 (Paper 2 in IPR2021-00251) dated Nov. 25, 2020 (117 pages).
Petition for Inter Partes Review of U.S. Pat. No. 10,632,466 (Paper 2 in IPR2021-00253) dated Nov. 25, 2020 (121 pages).
Declaration of Mark A. Burns, Ph.D. (Exhibit N1001 in IPR2021-00250, IPR2021-00251 and IPR2021-00253) dated Nov. 24, 2020 (311 pages).
Declaration of James L. Mullins, Ph.D. (Exhibit N1029 in IPR2021-00250, IPR2021-00251, and IPR2021-00253) dated Nov. 18, 2020 (54 pages).
Decision Denying Institution of Inter Partes Review of U.S. Pat. No. 8,273,308 (Paper 14 in IPR2020-01091) dated Dec. 4, 2020 (21 pages).
Decision Denying Institution of Inter Partes Review of U.S. Pat. No. 8,703,069 (Paper 14 in IPR2020-01095) dated Dec. 4, 2020 (22 pages).
Decision Denying Institution of Inter Partes Review of U.S. Pat. No. 8,703,069 (Paper 15 in IPR2020-01100) dated Dec. 4, 2020 (19 pages).
Decision Denying Institution of Inter Partes Review of U.S. Pat. No. 8,273,308 (Paper 14 in IPR2020-01083) dated Jan. 7, 2021 (24 pages).
Patent Owner's Preliminary Response to Petition for Inter Partes Review of U.S. Pat. No. 8,415,103 (Paper 20 in IPR2020-01133) dated Jan. 20, 2021 (67 pages).
Patent Owner's Preliminary Response to Petition for Inter Partes Review of U.S. Pat. No. 8,709,787 (Paper 19 in IPR2020-01132) dated Jan. 20, 2021 (78 pages).
Declaration of M. Allen Northrup, Ph.D. in support of Patent Owner Preliminary Responses in IPR2020-01132 and IPR2020-01133 (Exhibit H2016) dated Jan. 20, 2021 (154 pages).
Patent Owner's Preliminary Response to Petition for Inter Partes Review of U.S. Pat. No. 8,415,103 (Paper 19 in IPR2020-01136) dated Jan. 20, 2021 (77 pages).
Patent Owner's Preliminary Response to Petition for Inter Partes Review of U.S. Pat. No. 8,709,787 (Paper 19 in IPR2020-01137) dated Jan. 20, 2021 (69 pages).
Declaration of M. Allen Northrup, Ph.D. in support of Patent Owner Preliminary Responses in IPR2020-01136 and IPR2020-01137 (Exhibit H2016) dated Jan. 20, 2021 (111 pages).
Opening Brief [Corrected] of Appellants Qiagen North American Holdings, Inc. and NeuMoDx Molecular Inc. in Appeals from the USPTO, PTAB, in Nos. IPR2019-00488, IPR2019-00490, IPR2019-01493 and IPR2019-01494 filed Jan. 22, 2021 in U.S. Court of Appeals for the Federal Circuit Case Nos. 20-2249, 20-2250, 20-2273 and 20-2276 (82 pages).
Decision Granting Institution of Inter Partes Review of U.S. Pat. No. 8,709,787 (Paper 20 in IPR2020-01132) dated Apr. 19, 2021 (33 pages).
Decision Denying Institution of Inter Partes Review of U.S. Pat. No. 8,415,103 (Paper 21 in IPR2020-01133) dated Apr. 19, 2021 (24 pages).
Decision Denying Institution of Inter Partes Review of U.S. Pat. No. 8,415,103 (Paper 20 in IPR2020-01136) dated Apr. 19, 2021 (19 pages).
Decision Denying Institution of Inter Partes Review of U.S. Pat. No. 8,709,787 (Paper 20 in IPR2020-01137) dated Apr. 19, 2021 (14 pages).
Patent Owner's Preliminary Response to Petition for Inter Partes Review of U.S. Pat. No. 10,625,262 (Paper 6 in IPR2021-00250) dated Apr. 19, 2021 (71 pages).
Patent Owner's Preliminary Response to Petition for Inter Partes Review of U.S. Pat. No. 10,625,261 (Paper 6 in IPR2021-00251) dated Apr. 19, 2021 (82 pages).
Patent Owner's Preliminary Response to Petition for Inter Partes Review of U.S. Pat. No. 10,632,466 (Paper 6 in IPR2021-00253) dated Apr. 19, 2021 (66 pages).
Declaration of James P. Landers, Ph.D. in support of Patent Owner Preliminary Responses in IPR2021-00250, IPR2021-00251, and IPR2021-00253 (Exhibit H2003) dated Apr. 19, 2021 (189 pages).
Brief for Appellee HandyLab, Inc. in Appeals from the USPTO, PTAB, in Nos. IPR2019-00488, IPR2019-00490, IPR2019-01493 and IPR2019-01494 filed May 24, 2021 in U.S. Court of Appeals for the Federal Circuit Case Nos. 20-2249, 20-2250, 20-2273 and 20-2276 (74 pages).
Reply Brief of Appellants Qiagen North American Holdings, Inc. and NeuMoDx Molecular, Inc. in Appeals from the USPTO, PTAB, in Nos. IPR2019-00488, IPR2019-00490, IPR2019-01493 and IPR2019-

(56) References Cited

OTHER PUBLICATIONS 01494 filed Jun. 21, 2021 in U.S. Court of Appeals for the Federal Circuit Case Nos. 20- 2249, 20-2250, 20-2273 and 20-2276 (44 pages).
Decision Denying Institution of Inter Partes Review of U.S. Pat. No. 10,625,262 (Paper 7 in IPR2021-00250) dated Jul. 15, 2021 (15 pages).
Decision Denying Institution of Inter Partes Review of U.S. Pat. No. 10,632,466 (Paper 7 in IPR2021-00253) dated Jul. 15, 2021 (22 pages).
Decision Denying Institution of Inter Partes Review of U.S. Pat. No. 10,625,261 (Paper 7 in IPR2021-00251) dated Jul. 15, 2021 (24 pages).
Patent Owner's Response in Inter Partes Review of U.S. Pat. No. 8,709,787 and Exhibit List (Paper 29 in IPR 2020-01132) dated Jul. 15, 2021 (87 pages).
Decision Granting Institution of Inter Partes Review of U.S. Pat. No. 8,415,103 on Rehearing (Paper 23 in IPR2020-01133) dated Aug. 6, 2021 (20 pages).
Decision of U.S. Court of Appeal for the Federal Circuit Affirming Inter Partes Review Final Written Decisions Determining No Challenged Claims of U.S. Pat. Nos. 7,998,708 and 8,323,900 are Unpatentable (IPR2019-00488, IPR2019-00490, IPR2019-01493, and IPR2019-01494) dated Oct. 29, 2021 (12 pages).
Joint Motion to Terminate Inter Partes Review of U.S. Pat. No. 8,709,787 (Paper 37 in IPR 2020-01132) dated Nov. 15, 2021 (8 pages).
Joint Motion to Terminate Inter Partes Review of U.S. Pat. No. 8,415, 103 (Paper 35 in IPR 2020-01133) dated Nov. 15, 2021 (8 pages).
Complaint filed by *Becton, Dickinson et al*., v. *NeuModx Molecular, Inc*. on Jun. 18, 2019 in U.S. District Court, Delaware, Case #1:19-cv-01126-LPS, Infringement Action involving U.S. Pat. Nos. 7,998,708; 8,273,308; 8,323,900; 8,415,103; 8,703,069; and 8,709,787 (29 pages).
Answer to Complaint filed by NeuModx Molecular, Inc. on Aug. 9, 2019 in U.S. District Court, Delaware, Case #1:19-cv-01126-LPS (24 pages).
Amended Answer to Complaint filed by NeuModx Molecular, Inc. on Oct. 4, 2019 in U.S. District Court, Delaware, Case #1:19-cv-01126-LPS (31 pages).
First Amended and Supplemental Complaint filed by Becton, Dickinson and Company et al. on Jun. 25, 2020 in U.S. District Court, Delaware, Case #1:19-cv-01126-LPS, Infringement Action involving U.S. Pat. Nos. 7,998,708; 8,273,308; 8,323,900; 8,415,103; 8,703,069; 8,709,787; 10,494,663; 10,364,456; 10,443,088; 10,604,788; 10,625,261; 10,625,262; and 10,632,466 (55 pages).
Answer to First Amended and Supplemental Complaint filed by NeuModx Molecular, Inc. on Jul. 16, 2020 in U.S. District Court, Delaware, Case #1:19-cv-01126-LPS (42 pages).
Defendant NeuModx's Initial Invalidity Contentions filed Sep. 30, 2020 in U.S. District Court, Delaware, Case #1:19-cv-01126-LPS (47 pages).
Defendant NeuModx's Joint Claim Construction Chart [Exhibit N1023] filed Oct. 21, 2020 in U.S. District Court, Delaware, Case #1:19-cv-01126-LPS (25 pages).
Defendant NeuModx's Amended Answer, Affirmative Defenses, and Counterclaims to Plaintiffs' First Amended and Supplemental Complaint filed Dec. 11, 2020 in U.S. District Court, Delaware, Case #1:19-cv-01126-LPS (43 pages).
Second Amended and Supplemental Complaint filed by Becton, Dickinson and Company et al. on Feb. 25, 2021 in U.S. District Court, Delaware, Case #1:19-cv-01126-LPS (75 pages).
Defendant NeuMoDx's First Supplemental Invalidity Contentions filed Mar. 17, 2021 in U.S. District Court, Delaware, Case #1:19-cv-01126-LPS (55 pages).
Defendant NeuModx's Answer, Affirmative Defenses, and Counterclaims to Plaintiffs' Second and Supplemental Complaint filed Mar. 18, 2021 in U.S. District Court, Delaware, Case #1:19-cv-01126-LPS (67 pages).
Plaintiffs' Answer and/or Reply to Defendants' Counterclaims and Counterclaims-In-Reply filed Apr. 22, 2021 in U.S. District Court, Delaware, Case #1:19-cv-01126-LPS (127 pages).
Claim Construction (Markman) Order dated May 10, 2021 in in U.S. District Court, Delaware, Case #1:19-cv-01126-LPS (30 pages).
Stipulation of Dismissal filed by Plaintiffs Becton, Dickinson and Company, Geneohm Sciences Canada, Inc. and HandyLab, Inc. and Defendants NeuMoDx Molecular, Inc., Qiagen GmbH, and Qiagen North American Holdings, Inc. on Nov. 12, 2021 in U.S. District Court, Delaware, Case #1:19-cv-01226-LPS (3 pages).
Asymtek: High-Speed Dispensejet DJ-9000 Jet; ASI Adhesives & Sealants Industry; Press Release dated Nov. 17, 2003; 2 pages.
Yang et al., "Integrated Multiprocess Microfluidic Systems for Automating Analysis", JALA Jun. 2010;15(3): 198-209.

* cited by examiner

MICROFLUIDIC SYSTEM FOR AMPLIFYING AND DETECTING POLYNUCLEOTIDES IN PARALLEL

CROSS-REFERENCE TO RELATED APPLICATIONS

This application is a continuation of U.S. patent application Ser. No. 17/496,160, filed Oct. 7, 2021 and scheduled to issue as U.S. Pat. No. 11,959,126 on Apr. 16, 2024 which is a continuation of U.S. patent application Ser. No. 16/787,977, filed Feb. 11, 2020 and issued as U.S. Pat. No. 11,142,785 on Oct. 12, 2021, which is a continuation of U.S. patent application Ser. No. 14/796,239, filed Jul. 10, 2015, which is a continuation of U.S. patent application Ser. No. 13/692,929, filed Dec. 3, 2012 and issued as U.S. Pat. No. 9,080,207 on Jul. 14, 2015, which is a continuation of U.S. patent application Ser. No. 13/035,725, filed Feb. 25, 2011, issued as U.S. Pat. No. 8,323,900 on Dec. 4, 2012, which is a continuation of U.S. patent application Ser. No. 11/985,577, filed Nov. 14, 2007, issued as U.S. Pat. No. 7,998,708 on Aug. 16, 2011, which is a continuation-in-part of U.S. patent application Ser. No. 11/728,964, filed Mar. 26, 2007, issued as U.S. Pat. No. 9,040,288 on May 26, 2015, which claims the benefit of U.S. Provisional Patent Application No. 60/786,007, filed Mar. 24, 2006, and U.S. Provisional Patent Application No. 60/859,284, filed Nov. 14, 2006. U.S. patent application Ser. No. 11/985,577 claims the benefit of U.S. Provisional Patent Application No. 60/859,284, filed Nov. 14, 2006, and U.S. Provisional Patent Application No. 60/959,437, filed Jul. 13, 2007. The disclosures of U.S. patent application Ser. No. 13/692,929, U.S. patent application Ser. No. 13/035,725, U.S. patent application Ser. No. 11/985,577, U.S. patent application Ser. No. 11/728,964, U.S. Provisional Patent Application No. 60/859,284, and U.S. Provisional Patent Application No. 60/959,437 are considered part of the disclosure of this application, and are incorporated by reference herein in their entirety.

TECHNICAL FIELD

The technology described herein generally relates to systems for detecting polynucleotides in samples, particularly from biological samples. The technology more particularly relates to microfluidic systems that carry out PCR on nucleotides of interest within microfluidic channels, and detect those nucleotides.

BACKGROUND

The medical diagnostics industry is a critical element of today's healthcare infrastructure. At present, however, diagnostic analyses no matter how routine have become a bottleneck in patient care. There are several reasons for this. First, many diagnostic analyses can only be done with highly specialist equipment that is both expensive and only operable by trained clinicians. Such equipment is found in only a few locations-often just one in any given urban area. This means that most hospitals are required to send out samples for analyses to these locations, thereby incurring shipping costs and transportation delays, and possibly even sample loss. Second, the equipment in question is typically not available 'on-demand' but instead runs in batches, thereby delaying the processing time for many samples because they must wait for a machine to fill up before they can be run.

Understanding that sample flow breaks down into several key steps, it would be desirable to consider ways to automate as many of these as possible. For example, a biological sample, once extracted from a patient, must be put in a form suitable for a processing regime that typically involves using PCR to amplify a vector of interest. Once amplified, the presence of a nucleotide of interest from the sample needs to be determined unambiguously. Sample preparation is a process that is susceptible to automation but is also relatively routinely carried out in almost any location. By contrast, steps such as PCR and nucleotide detection have customarily only been within the compass of specially trained individuals having access to specialist equipment.

There is a need for a method and apparatus of carrying out PCR and detection on prepared biological samples, and preferably with high throughput. In particular there is a need for an easy-to-use device that can deliver a diagnostic result on several samples in a short time.

The discussion of the background to the technology herein is included to explain the context of the technology. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present technology addresses systems for detecting polynucleotides in samples, particularly from biological samples. In particular, the technology relates to microfluidic systems that carry out PCR on nucleotides of interest within microfluidic channels, and detect those nucleotides.

An apparatus, comprising: a receiving bay configured to receive a microfluidic cartridge; at least one heat source thermally coupled to the cartridge and configured to carry out PCR on a microdroplet of polynucleotide-containing sample, in the cartridge; a detector configured to detect presence of one or more polynucleotides in the sample; and a processor coupled to the detector and the heat source, configured to control heating of one or more regions of the microfluidic cartridge.

A method of carrying out PCR on a plurality of polynucleotide-containing samples, the method comprising: introducing the plurality of samples in to a microfluidic cartridge, wherein the cartridge has a plurality of PCR reaction chambers configured to permit thermal cycling of the plurality of samples independently of one another; moving the plurality of samples into the respective plurality of PCR reaction chambers; and amplifying polynucleotides contained with the plurality of samples, by application of successive heating and cooling cycles to the PCR reaction chambers.

The details of one or more embodiments of the technology are set forth in the accompanying drawings and further description herein. Other features, objects, and advantages of the technology will be apparent from the description and drawings, and from the claims.

Additional figures are illustrated within the examples, and are further described therein.

Like reference symbols in the various drawings indicate like elements.

DETAILED DESCRIPTION

Overview of Apparatus

The present technology relates to a system and related methods for amplifying, and carrying out diagnostic analyses on, polynucleotides (e.g., a DNA, RNA, mRNA, or rRNA) from biological samples. For example, the system and methods can determine whether a polynucleotide indicative of the presence of a particular pathogen (such as a bacterium or a virus) can be present. The polynucleotide may be a sample of genomic DNA, or may be a sample of mitochondrial DNA. The nucleotides are typically provided to the system having been isolated or released from particles such as cells in the sample. The system includes a disposable microfluidic cartridge containing multiple sample lanes in parallel and a reusable instrument platform (a PCR analyzer apparatus) that can actuate on-cartridge operations, can detect (e.g., by fluorescence detection) and analyze the products of the PCR amplification in each of the lanes separately, in all simultaneously, or in groups simultaneously, and, optionally, can display the results on a graphical user interface.

A system, microfluidic cartridge, heater unit, detector, kit, methods, and associated computer program product, are now further described.

By cartridge is meant a unit that may be disposable, or reusable in whole or in part, and that is configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 μl to about 999 μl, such as from 1-100 μl, or from 2-25 μl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide.

Figure 1:
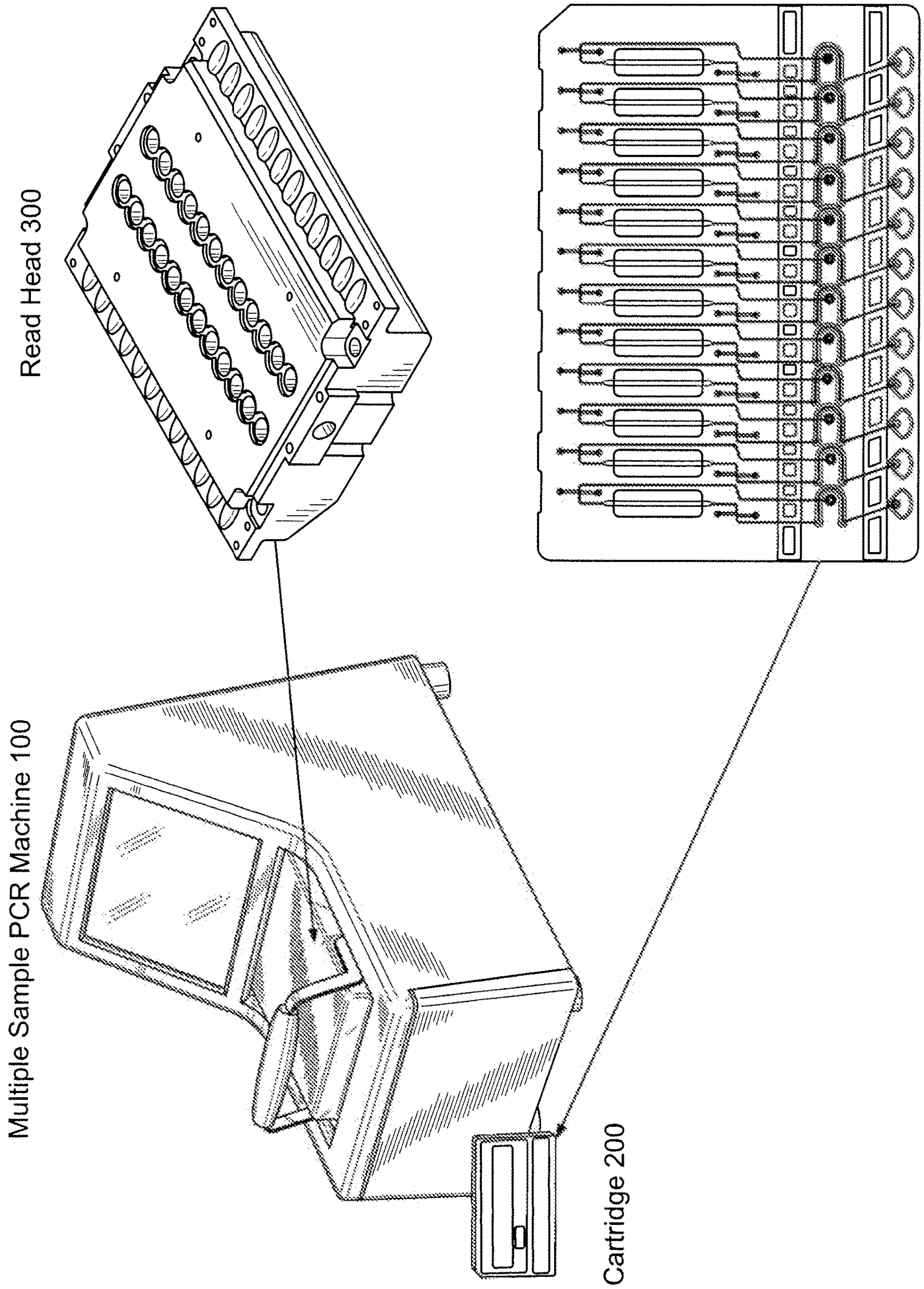
FIG. 1 shows an exemplary apparatus, a microfluidic cartridge, and a read head, as further described herein.
Figure 2:
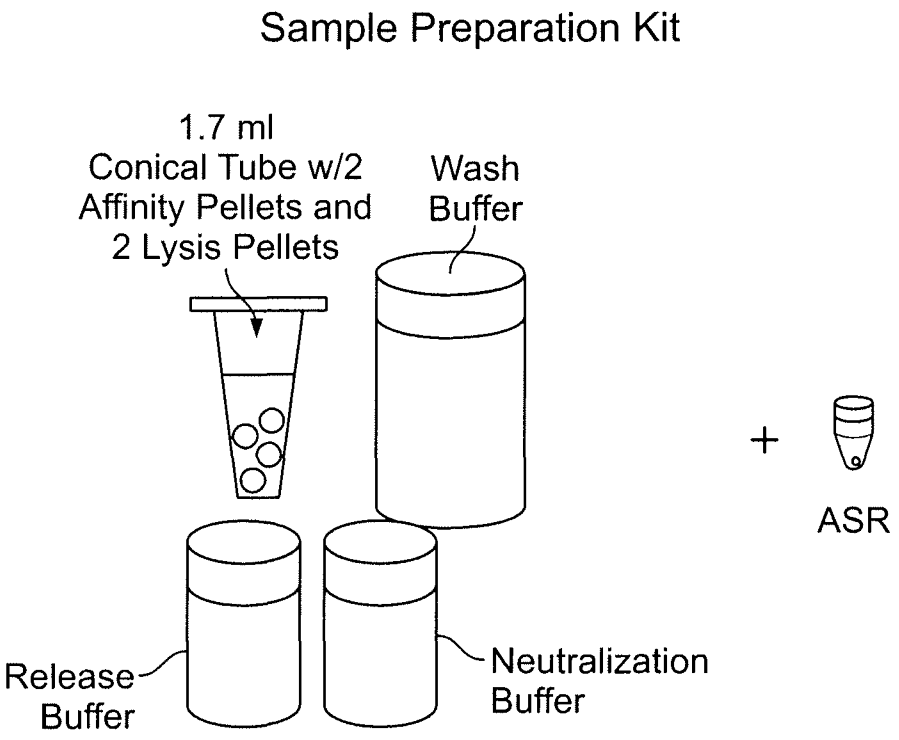
FIG. 2 shows an exemplary sample-preparation kit.

FIG. 1 shows a perspective view of an exemplary apparatus 100 consistent with those described herein, as well as various components thereof, such as exemplary cartridge 200 that contains multiple sample lanes, and exemplary read head 300 that contains detection apparatus for reading signals from cartridge 200. The apparatus 100 of FIG. 1 is able to carry out real-time PCR on a number of samples in cartridge 200 simultaneously. Preferably the number of samples is 12 samples, as illustrated with exemplary cartridge 200, though other numbers of samples such as 4, 8, 10, 16, 20, 24, 25, 30, 32, 36, 40, and 48 are within the scope of the present description. In preferred operation of the apparatus, a PCR-ready solution containing the sample, and, optionally, one or more analyte-specific reagents (ASR's) is prepared, as further described elsewhere (see, e.g., U.S. patent application publication 2006-0166233, incorporated herein by reference), prior to introduction into cartridge 200. An exemplary kit for preparing a PCR-ready sample, for use with the system described herein, the kit comprising buffers, lysis pellets, and affinity pellets, is shown in FIG. 2.

System Overview

Figure 3:
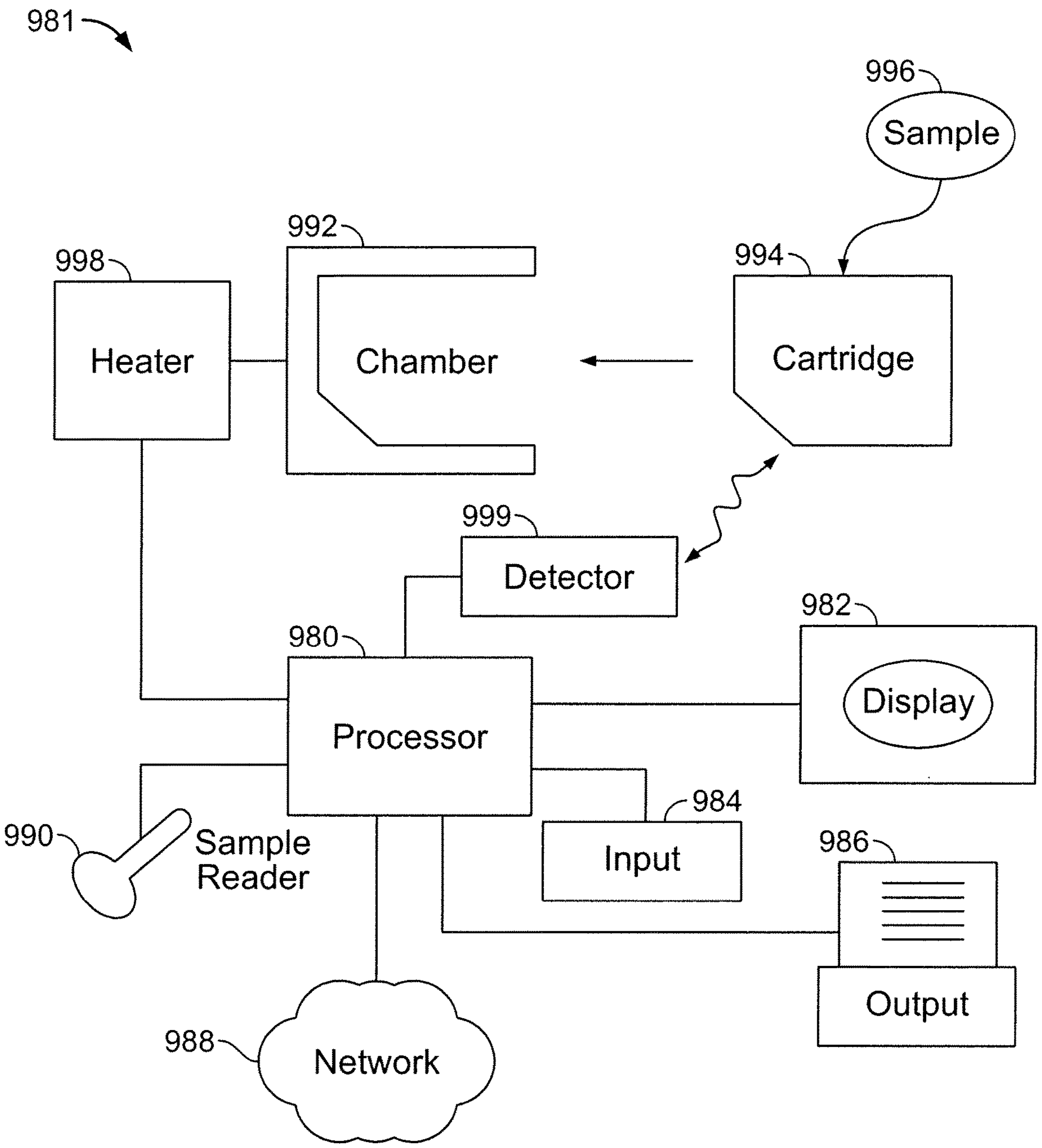
FIG. 3 shows a schematic diagram of an apparatus.

A schematic overview of a system 981 for carrying out analyses described herein is shown in FIG. 3. The geometric arrangement of the components of system 981 shown in FIG. 3, as well as their respective connectivities, is exemplary and not intended to be limiting.

A processor 980, such as a microprocessor, is configured to control functions of various components of the system as shown, and is thereby in communication with each such component. In particular, processor 980 is configured to receive data about a sample to be analyzed, e.g., from a sample reader 990, which may be a barcode reader, an optical character reader, or an RFID scanner (radio frequency tag reader). For example, the sample identifier can be a handheld bar code reader. Processor 980 can be configured to accept user instructions from an input 984, where such instructions may include instructions to start analyzing the sample, and choices of operating conditions.

Processor 980 can also be configured to communicate with an optional display 982, so that, for example, information including but not limited to the current status of the system, progress of PCR thermocycling, and any warning message in case of malfunction of either system or cartridge, as well as results of analysis, are transmitted to the display. Additionally, processor 980 may transmit one or more questions to be displayed on display 982 that prompt a user to provide input in response thereto. Thus, in certain embodiments, input 984 and display 982 are integrated with one another.

Processor 980 can be optionally further configured to transmit results of an analysis to an output device such as a printer, a visual display, or a speaker, or a combination thereof, the transmission being either directly through a directly dedicated printer cable, or wirelessly, or via a network connection.

Processor 980 is still further optionally connected via a communication interface such as a network interface to a computer network 988. The communication interface can be one or more interfaces selected from the group consisting of: a serial connection, a parallel connection, a wireless network connection and a wired network connection such as an ethernet, firewire, cable connection, or one using USB connectivity. Thereby, when the system is suitably addressed on the network, a remote user may access the processor and transmit instructions, input data, or retrieve data, such as may be stored in a memory (not shown) associated with the processor, or on some other computer-readable medium that is in communication with the processor. The computer network connection may also permit extraction of data to a remote location, such as a personal computer, personal digital assistant, or network storage device such as computer server or disk farm. The apparatus may further be configured to permit a user to e-mail results of an analysis directly to some other party, such as a healthcare provider, or a diagnostic facility, or a patient.

Although not shown in FIG. 3, in various embodiments, input 984 can include one or more input devices selected from the group consisting of: a keyboard, a touch-sensitive surface, a microphone, a track-pad, and a mouse. A suitable input device may further comprise a reader of formatted electronic media, such as, but not limited to, a flash memory card, memory stick, USB-stick, CD, or floppy diskette. An input device may further comprise a security feature such as a fingerprint reader, retinal scanner, magnetic strip reader, or bar-code reader, for ensuring that a user of the system is in fact authorized to do so, according to, for example, preloaded identifying characteristics of authorized users. An input device may additionally- and simultaneously-function as an output device for writing data in connection with sample analysis. For example, if an input device is a reader of formatted electronic media, it may also be a writer of such media. Data that may be written to such media by such a device includes, but is not limited to, environmental information, such as temperature or humidity, pertaining to an analysis, as well as a diagnostic result, and identifying data for the sample in question.

Additionally, in various embodiments, the apparatus can further comprise a data storage medium configured to receive data from one or more of the processor, an input device, and a communication interface, the data storage medium being one or more media selected from the group consisting of: a hard disk drive, an optical disk drive, or one or more removable storage media such as a CD-R, CD-RW, USB-drive, and a flash card.

Processor 980 is further configured to control various aspects of sample diagnosis, as follows in overview, and as further described in detail herein. The system is configured to operate in conjunction with a complementary cartridge 994, such as a microfluidic cartridge. The cartridge is itself configured, as further described herein, to receive one or more samples 996 containing one or more polynucleotides in a form suitable for amplification and diagnostic analysis. The cartridge has dedicated regions within which amplification, such as by PCR, of the polynucleotides is carried out when the cartridge is situated in the apparatus.

The microfluidic cartridge is received by a receiving bay 992 configured to selectively receive the cartridge. For example, the receiving bay and the microfluidic cartridge can be complementary in shape so that the microfluidic cartridge is selectively received in, e.g., a single orientation. The microfluidic cartridge can have a registration member that fits into a complementary feature of the receiving bay. The registration member can be, for example, a cut-out on an edge of the cartridge, such as a corner that is cut-off, or one or more notches that are made on one or more of the sides. By selectively receiving the cartridge, the receiving bay can help a user to place the cartridge so that the apparatus can properly operate on the cartridge. The receiving bay can also be configured so that various components of the apparatus that can operate on the microfluidic cartridge (heat sources, detectors, force members, and the like) are positioned to properly operate on the microfluidic cartridge. In some embodiments, the apparatus can further include a sensor coupled to the processor, the sensor configured to sense whether the microfluidic cartridge is selectively received.

The receiving bay is in communication with a heater unit 998 that itself is controlled by processor 980 in such a way that specific regions of the cartridge, such as individual sample lanes, are independently and selectively heated at specific times during amplification and analysis. The processor can be configured to control application of heat to the individual sample lanes, separately, in all simultaneously, or in groups simultaneously.

The heat source can be, for example, a contact heat source such as a resistive heater or a network of resistive heaters, or a Peltier device, and the like. The contact heat source can be configured to be in direct physical contact with one or more distinct locations of a microfluidic cartridge received in the receiving bay. In various embodiments, each contact source heater can be configured to heat a distinct location having an average diameter in 2 dimensions from about 1 millimeter (mm) to about 15 mm (typically about 1 mm to about 10 mm), or a distinct location having a surface area of between about 1 $mm^2$ about 225 $mm^2$ (typically between about 1 $mm^2$ and about 100 $mm^2$, or in some embodiments between about 5 $mm^2$ and about 50 $mm^2$).

In various embodiments, the heat source can be situated in an assembly that is removable from the apparatus, for example, to permit cleaning or to replace the heater configuration.

In various embodiments, the apparatus can include a compliant layer at the contact heat source configured to thermally couple the contact heat source with at least a portion of a microfluidic cartridge received in the receiving bay. The compliant layer at can have a thickness of between about 0.05 and about 2 millimeters and a Shore hardness of between about 25 and about 100.

In various embodiments, the apparatus can further include one or more force members (not shown in FIG. 3) configured to apply force to thermally couple the at least one heat source at least a portion of a microfluidic cartridge received in the receiving bay.

In various embodiments, the one or more force members are configured to apply force to a plurality of locations in the microfluidic cartridge. The force applied by the one or more force members can result in an average pressure at an interface between a portion of the receiving bay and a portion of the microfluidic cartridge of between about 5 kilopascals and about 50 kilopascals, for example, the average pressure can be at least about 7 kilopascals, and still more preferably at least about 14 kilopascals. At least one force member can be manually operated. At least one force member can be mechanically coupled to a lid at the receiving bay, whereby operation of the lid operates the force member. The application of force is important to ensure consistent thermal contact between the heater wafer and the PCR reactor and microvalves in the microfluidic cartridge.

In various embodiments, the apparatus can further include a lid at the receiving bay, the lid being operable to at least partially exclude ambient light from the receiving bay. The lid can be, for example, a sliding lid. The lid can include the optical detector. A major face of the lid at the optical detector or at the receiving bay can vary from planarity by less than about 100 micrometers, for example, less than about 25 micrometers. The lid can be configured to be removable from the apparatus. The lid can include a latching member that ensures that the lid is securely closed before amplification reactions are applied to the samples in the cartridge.

The processor is also configured to receive signals from and control a detector 999 configured to detect a polynucleotide in a sample in one or more of the individual sample lanes, separately or simultaneously. The processor thereby provides an indication of a diagnosis from the cartridge 994. Diagnosis can be predicated on the presence or absence of a specific polynucleotide in a particular sample. The diagnosis can be transmitted to the output device 986 and/or the display 982, as described hereinabove.

The detector can be, for example, an optical detector that includes a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof. Alternatively, for example, the optical detector can include a bandpass-filtered diode that selectively emits light in the absorption band of the fluorescent dye and a bandpass filtered photodiode that selectively detects light in the emission band of the fluorescent dye; or for example, the optical detector can be configured to independently detect a plurality of fluorescent dyes having different fluorescent emission spectra, wherein each fluorescent dye corresponds to a fluorescent polynucleotide probe or a fragment thereof; or for example, the optical detector can be configured to independently detect a plurality of fluorescent dyes at a plurality of different locations on a microfluidic cartridge, wherein each fluorescent dye corresponds to a fluorescent polynucleotide probe or a fragment thereof in a different sample.

A suitable processor 980 can be designed and manufactured according to, respectively, design principles and semiconductor processing methods known in the art.

The system in FIG. 3 is configured so that a cartridge with capacity to receive multiple samples can be acted upon by the system to analyze multiple samples- or subsets thereof- simultaneously, or to analyze the samples consecutively. It is also consistent that additional samples can be added to a cartridge, while previously added samples are being amplified and analyzed.

The system shown in outline in FIG. 3, as with other exemplary embodiments described herein, is advantageous at least because it does not require locations within the system suitably configured for storage of reagents. Neither does the system, or other exemplary embodiments herein, require inlet or outlet ports that are configured to receive reagents from, e.g., externally stored containers such as bottles, canisters, or reservoirs. Therefore, the system in FIG. 3 is self-contained and operates in conjunction with a microfluidic cartridge, wherein the cartridge has locations within it configured to receive mixtures of sample and PCR reagents.

The system of FIG. 3 may be configured to carry out operation in a single location, such as a laboratory setting, or may be portable so that it can accompany, e.g., a physician, or other healthcare professional, who may visit patients at different locations. The system is typically provided with a power-cord so that it can accept AC power from a mains supply or generator. An optional transformer (not shown) built into the system, or situated externally between a power socket and the system, transforms AC input power into a DC output for use by the system. The system may also be configured to operate by using one or more batteries and therefore is also typically equipped with a battery recharging system, and various warning devices that alert a user if battery power is becoming too low to reliably initiate or complete a diagnostic analysis.

The system of FIG. 3 may further be configured, for multiplexed cartridge analysis. In one such configuration, multiple instances of a system, as outlined in FIG. 3, are operated in conjunction with one another to accept and to process multiple cartridges, where each cartridge has been loaded with a different sample. Each component shown in FIG. 3 may therefore be present as many times as there are cartridges, though the various components may be configured in a common housing.

In still another configuration, a system is configured to accept and to process multiple cartridges, but one or more components in FIG. 3 is common to multiple cartridges. For example, a single device may be configured with multiple cartridge receiving bays, but a common processor and user interface suitably configured to permit concurrent, consecutive, or simultaneous, control of the various cartridges. In such an embodiment a single detector, for example, can scan across all of the multiple cartridges. It is further possible that such an embodiment, also utilizes a single sample reader, and a single output device.

In still another configuration, a system as shown in FIG. 3 is configured to accept a single cartridge, but wherein the single cartridge is configured to process more than 1, for example, 2, 3, 4, 5, or 6, samples in parallel, and independently of one another.

It is further consistent with the present technology that a cartridge can be tagged, e.g., with a molecular bar-code indicative of one or more of the samples, to facilitate sample tracking, and to minimize risk of sample mix-up. Methods for such tagging are described elsewhere, e.g., in U.S. patent application publication Ser. No. 10/360,854, incorporated herein by reference.

In various embodiments, the apparatus can further include an analysis port. The analysis port can be configured to allow an external sample analyzer to analyze a sample in the microfluidic cartridge; for example, the analysis port can be a hole or window in the apparatus which can accept an optical detection probe that can analyze a sample in situ in the microfluidic cartridge. In some embodiments, the analysis port can be configured to direct a sample from the microfluidic cartridge to an external sample analyzer; for example, the analysis port can include a conduit in fluid communication with the microfluidic cartridge that direct a liquid sample to a chromatography apparatus, an optical spectrometer, a mass spectrometer, or the like.

Apparatus 100 may optionally comprise one or more stabilizing feet that cause the body of the device to be elevated above a surface on which system 100 is disposed, thereby permitting ventilation underneath system 100, and also providing a user with an improved ability to lift system 100. There may be 2, 3, 4, 5, or 6, or more feet, depending upon the size of system 100. Such feet are preferably made of rubber, or plastic, or metal, and in some embodiments may elevate the body of system 100 by from about 2 to about 10 mm above a surface on which it is situated. The stabilizing function can also be provided by one or more runners that run along one or more edges—or are inwardly displaced from one or more edges—of the underside of the apparatus. Such runners can also be used in conjunction with one or more feet. In another embodiment, a turntable situated on the underside permits the apparatus to be rotated in a horizontal or near-horizontal plane when positioned on, e.g., a benchtop, to facilitate access from a number of angles by a user.

Figure 4:
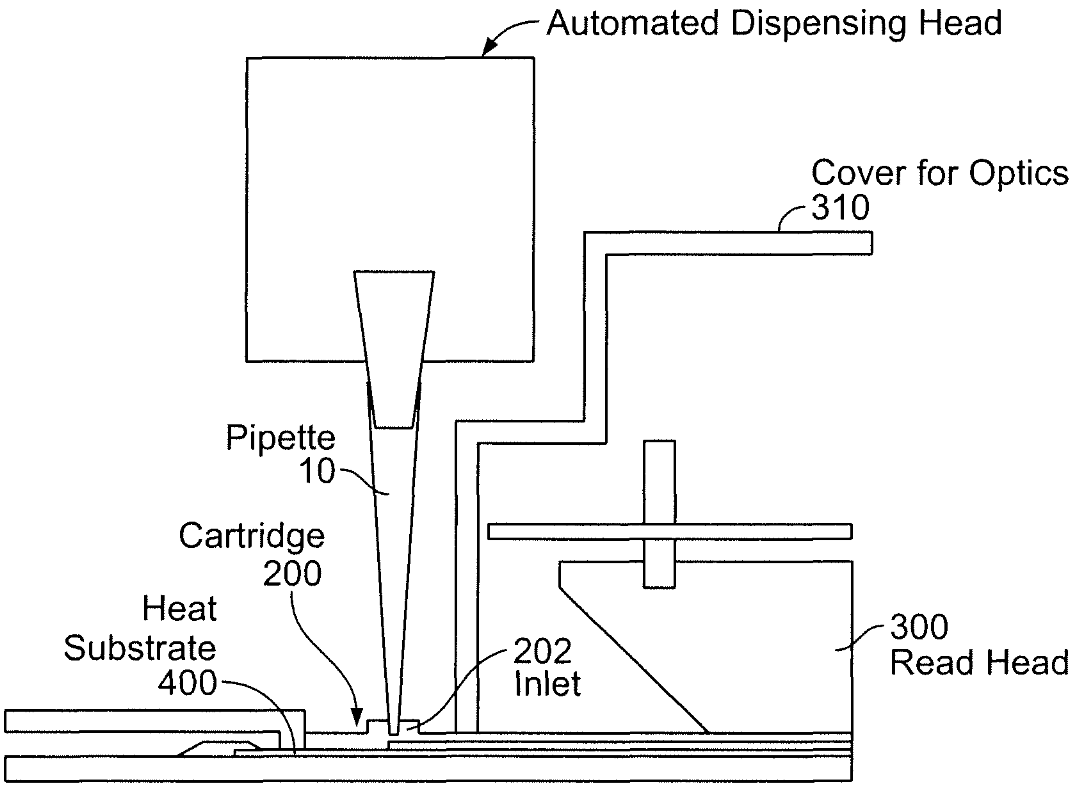
FIG. 4 shows a cross-section of a pipetting head and a cartridge in position in a microfluidic apparatus.

FIG. 4 shows a schematic cross-sectional view of a part of an apparatus as described herein, showing input of sample into a cartridge 200 via a pipette 10 (such as a disposable pipette) and an inlet 202. Inlet 202 is preferably configured to receive a pipette or the bottom end of a PCR tube and thereby accept sample for analysis with minimum waste, and with minimum introduction of air. Cartridge 200 is disposed on top of and in contact with a heater substrate 400. Read head 300 is positioned above cartridge 200 and a cover for optics 310 restricts the amount of ambient light that can be detected by the read head.

Figure 5:
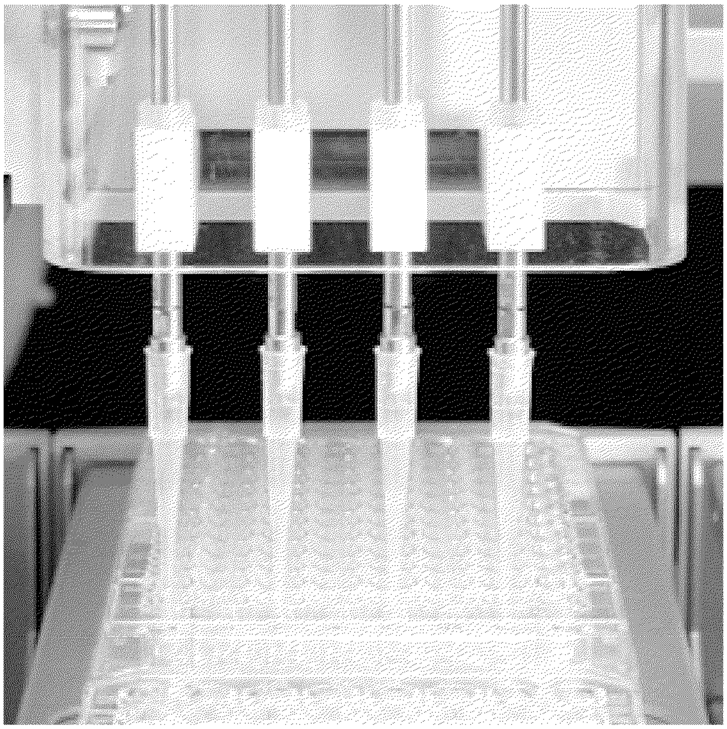
FIG. 5 shows introduction of a PCR-ready sample into a cartridge, situated in an instrument.

FIG. 5 shows an example of 4-pipette head used for attaching disposable pipette tips, prior to dispensing PCR-ready sample into a cartridge.

Exemplary Systems

Figure 6A:
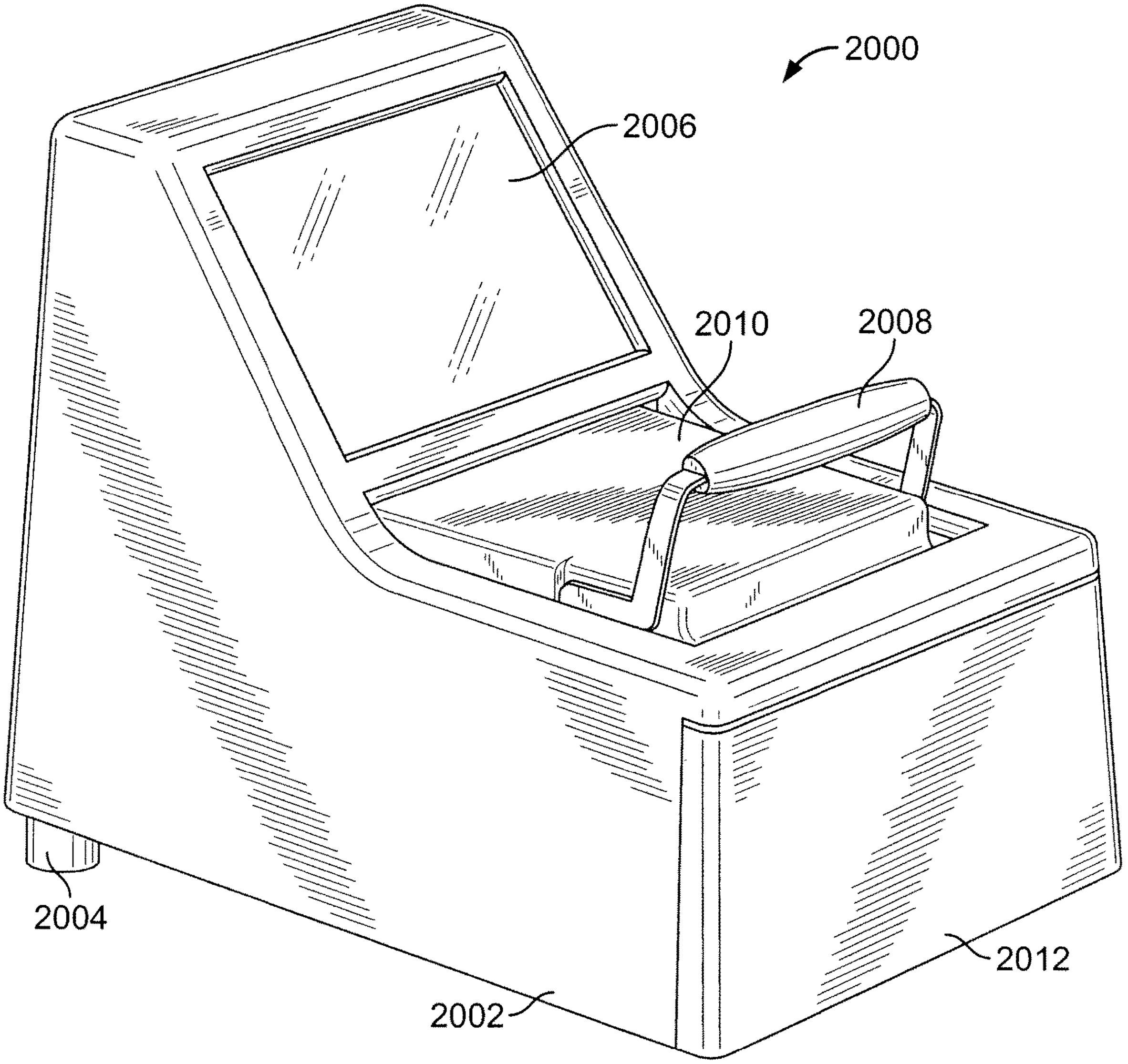
FIGS. 6A-6E show exemplary embodiments of an apparatus.

FIGS. 6A-6E show exterior perspective views of various configurations of an exemplary system, as further described herein. FIG. 6A shows a perspective view of a system 2000 for receiving microfluidic cartridge (not shown), and for causing and controlling various processing operations to be performed a sample introduced into the cartridge. The elements of system 2000 are not limited to those explicitly shown. For example, although not shown, system 2000 may be connected to a hand-held bar-code reader, as further described herein.

System 2000 comprises a housing 2002, which can-be made of metal, or a hardened plastic. The form of the housing shown in FIG. 6A embodies stylistic as well as functional features. Other embodiments of the technology may appear somewhat differently, in their arrangement of the components, as well as their overall appearance, in terms of smoothness of lines, and of exterior finish, and texture. System 2000 further comprises one or more stabilizing members 2004. Shown in FIG. 6A is a stabilizing foot, of which several are normally present, located at various regions of the underside of system 2000 so as to provide balance and support. For example, there may be three, four, five, six, or eight such stabilizing feet. The feet may be moulded into and made of the same material as housing 2002, or may be made of one or more separate materials and attached to the underside of system 2000. For example, the feet may comprise a rubber that makes it hard for system 2000 to slip on a surface on which it is situated, and also protects the surface from scratches. The stabilizing member of members may take other forms than feet, for example, rails, runners, or one or more pads.

System 2000 further comprises a display 2006, which may be a liquid crystal display, such as active matrix, an OLED, or some other suitable form. It may present images and other information in color or in black and white. Display 2006 may also be a touch-sensitive display and therefore may be configured to accept input from a user in response to various displayed prompts. Display 2006 may have an anti-reflective coating on it to reduce glare and reflections from overhead lights in an laboratory setting. Display 2006 may also be illuminated from, e.g., a back-light, to facilitate easier viewing in a dark laboratory.

Figure 6B:
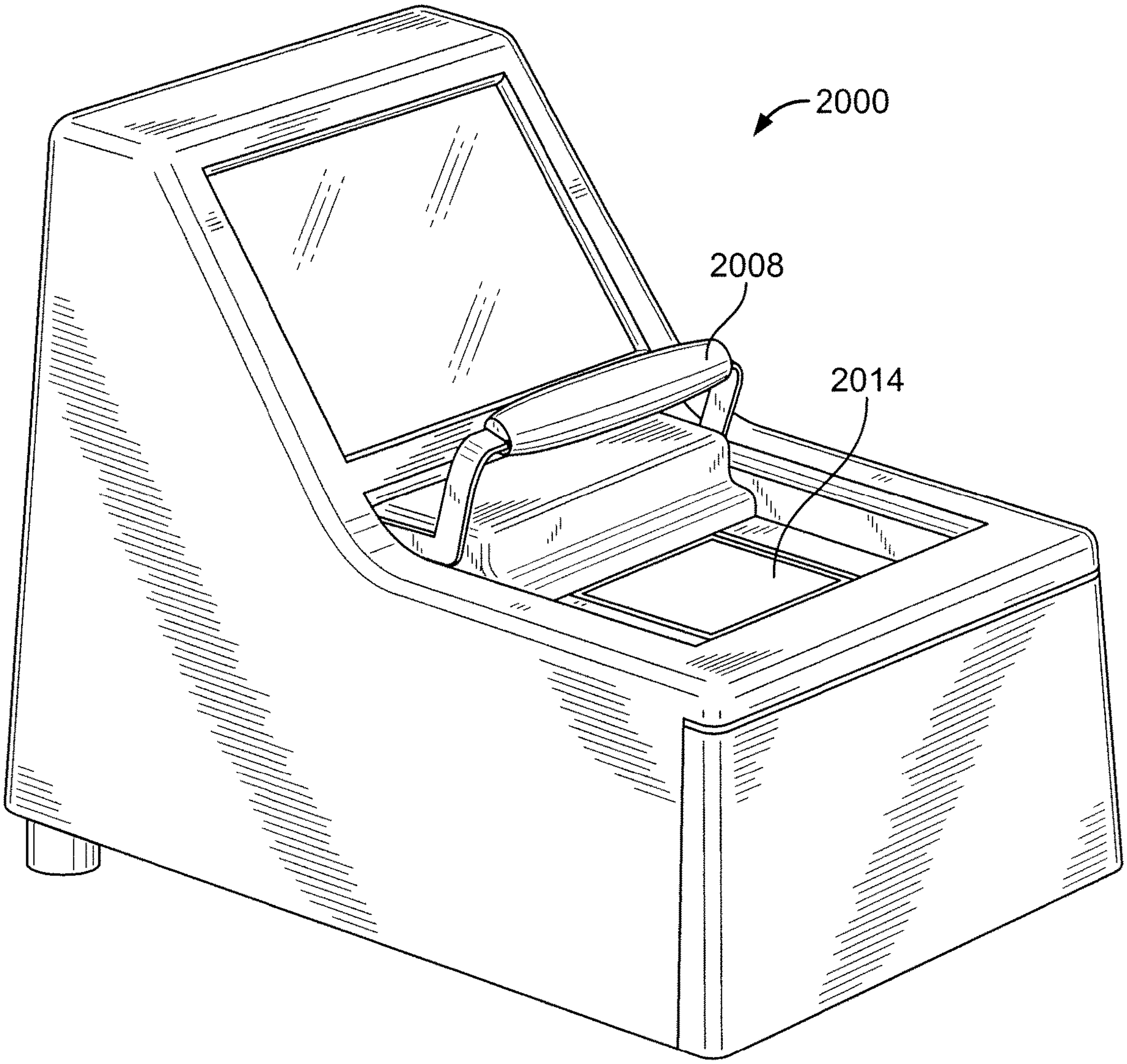

System 2000, as shown in FIG. 6A, also comprises a moveable lid 2010, having a handle 2008. The lid 2010 can slide back and forward. In FIG. 6A, the lid is in a forward position, whereby it is "closed". In FIG. 6B, the lid is shown in a back position, wherein the lid is "open" and reveals a receiving bay 2014 that is configured to receive a microfluidic cartridge. Of course, as one of ordinary skill in the art would appreciate, the technology described herein is not limited to a lid that slides, or one that slides back and forward. Side to side movement is also possible, as is a configuration where the lid is "open" when positioned forward in the device. It is also possible that the lid is a hinged lid, or one that is totally removable.

Figure 6C:
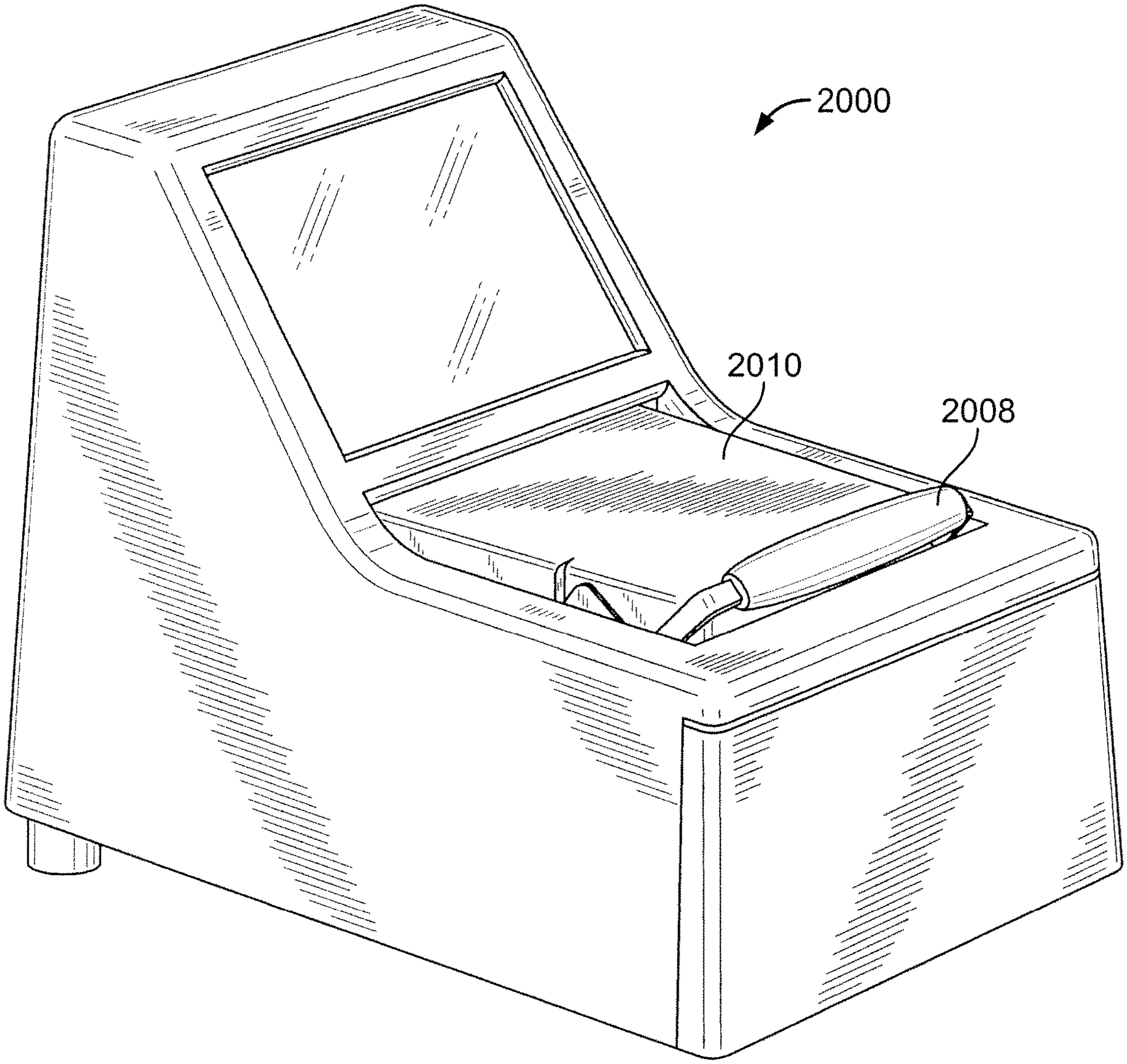

Handle 2008 performs a role of permitting a user to move lid 2010 from one position to another, and also performs a role of causing pressure to be forced down on the lid, when in a closed position, so that pressure can be applied to a cartridge in the receiving bay 2014. In FIG. 6C, handle 2008 is shown in a depressed position, wherein force is thereby applied to lid 2014, and thus pressure is applied to a cartridge received in the receiving bay beneath the lid.

In one embodiment, the handle and lid assembly are also fitted with a mechanical sensor that does not permit the handle to be depressed when there is no cartridge in the receiving bay. In another embodiment, the handle and lid assembly are fitted with a mechanical latch that does not permit the handle to be raised when an analysis is in progress.

Figure 6D:
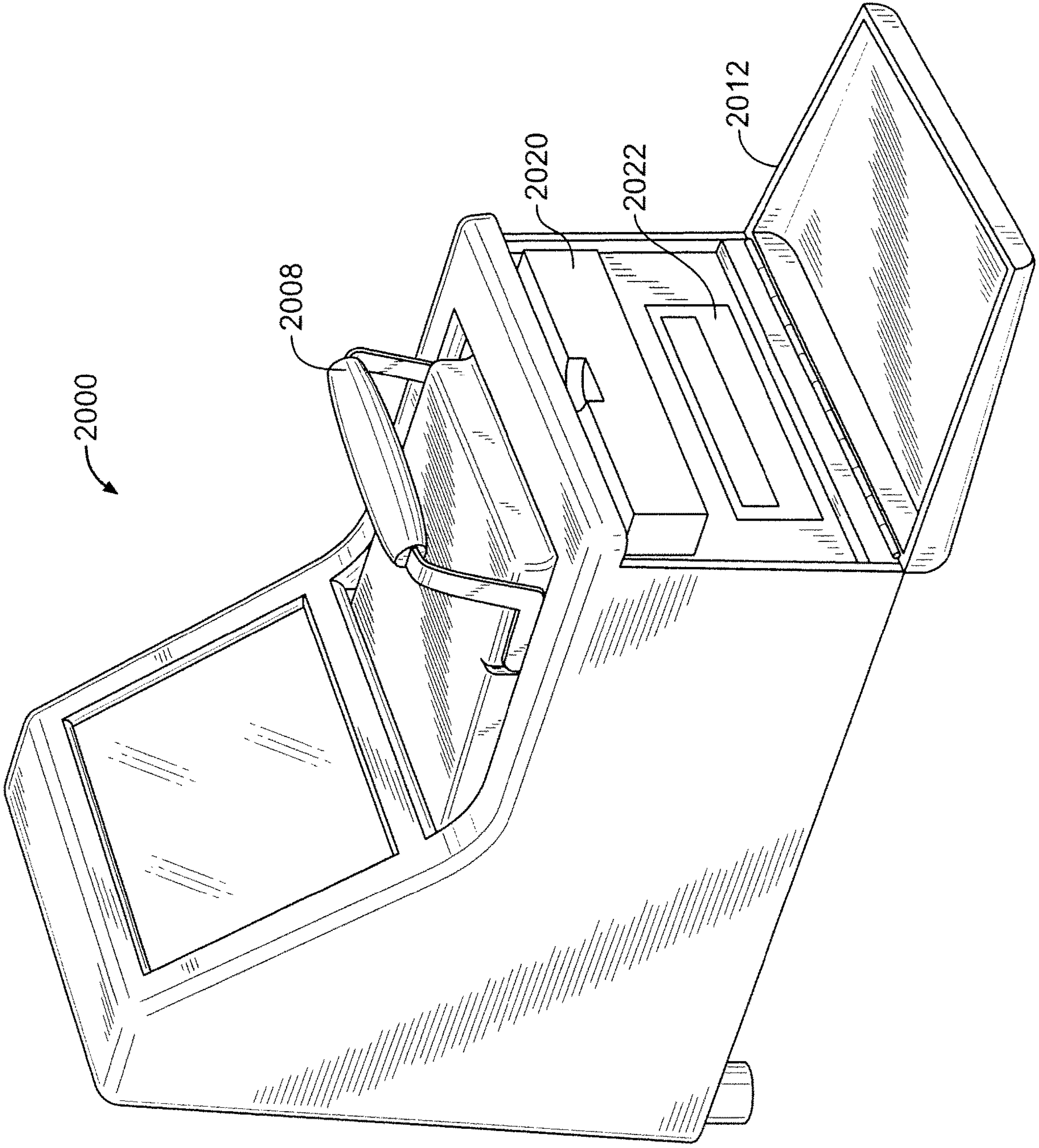

A further configuration of system 2000 is shown in FIG. 6D, wherein a door 2012 is in an open position. Door 2012 is shown in a closed position in FIGS. 6A-C. The door is an optional component that permits a user to access a heater module 2020, and also a computer-readable medium input tray 2022. System 2000 can function without a door that covers heater module 2020 and medium input 2022, but such a door has convenience attached to it. Although the door 2012 is shown hinged at the bottom, it may also be hinged at one of its sides, or at its upper edge. Door 2012 may alternatively be a removable cover, instead of being hinged. Door 2012, may also be situated at the rear, or side of system 2000 for example, if access to the heater module and/or computer readable medium input is desired on a different face of the system. It is also consistent with the system herein that the heater module, and the computer readable medium input are accessed by separate doors on the same or different sides of the device, and wherein such separate doors may be independently hinged or removable.

Heater module 2020 is preferably removable, and is further described hereinbelow.

Computer readable medium input 2022 may accept one or more of a variety of media. Shown in FIG. 2D is an exemplary form of input 2022, a CD-Rom tray for accepting a CD, DVD, or mini-CD, or mini-DVD, in any of the commonly used readable, read-writable, and writable formats. Also consistent with the description herein is an input that can accept another form of medium, such as a floppy disc, flash memory such as memory stick, compact flash, smart data-card, or secure-data card, a pen-drive, portable USB-drive, zip-disk, and others. Such an input can also be configured to accept several different forms of media. Such an input 2022 is in communication with a processor (as described in connection with FIG. 3, though not shown in FIGS. 6A-E), that can read data from a computer-readable medium when properly inserted into the input.

Figure 6E:
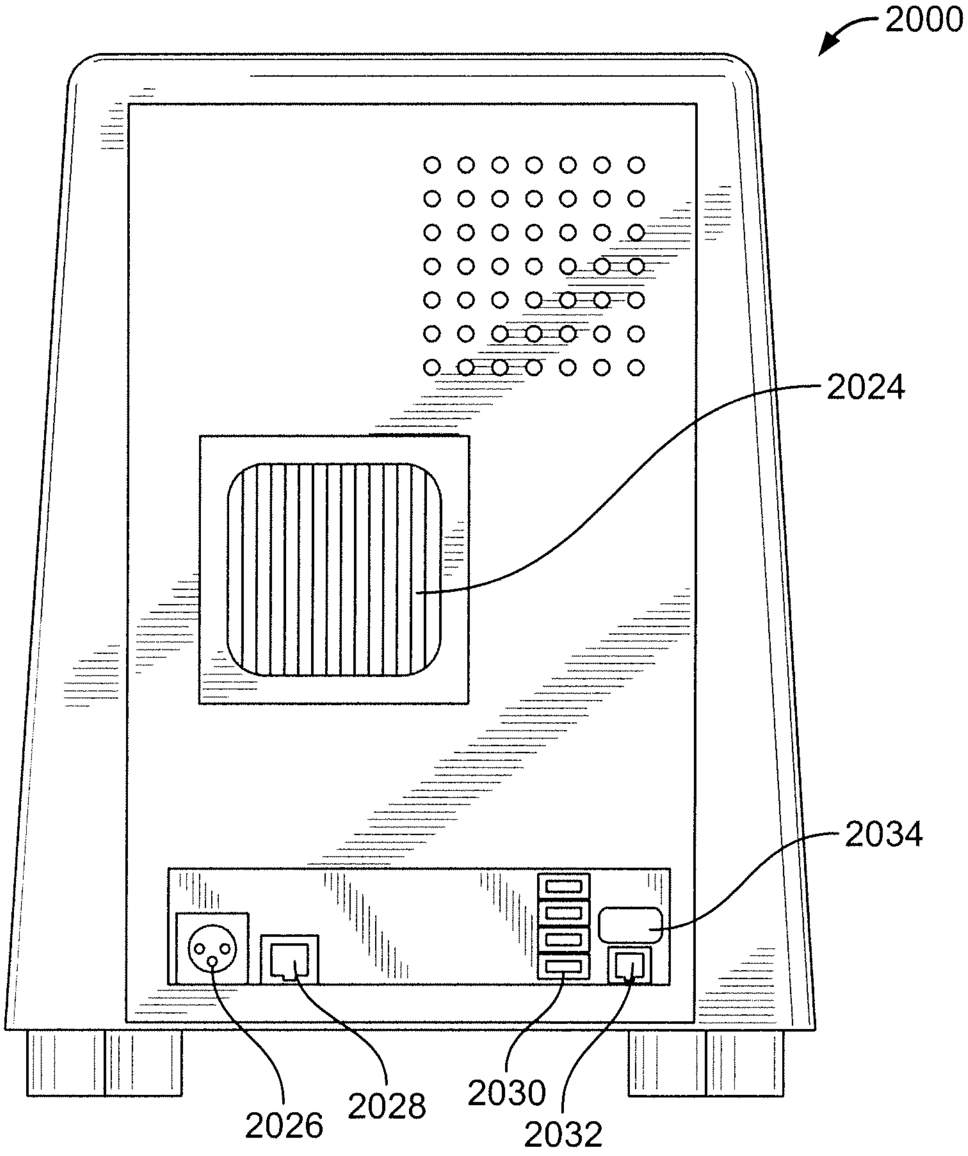

FIG. 6E shows a plan view of a rear of system 2000. Shown are an air vent 2024, or letting surplus heat escape during an analysis. Typically, on the inside of system 2000, and by air vent 2024 and not shown in FIG. 6E, is a fan. Other ports shown in FIG. 6E are as follows: a power socket 2026 for accepting a power cord that will connect system 2000 to a supply of electricity; an ethernet connection 2028 for linking system 2000 to a computer network such as a local area network; an phone-jack connection 2032 for linking system 2000 to a communication network such as a telephone network; one or more USB ports 2030, for connecting system 2000 to one or more peripheral devices such as a printer, or a computer hard drive; an infra-red port for communicating with, e.g., a remote controller (not shown), to permit a user to control the system without using a touch-screen interface. For example, a user could remotely issue scheduling commands to system 2000 to cause it to start an analysis at a specific time in the future.

Features shown on the rear of system 2000 may be arranged in any different manner, depending upon an internal configuration of various components. Additionally, features shown as being on the rear of system 2000, may be optionally presented on another face of system 2000, depending on design preference. Shown in FIG. 6E are exemplary connections. It would be understood that various other features, including inputs, outputs, sockets, and connections, may be present on the rear face of system 2000, though not shown, or on other faces of system 2000.

Figure 7:
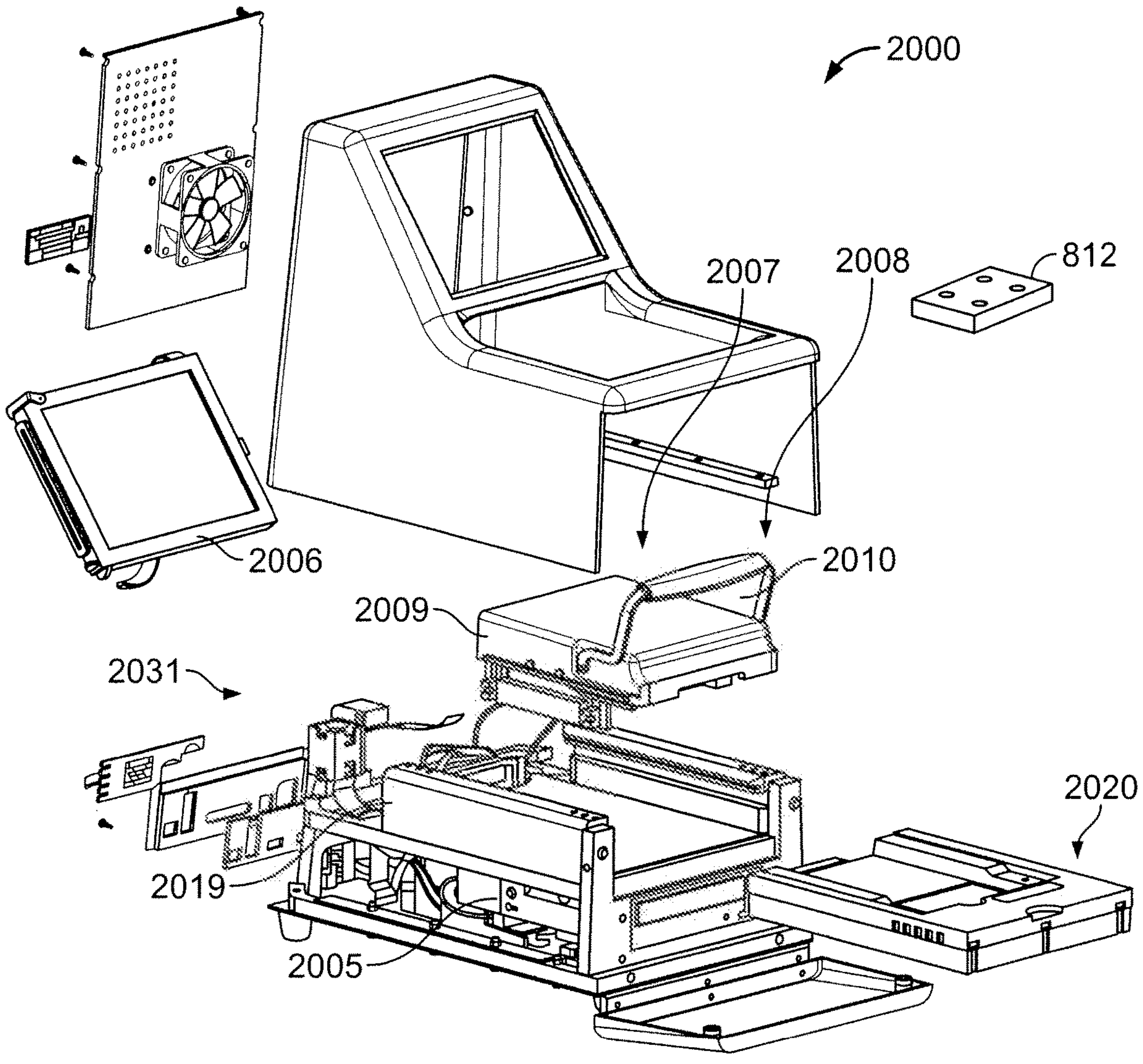
FIG. 7 shows an exploded view of an apparatus.

An exploded view of an exemplary embodiment of the apparatus is shown in FIG. 7, particularly showing internal features of apparatus 2000. Apparatus 2000 can comprise a computer readable medium configured with hardware/firmware that can be employed to drive and monitor the operations on a cartridge used therewith, as well as software to interpret, communicate and store the results of a diagnostic test performed on a sample processed in the cartridge. Referring to FIG. 7, typical components of the apparatus 2000 are shown and include, for example, control electronics 2005, removable heater/sensor module 2020, detector 2009 such as a fluorescent detection module, display screen or optionally combined display and user interface 2006 (e.g., a medical grade touch sensitive liquid crystal display (LCD)). In some embodiments, lid 2010, detector 2009, and handle 2008 can be collectively referred to as slider module 2007. Additional components of apparatus 2000 may include one or more mechanical fixtures such as frame 2019 to hold the various modules (e.g., the heater/sensor module 2020, and/or the slider module 2007) in alignment, and for providing structural rigidity. Detector module 2009 can be placed in rails to facilitate opening and placement of cartridge 2060 in the apparatus 2000, and to facilitate alignment of the optics upon closing. Heater/sensor module 2020 can be also placed on rails for easy removal and insertion of the assembly.

Embodiments of apparatus 2000 also include software (e.g., for interfacing with users, conducting analysis and/or analyzing test results), firmware (e.g., for controlling the hardware during tests on the cartridge 812), and one or more peripheral communication interfaces shown collectively as 2031 for peripherals (e.g., communication ports such as USB/Serial/Ethernet to connect to storage such as compact disc or hard disk, to connect input devices such as a bar code reader and/or a keyboard, to connect to other computers or storage via a network, and the like).

Figure 8:
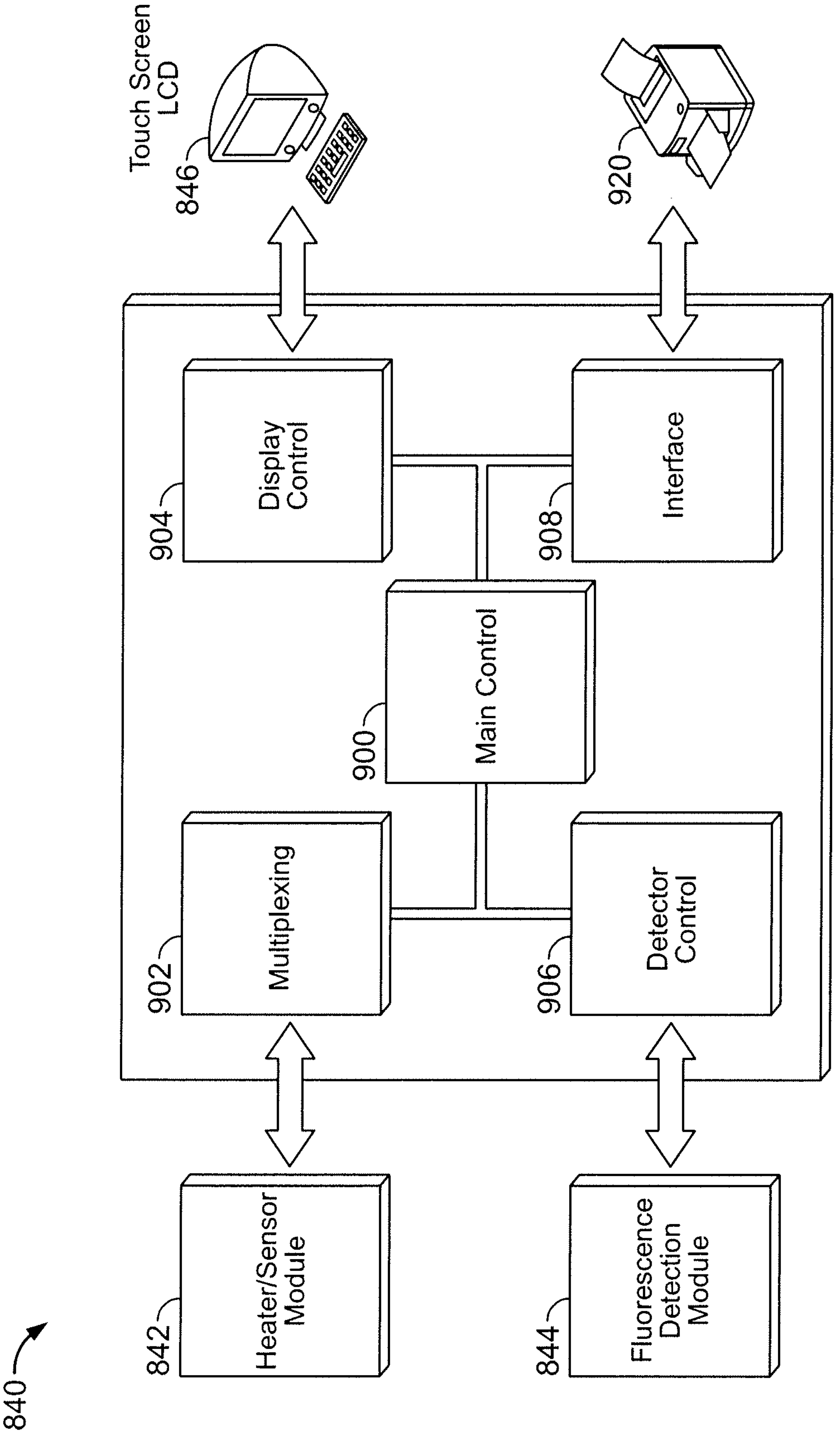
FIG. 8 shows a block diagram of control circuitry.

Control electronics 840, shown schematically in the block diagram in FIG. 8, can include one or more functions in various embodiments, for example for, main control 900, multiplexing 902, display control 904, detector control 906, and the like. The main control function may serve as the hub of control electronics 840 in apparatus 2000 and can manage communication and control of the various electronic functions. The main control function can also support electrical and communications interface 908 with a user or an output device such as a printer 920, as well as optional diagnostic and safety functions. In conjunction with main control function 900, multiplexer function 902 can control sensor data 914 and output current 916 to help control heater/sensor module 2020. The display control function 904 can control output to and, if applicable, interpret input from touch screen LCD 846, which can thereby provide a graphical interface to the user in certain embodiments. The detector function 906 can be implemented in control electronics 840 using typical control and processing circuitry to collect, digitize, filter, and/or transmit the data from a detector 2009 such as one or more fluorescence detection modules.

Microfluidic Cartridge

The present technology comprises a microfluidic cartridge that is configured to carry out an amplification, such as by PCR, of one or more polynucleotides from one or more samples. It is to be understood that, unless specifically made clear to the contrary, where the term PCR is used herein, any variant of PCR including but not limited to real-time and quantitative, and any other form of polynucleotide amplification is intended to be encompassed. The microfluidic cartridge need not be self-contained and can be designed so that it receives thermal energy from one or more heating elements present in an external apparatus with which the cartridge is in thermal communication. An exemplary such apparatus is further described herein; additional embodiments of such a system are found in U.S. patent application Ser. No. 11/940,310, entitled "Microfluidic Cartridge and Method of Making Same", and filed on even date herewith, the specification of which is incorporated herein by reference.

By cartridge is meant a unit that may be disposable, or reusable in whole or in part, and that is configured to be used in conjunction with some other apparatus that has been suitably and complementarily configured to receive and operate on (such as deliver energy to) the cartridge.

By microfluidic, as used herein, is meant that volumes of sample, and/or reagent, and/or amplified polynucleotide are from about 0.1 μl to about 999 μl, such as from 1-100 μl, or from 2-25 μl. Similarly, as applied to a cartridge, the term microfluidic means that various components and channels of the cartridge, as further described herein, are configured to accept, and/or retain, and/or facilitate passage of microfluidic volumes of sample, reagent, or amplified polynucleotide. Certain embodiments herein can also function with nanoliter volumes (in the range of 10-500 nanoliters, such as 100 nanoliters).

One aspect of the present technology relates to a microfluidic cartridge having two or more sample lanes arranged so that analyses can be carried out in two or more of the lanes in parallel, for example simultaneously, and wherein each lane is independently associated with a given sample.

A sample lane is an independently controllable set of elements by which a sample can be analyzed, according to methods described herein as well as others known in the art. A sample lane comprises at least a sample inlet, and a microfluidic network having one or more microfluidic components, as further described herein.

In various embodiments, a sample lane can include a sample inlet port or valve, and a microfluidic network that comprises, in fluidic communication one or more components selected from the group consisting of: at least one thermally actuated valve, a bubble removal vent, at least one thermally actuated pump, a gate, mixing channel, positioning element, microreactor, a downstream thermally actuated valve, and a PCR reaction chamber. The sample inlet valve can be configured to accept a sample at a pressure differential compared to ambient pressure of between about 70 and 100 kilopascals.

The cartridge can therefore include a plurality of microfluidic networks, each network having various components, and each network configured to carry out PCR on a sample in which the presence or absence of one or more polynucleotides is to be determined.

A multi-lane cartridge is configured to accept a number of samples in series or in parallel, simultaneously or consecutively, in particular embodiments 12 samples, wherein the samples include at least a first sample and a second sample, wherein the first sample and the second sample each contain one or more polynucleotides in a form suitable for amplification. The polynucleotides in question may be the same as, or different from one another, in different samples and hence in different lanes of the cartridge. The cartridge typically processes each sample by increasing the concentration of a polynucleotide to be determined and/or by reducing the concentration of inhibitors relative to the concentration of polynucleotide to be determined.

The multi-lane cartridge comprises at least a first sample lane having a first microfluidic network and a second lane having a second microfluidic network, wherein each of the first microfluidic network and the second microfluidic network is as elsewhere described herein, and wherein the first microfluidic network is configured to amplify polynucleotides in the first sample, and wherein the second microfluidic network is configured to amplify polynucleotides in the second sample.

In various embodiments, the microfluidic network can be configured to couple heat from an external heat source to a sample mixture comprising PCR reagent and neutralized polynucleotide sample under thermal cycling conditions suitable for creating PCR amplicons from the neutralized polynucleotide sample.

At least the external heat source may operate under control of a computer processor, configured to execute computer readable instructions for operating one or more components of each sample lane, independently of one another, and for receiving signals from a detector that measures fluorescence from one or more of the PCR reaction chambers.

Figure 9:
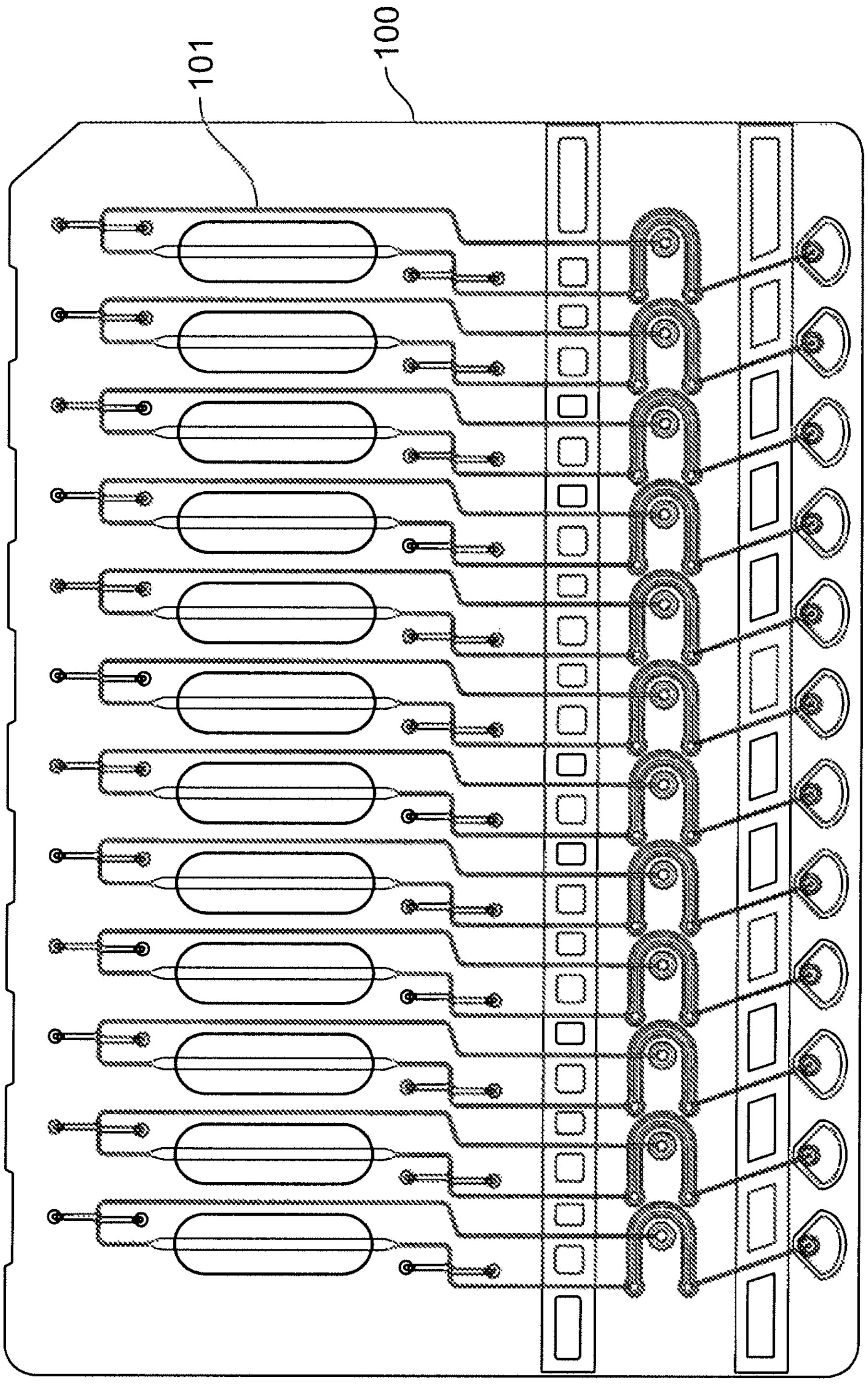
FIG. 9 shows a plan view of an exemplary multi-lane microfluidic cartridge.

For example, FIG. 9 shows a plan view of a microfluidic cartridge 100 containing twelve independent sample lanes 101 capable of simultaneous or successive processing. The microfluidic network in each lane is typically configured to carry out amplification, such as by PCR, on a PCR-ready sample, such as one containing nucleic acid extracted from a sample using other methods as further described herein. A PCR-ready sample is thus typically a mixture comprising the PCR reagents and the neutralized polynucleotide sample, suitable for subjecting to thermal cycling conditions that create PCR amplicons from the neutralized polynucleotide sample. For example, a PCR-ready sample can include a PCR reagent mixture comprising a polymerase enzyme, a positive control plasmid, a fluorogenic hybridization probe selective for at least a portion of the plasmid and a plurality of nucleotides, and at least one probe that is selective for a polynucleotide sequence. Exemplary probes are further described herein. Typically, the microfluidic network is configured to couple heat from an external heat source with the mixture comprising the PCR reagent and the neutralized polynucleotide sample under thermal cycling conditions suitable for creating PCR amplicons from the neutralized polynucleotide sample.

In various embodiments, the PCR reagent mixture can include a positive control plasmid and a plasmid fluorogenic hybridization probe selective for at least a portion of the plasmid, and the microfluidic cartridge can be configured to allow independent optical detection of the fluorogenic hybridization probe and the plasmid fluorogenic hybridization probe.

In various embodiments, the microfluidic cartridge can accommodate a negative control polynucleotide, wherein the microfluidic network can be configured to independently carry out PCR on each of a neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide. Each lane of a multi-lane cartridge as described herein can perform two reactions when used in conjunction with two fluorescence detection systems per lane. A variety of combinations of reactions can be performed in the cartridge, such as two sample reactions in one lane, a positive control and a negative control in two other lanes; or a sample reaction and an internal control in one lane and a negative control in a separate lane.

Figure 10A:
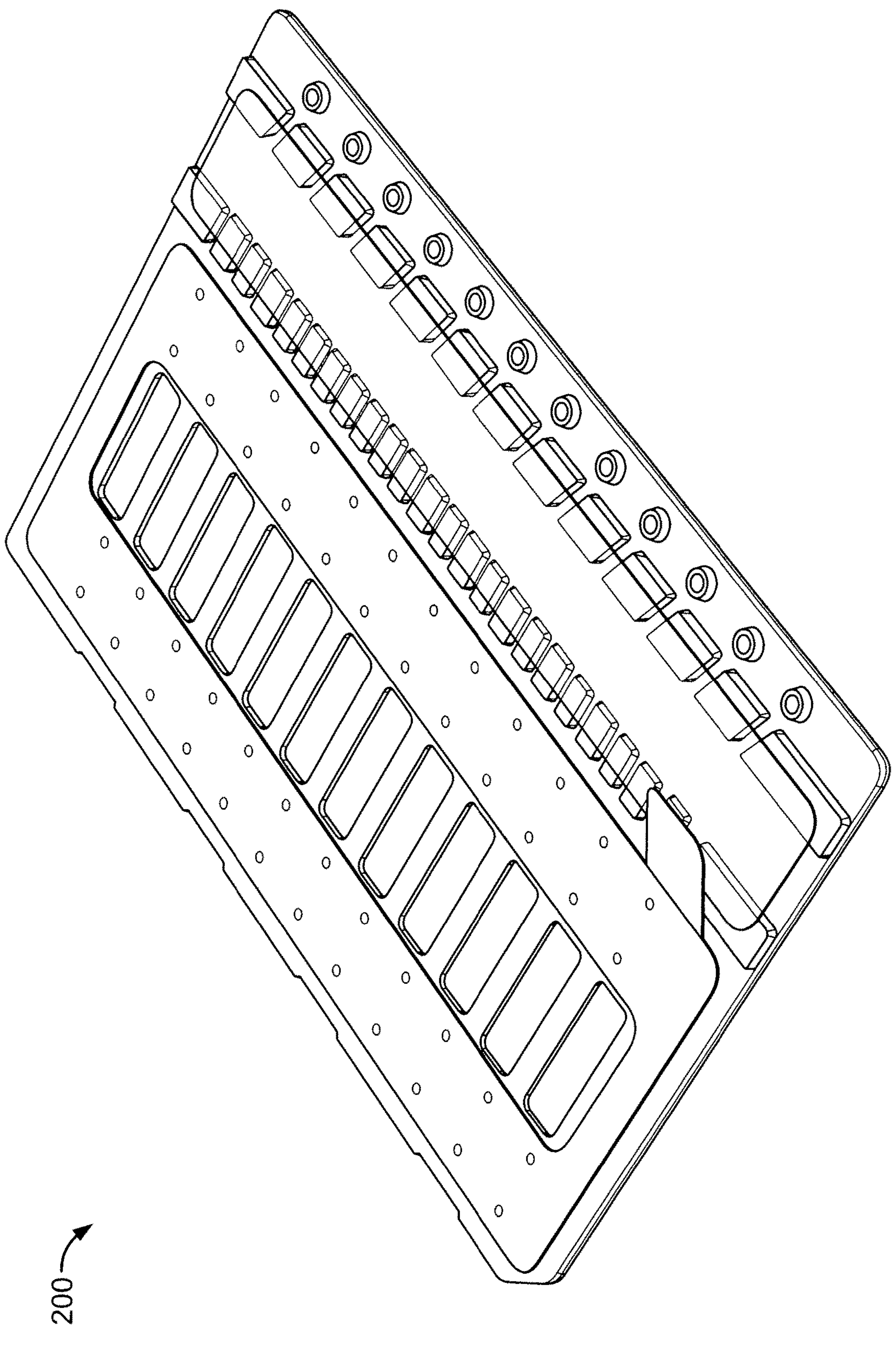
FIG. 10A shows an exemplary multi-lane cartridge.
Figure 10B:
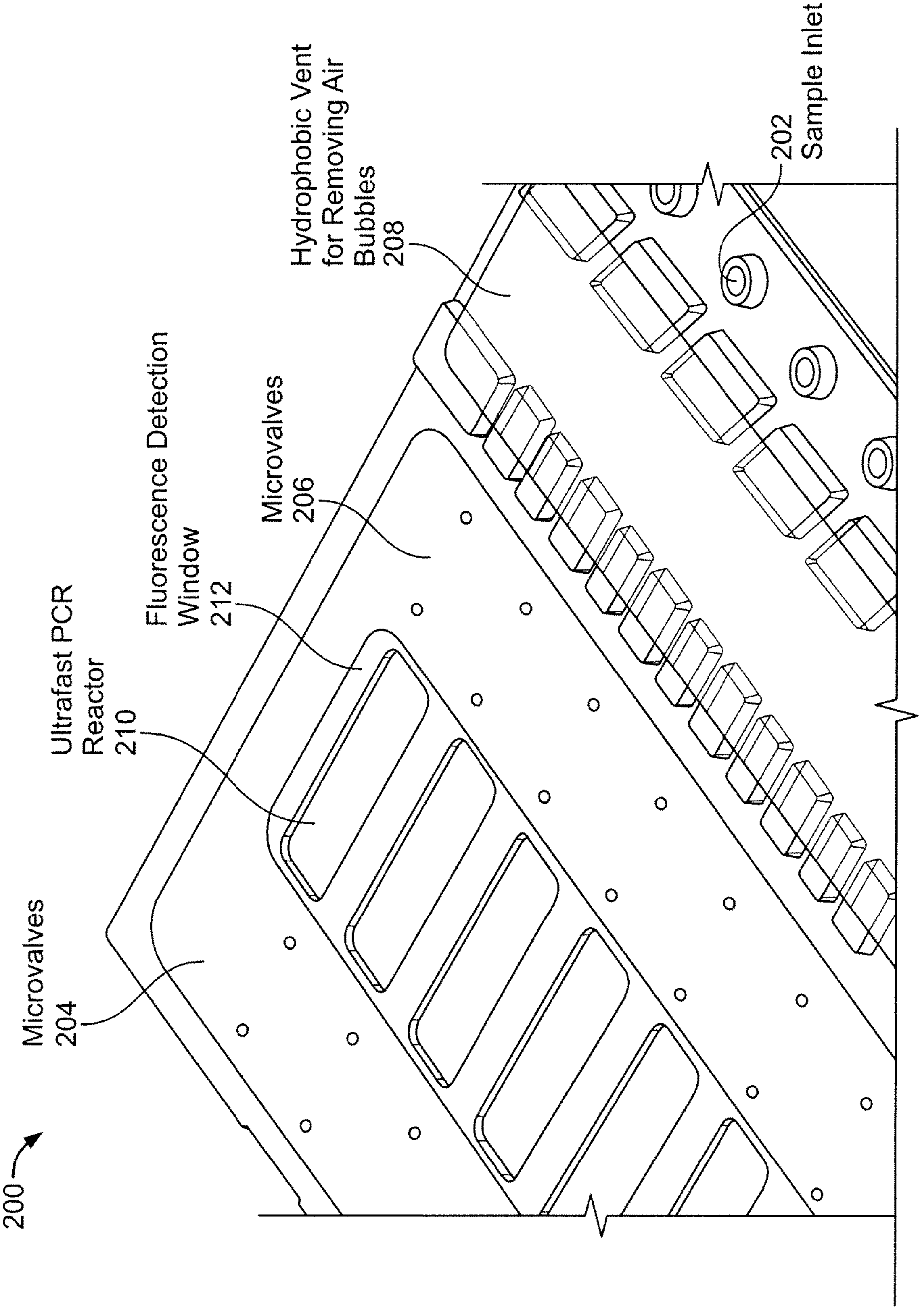
FIG. 10B shows a portion of an exemplary multi-lane cartridge.

FIG. 10A shows a perspective view of a portion of an exemplary microfluidic cartridge 200 according to the present technology. FIG. 10B shows a close-up view of a portion of the cartridge 200 of FIG. 10A illustrating various representative components. The cartridge 200 may be referred to as a multi-lane PCR cartridge with dedicated sample inlets 202. For example sample inlet 202 is configured to accept a liquid transfer member (not shown) such as a syringe, a pipette, or a PCR tube containing a PCR ready sample. More than one inlet 202 is shown in FIGS. 10A, 10B, wherein one inlet operates in conjunction with a single sample lane. Various components of microfluidic circuitry in each lane are also visible. For example, microvalves 204, and 206, and hydrophobic vents 208 for removing air bubbles, are parts of microfluidic circuitry in a given lane. Also shown is an ultrafast PCR reactor 210, which, as further described herein, is a microfluidic channel in a given sample lane that is long enough to permit PCR to amplify polynucleotides present in a sample. Above each PCR reactor 210 is a window 212 that permits detection of fluorescence from a fluorescent substance in PCR reactor 210 when a detector is situated above window 212. It is to be understood that other configurations of windows are possible including, but not limited to, a single window that straddles each PCR reactor across the width of cartridge 200.

In preferred embodiments, the multi-sample cartridge has a size substantially the same as that of a 96-well plate as is customarily used in the art. Advantageously, then, such a cartridge may be used with plate handlers used elsewhere in the art.

The sample inlets of adjacent lanes are reasonably spaced apart from one another to prevent any contamination of one sample inlet from another sample when a user introduces a sample into any one cartridge. In an embodiment, the sample inlets are configured so as to prevent subsequent inadvertent introduction of sample into a given lane after a sample has already been introduced into that lane. In certain embodiments, the multi-sample cartridge is designed so that a spacing between the centroids of sample inlets is 9 mm, which is an industry-recognized standard. This means that, in certain embodiments the center-to-center distance between inlet holes in the cartridge that accept samples from PCR tubes, as further described herein, is 9 mm. The inlet holes can be manufactured conical in shape with an appropriate conical angle so that industry-standard pipette tips (2 μl, 20 μl, 200 μl, volumes, etc.) fit snugly therein. The cartridge herein may be adapted to suit other, later-arising, industry standards not otherwise described herein, as would be understood by one of ordinary skill in the art.

In one embodiment, an exemplary microfluidic cartridge has 12 sample lanes. The inlet ports in this embodiment have a 6 mm spacing, so that, when used in conjunction with an automated sample loader having 4 heads, spaced equidistantly at 18 mm apart, the inlets can be loaded in three batches of four inlets: e.g., inlets 1, 4, 7, and 10 together, followed by 2, 5, 8, and 11, then finally 3, 6, 9, and 12, wherein the 12 inlets are numbered consecutively from one side of the cartridge to the other as shown.

A microfluidic cartridge as used herein may be constructed from a number of layers. Accordingly, one aspect of the present technology relates to a microfluidic cartridge that comprises a first, second, third, fourth, and fifth layers wherein one or more layers define a plurality of microfluidic networks, each network having various components configured to carry out PCR on a sample in which the presence or absence of one or more polynucleotides is to be determined. In various embodiments, one or more such layers are optional.

Figure 11A:
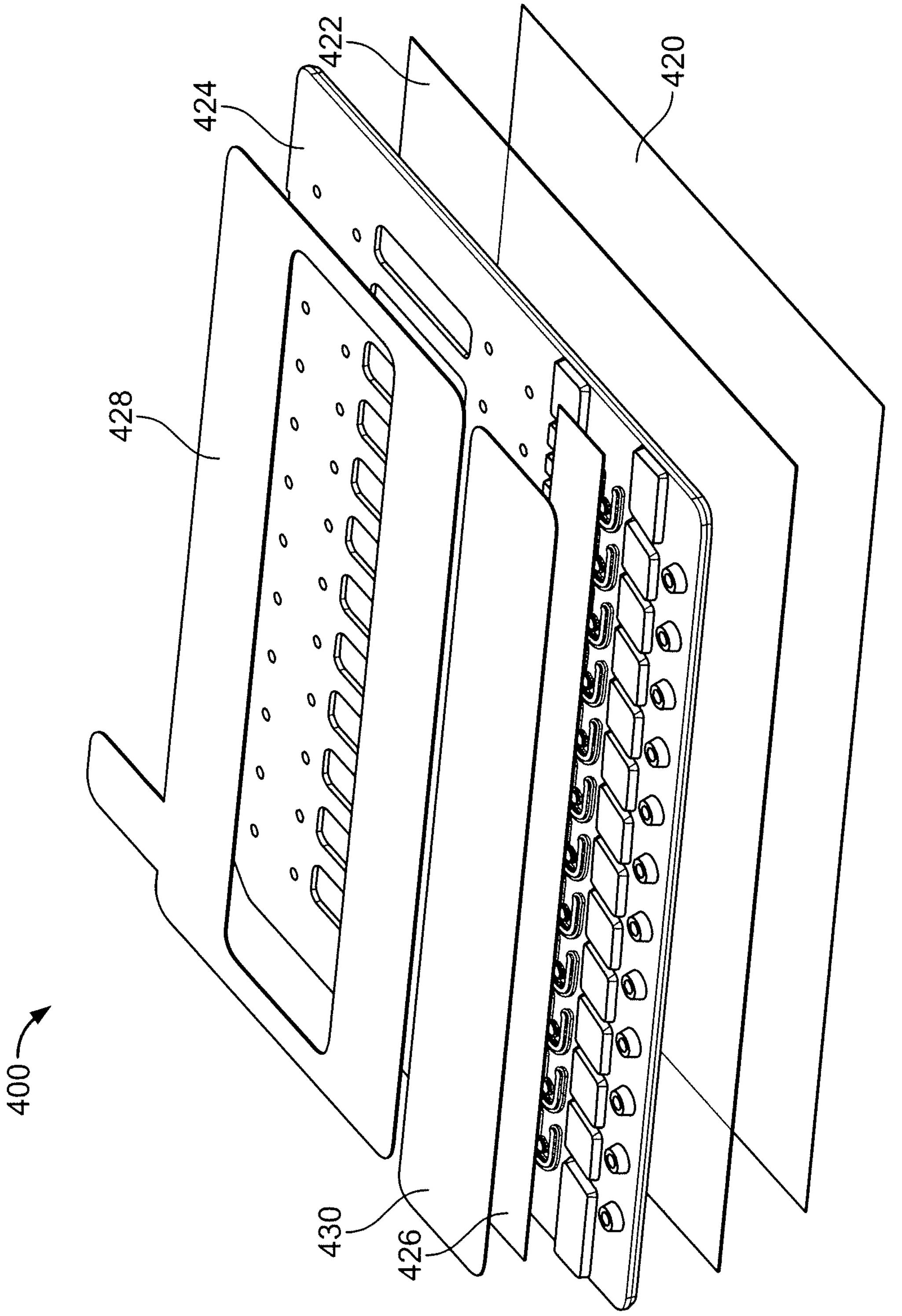
FIGS. 11A-C show exploded view of an exemplary microfluidic cartridge.
Figure 11B:
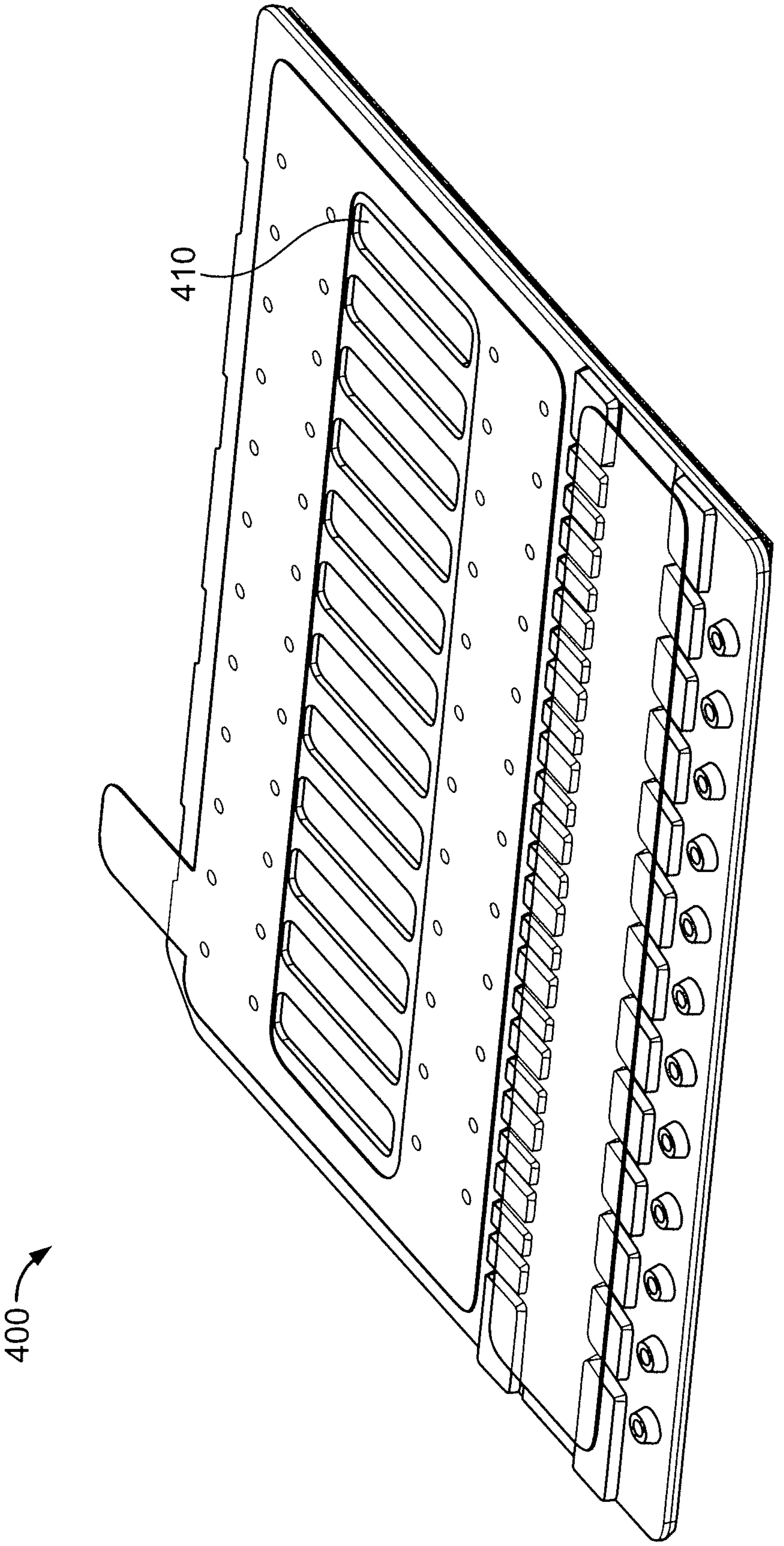
Figure 11C:
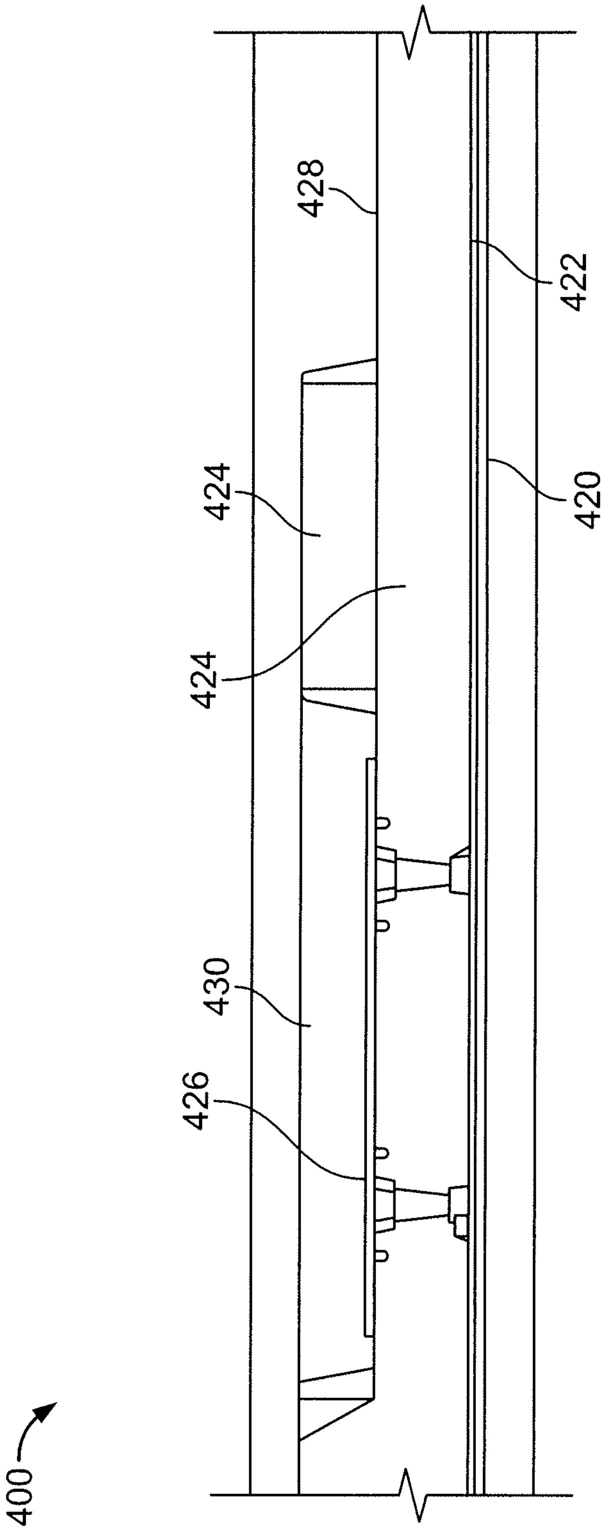

FIGS. 11A-C show various views of a layer structure of an exemplary microfluidic cartridge comprising a number of layers, as further described herein. FIG. 11A shows an exploded view; FIG. 11B shows a perspective view; and FIG. 11C shows a cross-sectional view of a sample lane in the exemplary cartridge. Referring to FIGS. 11A-C, an exemplary microfluidic cartridge 400 includes first 420, second 422, third 424, fourth 426, and fifth layers in two non-contiguous parts 428, 430 (as shown) that enclose a microfluidic network having various components configured to process multiple samples in parallel that include one or more polynucleotides to be determined.

Microfluidic cartridge 400 can be fabricated as desired. The cartridge can include a microfluidic substrate layer 424, typically injection molded out of a plastic, such as a zeonor plastic (cyclic olefin polymer), having a PCR channel and valve channels on a first side and vent channels and various inlet holes, including wax loading holes and liquid inlet holes, on a second side (disposed toward hydrophobic vent membrane 426). It is advantageous that all the microfluidic network defining structures, such as PCR reactors, valves, inlet holes, and air vents, are defined on the same single substrate 424. This attribute facilitates manufacture and assembly of the cartridge. Additionally, the material from which this substrate is formed is rigid or nondeformable, non-venting to air and other gases, and has a low autofluorescence to facilitate detection of polynucleotides during an amplification reaction performed in the microfluidic circuitry defined therein. Rigidity is advantageous because it facilitates effective and uniform contact with a heat unit as further described herein. Use of a non-venting material is also advantageous because it reduces the likelihood that the concentration of various species in liquid form will change during analysis. Use of a material having low auto-fluorescence is also important so that background fluorescence does not detract from measurement of fluorescence from the analyte of interest.

The cartridge can further include, disposed on top of the substrate 424, an oleophobic/hydrophobic vent membrane layer 426 of a porous material, such as 0.2 to 1.0 micron pore-size membrane of modified polytetrafluorethylene, the membrane being typically between about 25 and about 100 microns thick, and configured to cover the vent channels of microfluidic substrate 424, and attached thereto using, for example, heat bonding.

Typically, the microfluidic cartridge further includes a layer 428, 430 of polypropylene or other plastic label with pressure sensitive adhesive (typically between about 50 and 150 microns thick) configured to seal the wax loading holes of the valves in substrate 424, trap air used for valve actuation, and serve as a location for operator markings. In FIG. 4A, this layer is shown in two separate pieces, 428, 430, though it would be understood by one of ordinary skill in the art that a single piece layer would be appropriate.

In various embodiments, the label is a computer-readable label. For example, the label can include a bar code, a radio frequency tag or one or more computer-readable characters. The label can be formed of a mechanically compliant material. For example, the mechanically compliant material of the label can have a thickness of between about 0.05 and about 2 millimeters and a Shore hardness of between about 25 and about 100. The label can be positioned such that it can be read by a sample identification verifier as further described herein.

The cartridge can further include a heat sealable laminate layer 422 (typically between about 100 and about 125 microns thick) attached to the bottom surface of the microfluidic substrate 424 using, for example, heat bonding. This layer serves to seal the PCR channels and vent channels in substrate 424. The cartridge can further include a thermal interface material layer 420 (typically about 125 microns thick), attached to the bottom of the heat sealable laminate layer using, for example, pressure sensitive adhesive. The layer 420 can be compressible and have a higher thermal conductivity than common plastics, thereby serving to transfer heat across the laminate more efficiently. Typically, however, layer 420 is not present.

The application of pressure to contact the cartridge to the heater of an instrument that receives the cartridge generally assists in achieving better thermal contact between the heater and the heat-receivable parts of the cartridge, and also prevents the bottom laminate structure from expanding, as would happen if the PCR channel was only partially filled with liquid and the air entrapped therein would be thermally expanded during thermocycling.

In use, cartridge 400 is typically thermally associated with an array of heat sources configured to operate the components (e.g., valves, gates, actuators, and processing region 410) of the device. Exemplary such heater arrays are further described herein. Additional embodiments of heater arrays are described in U.S. patent application Ser. No. 11/940,315, entitled "Heater Unit for Microfluidic Diagnostic System" and filed on even date herewith, the specification of which is incorporated herein by reference in its entirety. In some embodiments, the heat sources are controlled by a computer processor and actuated according to a desired protocol. Processors configured to operate microfluidic devices are described in, e.g., U.S. application Ser. No. 09/819,105, filed Mar. 28, 2001, which application is incorporated herein by reference.

In various embodiments, during transport and storage, the microfluidic cartridge can be further surrounded by a sealed pouch. The microfluidic cartridge can be sealed in the pouch with an inert gas. The microfluidic cartridge can be disposable for example after one or more of its sample lanes have been used.

Highly Multiplexed Embodiments

Embodiments of the cartridge described herein may be constructed that have high-density microfluidic circuitry on a single cartridge that thereby permit processing of multiple samples in parallel, or in sequence, on a single cartridge. Preferred numbers of such multiple samples include 20, 24, 36, 40, 48, 50, 60, 64, 72, 80, 84, 96, and 100, but it would be understood that still other numbers are consistent with the apparatus and cartridge herein, where deemed convenient and practical.

Accordingly, different configurations of lanes, sample inlets, and associated heater networks than those explicitly depicted in the FIGs and examples that can facilitate processing such numbers of samples on a single cartridge are within the scope of the instant disclosure. Similarly, alternative configurations of detectors and heating elements for use in conjunction with such a highly multiplexed cartridge are also within the scope of the description herein.

It is also to be understood that the microfluidic cartridges described herein are not to be limited to rectangular shapes, but can include cartridges having circular, elliptical, triangular, rhombohedral, square, and other shapes. Such shapes may also be adapted to include some irregularity, such as a cut-out, to facilitate placement in a complementary apparatus as further described herein.

Figure 12:
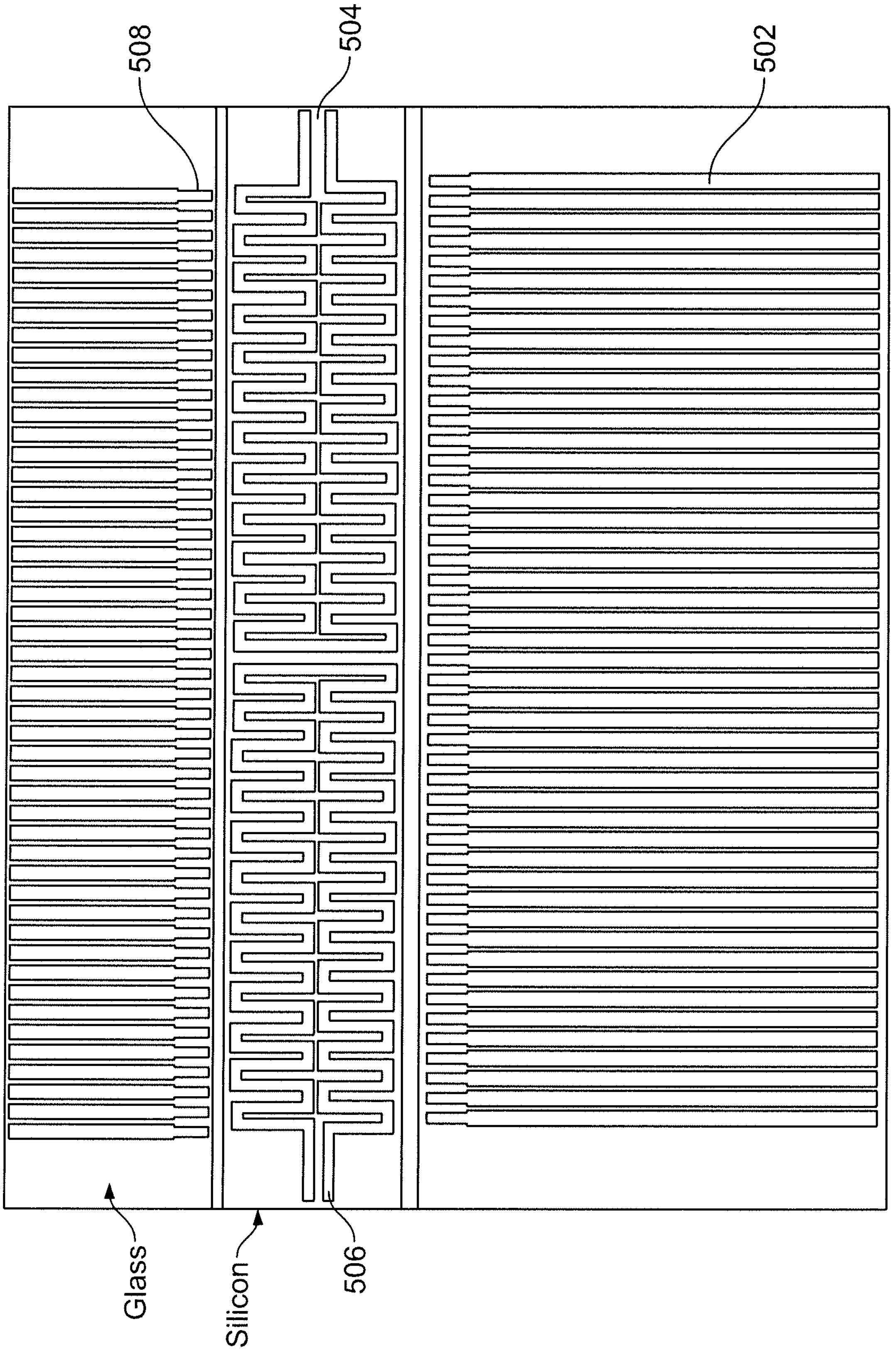
FIG. 12 shows an exemplary highly-multiplexed microfluidic cartridge.

In an exemplary embodiment, a highly multiplexed cartridge has 48 sample lanes, and permits independent control of each valve in each lane by suitably configured heater circuitry, with 2 banks of thermo cycling protocols per lane, as shown in FIG. 12. In the embodiment in FIG. 12, the heaters (shown superimposed on the lanes) are arranged in three arrays 502, 504, with 506, and 508. The heaters are themselves disposed within one or more substrates. Heater arrays 502, 508 in two separate glass regions only apply heat to valves in the microfluidic networks in each lane. Because of the low thermal conductivity of glass, the individual valves may be heated separately from one another. This permits samples to be loaded into the cartridge at different times, and passed to the PCR reaction chambers independently of one another. The PCR heaters 504, 506 are mounted on a silicon substrate- and are not readily heated individually, but thereby permit batch processing of PCR samples, where multiple samples from different lanes are amplified by the same set of heating/cooling cycles. It is preferable for the PCR heaters to be arranged in 2 banks (the heater arrays 506 on the left and right 508 are not in electrical communication with one another), thereby permitting a separate degree of sample control.

Figure 13:
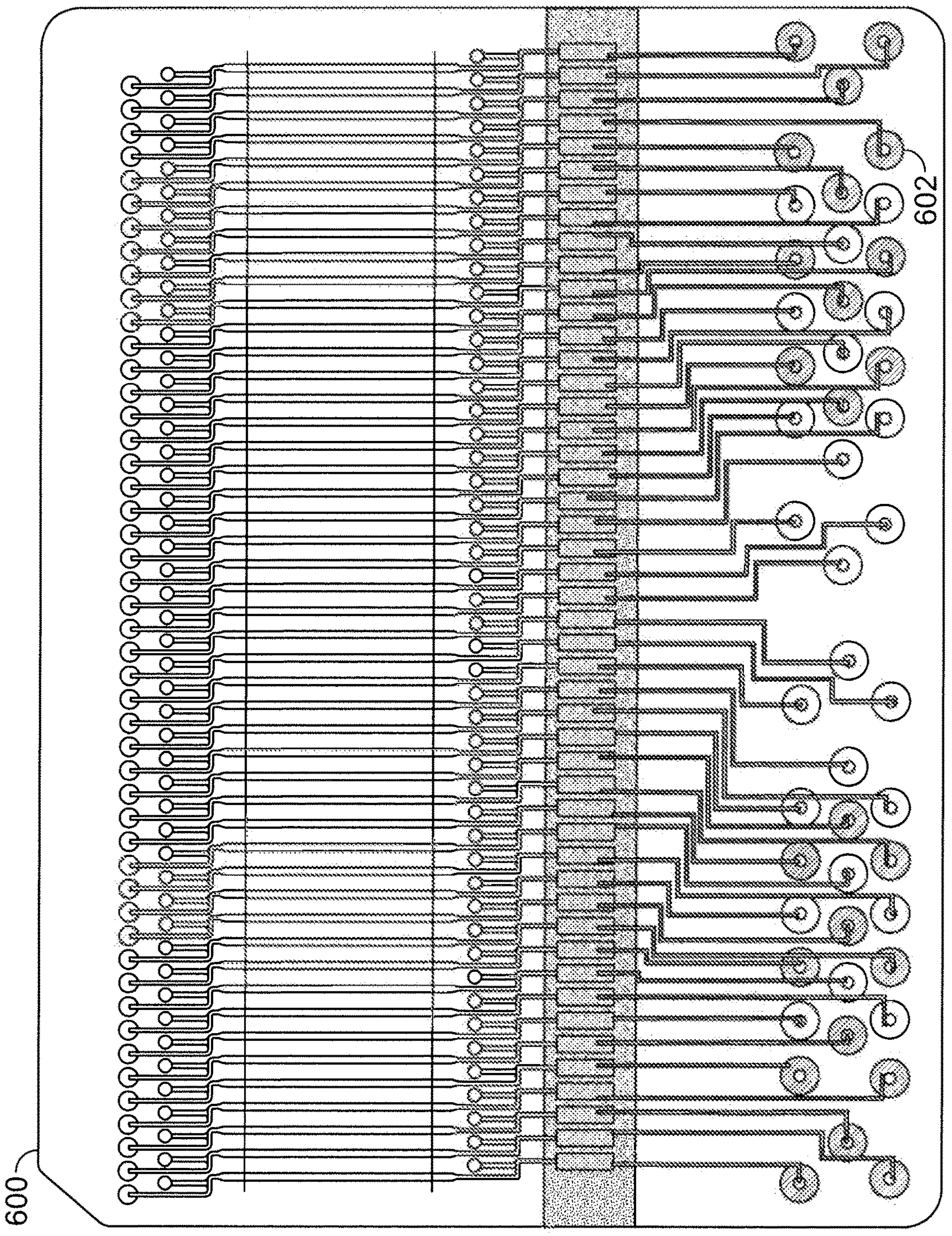
FIGS. 13-16 show various aspects of exemplary highly multiplexed microfluidic cartridges.

FIG. 13 shows a representative 48-sample cartridge 600 compatible with the heater arrays of FIG. 12, and having a configuration of inlets 602 different to that depicted o other cartridges herein. The inlet configuration is exemplary and has been designed to maximize efficiency of space usage on the cartridge. The inlet configuration can be compatible with an automatic pipetting machine that has dispensing heads situated at a 9 mm spacing. For example, such a machine having 4 heads can load 4 inlets at once, in 12 discrete steps, for the cartridge of FIG. 13. Other configurations of inlets though not explicitly described or depicted are compatible with the technology described herein.

Figure 14:
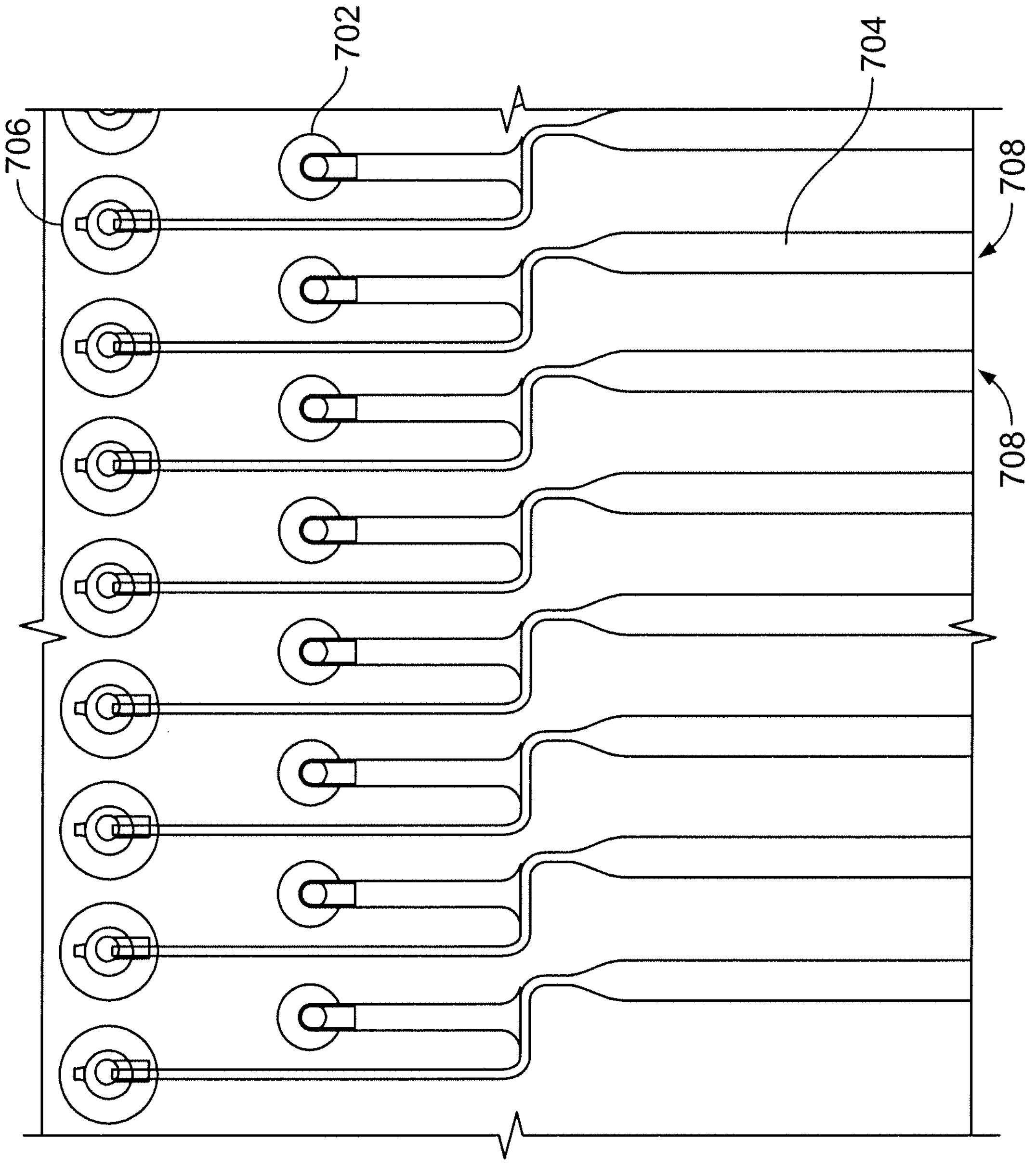

FIG. 14 shows, in close up, an exemplary spacing of valves 702, channels 704, and vents 796, in adjacent lanes 708 of a multi-sample microfluidic cartridge for example as shown in FIG. 13.

Figure 15:
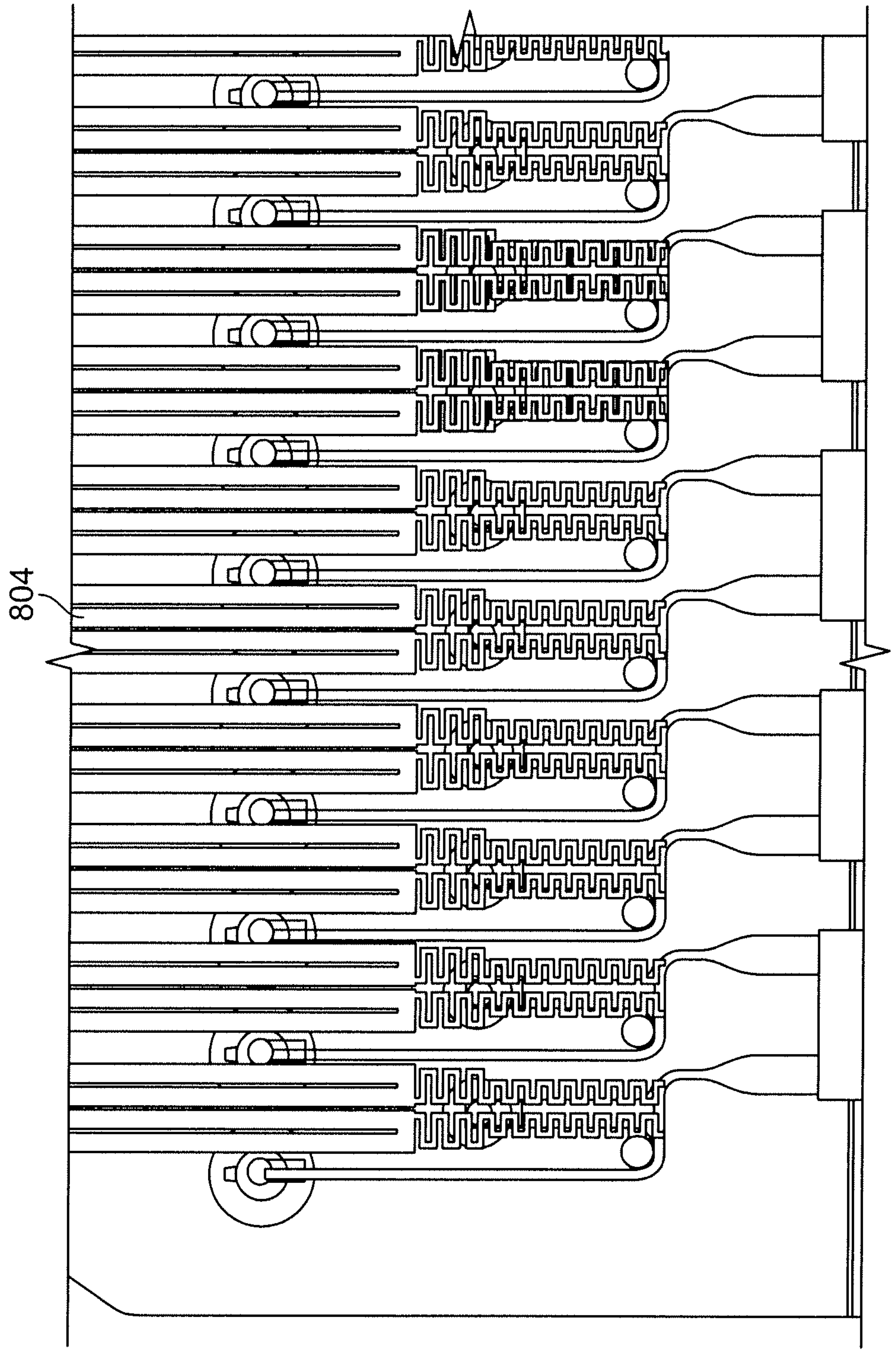
Figure 16:
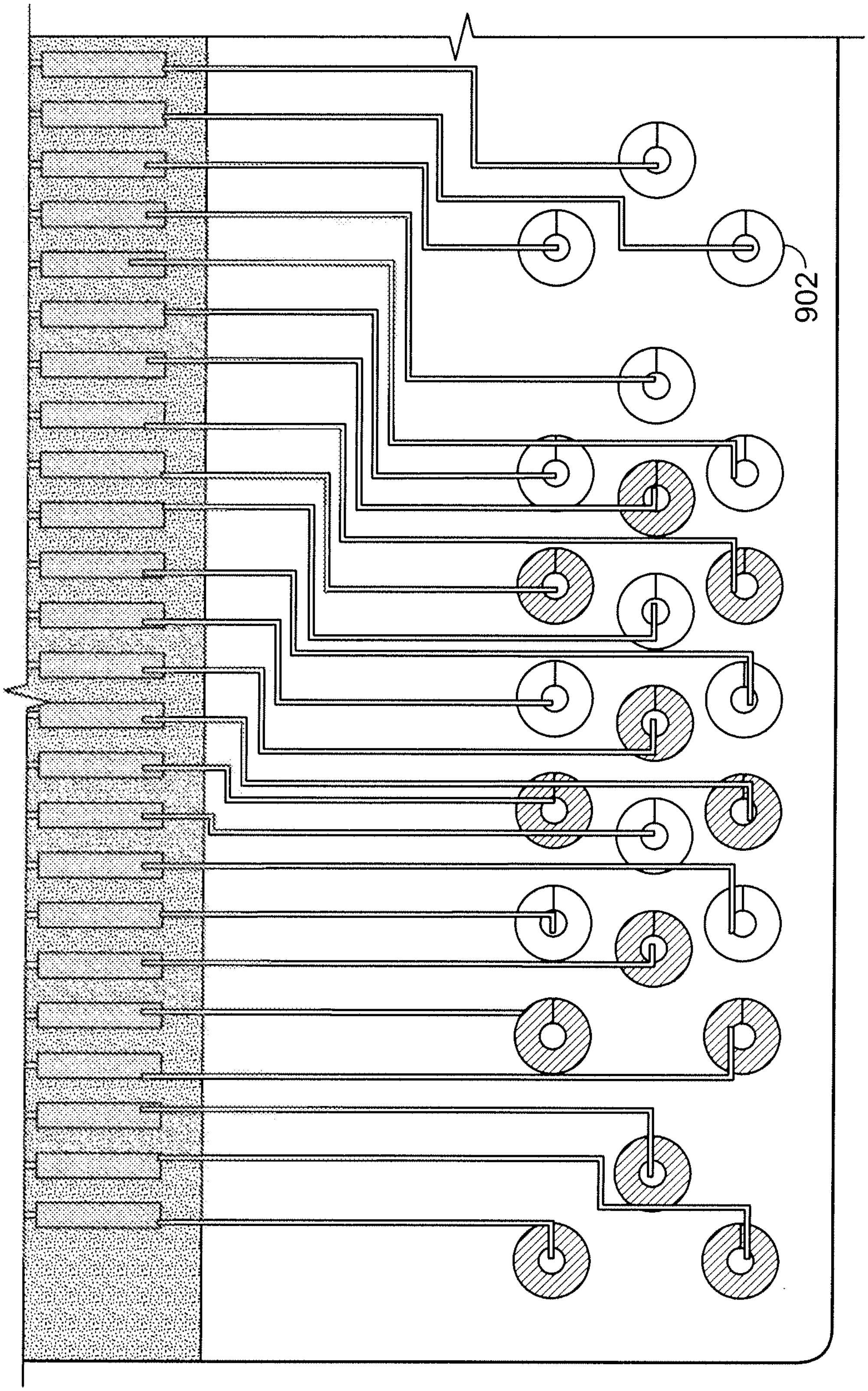

FIGS. 15 and 16 show close-ups of, respectively, heater arrays 804 compatible with, and inlets 902 on, the exemplary cartridge shown in FIG. 14.

Figure 17A:
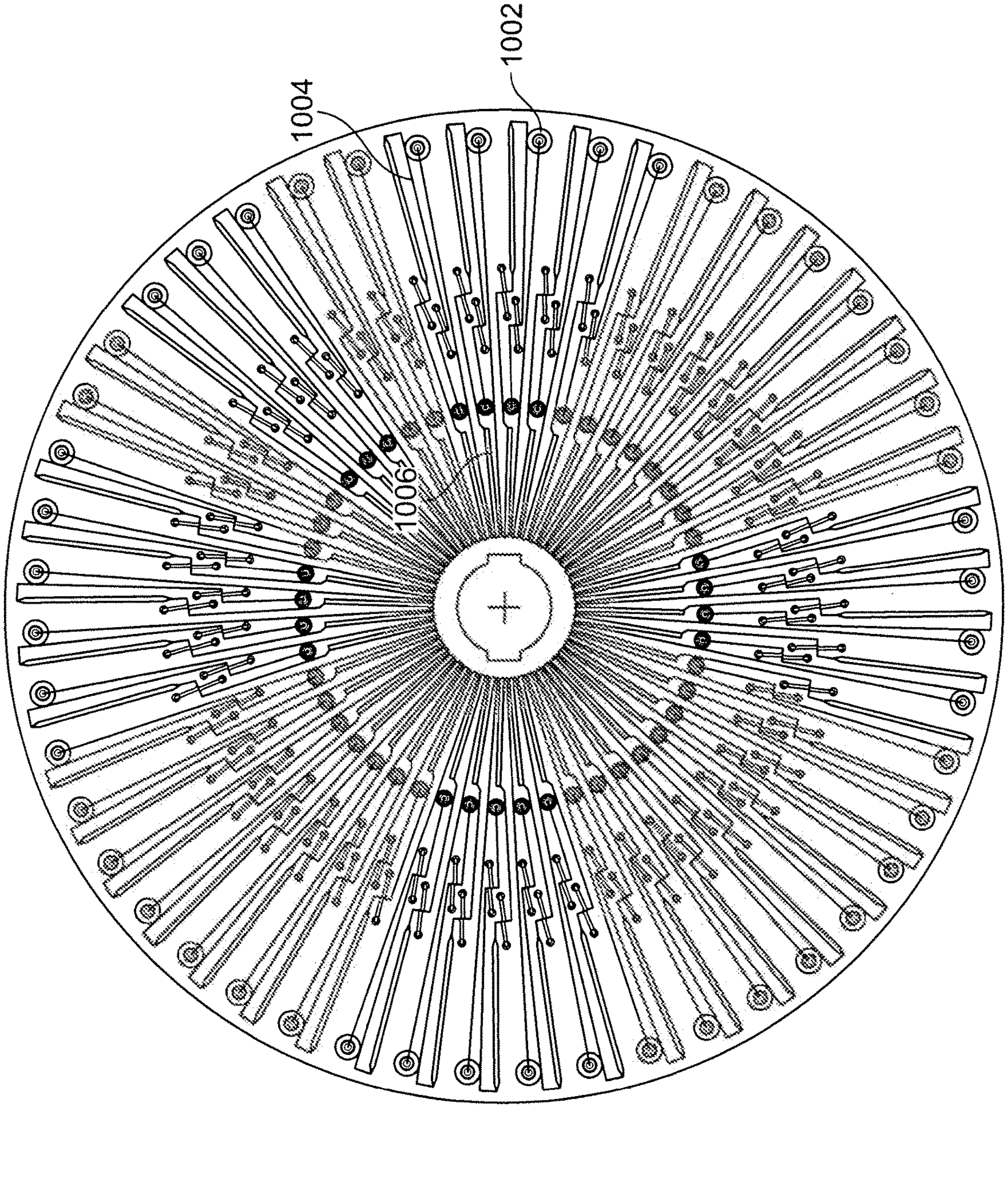
FIGS. 17A-C show various aspects of a radially configured highly multiplexed microfluidic cartridge.
Figure 17B:
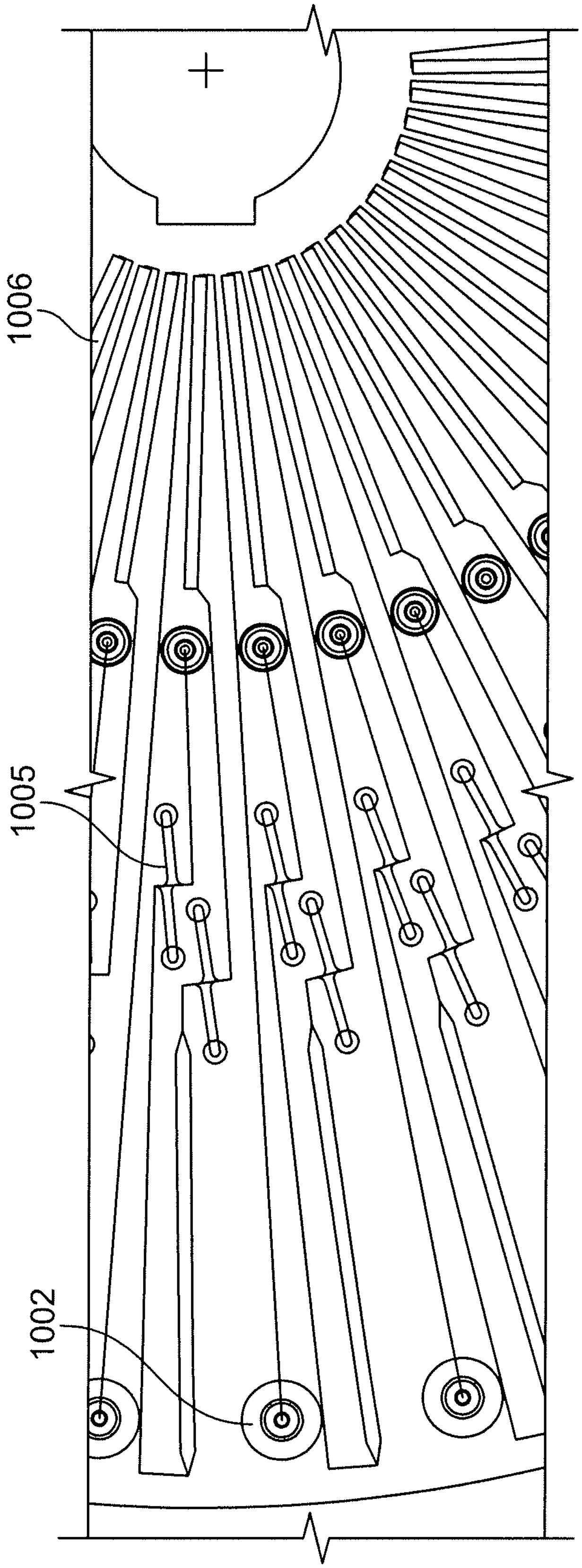
Figure 17C:
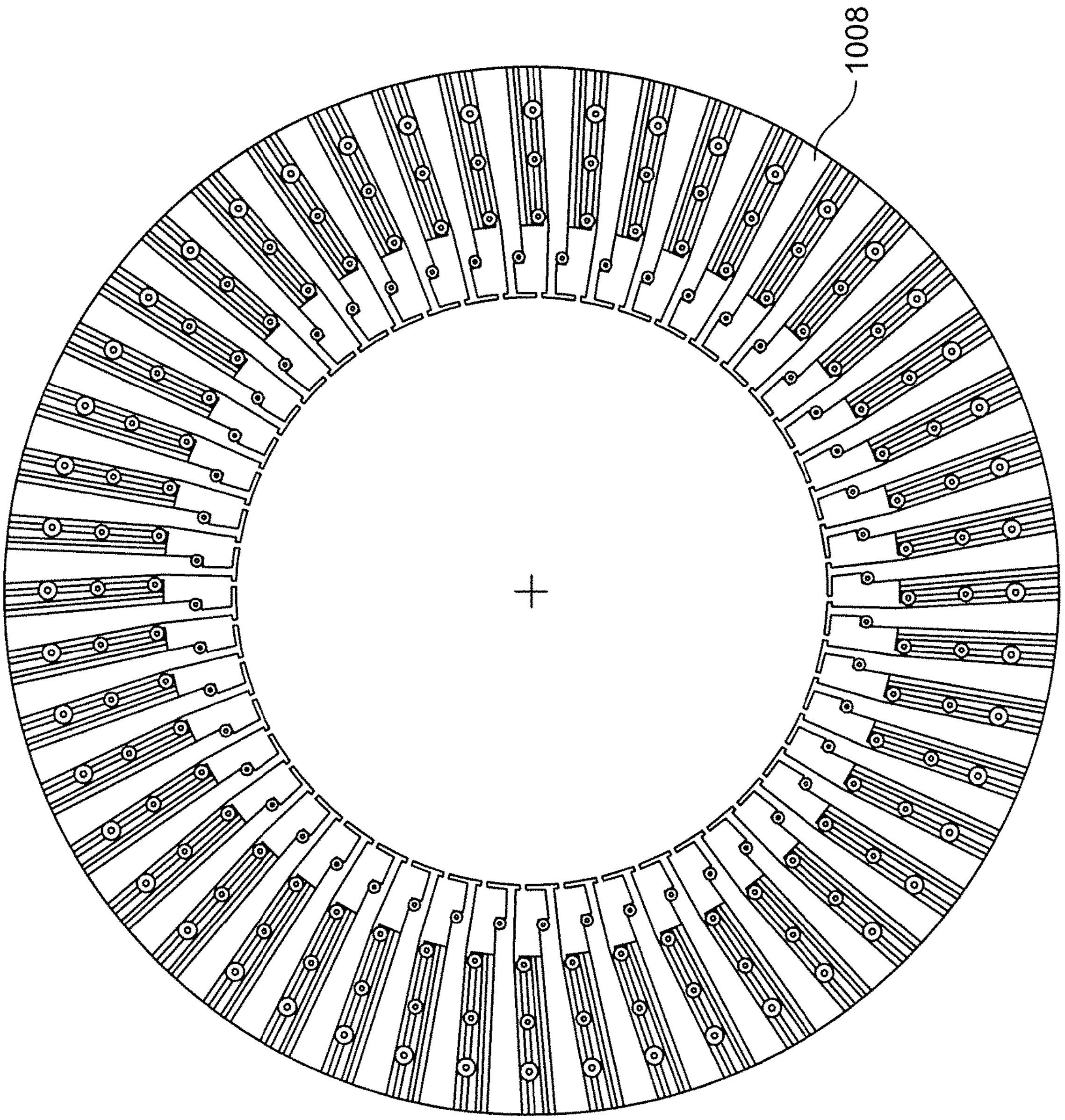

FIGS. 17A and 17B show various views of an embodiment of a radially-configured highly-multiplexed cartridge, having a number of inlets 1002, microfluidic lanes 1004, valves 1005, and PCR reaction chambers 1006. FIG. 17C shows an array of heater elements 1008 compatible with the cartridge layout of FIG. 17A.

The various embodiments shown in FIGS. 12-17C are compatible with liquid dispensers, receiving bays, and detectors that are configured differently from the other specific examples described herein.

During the design and manufacture of highly multiplexed cartridges, photolithographic processing steps such as etching, hole drilling/photo-chemical drilling/sand-blasting/ion-milling processes should be optimized to give well defined holes and microchannel pattern. Proper distances between channels should be identified and maintained to obtain good bonding between the microchannel substate and the heat conducting substrate layer. In particular, it is desirable that minimal distances are maintained between pairs of adjacent microchannels to promote, reliable bonding of the laminate in between the channels.

The fabrication by injection molding of these complicated microfluidic structures having multiple channels and multiple inlet holes entails proper consideration of dimensional repeatability of these structures over multiple shots from the injection molding master pattern. Proper consideration is also attached to the placement of ejector pins to push out the structure from the mold without causing warp, bend or stretching of it. For example, impression of the ejector pins on the microfluidic substrate should not sink into the substrate thereby preventing planarity of the surface of the cartridge. The accurate placement of various inlet holes (such as sample inlet holes, valve inlet holes and vent holes) relative to adjacent microfluidic channels is also important because the presence of these holes can cause knit-lines to form that might cause unintended leak from a hole to a microchannel. Highly multiplexed microfluidic substrates may be fabricated in other materials such as glass, silicon.

The size of the substrate relative to the number of holes is also factor during fabrication because it is easy to make a substrate having just a simple microfluidic network with a few holes (maybe fewer than 10 holes) and a few microchannels, but making a substrate having over 24, or over 48, or over 72 holes, etc., is more difficult.

Microfluidic Networks

Particular components of exemplary microfluidic networks are further described herein.

Channels of a microfluidic network in a lane of cartridge typically have at least one sub-millimeter cross-sectional dimension. For example, channels of such a network may have a width and/or a depth of about 1 mm or less (e.g., about 750 microns or less, about 500 microns, or less, about 250 microns or less).

Figure 18:
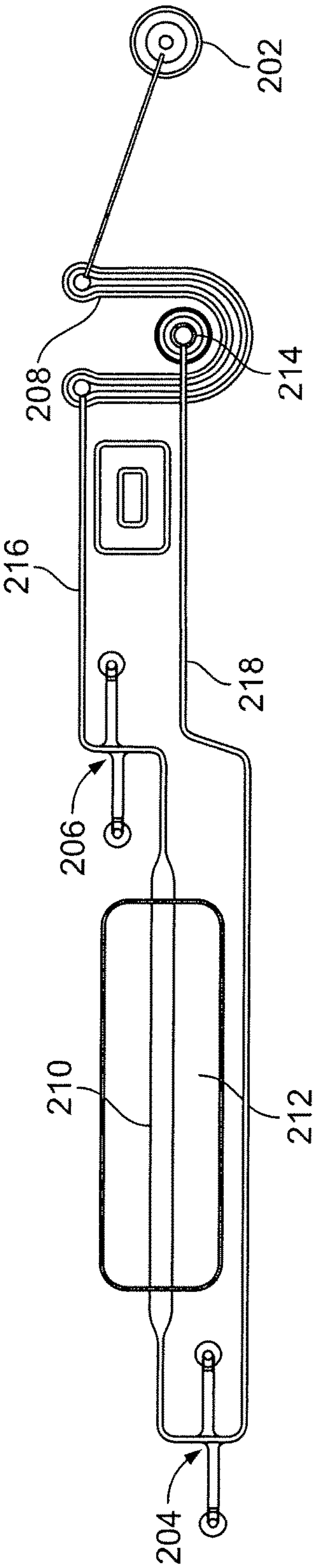
FIG. 18 shows an exemplary microfluidic network in a lane of a multi-lane cartridge.

FIG. 18 shows a plan view of a representative microfluidic circuit found in one lane of a multi-lane cartridge such as shown in FIGS. 10A and 10B. It would be understood by one skilled in the art that other configurations of microfluidic network would be consistent with the function of the cartridges and apparatus described herein. In operation of the cartridge, in sequence, sample is introduced through liquid inlet 202, optionally flows into a bubble removal vent channel 208 (which permits adventitious air bubbles introduced into the sample during entry, to escape), and continues along a channel 216. Typically, when using a robotic dispenser of liquid sample, the volume is dispensed accurately enough that formation of bubbles is not a significant problem, and the presence of vent channel 208 is not necessary. Thus, in certain embodiments, the bubble removal vent channel 208 is not present and sample flows directly into channel 216. Throughout the operation of cartridge 200, the fluid is manipulated as a microdroplet (not shown in the FIGs). Valves 204 and 206 are initially both open, so that a microdroplet of sample-containing fluid can be pumped into PCR reactor channel 210 from inlet hole 202 under influence of force from the sample injection operation. Upon initiating of processing, the detector present on top of the PCR reactor 210 checks for the presence of liquid in the PCR channel, and then valves 204 and 206 are closed to isolate the PCR reaction mix from the outside. In one embodiment, the checking of the presence of liquid in the PCR channel is by measuring the heat ramp rate, such as by one or more temperature sensors in the heating unit. A channel with liquid absent will heat up faster than one in which, e.g., a sample, is present.

Both valves 204 and 206 are closed prior to thermocycling to prevent or reduce any evaporation of liquid, bubble generation, or movement of fluid from the PCR reactor. End vent 214 is configured to prevent a user from introducing an excess amount of liquid into the microfluidic cartridge, as well as playing a role of containing any sample from spilling over to unintended parts of the cartridge. A user may input sample volumes as small as an amount to fill the region from the bubble removal vent (if present) to the middle of the microreactor, or up to valve 204 or beyond valve 204. The use of microvalves prevents both loss of liquid or vapor thereby enabling even a partially filled reactor to successfully complete a PCR thermocycling reaction.

The reactor 210 is a microfluidic channel that is heated through a series of cycles to carry out amplification of nucleotides in the sample, as further described herein, and according to amplification protocols known to those of ordinary skill in the art. The inside walls of the channel in the PCR reactor are typically made very smooth and polished to a shiny finish (for example, using a polish selected from SPI A1, SPI A2, SPI A3, SPI B1, or SPI B2) during manufacture. This is in order to minimize any microscopic quantities of air trapped in the surface of the PCR channel, which would causing bubbling during the thermocycling steps. The presence of bubbles especially in the detection region of the PCR channel could also cause a false or inaccurate reading while monitoring progress of the PCR. Additionally, the PCR channel can be made shallow such that the temperature gradient across the depth of the channel is minimized.

The region of the cartridge 212 above PCR reactor 210 is a thinned down section to reduce thermal mass and autofluorescence from plastic in the cartridge. It permits a detector to more reliably monitor progress of the reaction and also to detect fluorescence from a probe that binds to a quantity of amplified nucleotide. Exemplary probes are further described herein. The region 212 can be made of thinner material than the rest of the cartridge so as to permit the PCR channel to be more responsive to a heating cycle (for example, to rapidly heat and cool between temperatures appropriate for denaturing and annealing steps), and so as to reduce glare, autofluorescence, and undue absorption of fluorescence.

After PCR has been carried out on a sample, and presence or absence of a polynucleotide of interest has been determined, it is preferred that the amplified sample remains in the cartridge and that the cartridge is either used again (if one or more lanes remain unused), or disposed of. Should a user wish to run a post amplification analysis, such as gel electrophoresis, the user may pierce a hole through the laminate of the cartridge, and recover an amount—typically about 1.5 microliter—of PCR product. The user may also place the individual PCR lane on a special narrow heated plate, maintained at a temperature to melt the wax in the valve, and then aspirate the reacted sample from the inlet hole of that PCR lane.

In various embodiments, the microfluidic network can optionally include at least one reservoir configured to contain waste.

Table 1 outlines typical volumes, pumping pressures, and operation times associated with various components of a microfluidic cartridge described herein.

TABLE 1

| Operation | Pumping Pressure | Displacement Volume | Time of Operation |
|---|---|---|---|
| Moving valve wax plugs | ~1-2 psi | <1 μl | 5-15 seconds |

| Operation | Pump Used | Pump Design | Pump Actuation |
|---|---|---|---|
| Moving valve wax plugs | Thermopneumatic pump | 1 μl of trapped air | Heat trapped air to ~70-90 C. |

Valves

A valve (sometimes referred to herein as a microvalve) is a component in communication with a channel, such that the valve has a normally open state allowing material to pass along a channel from a position on one side of the valve (e.g., upstream of the valve) to a position on the other side of the valve (e.g., downstream of the valve). Upon actuation of the valve, the valve transitions to a closed state that prevents material from passing along the channel from one side of the valve to the other. For example, in one embodiment, a valve can include a mass of a thermally responsive substance (TRS) that is relatively immobile at a first temperature and more mobile at a second temperature. The first and second temperatures are insufficiently high to damage materials, such as polymer layers of a microfluidic cartridge in which the valve is situated. A mass of TRS can be an essentially solid mass or an agglomeration of smaller particles that cooperate to obstruct the passage when the valve is closed. Examples of TRS's include a eutectic alloy (e.g., a solder), wax (e.g., an olefin), polymers, plastics, and combinations thereof. The TRS can also be a blend of variety of materials, such as an emulsion of thermoelastic polymer blended with air microbubbles (to enable higher thermal expansion, as well as reversible expansion and contraction), polymer blended with expancel material (offering higher thermal expansion), polymer blended with heat conducting microspheres (offering faster heat conduction and hence, faster melting profiles), or a polymer blended with magnetic microspheres (to permit magnetic actuation of the melted thermoresponsive material).

Generally, for such a valve, the second temperature is less than about 90° C. and the first temperature is less than the second temperature (e.g., about 70° C. or less). Typically, a chamber is in gaseous communication with the mass of TRS. The valve is in communication with a source of heat that can be selectively applied to the chamber of air and to the TRS. Upon heating gas (e.g., air) in the chamber and heating the mass of TRS to the second temperature, gas pressure within the chamber due to expansion of the volume of gas, forces the mass to move into the channel, thereby obstructing material from passing therealong.

Figure 19A:
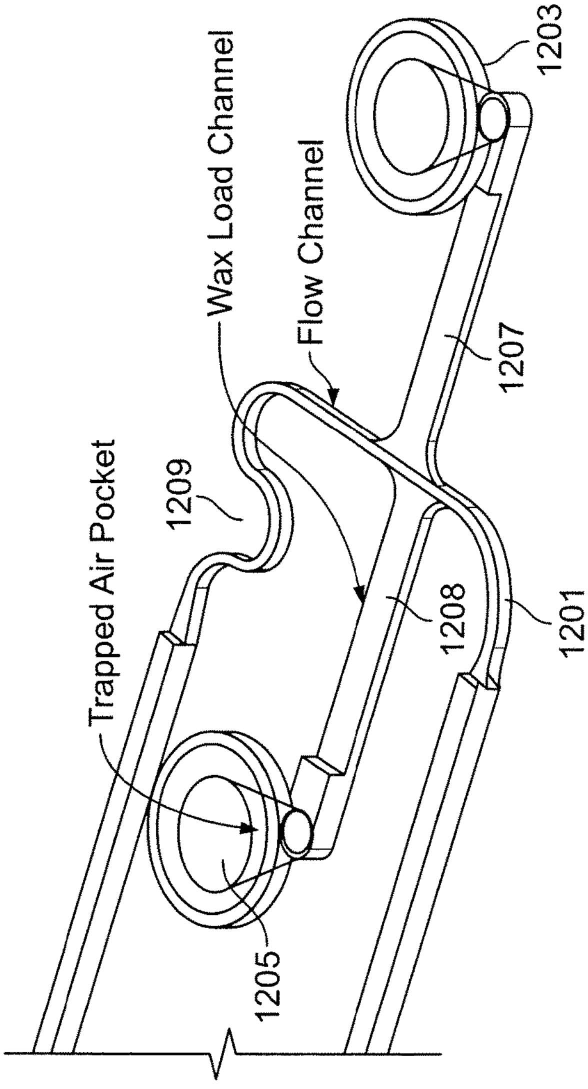
FIGS. 19A-19D show exemplary microfluidic valves.

An exemplary valve is shown in FIG. 19A. The valve of FIG. 19A has two chambers of air 1203, 1205 in contact with, respectively, each of two channels 1207, 1208 containing TRS. The air chambers also serve as loading ports for TRS during manufacture of the valve, as further described herein. In order to make the valve sealing very robust and reliable, the flow channel 1201 (along which, e.g., sample passes) at the valve junction is made narrow (typically 150 μm wide, and 150 μm deep or narrower), and the constricted portion of the flow channel is made at least 0.5 or 1 mm long such that the TRS seals up a long narrow channel thereby reducing any leakage through the walls of the channel. In the case of a bad seal, there may be leakage of fluid around walls of channel, past the TRS, when the valve is in the closed state. In order to minimize this, the flow channel is narrowed and elongated as much as possible. In order to accommodate such a length of channel on a cartridge where space may be at a premium, the flow channel can incorporate one or more curves 1209 as shown in FIG. 19A. The valve operates by heating air in the TRS-loading port, which forces the TRS forwards into the flow-channel in a manner so that it does not come back to its original position. In this way, both air and TRS are heated during operation.

Figure 19B:
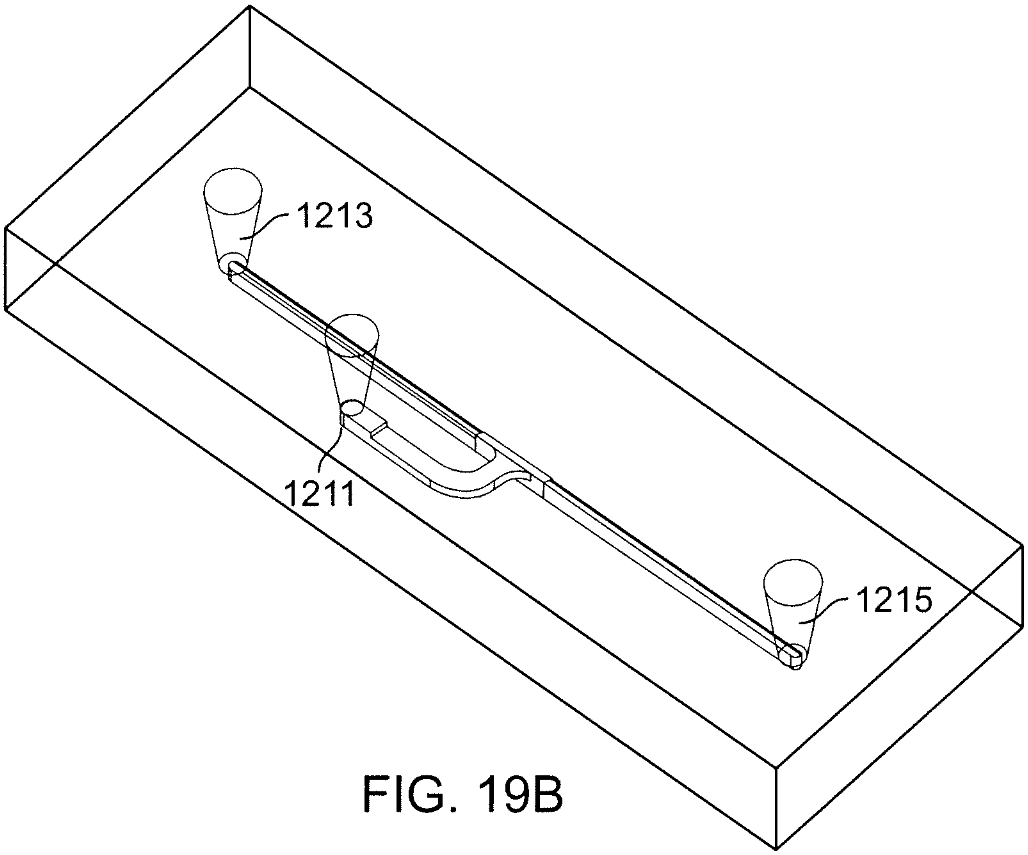

In various other embodiments, a valve for use with a microfluidic network in a microfluidic cartridge herein can be a bent valve as shown in FIG. 19B. Such a configuration reduces the footprint of the valve and hence reduces cost per part for highly dense microfluidic cartridges. A single valve loading hole 1211 is positioned in the center, that serves as an inlet for thermally responsive substance. The leftmost vent 1213 can be configured to be an inlet for, e.g., sample, and the rightmost vent 1215 acts as an exit for, e.g., air. This configuration can be used as a prototype for testing such attributes as valve and channel geometry and materials.

Figure 19C:
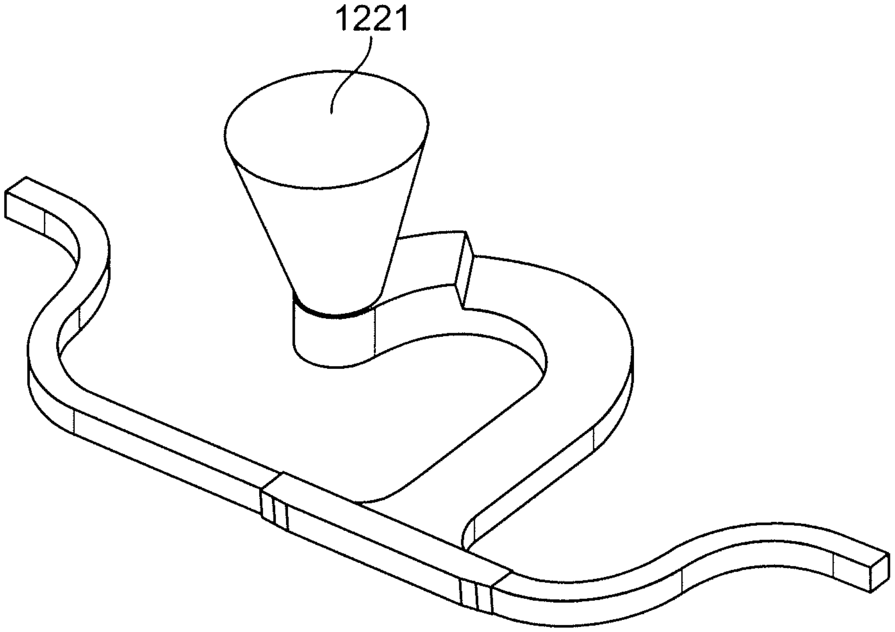

In various other embodiments, a valve for use with a microfluidic network can include a curved valve as shown in FIG. 19C, in order to reduce the effective cross-section of the valve, thereby enabling manufacture of cheaper dense microfluidic devices. Such a valve can function with a single valve loading hole and air chamber 1221 instead of a pair as shown in FIG. 19A.

Gates

Figure 19D:
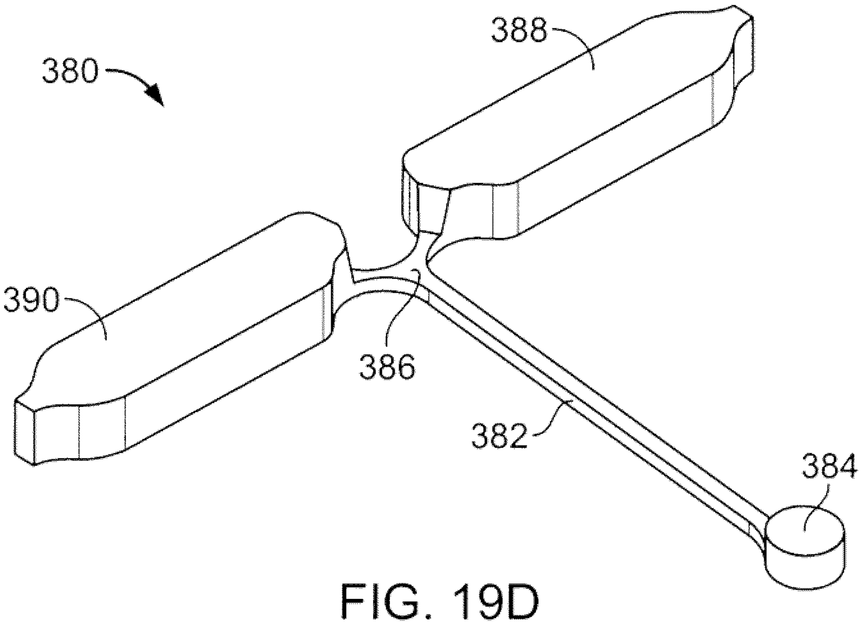

FIG. 19D shows an exemplary gate as may optionally be used in a microfluidic network herein. A gate can be a component that can have a closed state that does not allow material to pass along a channel from a position on one side of the gate to another side of the gate, and an open state that does allow material to pass along a channel from a position on one side of the gate to another side of the gate. Actuation of an open gate can transition the gate to a closed state in which material is not permitted to pass from one side of the gate (e.g., upstream of the gate) to the other side of the gate (e.g., downstream of the gate). Upon actuation, a closed gate can transition to an open state in which material is permitted to pass from one side of the gate (e.g., upstream of the gate) to the other side of the gate (e.g., downstream of the gate).

In various embodiments, a microfluidic network can include a narrow gate 380 as shown in FIG. 19D where a gate loading channel 382 used for loading wax from a wax loading hole 384 to a gate junction 386 can be narrower (e.g., approximately 150 μm wide and 100 microns deep). An upstream channel 388 as well as a downstream channel 390 of the gate junction 386 can be made wide (e.g., ~500 μm) and deep (e.g., ~500 μm) to help ensure the wax stops at the gate junction 386. The amount of gate material melted and moved out of the gate junction 386 may be minimized for optimal gate 380 opening. As an off-cartridge heater may be used to melt the thermally responsive substance in gate 380, a misalignment of the heater could cause the wax in the gate loading channel 382 to be melted as well. Therefore, narrowing the dimension of the loading channel may increase reliability of gate opening. In the case of excessive amounts of wax melted at the gate junction 386 and gate loading channel 382, the increased cross-sectional area of the downstream channel 390 adjacent to the gate junction 386 can prevent wax from clogging the downstream channel 390 during gate 380 opening. The dimensions of the upstream channel 388 at the gate junction 386 can be made similar to the downstream channel 390 to ensure correct wax loading during gate fabrication.

In various embodiments, the gate can be configured to minimize the effective area or footprint of the gate within the network and thus bent gate configurations, although not shown herein are consistent with the foregoing description.

Vents

In various embodiments, the microfluidic network can include at least one hydrophobic vent in addition to an end vent. A vent is a general outlet (hole) that may or may not be covered with a hydrophobic membrane. An exit hole is an example of a vent that need not be covered by a membrane.

A hydrophobic vent (e.g., a vent in FIG. 20) is a structure that permits gas to exit a channel while limiting (e.g., preventing) quantities of liquid from exiting the channel.

Typically, hydrophobic vents include a layer of porous hydrophobic material (e.g., a porous filter such as a porous hydrophobic membrane from GE Osmonics, Minnetonka, MN) that defines a wall of the channel. As described elsewhere herein, hydrophobic vents can be used to position a microdroplet of sample at a desired location within a microfluidic network.

The hydrophobic vents of the present technology are preferably constructed so that the amount of air that escapes through them is maximized while minimizing the volume of the channel below the vent surface. Accordingly, it is preferable that the vent is constructed so as to have a hydrophobic membrane 1303 of large surface area and a shallow cross section of the microchannel below the vent surface.

Hydrophobic vents are useful for bubble removal and typically have a length of at least about 2.5 mm (e.g., at least about 5 mm, at least about 7.5 mm) along a channel 1305 (see FIG. 13). The length of the hydrophobic vent is typically at least about 5 times (e.g., at least about 10 times, at least about 20 times) larger than a depth of the channel within the hydrophobic vent. For example, in some embodiments, the channel depth within the hydrophobic vent is about 300 microns or less (e.g., about 250 microns or less, about 200 microns or less, about 150 microns or less).

The depth of the channel within the hydrophobic vent is typically about 75% or less (e.g., about 65% or less, about 60% or less) of the depth of the channel upstream 1301 and downstream (not shown) of the hydrophobic vent. For example, in some embodiments the channel depth within the hydrophobic vent is about 150 microns and the channel depth upstream and downstream of the hydrophobic vent is about 250 microns. Other dimensions are consistent with the description herein.

A width of the channel within the hydrophobic vent is typically at least about 25% wider (e.g., at least about 50% wider) than a width of the channel upstream from the vent and downstream from the vent. For example, in an exemplary embodiment, the width of the channel within the hydrophobic vent is about 400 microns, and the width of the channel upstream and downstream from the vent is about 250 microns. Other dimensions are consistent with the description herein.

Figure 20:
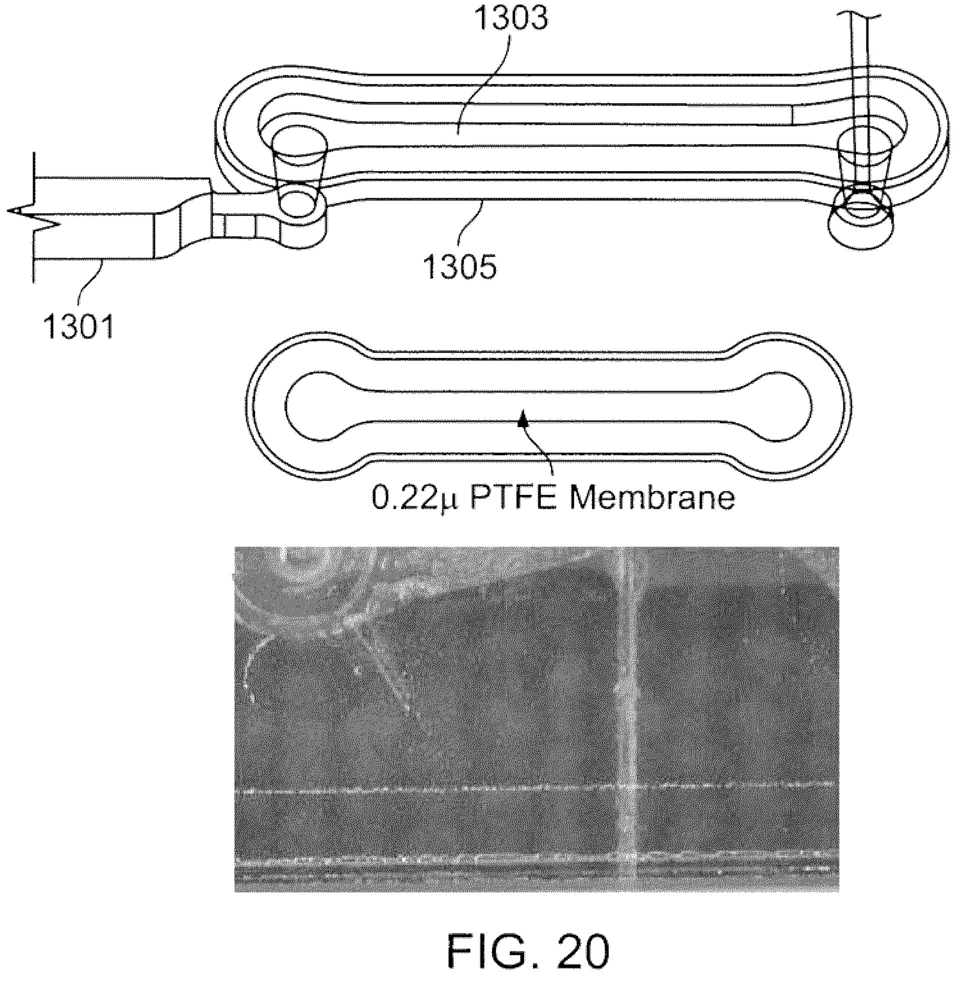
FIG. 20 shows an exemplary bubble vent.

The vent in FIG. 20 is shown in a linear configuration though it would be understood that it need not be so. A bent, kinked, curved, S-shaped, V-shaped, or U-shaped (as in item 208 FIG. 11) vent is also consistent with the manner of construction and operation described herein.

Figure 21:
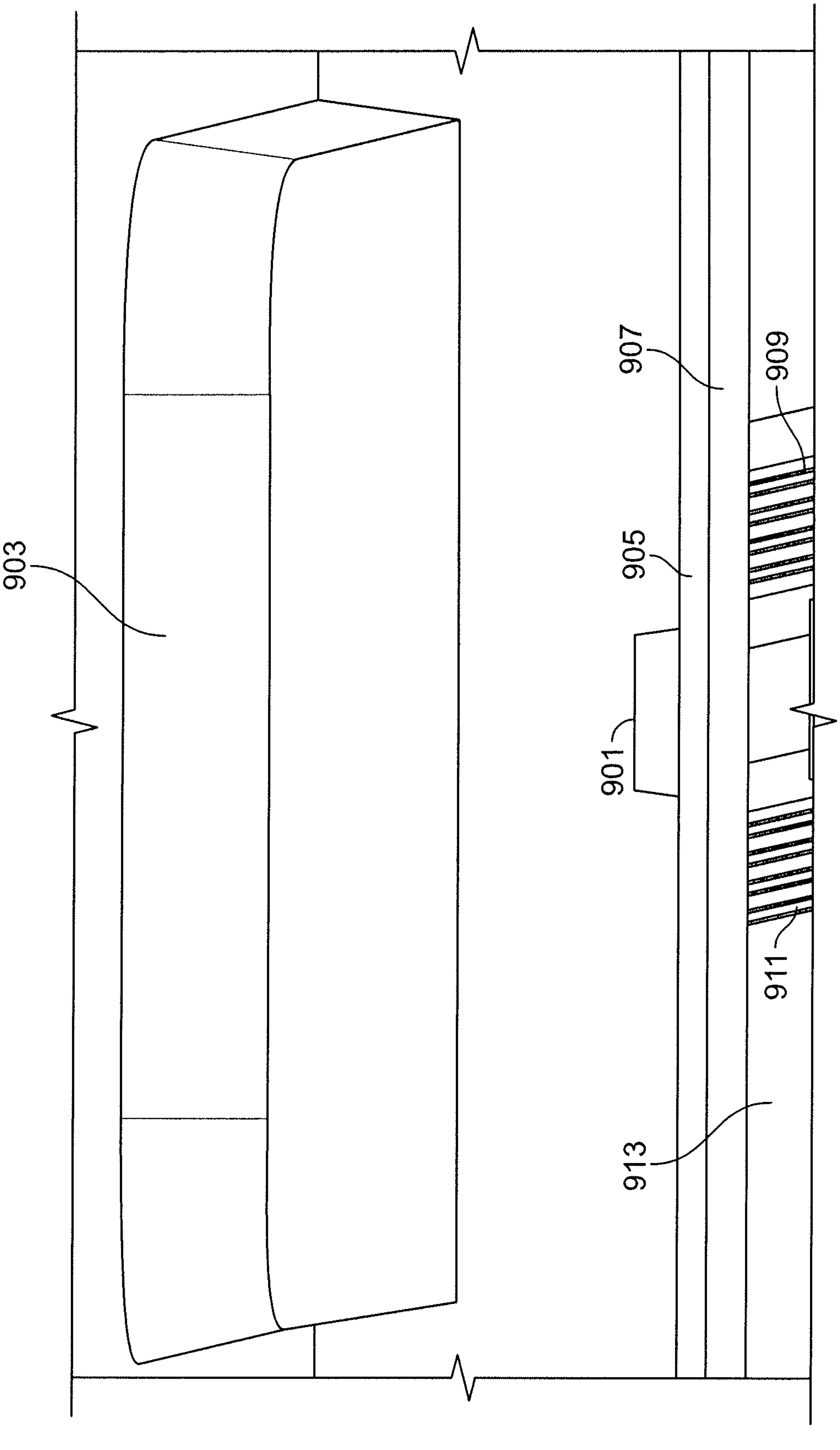
FIG. 21 shows a cross-section of a microfluidic cartridge, when in contact with a heater substrate.

Use of Cutaways in Cartridge and Substrate To Improve Rate of Cooling During PCR Cycling During a PCR amplification of a nucleotide sample, a number of thermal cycles are carried out. For improved efficiency, the cooling between each application of heat is preferably as rapid as possible. Improved rate of cooling can be achieved with various modifications to the heating substrate and/or the cartridge, as shown in FIG. 21.

Figure 22A:
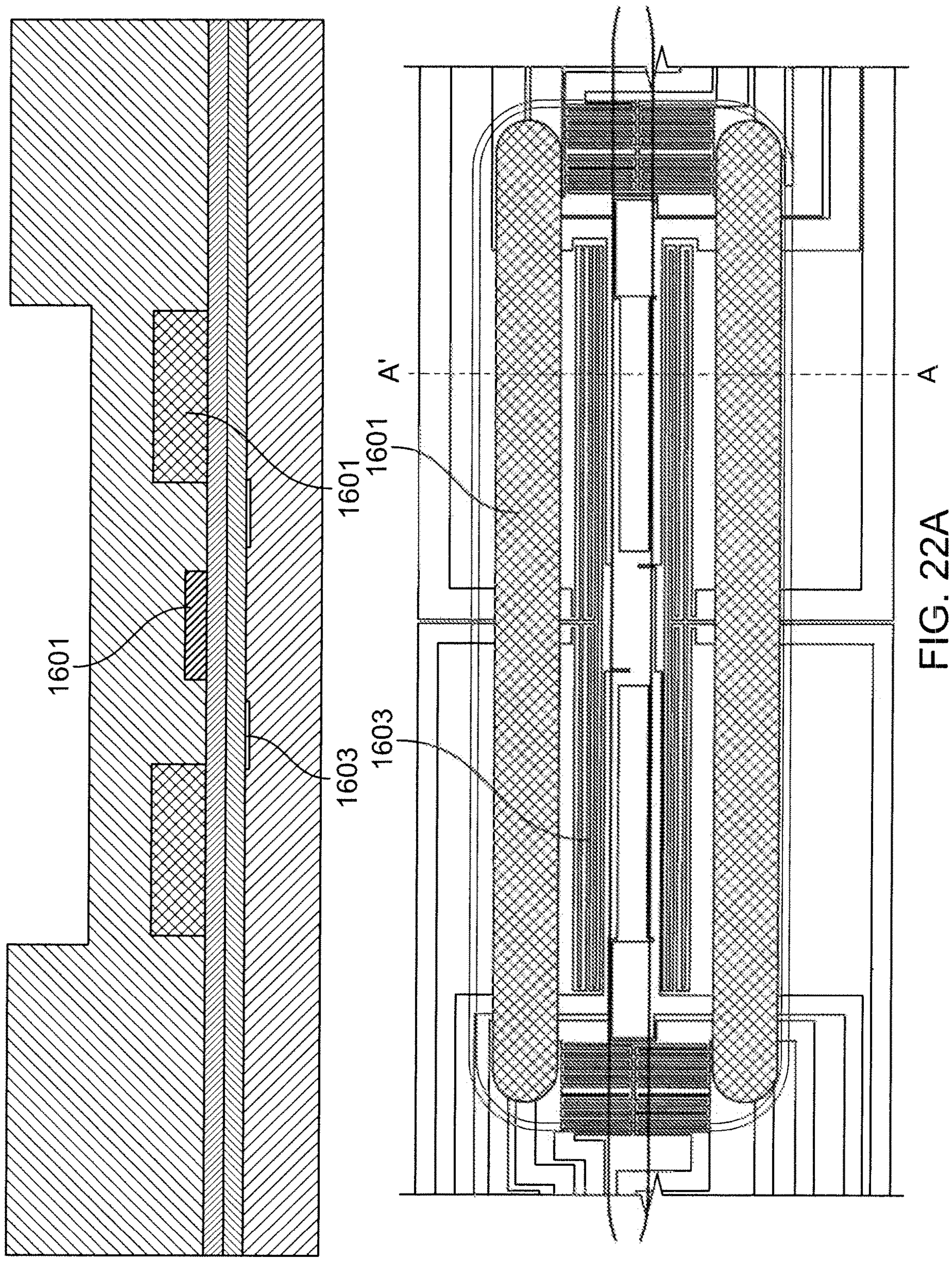
FIGS. 22A-22C shows various cut-away sections that can be used to improve cooling rates during PCR thermal cycling.

One way to achieve rapid cooling is to cutaway portions of the microfluidic cartridge substrate, as shown in FIG. 22A. The upper panel of FIG. 22A is a cross-section of an exemplary microfluidic cartridge taken along the dashed line A-A' as marked on the lower panel of FIG. 22A. PCR reaction chamber 1601, and representative heaters 1603 are shown. Also shown are two cutaway portions, one of which labeled 1601, that are situated alongside the heaters that are positioned along the long side of the PCR reaction chamber. Cutaway portions such as 1601 reduce the thermal mass of the cartridge, and also permit air to circulate within the cutaway portions. Both of these aspects permit heat to be conducted away quickly from the immediate vicinity of the PCR reaction chamber. Other configurations of cutouts, such as in shape, position, and number, are consistent with the present technology.

Figure 22B:
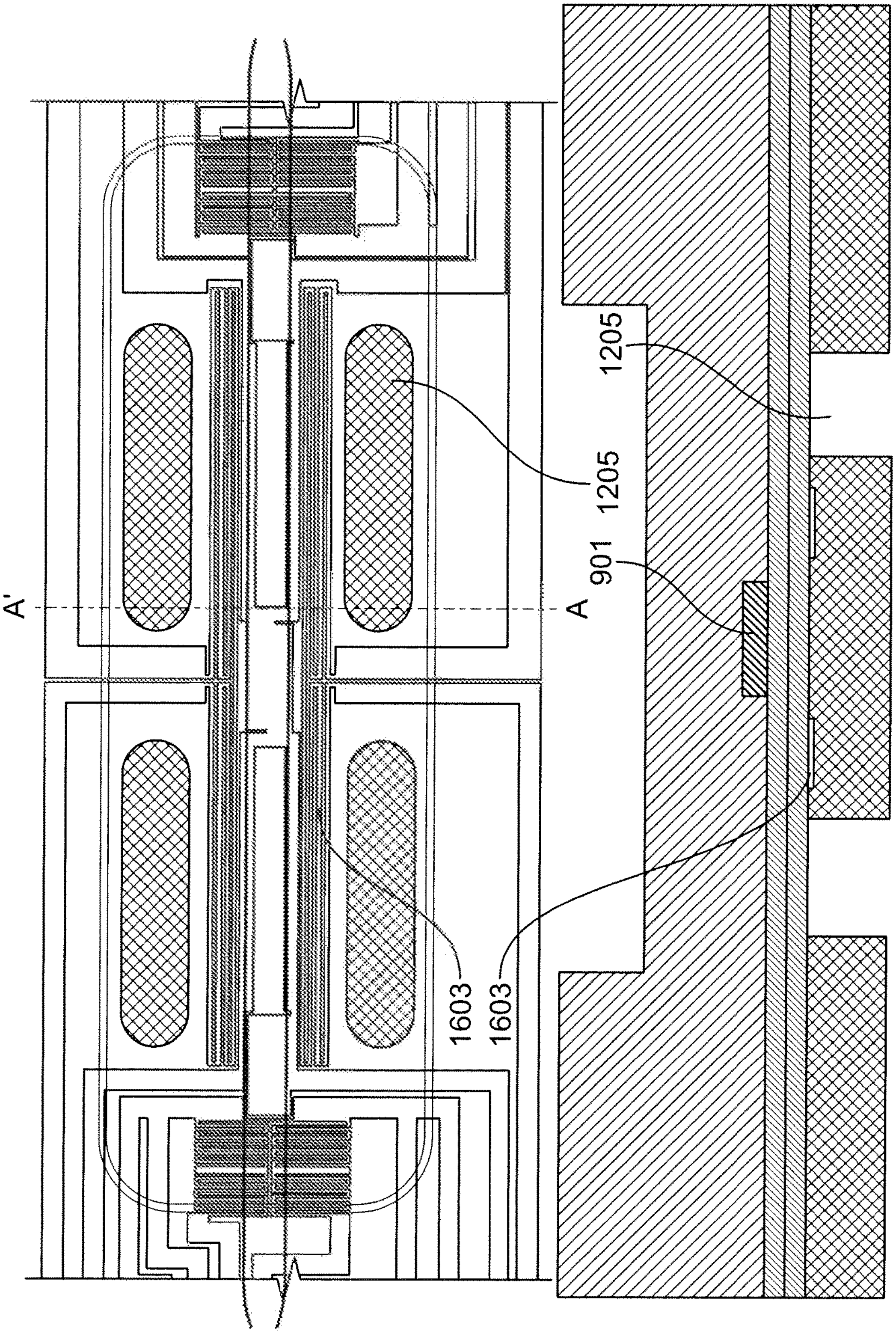

Another way to achieve rapid cooling is to cutaway portions of the heater substrate, as shown in FIG. 22B. The lower panel of FIG. 22B is a cross-section of an exemplary microfluidic cartridge and heater substrate taken along the dashed line A-A' as marked on the upper panel of FIG. 22B. PCR reaction chamber 901, and representative heaters 1003 are shown. Also shown are four cutaway portions, one of which labeled 1205, that are situated alongside the heaters that are situated along the long side of the PCR reaction chamber. Cutaway portions such as 1205 reduce the thermal mass of the heater substrate, and also permit air to circulate within the cutaway portions. Both of these aspects permit heat to be conducted away quickly from the immediate vicinity of the PCR reaction chamber. Four separate cutaway portions are shown in FIG. 22A so that control circuitry to the various heaters is not disrupted. Other configurations of cutouts, such as in shape, position, and number, are consistent with the present technology. These cutouts may be created by a method selected from: selective etching using wet etching processes, deep reactive ion etching, selective etching using $CO_2$ laser or femtosecond laser (to prevent surface cracks or stress near the surface), selective mechanical drilling, selective ultrasonic drilling, or selective abrasive particle blasting. Care has to be taken to maintain mechanically integrity of the heater while reducing as much material as possible.

Figure 22C:
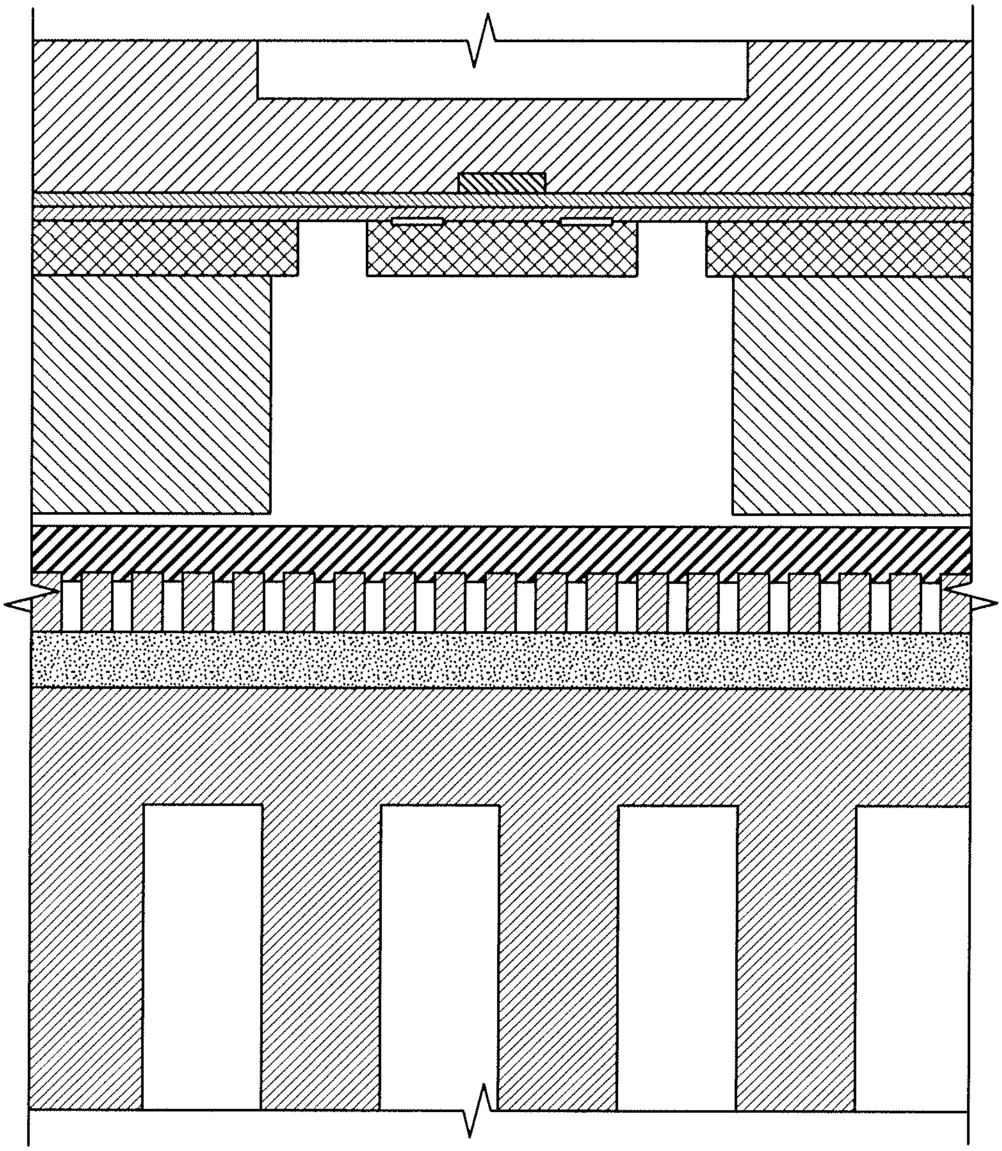

FIG. 22C shows a combination of cutouts and use of ambient air cooling to increase the cooling rate during the cooling stage of thermocycling. A substantial amount of cooling happens by convective loss from the bottom surface of the heater surface to ambient air. The driving force for this convective loss is the differential in temperatures between the glass surface and the air temperature. By decreasing the ambient air temperature by use of, for example, a peltier cooler, the rate of cooling can be increased. The convective heat loss may also be increased by keeping the air at a velocity higher than zero.

Figure 23:
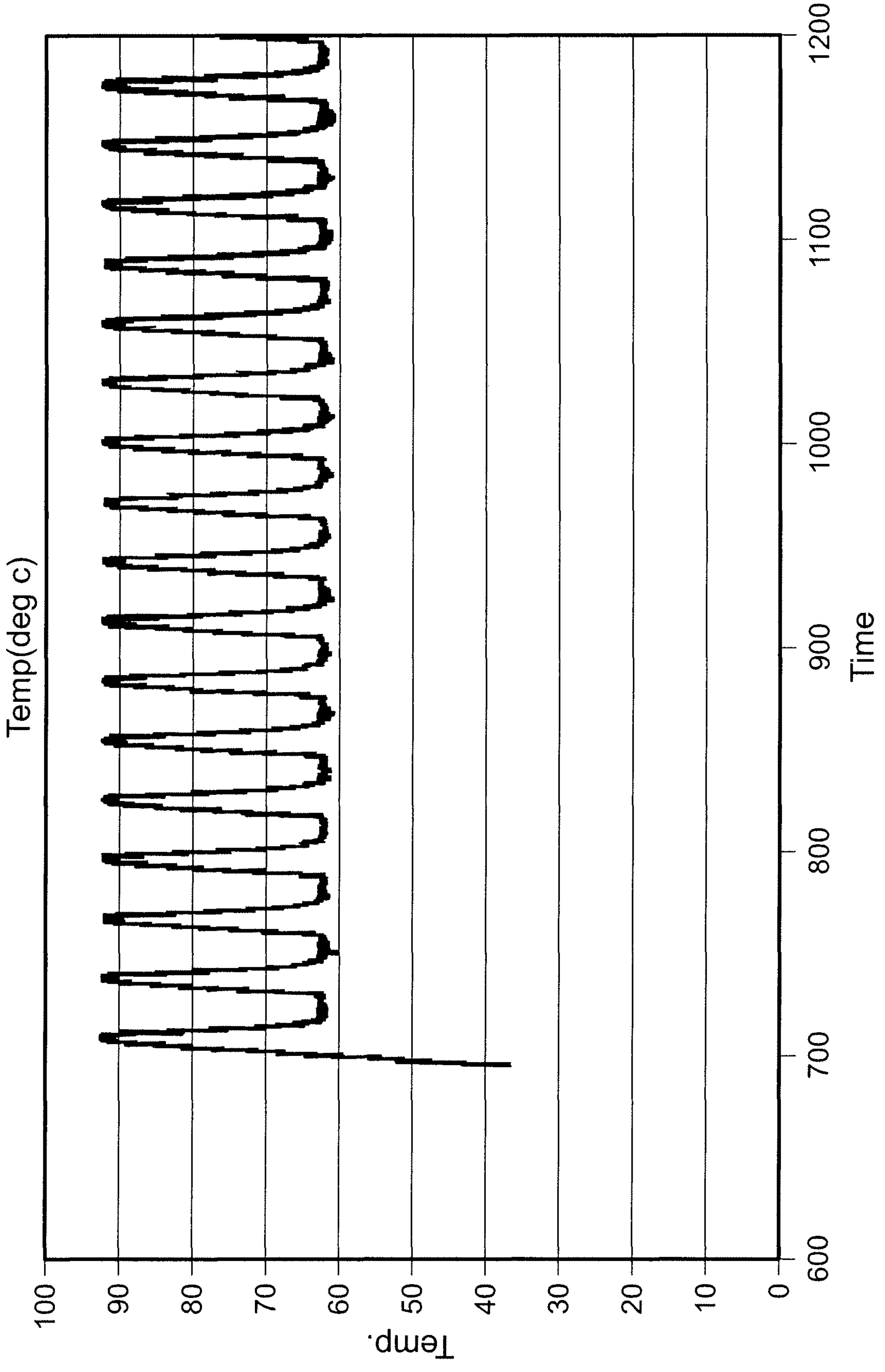
FIG. 23 shows a plot of temperature against time during a PCR process, as performed on a microfluidic cartridge as described herein.

An example of thermal cycling performance in a PCR reaction chamber obtained with a configuration as described herein, is shown in FIG. 23 for a protocol that is set to heat up the reaction mixture to 92° C., and maintain the temperature for 1 second, then cool to 62° C., and stay for 10 seconds. The cycle time shown is about 29 seconds, with 8 seconds required to heat from 62° C. and stabilize at 92° C., and 10 seconds required to cool from 92° C., and stabilize at 62° C. To minimize the overall time required for a PCR effective to produce detectable quantities of amplified material, it is important to minimize the time required for each cycle. Cycle times in the range 15-30 s, such as 18-25 s, and 20-22 s, are desirable. In general, an average PCR cycle time of 25 seconds as well as cycle times as low as 20 seconds are typical with the technology described herein. Using reaction volumes less than a microliter (such as a few hundred nanoliters or less) permits use of an associated smaller PCR chamber, and enables cycle times as low as 15 seconds. An average cycle time of 25 seconds and as low as 20 seconds can be achieved by technology described herein, even without any forced cooling or implementing any thermal mass reductions described elsewhere herein.

Manufacturing Process for Cartridge

Figure 24:
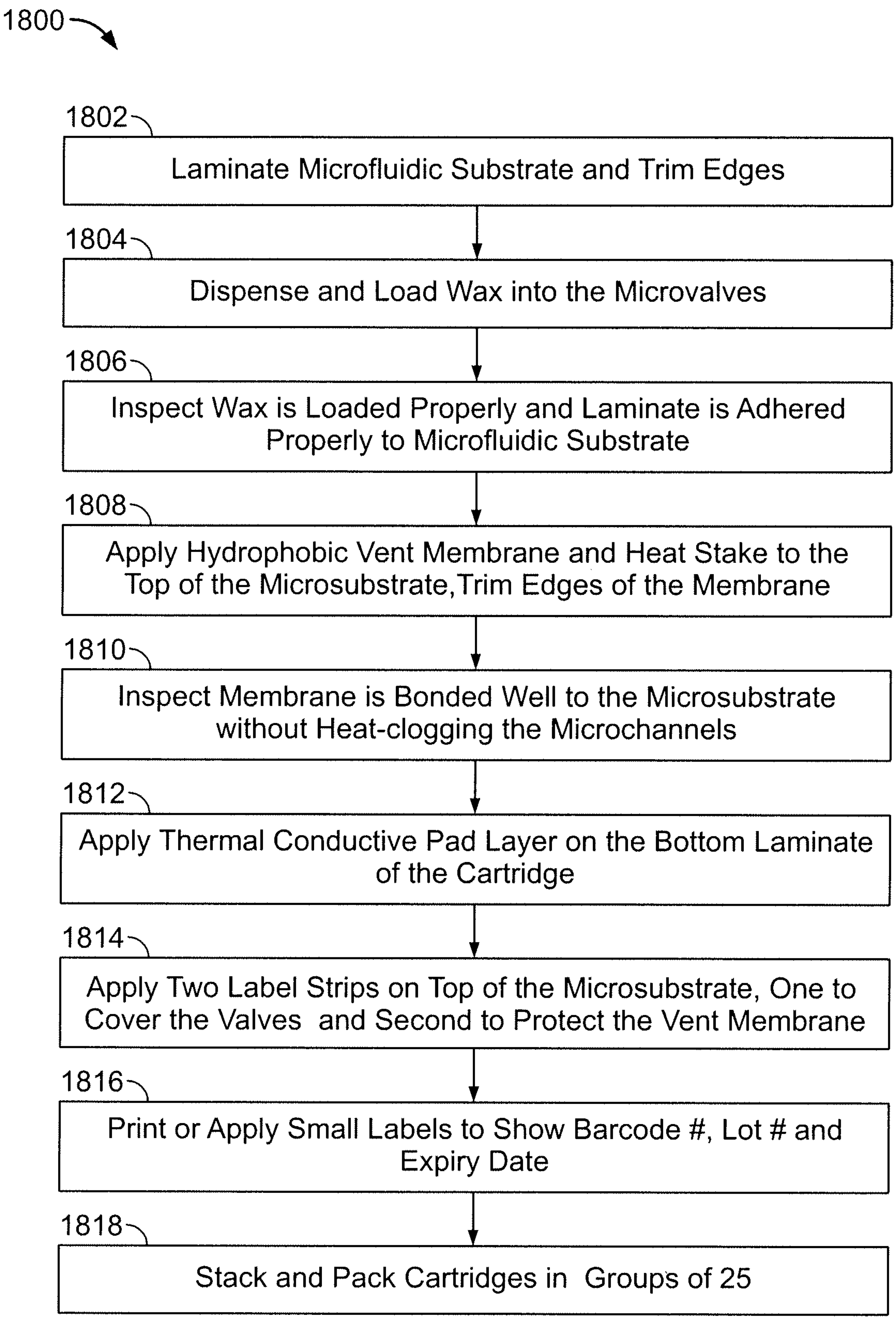
FIG. 24 shows an assembly process for a cartridge as further described herein.

FIG. 24 shows a flow-chart 1800 for an embodiment of an assembly process for an exemplary cartridge as shown in FIG. 11A herein. It would be understood by one of ordinary skill in the art, both that various steps may be performed in a different order from the order set forth in FIG. 24, and additionally that any given step may be carried out by alternative methods to those described in the figure. It would also be understood that, where separate serial steps are illustrated for carrying out two or more functions, such functions may be performed synchronously and combined into single steps and remain consistent with the overall process described herein.

At 1802, a laminate layer is applied to a microfluidic substrate that has previously been engineered, for example by injection molding, to have a microfluidic network constructed in it; edges are trimmed from the laminate where they spill over the bounds of the substrate.

At 1804, wax is dispensed and loaded into the microvalves of the microfluidic network in the microfluidic substrate. An exemplary process for carrying this out is further described herein.

At 1806, the substrate is inspected to ensure that wax from step 1804 is loaded properly and that the laminate from step 1802 adheres properly to it. If a substrate does not satisfy either or both of these tests, it is usually discarded. If substrates repeatedly fail either or both of these tests, then the wax dispensing, or laminate application steps, as applicable, are reviewed.

At 1808, a hydrophobic vent membrane is applied to, and heat bonded to, the top of the microfluidic substrate covering at least the one or more vent holes, and on the opposite face of the substrate from the laminate. Edges of the membrane that are in excess of the boundary of the substrate are trimmed.

At 1810, the assembly is inspected to ensure that the hydrophobic vent membrane is bonded well to the microfluidic substrate without heat-clogging the microfluidic channels. If any of the channels is blocked, or if the bond between the membrane and the substrate is imperfect, the assembly is discarded, and, in the case of repeated discard events, the foregoing process step 1808 is reviewed.

At 1812, optionally, a thermally conductive pad layer is applied to the bottom laminate of the cartridge.

At 1814, two label strips are applied to the top of the microfluidic substrate, one to cover the valves, and a second to protect the vent membranes. It would be understood that a single label strip may be devised to fulfill both of these roles.

At 1816, additional labels are printed or applied to show identifying characteristics, such as a barcode #, lot # and expiry date on the cartridge. Preferably one or more of these labels has a space and a writable surface that permits a user to make an identifying annotation on the label, by hand.

Optionally, at 1818, to facilitate transport and delivery to a customer, assembled and labeled cartridges are stacked, and cartridges packed into groups, such as groups of 25, or groups of 10, or groups of 20, or groups of 48 or 50. Preferably the packaging is via an inert and/or moisture-free medium.

Wax Loading in Valves

Figure 25A:
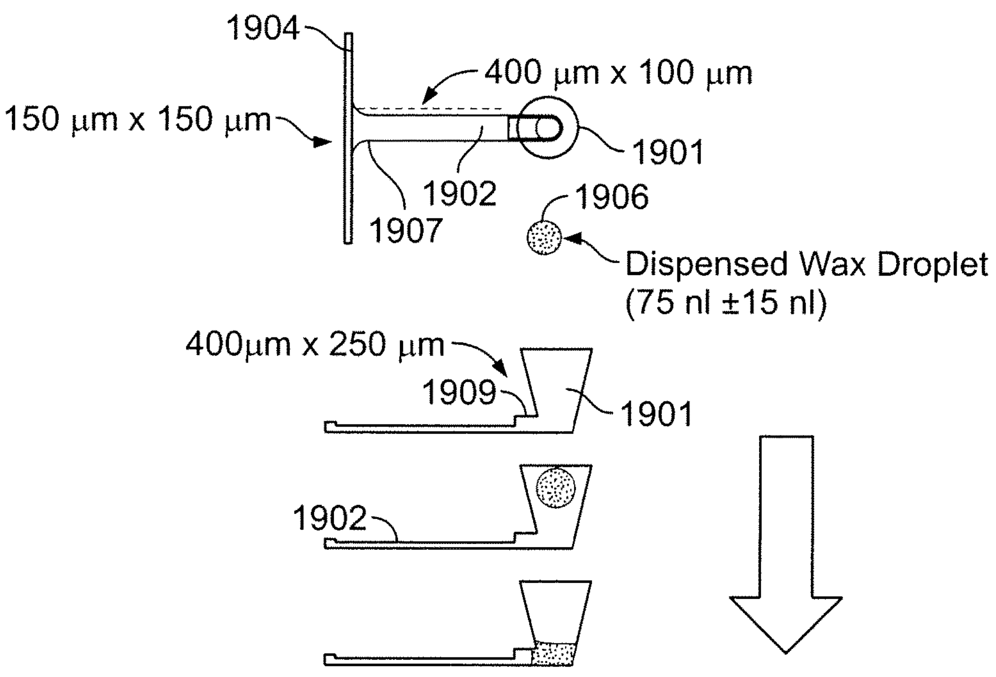
FIGS. 25A and 25B show exemplary deposition of wax droplets into microfluidic valves.
Figure 25B:
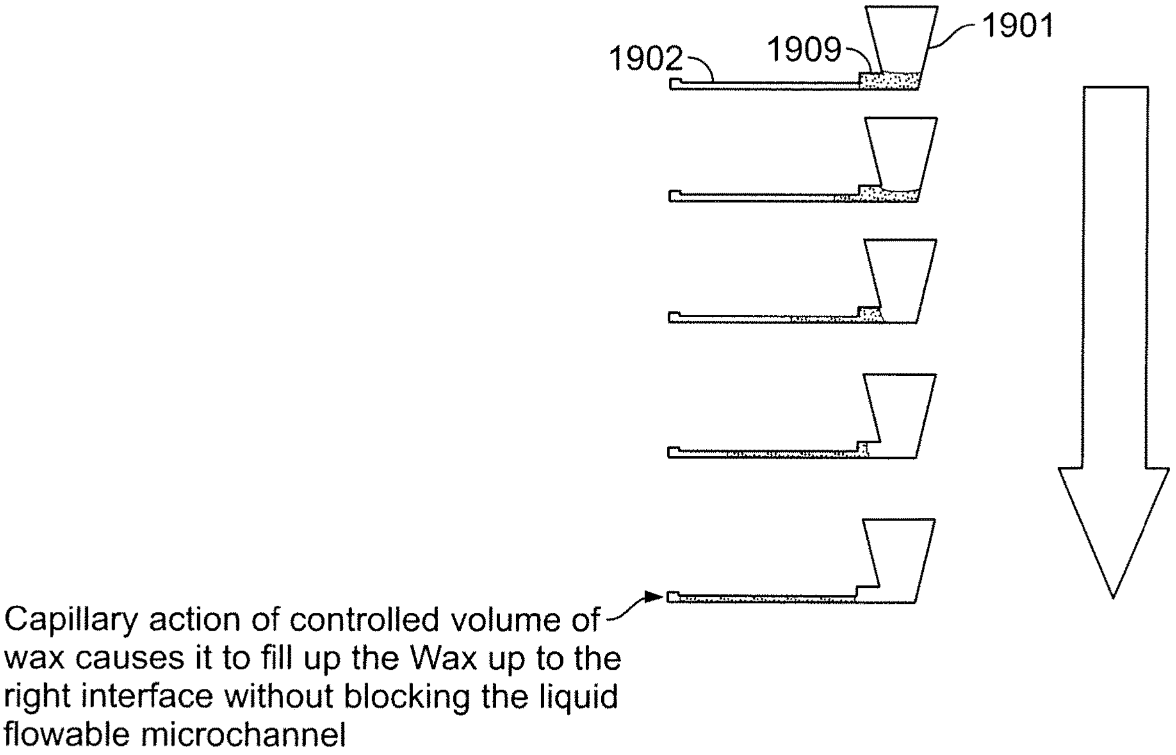

In general, a valve as shown in, e.g., FIGS. 25A-C, is constructed by depositing a precisely controlled amount of a TRS (such as wax) into a loading inlet machined in the microfluidic substrate. FIGS. 25A and 25B show how a combination of controlled hot drop dispensing into a heated microchannel device of the right dimensions and geometry is used to accurately load wax into a microchannel of a microfluidic cartridge to form a valve. The top of FIG. 25A shows a plan view of a valve inlet 190 and loading channel 1902, connecting to a flow channel 1904. The lower portions of FIG. 25A show the progression of a dispensed wax droplet 1906 (having a volume of 75 nl±15 nl) through the inlet 1901 and into the loading channel 1902.

To accomplish those steps, a heated dispenser head can be accurately positioned over the inlet hole of the micro channel in the microfluidic device, and can dispense molten wax drops in volumes as small as 75 nanoliters with an accuracy of 20%. A suitable dispenser is also one that can deposit amounts smaller than 100 nl with a precision of +/−20%. The dispenser should also be capable of heating and maintaining the dispensing temperature of the TRS to be dispensed. For example, it may have a reservoir to hold the solution of TRS. It is also desirable that the dispense head can have freedom of movement at least in a horizontal (x-y) plane so that it can easily move to various locations of a microfluidic substrate and dispense volumes of TRS into valve inlets at such locations without having to be re-set, repositioned manually, or recalibrated in between each dispense operation.

The inlet hole of the microfluidic cartridge, or other microchannel device, is dimensioned in such a way that the droplet of 75 nl can be accurately propelled to the bottom of the inlet hole using, for example, compressed air, or in a manner similar to an inkjet printing method. The microfluidic cartridge is maintained at a temperature above the melting point of the wax thereby permitting the wax to stay in a molten state immediately after it is dispensed. After the drop falls to the bottom of the inlet hole 1901, the molten wax is drawn into the narrow channel by capillary action, as shown in the sequence of views in FIG. 25B. A shoulder between the inlet hole 1901 and the loading channel can facilitate motion of the TRS. The volume of the narrow section can be designed to be approximately equal to a maximum typical amount that is dispensed into the inlet hole. The narrow section can also be designed so that even though the wax dispensed may vary considerably between a minimum and a maximum shot size, the wax always fills up to, and stops at, the micro channel junction 1907 because the T-junction provides a higher cross section than that of the narrow section and thus reduces the capillary forces.

PCR Reagent Mixtures

In various embodiments, the sample for introduction into a lane of the microfluidic cartridge can include a PCR reagent mixture comprising a polymerase enzyme and a plurality of nucleotides.

In various embodiments, preparation of a PCR-ready sample for use with an apparatus and cartridge as described herein can include contacting a neutralized polynucleotide sample with a PCR reagent mixture comprising a polymerase enzyme and a plurality of nucleotides (in some embodiments, the PCR reagent mixture can further include a positive control plasmid and a fluorogenic hybridization probe selective for at least a portion of the plasmid).

The PCR-ready sample can be prepared, for example, using the following steps: (1) collect sample in sample collection buffer, (2) transfer entire sample to lysis tube, mix, heat, and incubate for seven minutes, (3) place on magnetic rack, allow beads to separate, aspirate supernatant, (4) add 100 μl of Buffer 1, mix, place on magnetic rack, allow beads to separate, aspirate supernatant, (5) add 10 μl of Buffer 2, mix, place in high temperature heat block for 3 minutes, place on magnetic rack, allow beads to separate, transfer 5 μl supernatant, and (6) Add 5 μl of Buffer 3, transfer 1 to 10 μl of supernatant for PCR amplification and detection.

The PCR reagent mixture can be in the form of one or more lyophilized pellets and the steps by which the PCR-ready sample is prepared can involve reconstituting the PCR pellet by contacting it with liquid to create a PCR reagent mixture solution. In yet another embodiment, each of the PCR lanes may have dried down or lyophilized ASR reagents preloaded such that the user only needs to input prepared polynucleotide sample into the PCR. In another embodiment, the PCR lanes may have only the application-specific probes and primers pre-measured and pre-loaded, and the user inputs a sample mixed with the PCR reagents.

In various embodiments, the PCR-ready sample can include at least one probe that can be selective for a polynucleotide sequence, wherein the steps by which the PCR-ready sample is prepared involve contacting the neutralized polynucleotide sample or a PCR amplicon thereof with the probe. The probe can be a fluorogenic hybridization probe. The fluorogenic hybridization probe can include a polynucleotide sequence coupled to a fluorescent reporter dye and a fluorescence quencher dye.

In various embodiments, the PCR-ready sample further includes a sample buffer.

In various embodiments, the PCR-ready sample includes at least one probe that is selective for a polynucleotide sequence, e.g., the polynucleotide sequence that is characteristic of a pathogen selected from the group consisting of gram positive bacteria, gram negative bacteria, yeast, fungi, protozoa, and viruses.

In various embodiments, the PCR reagent mixture can further include a polymerase enzyme, a positive control plasmid and a fluorogenic hybridization probe selective for at least a portion of the plasmid.

In various embodiments, the probe can be selective for a polynucleotide sequence that is characteristic of an organism, for example any organism that employs deoxyribonucleic acid or ribonucleic acid polynucleotides. Thus, the probe can be selective for any organism. Suitable organisms include mammals (including humans), birds, reptiles, amphibians, fish, domesticated animals, wild animals, extinct organisms, bacteria, fungi, viruses, plants, and the like. The probe can also be selective for components of organisms that employ their own polynucleotides, for example mitochondria. In some embodiments, the probe is selective for microorganisms, for example, organisms used in food production (for example, yeasts employed in fermented products, molds or bacteria employed in cheeses, and the like) or pathogens (e.g., of humans, domesticated or wild mammals, domesticated or wild birds, and the like). In some embodiments, the probe is selective for organisms selected from the group consisting of gram positive bacteria, gram negative bacteria, yeast, fungi, protozoa, and viruses.

In various embodiments, the probe can be selective for a polynucleotide sequence that is characteristic of an organism selected from the group consisting of *Staphylococcus* spp., e.g., *S. epidermidis, S. aureus*, Methicillin-resistant *Staphylococcus aureus* (MRSA), Vancomycin-resistant *Staphylococcus; Streptococcus* (e.g., α, β or γ-hemolytic, Group A, B, C, D or G) such as *S. pyogenes, S. agalactiae; E. faccalis, E. durans*, and *E. faccium* (formerly *S. faccalis, S. durans, S. faccium*); nonenterococcal group D *Streptococci*, e.g., *S. bovis* and *S. equines; Streptococci viridans*, e.g., *S. mutans, S. sanguis, S. salivarius, S. mitior, A. milleri, S. constellatus, S. intermedius*, and *S. anginosus; S. iniac; S. pneumoniac; Neisseria*, e.g., *N. meningitides, N. gonorrhoeae*, saprophytic *Neisseria* sp; *Erysipelothrix*, e.g., *E. rhusiopathiae; Listeria* spp., e.g., *L. monocytogenes*, rarely *L. ivanovii* and *L. secligeri; Bacillus*, e.g., *B. anthracis, B. cereus, B. subtilis, B. subtilus niger, B. thuringiensis; Nocardia* asteroids; *Legionella*, e.g., *L. pneumonophilia, Pneumocystis*, e.g., *P. carinii*; Enterobacteriaceae such as *Salmonella, Shigella, Escherichia* (e.g., *E. coli, E. coli*O157: H7); *Klebsiella, Enterobacter, Serratia, Proteus, Morganella, Providencia, Yersinia*, and the like, e.g., *Salmonella*, e.g., *S. typhi S. paratyphi* A, B (*S. schottmuelleri*), and C (*S. hirschfeldii*), *S. dublin S. choleraesuis, S. enteritidis, S. typhimurium, S. heidelberg, S. newport, S. infantis, S. agona, S. montevideo*, and *S. saint-paul; Shigella* e.g., subgroups: A, B, C, and D, such as *S. flexneri, S. sonnei, S. boydii, S. dysenteriac; Proteus* (*P. mirabilis, P. vulgaris*, and *P. myxofaciens*), *Morganella* (*M. morganii*); *Providencia* (*P. rettgeri, P. alcalifaciens*, and *P. stuartii*); *Yersinia*, e.g., *Y. pestis, Y. enterocolitica; Hacmophilus*, e.g., *H. influenzac, H. parainfluenzae H. aphrophilus, H. ducreyi; Brucella*, e.g., *B. abortus, B. melitensis, B. suis, B. canis; Francisella*, e.g., *F. tularensis; Pseudomonas*, e.g., *P. acruginosa, P. paucimobilis, P. putida, P. fluorescens, P. acidovorans, Burkholderia* (*Pseudomonas*) *pseudomallei, Burkholderia mallei, Burkholderia cepacia* and *Stenotrophomonas maltophilia; Campylobacter*, e.g., *C. fetus fetus, C. jejuni, C. pylori* (*Helicobacter pylori*); *Vibrio*, e.g., *V. cholerae, V. parahaemolyticus, V. mimicus, V. alginolyticus, V. hollisae, V. vulnificus*, and the nonagglutinable vibrios; *Clostridia*, e.g., *C. perfringens, C. tetani, C. difficile, C. botulinum; Actinomyces*, e.g., *A. israelii; Bacteroides*, e.g., *B. fragilis, B. thetaiotaomicron, B. distasonis, B. vulgatus, B. ovatus, B. caccae*, and *B. merdac; Prevotella*, e.g., *P. melaninogenica*; genus *Fusobacterium; Treponema*, e.g. *T. pallidum* subspecies *endemicum, T. pallidum* subspecies *pertenue, T. carateum*, and *T. pallidum* subspecies *pallidum*; genus *Borrelia*, e.g., *B burgdorferi*; genus *Leptospira; Streptobacillus*, e.g., *S. moniliformis; Spirillum*, e.g., *S. minus; Mycobacterium*, e.g., *M. tuberculosis, M. bovis, M. africanum, M. avium M. intracellulare, M . . . kansasii, M. xenopi, M. marinum, M. ulcerans*, the *M. fortuitum* complex (*M. fortuitum* and *M. chelonei*), *M. leprae, M. asiaticum, M. chelonei* subsp. *abscessus, M. fallax, M. fortuitum, M. malmoense, M. shimoidei, M. simiac, M. szulgai, M. xenopi; Mycoplasma*, e.g., *M. hominis, M. orale, M. salivarium, M. fermentans, M. pneumoniac, M. bovis, M. tuberculosis, M. avium, M. leprae; Mycoplasma*, e.g., *M. genitalium; Ureaplasma*, e.g., *U. urealyticum; Trichomonas*, e.g., *T. vaginalis; Cryptococcus*, e.g., *C. ncoformans; Histoplasma*, e.g., *H. capsulatum; Candida*, e.g., *C. albicans; Aspergillus* sp; *Coccidioides*, e.g., *C. immitis; Blastomyces*, e.g. *B. dermatitidis; Paracoccidioides*, e.g., *P. brasiliensis; Penicillium*, e.g., *P. marneffei; Sporothrix*, e.g., *S. schenckii; Rhizopus, Rhizomucor, Absidia*, and *Basidiobolus*; diseases caused by *Bipolaris, Cladophialophora, Cladosporium, Drechslera, Exophiala, Fonsecaca, Phialophora, Xylohypha, Ochroconis, Rhinocladiella, Scolecobasidium*, and *Wangiella; Trichosporon*, e.g., *T. beigelii; Blastoschizomyces*, e.g., *B. capitatus; Plasmodium*, e.g., *P. falciparum, P. vivax, P. ovale*, and *P. malariae; Babesia* sp; protozoa of the genus *Trypanosoma*, e.g., *T. cruzi; Leishmania*, e.g., *L. donovani, L. major L. tropica, L. mexicana, L. braziliensis*, L. viannia *braziliensis; Toxoplasma*, e.g., *T. gondii*; Amoebas of the genera *Naegleria* or Acanthamocba; *Entamoeba histolytica; Giardia lamblia*; genus *Cryptosporidium*, e.g., *C. parvum; Isospora belli; Cyclospora cayetanensis; Ascaris lumbricoides; Trichuris trichiura; Ancylostoma duodenale* or *Necator americanus; Strongyloides stercoralis Toxocara*, e.g., *T. canis, T. cati; Baylisascaris*, e.g., *B. procyonis; Trichinella*, e.g., *T. spiralis; Dracunculus*, e.g., *D. medinensis*; genus *Filarioidea; Wuchereria bancrofti; Brugia*, e.g., *B. malayi*, or *B. timori; Onchocerca volvulus; Loa loa; Dirofilaria immitis*; genus *Schistosoma*, e.g., *S. japonicum, S. mansoni, S.*

*mekongi, S. intercalatum, S. haematobium; Paragonimus*, e.g., *P. Westermani, P. Skriabini; Clonorchis sinensis; Fasciola hepatica; Opisthorchis* sp; *Fasciolopsis buski; Diphyllobothrium latum; Taenia*, e.g., *T. saginata, T. solium; Echinococcus*, e.g., *E. granulosus, E. multilocularis*; Picornaviruses, rhinoviruses echoviruses, coxsackieviruses, influenza virus; paramyxoviruses, e.g., types 1, 2, 3, and 4; adnoviruses; Herpesviruses, e.g., HSV-1 and HSV-2; varicella-zoster virus; human T-lymphotrophic virus (type I and type II); Arboviruses and Arenaviruses; Togaviridae, Flaviviridae, Bunyaviridae, Reoviridae; Flavivirus; Hantavirus; Viral encephalitis (alphaviruses [e.g., Venezuelan equine encephalitis, eastern equine encephalitis, western equine encephalitis]); Viral hemorrhagic fevers (filoviruses [e.g., Ebola, Marburg] and arenaviruses [e.g., Lassa, Machupo]); Smallpox (variola); retroviruses e.g., human immunodeficiency viruses 1 and 2; human papillomavirus [HPV] types 6, 11, 16, 18, 31, 33, and 35.

In various embodiments, the probe can be selective for a polynucleotide sequence that is characteristic of an organisms selected from the group consisting of *Pseudomonas aeruginosa, Proteus mirabilis, Klebsiella oxytoca, Klebsiella pneumoniae, Escherichia coli, Acinetobacter Baumannii, Serratia marcescens, Enterobacter aerogenes, Enterococcus faecium*, vancomycin-resistant *enterococcus* (VRE), *Staphylococcus aureus*, methecillin-resistant *Staphylococcus aureus* (MRSA), *Streptococcus viridans, Listeria monocytogenes, Enterococcus* spp., *Streptococcus* Group B, *Streptococcus* Group C, *Streptococcus* Group G, *Streptococcus* Group F, *Enterococcus faecalis, Streptococcus pneumoniae, Staphylococcus epidermidis, Gardenerella vaginalis, Micrococcus* sps., *Haemophilus influenzae, Neisseria gonorrhoeee, Moraxella catarrahlis, Salmonella* sps., *Chlamydia trachomatis, Peptostreptococcus productus, Peptostreptococcus anaerobius, Lactobacillus fermentum, Eubacterium lentum, Candida glabrata, Candida albicans, Chlamydia* spp., *Camplobacter* spp., *Salmonella* spp., smallpox (variola major), Yersina Pestis, Herpes Simplex Virus I (HSV I), and Herpes Simplex Virus II (HSV II).

In various embodiments, the probe can be selective for a polynucleotide sequence that is characteristic of Group B *Streptococcus*.

In various embodiments, a method of carrying out PCR on a sample can further include one or more of the following steps: heating the biological sample in the microfluidic cartridge; pressurizing the biological sample in the microfluidic cartridge at a pressure differential compared to ambient pressure of between about 20 kilopascals and 200 kilopascals, or in some embodiments, between about 70 kilopascals and 110 kilopascals.

In some embodiments, the method for sampling a polynucleotide can include the steps of: placing a microfluidic cartridge containing a PCR-ready sample in a receiving bay of a suitably configured apparatus; carrying out PCR on the sample under thermal cycling conditions suitable for creating PCR amplicons from the neutralized polynucleotide in the sample, the PCR-ready sample comprising a polymerase enzyme, a positive control plasmid, a fluorogenic hybridization probe selective for at least a portion of the plasmid, and a plurality of nucleotides; contacting the neutralized polynucleotide sample or a PCR amplicon thereof with the at least one fluorogenic probe that is selective for a polynucleotide sequence, wherein the probe is selective for a polynucleotide sequence that is characteristic of an organism selected from the group consisting of gram positive bacteria, gram negative bacteria, yeast, fungi, protozoa, and viruses; and detecting the fluorogenic probe, the presence of the organism for which the one fluorogenic probe is selective is determined.

Carrying out PCR on a PCR-ready sample can additionally include: independently contacting each of the neutralized polynucleotide sample and a negative control polynucleotide with the PCR reagent mixture under thermal cycling conditions suitable for independently creating PCR amplicons of the neutralized polynucleotide sample and PCR amplicons of the negative control polynucleotide; and/or contacting the neutralized polynucleotide sample or a PCR amplicon thereof and the negative control polynucleotide or a PCR amplicon thereof with at least one probe that is selective for a polynucleotide sequence.

In various embodiments, a method of using the apparatus and cartridge described herein can further include one or more of the following steps: determining the presence of a polynucleotide sequence in the biological sample, the polynucleotide sequence corresponding to the probe, if the probe is detected in the neutralized polynucleotide sample or a PCR amplicon thereof; determining that the sample was contaminated if the probe is detected in the negative control polynucleotide or a PCR amplicon thereof; and/or in some embodiments, wherein the PCR reagent mixture further comprises a positive control plasmid and a plasmid probe selective for at least a portion of the plasmid, the method further including determining that a PCR amplification has occurred if the plasmid probe is detected.

Kit

In various embodiments, the microfluidic cartridge as described herein can be provided in the form of a kit, wherein the kit can include a microfluidic cartridge, and a liquid transfer member (such as a syringe or a pipette). In various embodiments, the kit can further include instructions to employ the liquid transfer member to transfer a sample containing extracted nucleic acid from a sample container via a sample inlet to the microfluidic network on the microfluidic cartridge. In some embodiments, the microfluidic cartridge and the liquid transfer member can be sealed in a pouch with an inert gas.

Typically when transferring a sample from liquid dispenser, such as a pipette tip, to an inlet on the microfluidic cartridge, a volume of air is simultaneously introduced into the microfluidic network, the volume of air being between about 0.5 mL and about 5 mL. Presence of air in the microfluidic network, however, is not essential to operation of the cartridge described herein.

In various embodiments, the kit can further include at least one computer-readable label on the cartridge. The label can include, for example, a bar code, a radio frequency tag or one or more computer-readable characters. When used in conjunction with a similar computer-readable label on a sample container, such as a vial or a pouch, matching of diagnostic results with sample is thereby facilitated.

In some embodiments, a sample identifier of the apparatus described elsewhere herein is employed to read a label on the microfluidic cartridge and/or a label on the biological sample.

Heater Unit

Figure 26:
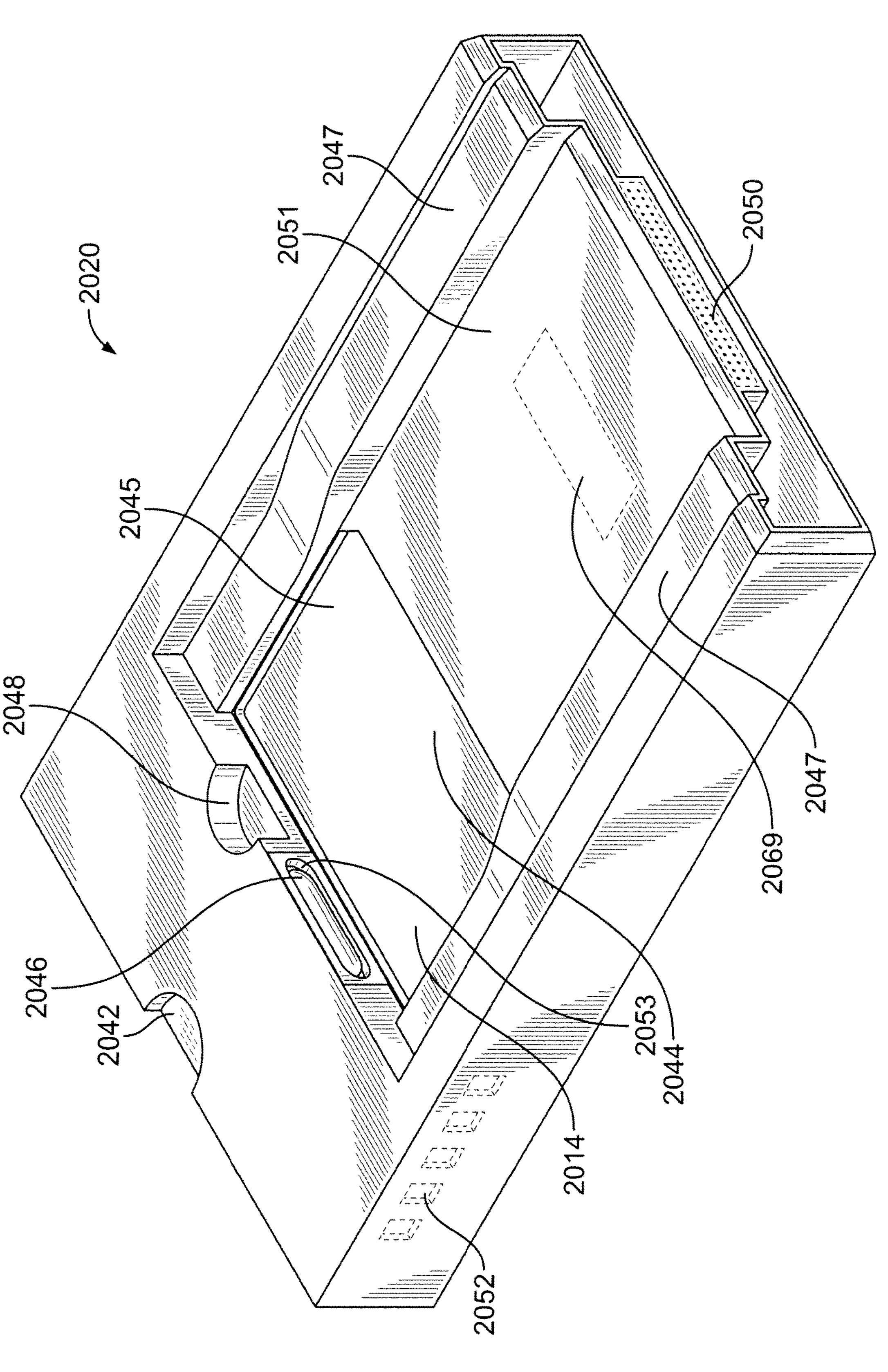
FIG. 26 shows an exemplary heater unit.

An exemplary heater unit 2020 is shown in FIG. 26. The unit is configured to deliver localized heat to various selected regions of a cartridge received in a receiving bay 2014. Heater unit 2020 is configured to be disposed within a diagnostic apparatus during operation, as further described herein, and in certain embodiments is removable from that apparatus, for example to facilitate cleaning, or to permit reconfiguration of the heater circuitry. In various embodiments, heater unit 2020 can be specific to particular designs of microfluidic networks and microfluidic substrate layouts.

Shown in FIG. 26 is a heater unit having a recessed surface 2044 that provides a platform for supporting a microfluidic cartridge when in receiving bay 2014. In one embodiment, the cartridge rests directly on surface 2044. Surface 2044 is shown as recessed, in FIG. 2, but need not be so and, for example, may be raised or may be flush with the surrounding area of the heater unit. Surface 2044 is typically a layer of material that overlies a heater chip or board, or a heater substrate, that contains heater micro-circuitry configured to selectively and specifically heat regions of a microfluidic substrate, such as in a cartridge, in the receiving bay 2014.

Area 2044 is configured to accept a microfluidic cartridge in a single orientation. Therefore area 2044 can be equipped with a registration member such as a mechanical key that prevents a user from placing a cartridge into receiving bay 2014 in the wrong configuration. Shown in FIG. 26 as an exemplary mechanical key 2045 is a diagonally cutout corner of area 2044 into which a complementarily cutoff corner of a microfluidic cartridge fits. Other registration members are consistent with the heater unit described herein, for example, a feature engineered on one or more edges of a cartridge including but not limited to: several, such as two or more, cut-out corners, one or more notches cut into one or more edges of the cartridge; or one or more protrusions fabricated into one or more edges of the cartridge. Alternative registration members include one or more lugs or bumps engineered into an underside of a cartridge, complementary to one or more recessed sockets or holes in surface 2044 (not shown in the embodiment of FIG. 26). Alternative registration members include one or more recessed sockets or holes engineered into an underside of a cartridge, complementary to one or more lugs or bumps on surface 2044. In general, the pattern of features is such that the cartridge possesses at least one element of asymmetry so that it can only be inserted in a single orientation into the receiving bay.

Also shown in FIG. 26 is a hand-grasp 2042 that facilitates removal and insertion of the heater unit into an apparatus by a user. Cutaway 2048 permits a user to easily remove a cartridge from receiving bay 2014 after a processing run where, e.g., a user's thumb or finger when grabbing the top of the cartridge, is afforded comfort space by cutaway 2048. Both cutaways 2042 and 2048 are shown as semicircular recesses in the embodiment of FIG. 26, but it would be understood that they are not so limited in shape. Thus, rectangular, square, triangular, half-oval, contoured, and other shaped recesses are also consistent with a heater unit as described herein.

In the embodiment of FIG. 26, which is designed to be compatible with an exemplary apparatus as further described herein, the front of the heater unit is at the left of the figure. At the rear of heater unit 2020 is an electrical connection 2050, such as an RS-232 connection, that permits electrical signals to be directed to heaters located at specific regions of area 2044 during sample processing and analysis, as further described herein. Thus, underneath area 2044 and not shown in FIG. 2 can be an array of heat sources, such as resistive heaters, that are configured to align with specified locations of a microfluidic cartridge properly inserted into the receiving bay. Surface 2044 is able to be cleaned periodically, for example with common cleaning agents (e.g., a 10% bleach solution), to ensure that any liquid spills that may occur during sample handling do not cause any short circuiting. Such cleaning can be carried out frequently when the heater unit is disposed in a diagnostic apparatus, and less frequently but more thoroughly when the unit is removed.

Other non-essential features of heater unit 2020 are as follows. One or more air vents 2052 can be situated on one or more sides (such as front, rear, or flanking) or faces (such as top or bottom) of heater unit 2020, to permit excess heat to escape, when heaters underneath receiving bay 2014, are in operation. The configuration of air vents in FIG. 26, as a linear array of square vents, is exemplary and it would be understood that other numbers and shapes thereof are consistent with routine fabrication and use of a heater unit. For example, although 5 square air vents are shown, other numbers such as 1, 2, 3, 4, 6, 8, or 10 air vents are possible, arranged on one side, or spread over two or more sides and/or faces of the heater unit. In further embodiments, air vents may be circular, rectangular, oval, triangular, polygonal, and having curved or squared vertices, or still other shapes, including irregular shapes. In further embodiments two or more vents need not be disposed in a line, parallel with one another and with an edge of the heater unit but may be disposed offset from one another.

Heater unit 2020 may further comprise one or more guiding members 2047 that facilitate inserting the heater unit into an apparatus as further described herein, for an embodiment in which heater unit 2020 is removable by a user. Heater unit is advantageously removable because it permits system 2000 to be easily reconfigured for a different type of analysis, such as employing a different cartridge with a different registration member and/or microfluidic network, in conjunction with the same or a different sequence of processing operations. In other embodiments, heater unit 2020 is designed to be fixed and only removable, e.g., for cleaning, replacement, or maintenance, by the manufacturer or an authorized maintenance agent, and not routinely by the user. Guiding members 2047 may perform one or more roles of ensuring that the heater unit is aligned correctly in the apparatus, and ensuring that the heater unit makes a tight fit and does not significantly move during processing and analysis of a sample, or during transport of the apparatus.

Guiding members shown in the embodiment of FIG. 26 are on either side of receiving bay 2044 and stretch along a substantial fraction of the length of unit 2020, but such an arrangement of guiding members is exemplary. Other guiding members are consistent with use herein, and include but are not limited to other numbers of guiding members such as 1, 3, 4, 5, 6, or 8, and other positions thereof, including positioned in area 2051 of unit 2020, and need not stretch along as much of the length of unit 2020 as shown in FIG. 26, or may stretch along its entire length. Guiding members 2047 are shown having a non-constant thickness along their lengths. It is consistent herein that other guiding members may have essentially constant thickness along their lengths. At the end of the heater unit that is inserted into an apparatus, in the embodiment shown, the edges are beveled to facilitate proper placement.

Also shown in FIG. 26 is an optional region of fluorescent material, such as optically fluorescent material 2069, on area 2051 of heater unit 2020. The region of fluorescent material is configured to be detected by a detection system further described herein. The region 2069 is used for verifying the state of optics in the detection system prior to sample processing and analysis and therefore acts as a control, or a standard. For example, in one embodiment a lid of the apparatus in which the heater unit is disposed, when in an open position, permits ambient light to reach region 2069 and thereby cause the fluorescent material to emit a characteristic frequency or spectrum of light that can be measured by the detector for, e.g., standardization or calibration purposes. In another embodiment, instead of relying on ambient light to cause the fluorescent material to fluoresce, light source from the detection system itself, such as one or more LED's, is used to shine on region 2069. The region 2069 is therefore positioned to align with a position of a detector. Region 2069 is shown as rectangular, but may be configured in other shapes such as square, circular, elliptical, triangular, polygonal, and having curved or squared vertices. It is also to be understood that the region 2069 may be situated at other places on the heater unit 2020, according to convenience and in order to be complementary to the detection system deployed.

In particular and not shown in FIG. 26, heater/sensor unit 2020 can include, for example, a multiplexing function in a discrete multiplexing circuit board (MUX board), one or more heaters (e.g., a microheater), one or more temperature sensors (optionally combined together as a single heater/sensor unit with one or more respective microheaters, e.g., as photolithographically fabricated on fused silica substrates). The micro-heaters can provide thermal energy that can actuate various microfluidic components on a suitably positioned microfluidic cartridge. A sensor (e.g., as a resistive temperature detector (RTD)) can enable real time monitoring of the micro-heaters, for example through a feedback based mechanism to allow for rapid and accurate control of the temperature. One or more microheaters can be aligned with corresponding microfluidic components (e.g., valves, pumps, gates, reaction chambers) to be heated on a suitably positioned microfluidic cartridge. A microheater can be designed to be slightly bigger than the corresponding microfluidic component(s) on the microfluidic cartridge so that even though the cartridge may be slightly misaligned, such as off-centered, from the heater, the individual components can be heated effectively.

Heater Configurations to Ensure Uniform Heating of a Region

The microfluidic substrates described herein are configured to accept heat from a contact heat source, such as found in a heater unit described herein. The heater unit typically comprises a heater board or heater chip that is configured to deliver heat to specific regions of the microfluidic substrate, including but not limited to one or more microfluidic components, at specific times. For example, the heat source is configured so that particular heating elements are situated adjacent to specific components of the microfluidic network on the substrate. In certain embodiments, the apparatus uniformly controls the heating of a region of a microfluidic network. In an exemplary embodiment, multiple heaters can be configured to simultaneously and uniformly heat a region, such as the PCR reaction chamber, of the microfluidic substrate. The term heater unit, as used herein, may be used interchangeably to describe either the heater board or an item such as shown in FIG. 26.

Figure 27A:
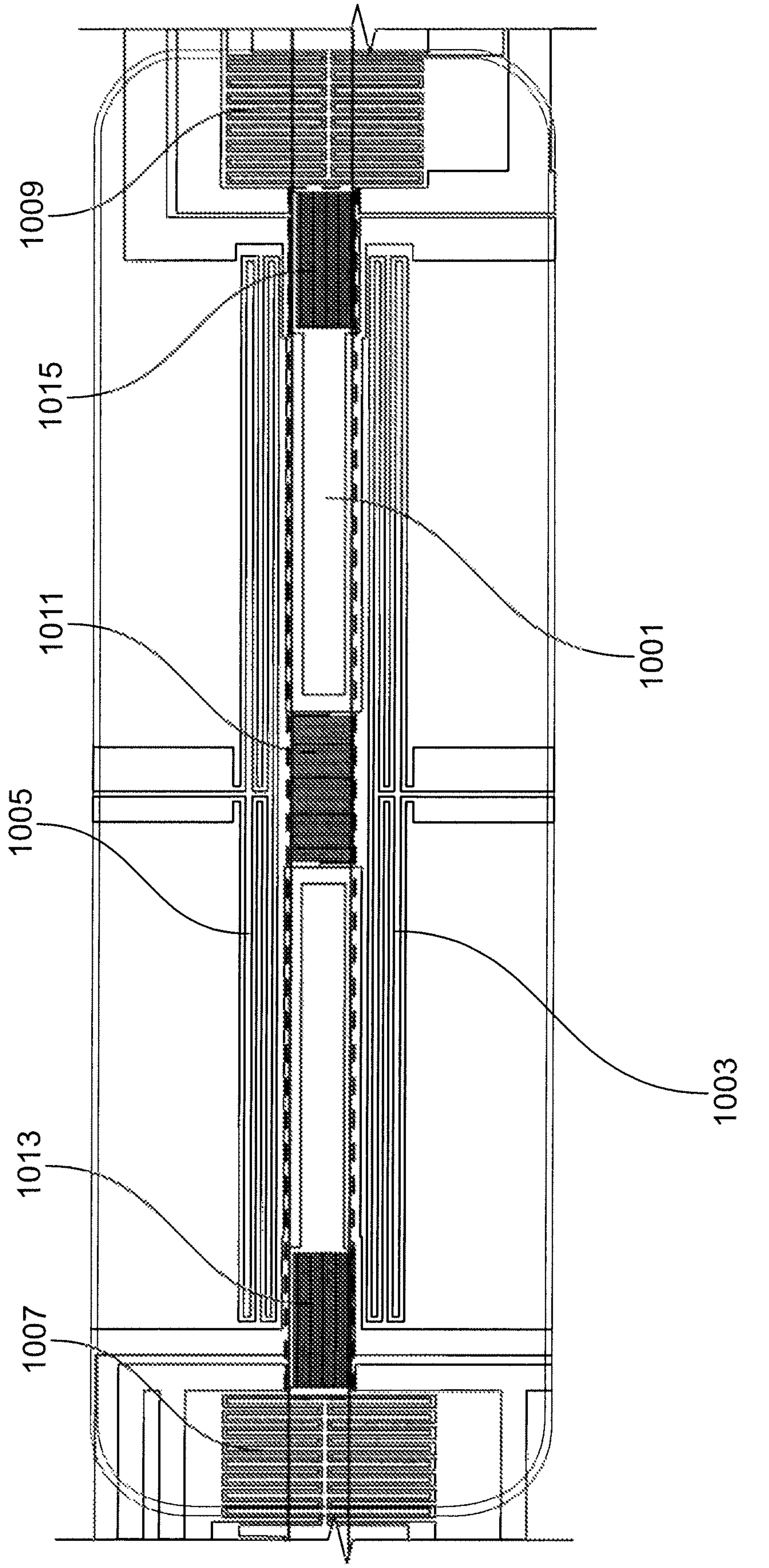
FIGS. 27A and 27B show a plan view of heater circuitry adjacent to a PCR reaction chamber.
Figure 27B:
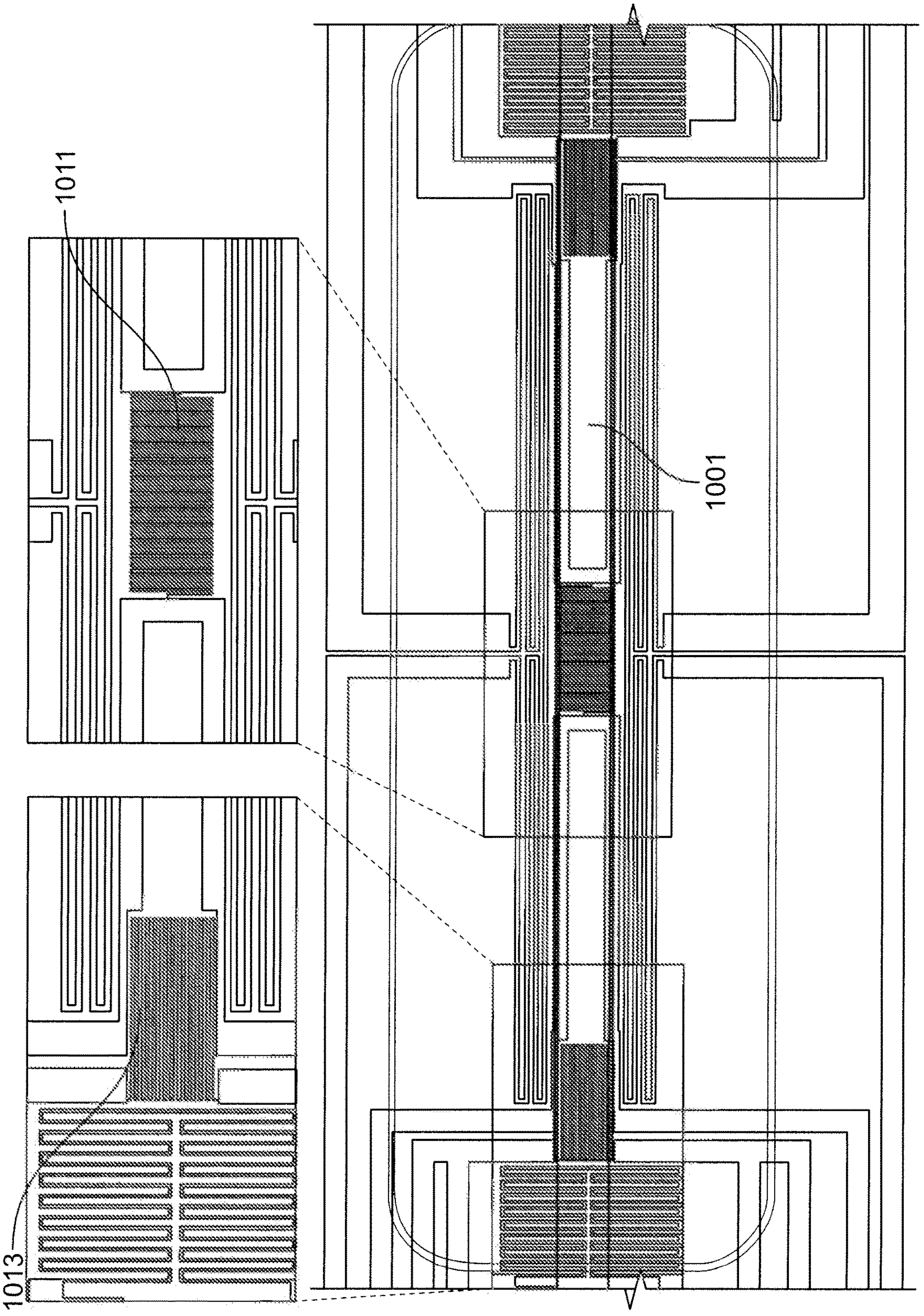

Referring to FIGS. 27A and 27B, an exemplary set of heaters configured to heat, cyclically, PCR reaction chamber 1001 is shown. It is to be understood that heater configurations to actuate other regions of a microfluidic cartridge such as other gates, valves, and actuators, may be designed and deployed according to similar principles to those governing the heaters shown in FIGS. 27A and 27B.

Referring to FIGS. 27A and 27B, an exemplary PCR reaction chamber 1001 in a microfluidic substrate, typically a chamber or channel having a volume ~1.6 μl, is configured with a long side and a short side, each with an associated heating element. A PCR reaction chamber may also be referred to as a PCR reactor, herein, and the region of a cartridge in which the reaction chamber is situated may be called a zone. The heater substrate therefore includes four heaters disposed along the sides of, and configured to heat, a given PCR reaction chamber, as shown in the exemplary embodiment of FIG. 27A: long top heater 1005, long bottom heater 1003, short left heater 1007, and short right heater 1009. The small gap between long top heater 1005 and long bottom heater 1003 results in a negligible temperature gradient (less than 1° C. difference across the width of the PCR channel at any point along the length of the PCR reaction chamber) and therefore an effectively uniform temperature throughout the PCR reaction chamber. The heaters on the short edges of the PCR reactor provide heat to counteract the gradient created by the two long heaters from the center of the reactor to the edge of the reactor.

It would be understood by one of ordinary skill in the art that still other configurations of one or more heater(s) situated about a PCR reaction chamber are consistent with the methods and apparatus described herein. For example, a 'long' side of the reaction chamber can be configured to be heated by two or more heaters. Specific orientations and configurations of heaters are used to create uniform zones of heating even on substrates having poor thermal conductivity because the poor thermal conductivity of glass, or quartz, polyimide, FR4, ceramic, or fused silica substrates is utilized to help in the independent operation of various microfluidic components such as valves and independent operation of the various PCR lanes. It would be further understood by one of ordinary skill in the art, that the principles underlying the configuration of heaters around a PCR reaction chamber are similarly applicable to the arrangement of heaters adjacent to other components of the microfluidic cartridge, such as actuators, valves, and gates.

Generally, the heating of microfluidic components, such as a PCR reaction chamber, is controlled by passing currents through suitably configured microfabricated heaters. Under control of suitable circuitry, the lanes of a multi-lane cartridge can then be controlled independently of one another. This can lead to a greater energy efficiency of the apparatus, because not all heaters are heating at the same time, and a given heater is receiving current for only that fraction of the time when it is required to heat. Control systems and methods of controllably heating various heating elements are further described in U.S. patent application Ser. No. 11/940,315, filed Nov. 14, 2007 and entitled "Heater Unit for Microfluidic Diagnostic System".

In certain embodiments, each heater has an associated temperature sensor. In the embodiment of FIG. 27A, a single temperature sensor 1011 is used for both long heaters. A temperature sensor 1013 for short left heater, and a temperature sensor 1015 for short right heater are also shown. The temperature sensor in the middle of the reactor is used to provide feedback and control the amount of power supplied to the two long heaters, whereas each of the short heaters has a dedicated temperature sensor placed adjacent to it in order to control it. As further described herein, temperature sensors are preferably configured to transmit information about temperature in their vicinity to a processor in the apparatus at such times as the heaters are not receiving current that causes them to heat. This can be achieved with appropriate control of current cycles.

In order to reduce the number of sensor or heater elements required to control a PCR heater, the heaters may be used to sense as well as heat, and thereby obviate the need to have a separate dedicated sensor for each heater. In another embodiment, each of the four heaters may be designed to have an appropriate wattage, and connect the four heaters in series or in parallel to reduce the number of electronically-controllable elements from four to just one, thereby reducing the burden on the associated electronic circuitry.

FIG. 27B shows expanded views of heaters and temperature sensors used in conjunction with a PCR reaction chamber of FIG. 27A. Temperature sensors 1001 and 1013 are designed to have a room temperature resistance of approximately 200-300 ohms. This value of resistance is determined by controlling the thickness of the metal layer deposited (e.g., a sandwich of 400 Å TiW/3,000 Å Au/400 Å TiW), and etching the winding metal line to have a width of approximately 10-25 μm and 20-40 mm length. The use of metal in this layer gives it a temperature coefficient of resistivity of the order of 0.5-20° C./ohms, preferably in the range of 1.5-3° C./ohms. Measuring the resistance at higher temperatures enables determination of the exact temperature of the location of these sensors.

The configuration for uniform heating, shown in FIG. 27A for a single PCR reaction chamber, can also be applied to a multi-lane PCR cartridge in which multiple independent PCR reactions occur.

Figure 27C:
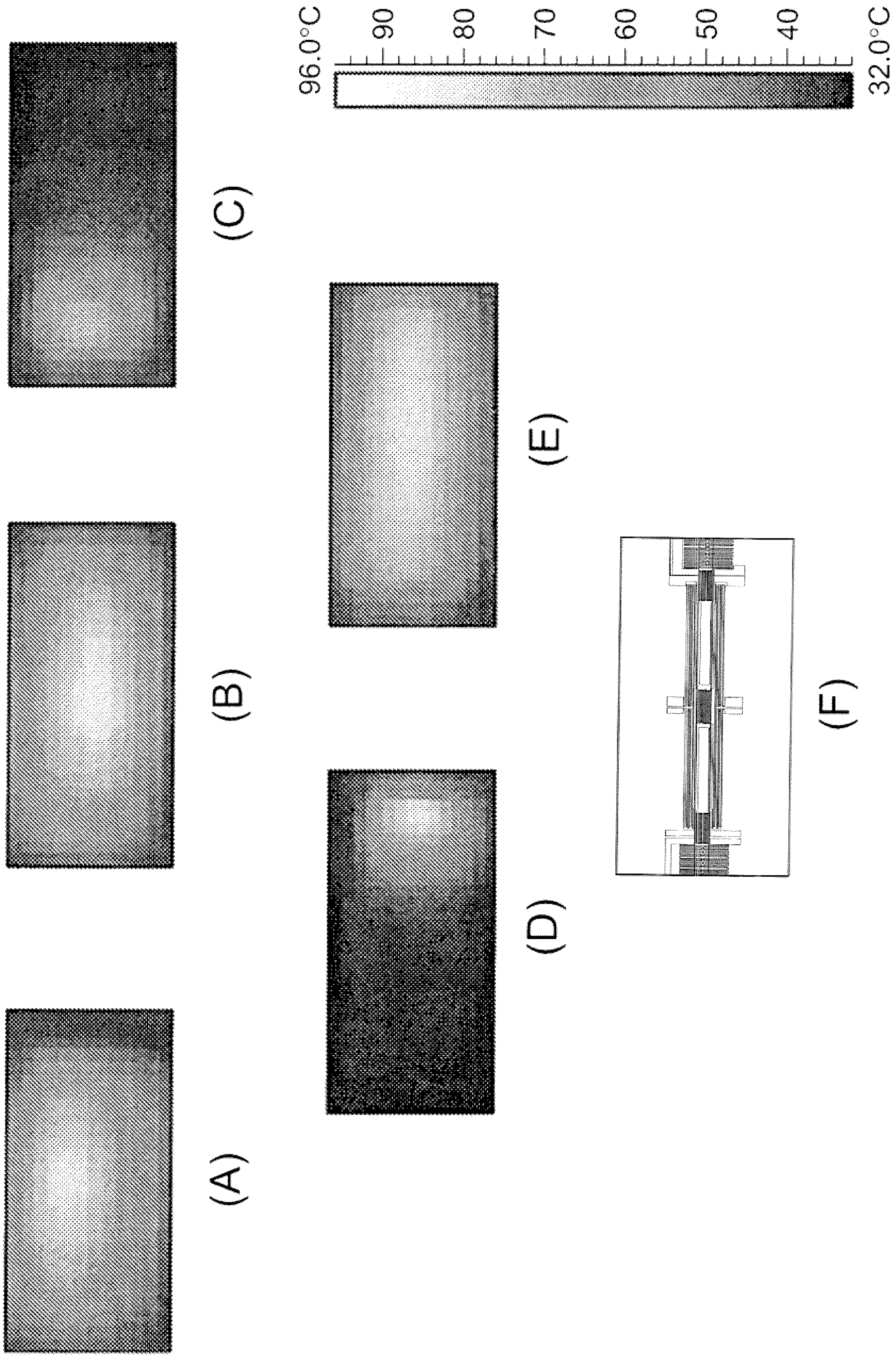
FIG. 27C shows thermal images of heater circuitry in operation.

Each heater can be independently controlled by a processor and/or control circuitry used in conjunction with the apparatus described herein. FIG. 27C shows thermal images, from the top surface of a microfluidic cartridge when heated by heaters configured as in FIGS. 27A and 27B, when each heater in turn is activated, as follows: (A): Long Top only; (B) Long Bottom only; (C) Short Left only; (D) Short Right only; and (E) All Four Heaters on. Panel (F) shows a view of the reaction chamber and heaters on the same scale as the other image panels in FIG. 27C. Also shown in the figure is a temperature bar.

The configuration for uniform heating, shown in FIG. 27A for a single PCR reaction chamber, can be applied to a multi-lane PCR cartridge in which multiple independent PCR reactions occur. See, e.g., FIG. 28, which shows an array of heater elements suitable to heat a cartridge herein.

Heater Multiplexing (Under Software Control)

Another aspect of the heater unit described herein, relates to a control of heat within the system and its components. The method leads to a greater energy efficiency of the apparatus described herein, because not all heaters are heating at the same time, and a given heater is receiving current for only part of the time.

Generally, the heating of microfluidic components, such as a PCR reaction chamber, is controlled by passing currents through suitably configured microfabricated heaters. The heating can be further controlled by periodically turning the current on and off with varying pulse width modulation (PWM), wherein pulse width modulation refers to the on-time/off-time ratio for the current. The current can be supplied by connecting a microfabricated heater to a high voltage source (for example, 30 V), which can be gated by the PWM signal. In some embodiments, the device includes 48 PWM signal generators. Operation of a PWM generator includes generating a signal with a chosen, programmable, period (the end count) and a particular granularity. For instance, the signal can be 4000 μs (micro-seconds) with a granularity of 1 μs, in which case the PWM generator can maintain a counter beginning at zero and advancing in increments of 1 us until it reaches 4000 μs, when it returns to zero. Thus, the amount of heat produced can be adjusted by adjusting the end count. A high end count corresponds to a greater length of time during which the microfabricated heater receives current and therefore a greater amount of heat produced. It would be understood that the granularity and signal width can take values other than those provided here without departing from the principles described herein.

Fluorescence Detection System, Including Lenses and Filters, and Multiple Parallel Detection for a Multi-Lane Cartridge The detection system herein is configured to monitor fluorescence coming from one or more species involved in a biochemical reaction. The system can be, for example, an optical detector having a light source that selectively emits light in an absorption band of a fluorescent dye, and a light detector that selectively detects light in an emission band of the fluorescent dye, wherein the fluorescent dye corresponds to a fluorescent polynucleotide probe or a fragment thereof, as further described elsewhere herein. Alternatively, the optical detector can include a bandpass-filtered diode that selectively emits light in the absorption band of the fluorescent dye and a bandpass filtered photodiode that selectively detects light in the emission band of the fluorescent dye. For example, the optical detector can be configured to independently detect a plurality of fluorescent dyes having different fluorescent emission spectra, wherein each fluorescent dye corresponds to a fluorescent polynucleotide probe or a fragment thereof. For example, the optical detector can be configured to independently detect a plurality of fluorescent dyes at a plurality of different locations of, for example, a microfluidic substrate, wherein each fluorescent dye corresponds to a fluorescent polynucleotide probe or a fragment thereof. The detector further has potential for 2, 3 or 4 color detection and is controlled by software, preferably custom software, configured to sample information from the detector.

The detection system described herein is capable of detecting a fluorescence signal from nanoliter scale PCR reactions. Advantageously, the detector is formed from inexpensive components, having no moving parts. The detector can be configured to couple to a microfluidic cartridge as further described herein, and can also be part of a pressure application system, such as a sliding lid on an apparatus in which the detector is situated, that keeps the cartridge in place.

Figure 31A:
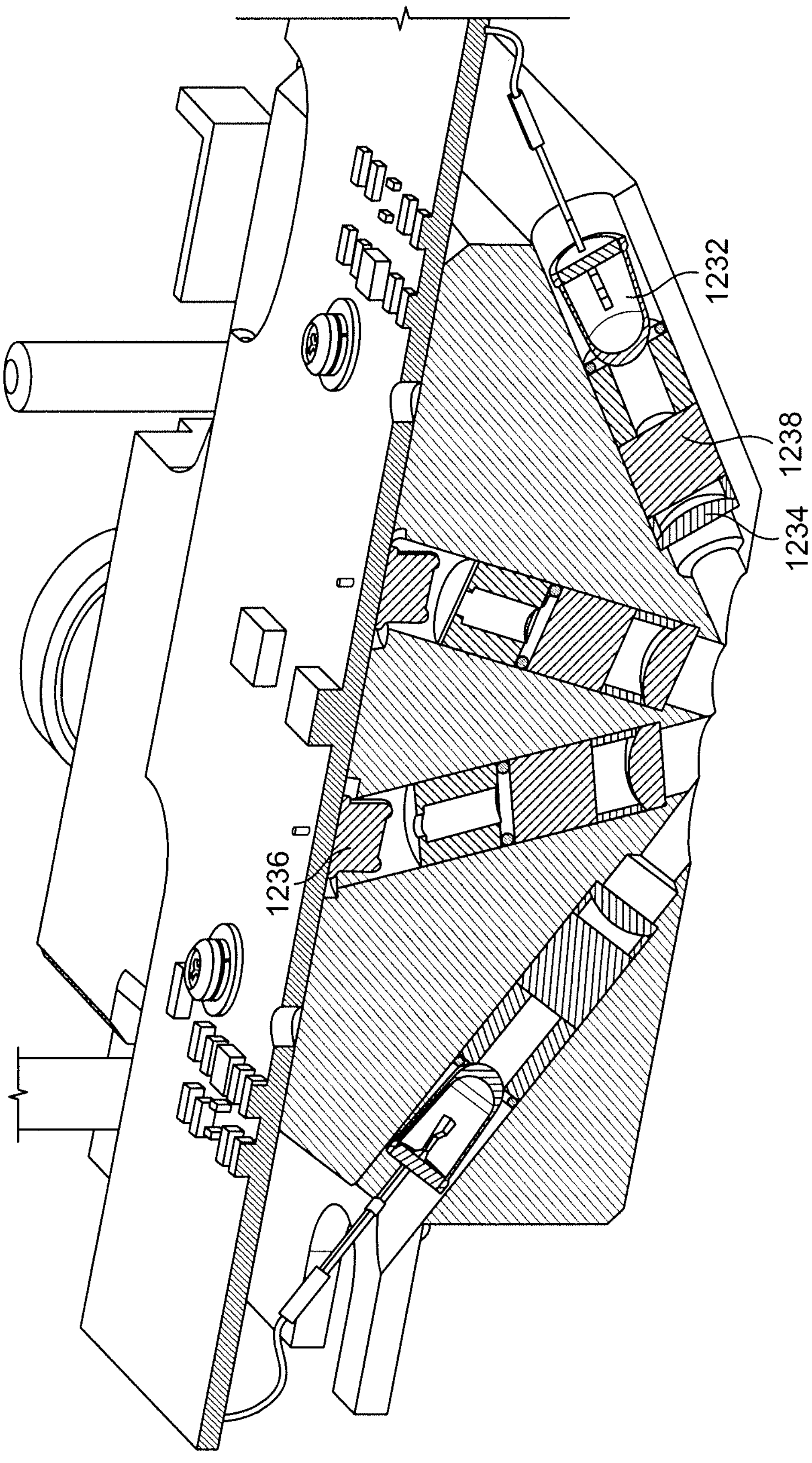
FIG. 31A, 31B shows a cutaway view of an exemplary detector in a read-head.
Figure 31B:
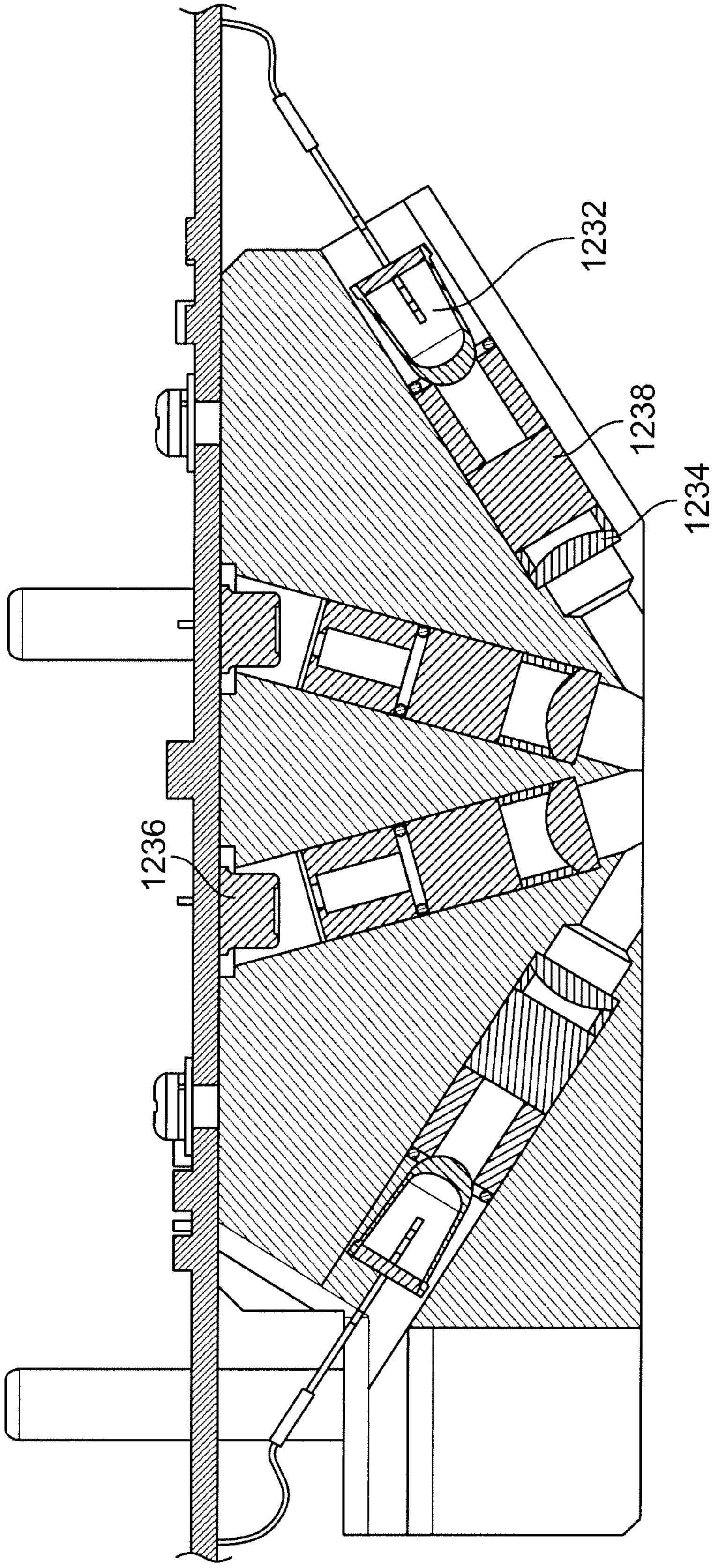

FIGS. 29-31B depict an embodiment of a highly sensitive fluorescence detection system that includes light emitting diodes (LED's), photodiodes, and filters/lenses for monitoring, in real-time, one or more fluorescent signals emanating from the microfluidic channel. The embodiment in FIGS. 29-31B displays a two-color detection system having a modular design that couples with a single microfluidic channel found, for example, in a microfluidic cartridge. It would be understood by one skilled in the art that the description herein could also be adapted to create a detector that just detects a single color of light. FIGS. 31A and 31B show elements of optical detector elements 1220 including light sources 1232 (for example, light emitting diodes), lenses 1234, light detectors 1236 (for example, photodiodes) and filters 1238. The detector comprises two LED's (blue and red, respectively) and two photodiodes. The two LED's are configured to transmit a beam of focused light on to a particular region of the cartridge. The two photo diodes are configured to receive light that is emitted from the region of the cartridge. One photodiode is configured to detect emitted red light, and the other photodiode is configured to detect emitted blue light. Thus, in this embodiment, two colors can be detected simultaneously from a single location. Such a detection system can be configured to receive light from multiple microfluidic channels by being mounted on an assembly that permits it to slide over and across the multiple channels. The filters can be, for example, bandpass filters, the filters at the light sources corresponding to the absorption band of one or more fluorogenic probes and the filters at the detectors corresponding to the emission band of the fluorogenic probes.

Figure 32:
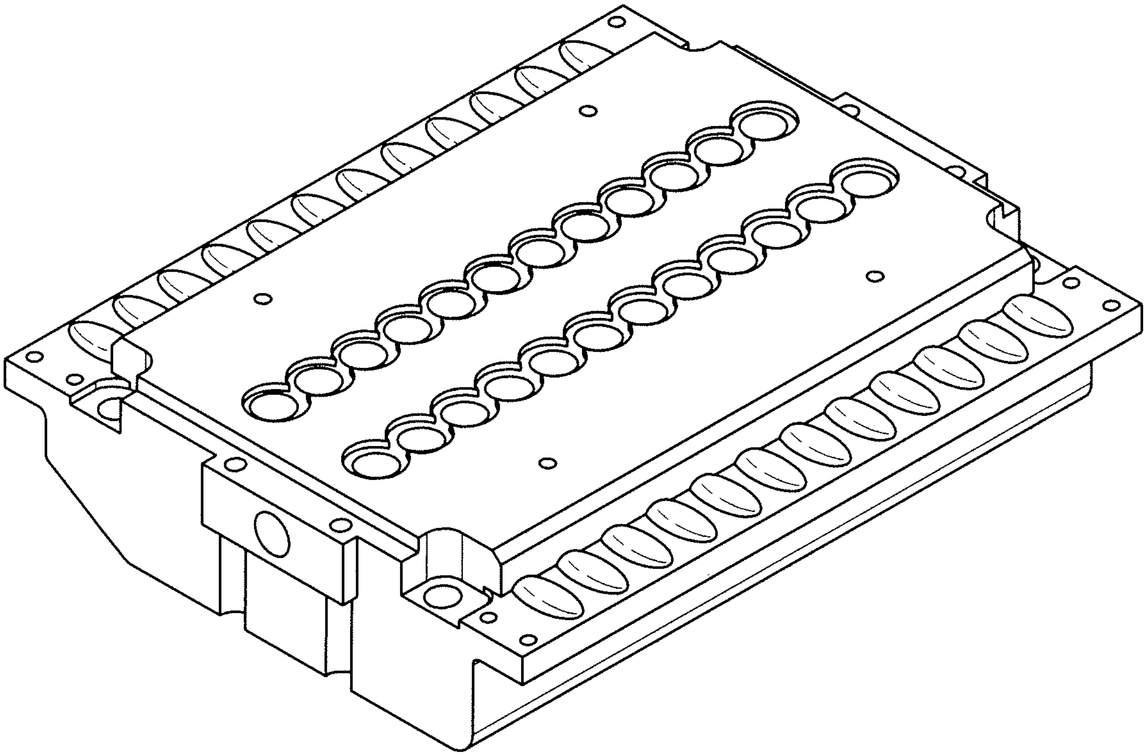
FIG. 32 shows an exterior view of an exemplary multiplexed read-head with an array of detectors therein.
Figure 33:
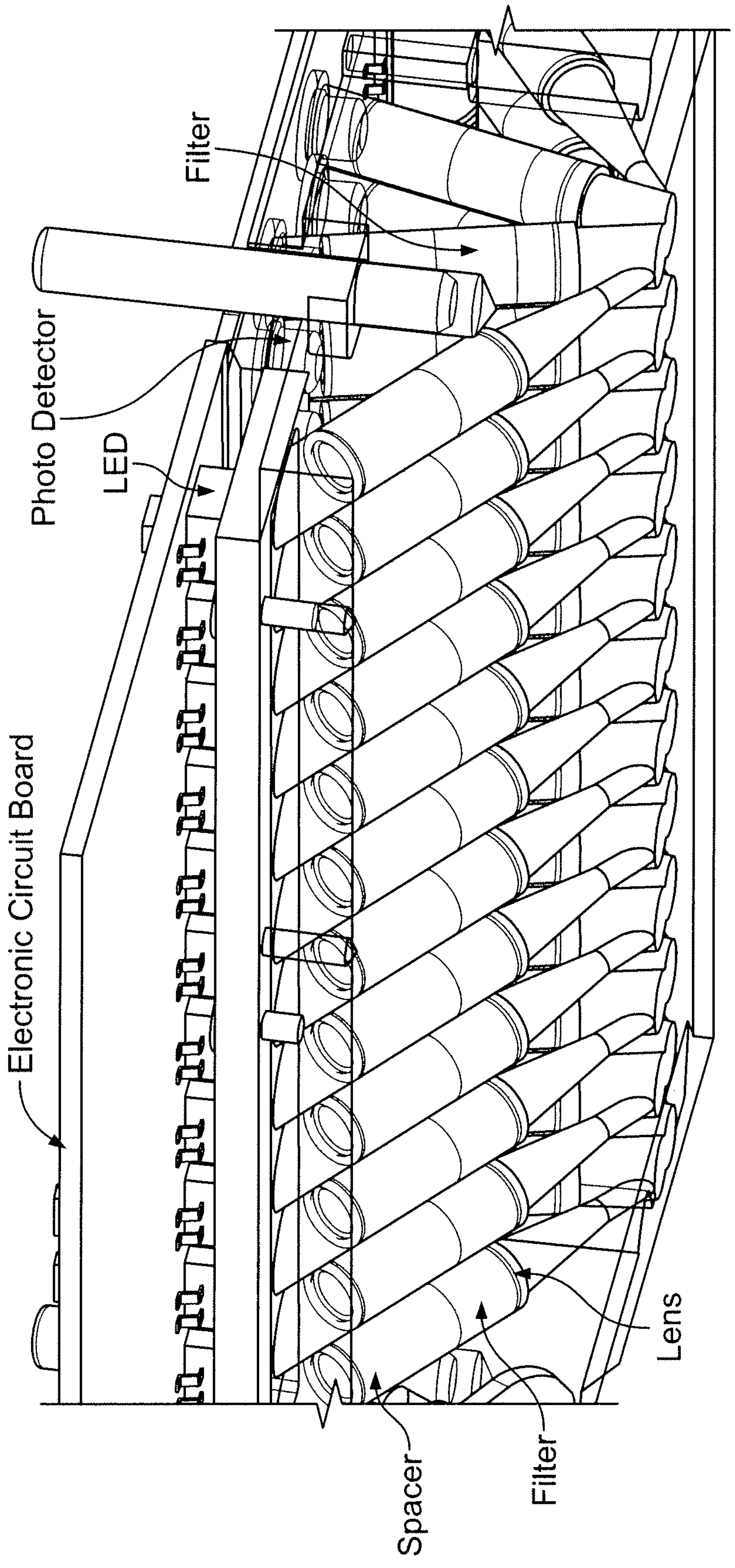
FIG. 33 shows a cutaway view of an exemplary multiplexed read-head, as in FIG. 18.

FIGS. 32 and 33 show an exemplary read-head comprising a multiplexed 2 color detection system that is configured to mate with a multi-lane microfluidic cartridge. FIG. 32 shows a view of the exterior of a multiplexed read-head. FIG. 33 is an exploded view that shows how various detectors are configured within an exemplary multiplexed read head, and in communication with an electronic circuit board.

Each of the detection systems multiplexed in the assembly of FIGS. 32 and 33 is similar in construction to the embodiment of FIGS. 29-31B. The module in FIGS. 32 and 33 is configured to detect fluorescence from each of 12 microfluidic channels, as found in, for example, the respective lanes of a 12-lane microfluidic cartridge. Such a module therefore comprises 24 independently controllable detectors, arranged as 12 pairs of identical detection elements. Each pair of elements is then capable of dual-color detection of a predetermined set of fluorescent probes. It would be understood by one of ordinary skill in the art that other numbers of pairs of detectors are consistent with the apparatus described herein. For example, 4, 6, 8, 10, 16, 20, 24, 25, 30, 32, 36, 40, and 48 pairs are also consistent and can be configured according to methods and criteria understood by one of ordinary skill in the art.

Detection Sensitivity, Time Constant and Gain

A typical circuit that includes a detector as described herein includes, in series, a preamplifier, a buffer/inverter, a filter, and a digitizer. Sensitivity is important so that high gain is very desirable. In one embodiment of the preamplifier, a very large, for example 100 GΩ, resistor is placed in parallel with the diode. Other values of a resistor would be consistent with the technology herein: such values typically fall in the range 0.5-100 GΩ, such as 1-50 GΩ, or 2-10 GΩ. An exemplary pre-amplifier circuit configured in this way is shown in FIG. 7. Symbols in the figure have their standard meanings in electronic circuit diagrams.

Figure 34:
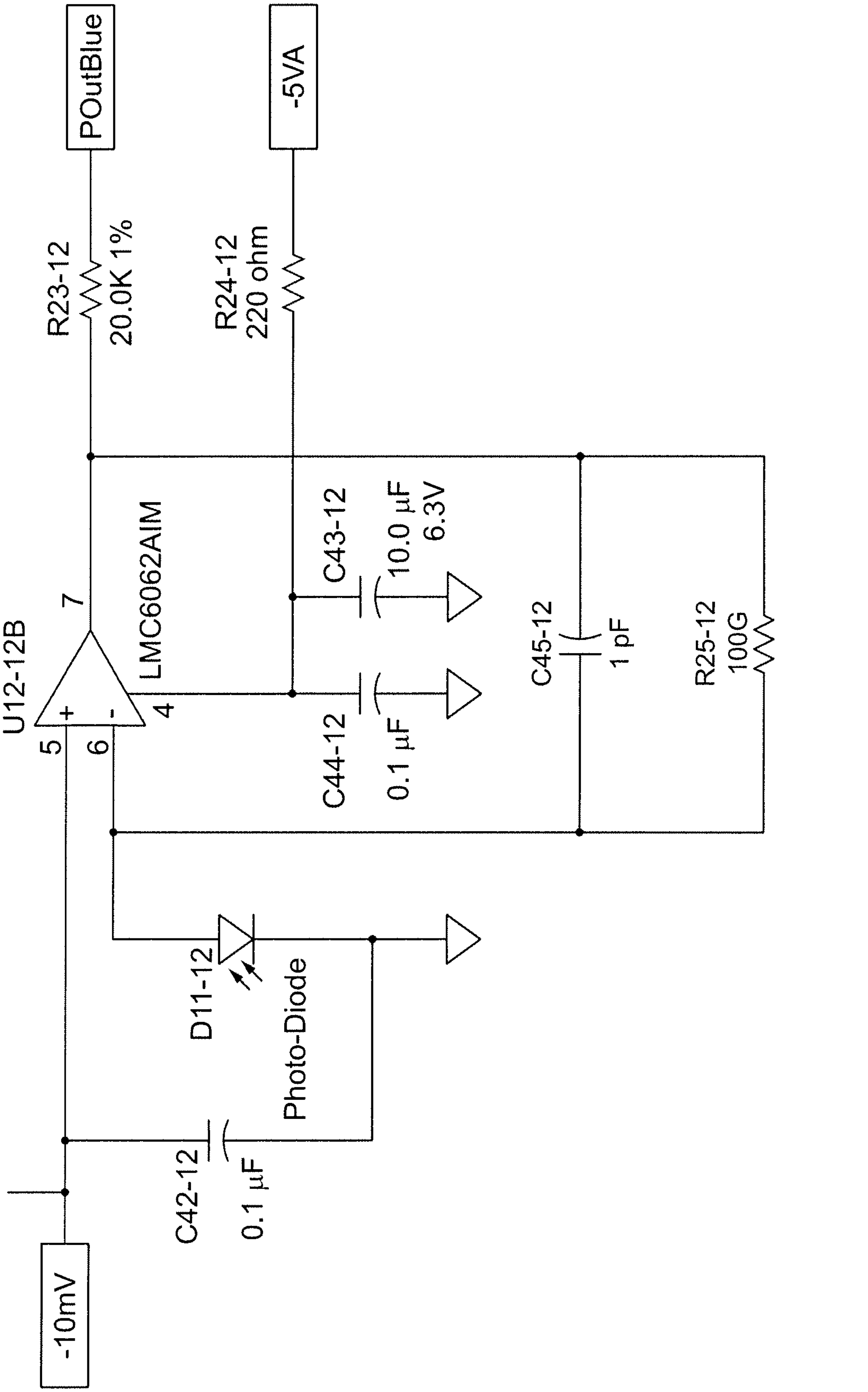
FIG. 34 shows exemplary pre-amplifier circuitry for a fluorescence detector.

The FIG. 34 shows a current-to-voltage converter/pre-amplifier circuit suitable for use with the detection system. D11 is the photodetector that collects the fluorescent light coming from the microfluidic channel and converts it into an electric current. The accompanying circuitry is used to convert these fluorescent currents into voltages suitable for measurement and output as a final measure of the fluorescence.

A resistor-capacitor circuit in FIG. 34 contains capacitor C45 and resistor R25. Together, the values of capacitance of C45 and resistance of R25 are chosen so as to impact the time constant $\tau_c$ (equal to the product of R25 and C45) of the circuit as well as gain of the detection circuit. The higher the time constant, the more sluggish is the response of the system to incident light. It typically takes the duration of a few time constants for the photodetector to completely charge to its maximum current or to discharge to zero from its saturation value. It is important for the photo current to decay to zero between measurements, however. As the PCR systems described herein are intended to afford rapid detection measurements, the product $R_{25}C_{45}$ should therefore be made as low as possible. However, the gain of the pre-amplifier whose circuitry is shown is directly proportional to the (fluorescent-activated) current generated in the photodetector and the resistance $R_{25}$. As the fluorescence signal from the microfluidic channel device is very faint (due to low liquid volume as well as small path lengths of excitation), it is thus important to maximize the value of $R_{25}$. In some embodiments, $R_{25}$ is as high as 100 Giga-Ohms (for example, in the range 10-100 GΩ, effectively behaving as an open-circuit. With such values, the time-constant can take on a value of approximately 50-100 ms by using a low-value capacitor for C45. For example, the lowest possible available standard off-the-shelf capacitor has a value of 1 pF (1 picoFarad). A time-constant in the range 50-100 ms ensures that the photocurrent decays to zero in approximately 0.5 s (approx. 6 cycles) and therefore that approximately 2 samplings can be made per second. Other time constants are consistent with effective use of the technology herein, such as in the range 10 ms-1 s, or in the range 50 ms-500 ms, or in the range 100-200 ms. The actual time constant suitable for a given application will vary according to circumstance and choice of capacitor and resistor values. Additionally, the gain achieved by the pre-amplifier circuit herein may be in the range of $10^7$-$5\times10^9$, for example may be $1\times10^9$.

As the resistance value for R25 is very high (~100 GΩ, the manner of assembly of this resistor on the optics board is important for the overall efficiency of the circuit. Effective cleaning of the circuit during assembly and before use is important to achieve an optimal time-constant and gain for the optics circuit.

It is also important to test each photo-diode that is used, because many do not perform according to specification.

Sensitivity and Aperturing

The LED light passes through a filter before passing through the sample in the microfluidic channel (as described herein, typically 300μ deep). This is a very small optical path-length for the light in the sample. The generated fluorescence then also goes through a second filter, and into a photo-detector. Ultimately, then, the detector must be capable of detecting very little fluorescence. Various aspects of the detector configuration can improve sensitivity, however.

Figure 35A:
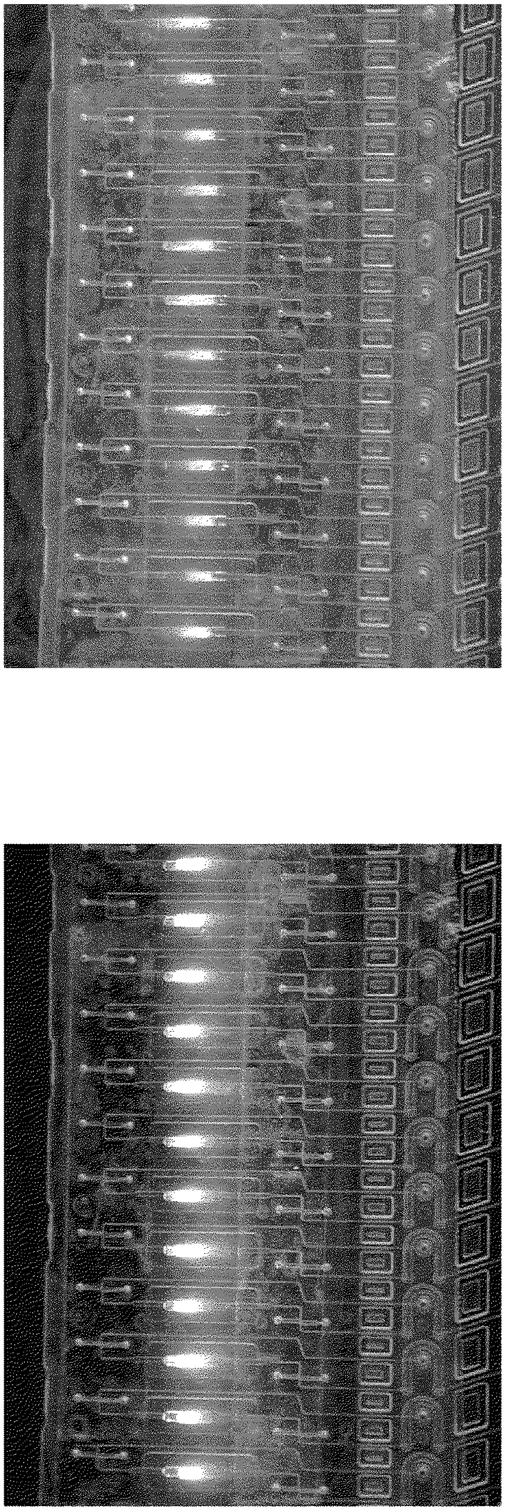
FIG. 35A shows effects of aperturing on fluorescence intensity.
Figure 35B:
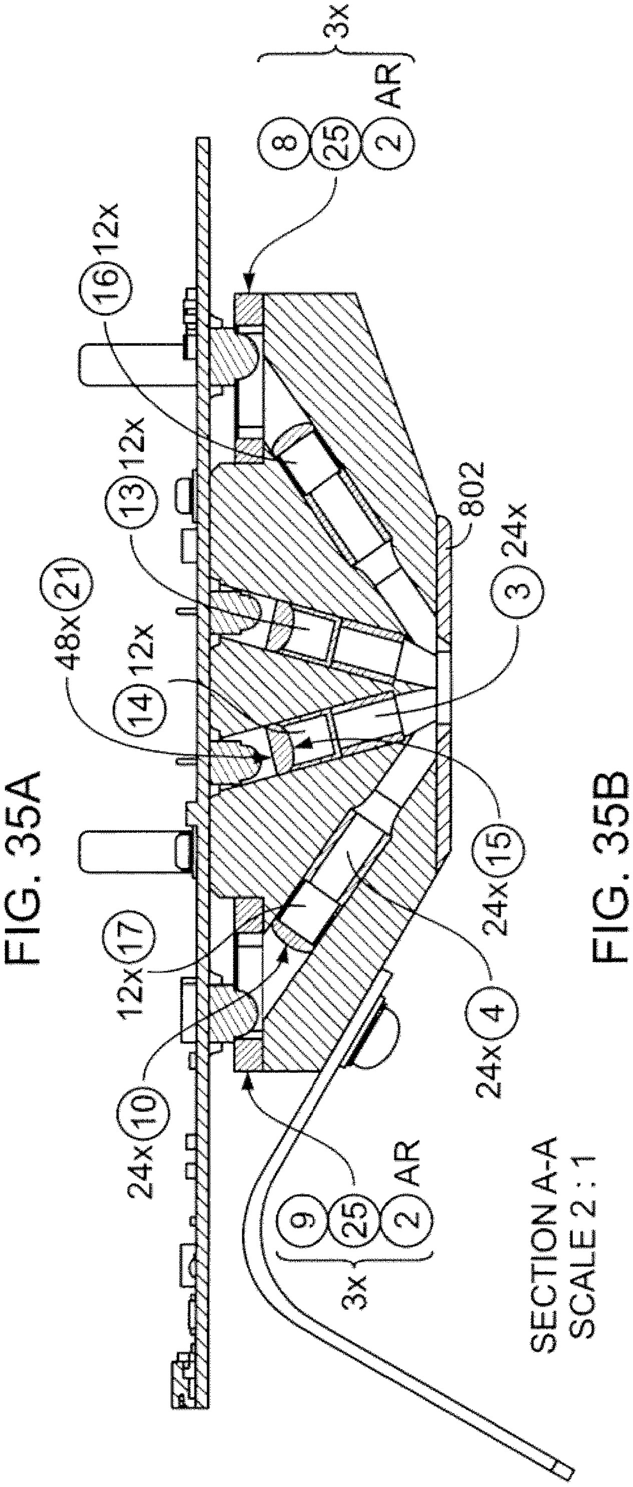
FIG. 35B shows a detector in cross section with an exemplary aperture.

The illumination optics can be designed so that the excitation light falling on the PCR reactor is incident along an area that is similar to the shape of the reactor. As the reactor is typically long and narrow, the illumination spot should be long and narrow, i.e., extended, as well. The length of the spot can be adjusted by altering a number of factors, including: the diameter of the bore where the LED is placed (the tube that holds the filter and lens has an aperturing effect); the distance of the LED from the PCR reactor; and the use of proper lens at the right distance in between. As the width of the beam incident on the reactor is determined by the bore of the optical element (approximately 6 mm in diameter), it is typical to use an aperture (a slit having a width approximately equal to the width of the reactor, and a length equal to the length of the detection volume) to make an optimal illumination spot. A typical spot, then, is commensurate with the dimensions of a PCR reaction chamber, for example 1.5 mm wide by 7 mm long. FIG. 35A shows the illumination spot across 12 PCR reactors for the two different colors used. A typical aperture is made of anodized aluminum and has very low autofluorescence in the wavelengths of interest. FIG. 35B illustrates a cross-section of a detector, showing an exemplary location for an aperture 802.

The optimal spot size and intensity is importantly dependent on the ability to maintain the correct position of the LED's with respect to the center of the optical axis. Special alignment procedures and checks can be utilized to optimize this. The different illuminations can also be normalized with respect to each other by adjusting the power current through each of the LED's or adjusting the fluorescence collection time (the duration for which the photodetector is on before measuring the voltage) for each detection spot. It is also important to align the detectors with the axis of the micro-channels.

The aperturing is also important for successful fluorescence detection because as the cross-sectional area of the incident beam increases in size, so the background fluorescence increases, and the fluorescence attributable only to the molecules of interest (PCR probes) gets masked. Thus, as the beam area increases, the use of an aperture increases the proportion of collected fluorescence that originates only from the PCR reactor. Note that the aperture used in the detector herein not only helps collect fluorescence only from the reaction volume but it correspondingly adjusts the excitation light to mostly excite the reaction volume. The excitation and emission aperture is, of course, the same.

Based on a typical geometry of the optical excitation and emission system and aperturing, show spot sizes as small as 0.5 mm by 0.5 mm and as long as 8 mm×1.5 mm have been found to be effective. By using a long detector (having an active area 6 mm by 1 mm) and proper lensing, the aperture design can extend the detection spot to as long as 15-20 mm, while maintaining a width of 1-2 mm using an aperture. Correspondingly, the background fluorescence decreases as the spot size is decreased, thereby increasing the detection sensitivity.

Use of Detection System to Measure/Detect Fluid in PCR Chamber

The fluorescence detector is sensitive enough to be able to collect fluorescence light from a PCR chamber of a microfluidic substrate. The detector can also be used to detect the presence of liquid in the chamber, a measurement that provides a determination of whether or not to carry out a PCR cycle for that chamber. For example, in a multi-sample cartridge, not all chambers will have been loaded with sample; for those that are not, it would be unnecessary to apply a heating protocol thereto. One way to determine presence or absence of a liquid is as follows. A background reading is taken prior to filling the chamber with liquid. Another reading is taken after microfluidic operations have been performed that should result in filling the PCR chamber with liquid. The presence of liquid alters the fluorescence reading from the chamber. A programmable threshold value can be used to tune an algorithm programmed into a processor that controls operation of the apparatus as further described herein (for example, the second reading has to exceed the first reading by 20%). If the two readings do not differ beyond the programmed margin, the liquid is deemed to not have entered the chamber, and a PCR cycle is not initiated for that chamber. Instead, a warning is issued to a user.

Exemplary Electronics and Software

Figure 36:
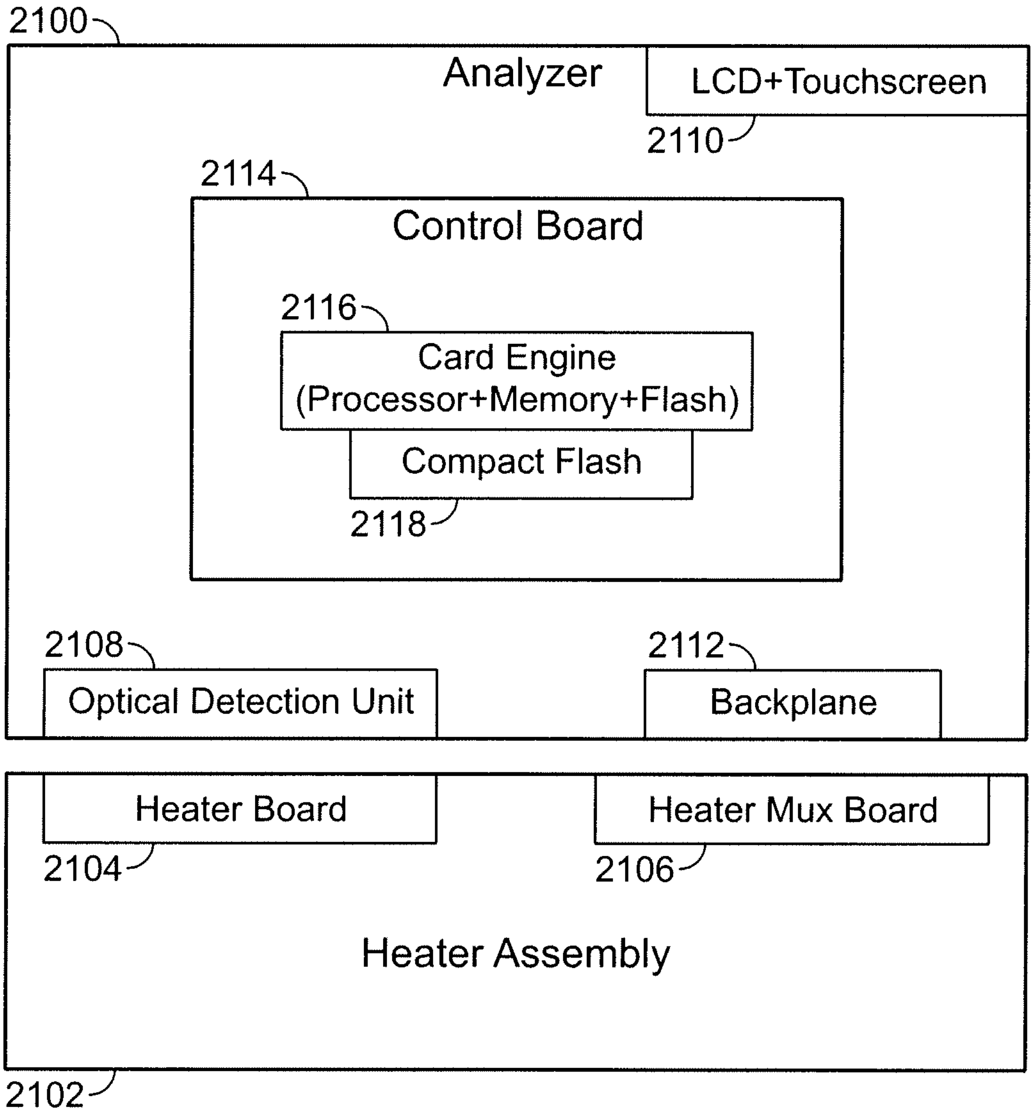
FIG. 36 shows an exemplary layout for electronics and software components, as further described herein.

The heater unit described herein can be controlled by various electronics circuitry, itself operating on receipt of computer-controlled instructions. FIG. 36 illustrates exemplary electronics architecture modules for operating a heater unit and diagnostic apparatus. It would be understood by one of ordinary skill in the art that other configurations of electronics components are consistent with operation of the apparatus as described herein. In the exemplary embodiment, the electronics architecture is distributed across two components of the apparatus: the Analyzer 2100 and a Heater unit 2102. The Analyzer apparatus as further described herein contains, for example, an Optical Detection Unit 2108, a Control Board 2114, a Backplane 2112, and a LCD Touchscreen 2110. The Control Board includes a Card Engine 2116 further described herein, and Compact Flash memory 2118, as well as other components. The Heater Assembly includes a Heater Board 2104 and a Heater Mux Board 2106, both further described herein.

In one embodiment, the Card Engine electronics module 2116 is a commercial, off the shelf "single board computer" containing a processor, memory, and flash memory for operating system storage.

The optional LCD+Touchscreen electronics module 2110 is a user interface, for example, driven through a touchscreen, such as a 640 pixel by 480 pixel 8 inch LCD and 5-wire touchscreen.

The Compact Flash electronics module 2118 is, for example, a 256 megabyte commercial, off the shelf, compact flash module for application and data storage. Other media are alternatively usable, such as USB-drive, smart media card, memory stick, and smart data-card having the same or other storage capacities.

The Backplane electronics module 2112 is a point of connection for the removable heater assembly 2102. Bare PC boards with two connectors are sufficient to provide the necessary level of connectivity.

The Control Board electronics module 2114 supports peripherals to the Card Engine electronics module 2116. In one embodiment, the peripherals include such devices as a USB host+slave or hub, a USB CDROM interface, serial ports, and ethernet ports. The Control Board 2114 can include a power monitor with a dedicated processor. The Control Board may also include a real time clock. The Control Board may further include a speaker. The Control Board 2114 also includes a CPLD to provide SPI access to all other modules and programming access to all other modules. The Control Board includes a programmable high voltage power supply. The Control Board includes a Serial-Deserializer interface to the LCD+Touchscreen electronics module 2110 and to the Optical Detection Unit electronics module 2108. The Control Board also includes module connectors.

In the exemplary embodiment, the optical detection unit electronics module 2108 contains a dedicated processor. The optical detection unit 2108 contains a serializer-deserializer interface. The optical detection unit 2108 contains LED drivers. The optical detection unit also contains high gain-low noise photodiode amplifiers. The optical detection unit can have power monitoring capability. The optical detection unit can also be remotely reprogrammable.

The Heater Board electronics module 2104 is preferably a glass heater board. The Heater Board has PCB with bonding pads for glass heater board and high density connectors.

In one embodiment, the heater mux ('multiplex') board electronics module 2106 has 24 high-speed ADC, 24 precision current sources, and 96 optically isolated current drivers for heating. The heater mux board has the ability to time-multiplex heating/measurement. The heater mux board has multiplexer banks to multiplex inputs to ADC, and to multiplex current source outputs. The heater mux board has a FPGA with a soft processor core and SDRAM. The heater mux board has a Power Monitor with a dedicated processor. The Heater Mux Board can be remotely reprogrammable.

In another embodiment, control electronics can be spread over four different circuit board assemblies. These include the MAIN board: Can serve as the hub of the Analyzer control electronics and manages communication and control of the other various electronic subassemblies. The main board can also serve as the electrical and communications interface with the external world. An external power supply (12V DC/10 A; UL certified) can be used to power the system. The unit can communicate via 5 USB ports, a serial port and an Ethernet port. Finally, the main board can incorporate several diagnostic/safety features to ensure safe and robust operation of the Analyzer.

MUX Board: Upon instruction from the main board, the MUX board can perform all the functions typically used for accurate temperature control of the heaters and can coordinate the collection of fluorescence data from the detector board.

LCD Board: Can contain the typical control elements to light up the LCD panel and interpret the signals from the touch sensitive screen. The LCD/touch screen combination can serve as a mode of interaction with the user via a Graphical User Interface.

Detector Board: Can house typical control and processing circuitry that can be employed to collect, digitize, filter, and transmit the data from the fluorescence detection modules.

Certain software can be executed in each electronics module. The Control Board Electronics Module executes, for example, Control Board Power Monitor software. The Card Engine electronics module executes an operating system, graphical user interface (GUI) software, an analyzer module, and an application program interface (api). The Optical Detection Unit electronics module executes an optics software module. The Heater Mux Board electronics module executes dedicated Heater Mux software, and Heater Mux Power Monitor software. Each of the separate instances of software can be modular and under a unified control of, for example, driver software.

The exemplary electronics can use Linux, UNIX, Windows, or MacOS, including any version thereof, as the operating system. The operating system is preferably loaded with drivers for USB, Ethernet, LCD, touchscreen, and removable media devices such as compact flash. Miscellaneous programs for configuring the Ethernet interface, managing USB connections, and updating via CD-ROM can also be included.

In the embodiment of FIG. 36, the analyzer module is the driver for specific hardware. The analyzer module provides access to the Heater Mux Module, the Optical Detection Unit, the Control Board Power Monitor, the Real Time Clock, the High Voltage Power Supply, and the LCD backlight. The analyzer module provides firmware programming access to the Control Board power monitor, the Optical Detection Unit, and the Heater Mux Module.

The API provides uniform access to the analyzer module driver. The API is responsible for error trapping, and interrupt handling. The API is typically programmed to be thread safe.

The GUI software can be based on a commercial, off-the-shelf PEG graphics library. The GUI can use the API to coordinate the self-test of optical detection unit and heater assembly. The GUI starts, stops, and monitors test progress. The GUI can also implement an algorithm to arrive on diagnosis from fluorescence data. The GUI provides access control to unit and in some embodiments has an HIS/LIS interface.

The Control Board Power Monitor software monitors power supplies, current and voltage, and signals error in case of a fault.

The Optics Software performs fluorescence detection which is precisely timed to turn on/off of LED with synchronous digitization of the photodetector outputs. The Optics Software can also monitor power supply voltages. The Optics Software can also have self test ability.

The Heater Mux Module software implements a "protocol player" which executes series of defined "steps" where each "step" can turn on sets of heaters to implement a desired microfluidic action. The Heater Mux Module software also has self test ability. The Heater Mux Module software contains a fuzzy logic temperature control algorithm.

The Heater Mux Power Monitor software monitors voltage and current levels. The Heater Mux Power Monitor software can participate in self-test, synchronous, monitoring of the current levels while turning on different heaters.

EXAMPLES

The following are exemplary aspects of various parts and functions of the system described herein.

Additional embodiments of a cartridge are found in U.S. patent application Ser. No. 11/940,310, entitled "Microfluidic Cartridge and Method of Making Same", and filed on even date herewith, the specification of which is incorporated herein by reference.

Additional embodiments of heater units and arrays are described in U.S. patent application Ser. No. 11/940,315, entitled "Heater Unit for Microfluidic Diagnostic System" and filed on even date herewith, the specification of which is incorporated herein by reference in its entirety.

Further description of suitably configured detectors are described in U.S. patent application Ser. No. 11/940,321, filed on Nov. 14, 2007 and entitled "Fluorescence Detector for Microfluidic Diagnostic System", incorporated herein by reference.

Example 1: Analyzer Having Removable Heater Unit

This non-limiting example describes pictorially, various embodiments of an apparatus, showing incorporation of a heater unit and a microfluidic cartridge operated on by the heater unit.

Figure 37:
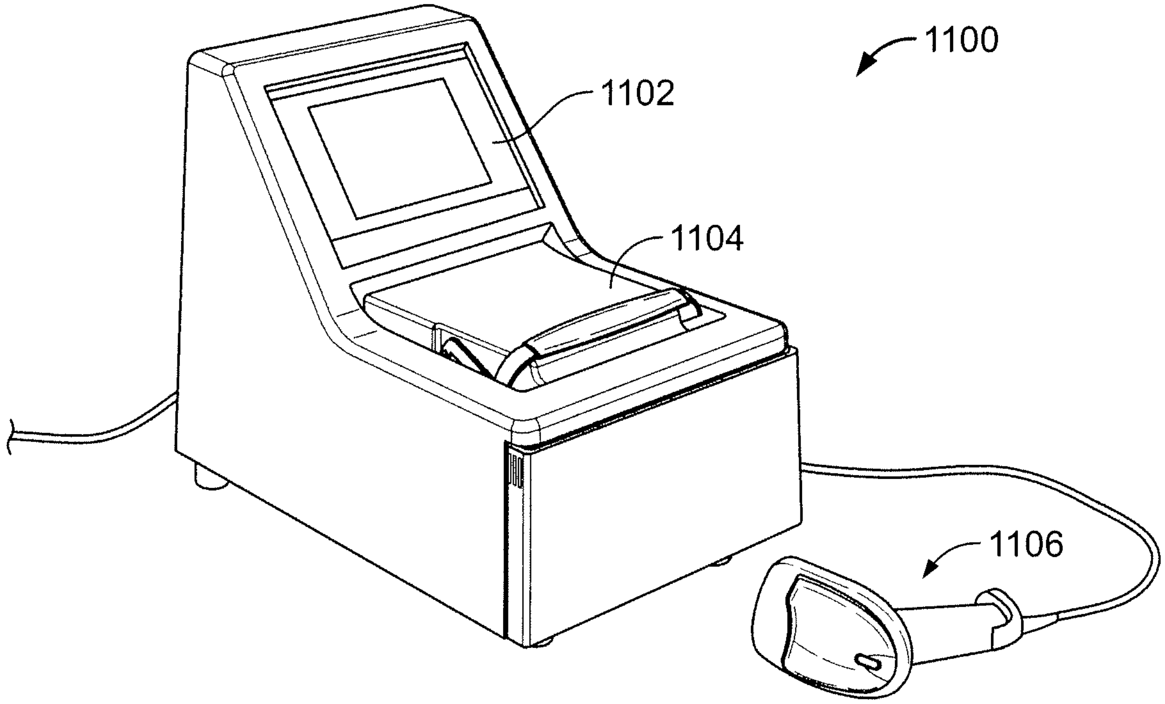
FIG. 37 shows an exemplary apparatus, a microfluidic cartridge, and a read head, as further described herein.
Figure 38:
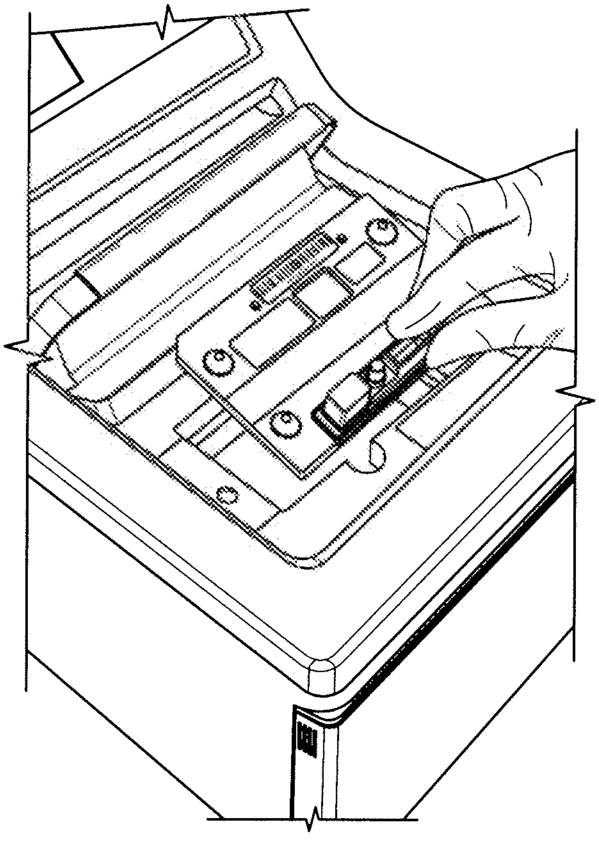
FIGS. 38-39 show positioning of a cartridge in an exemplary apparatus.
Figure 39:
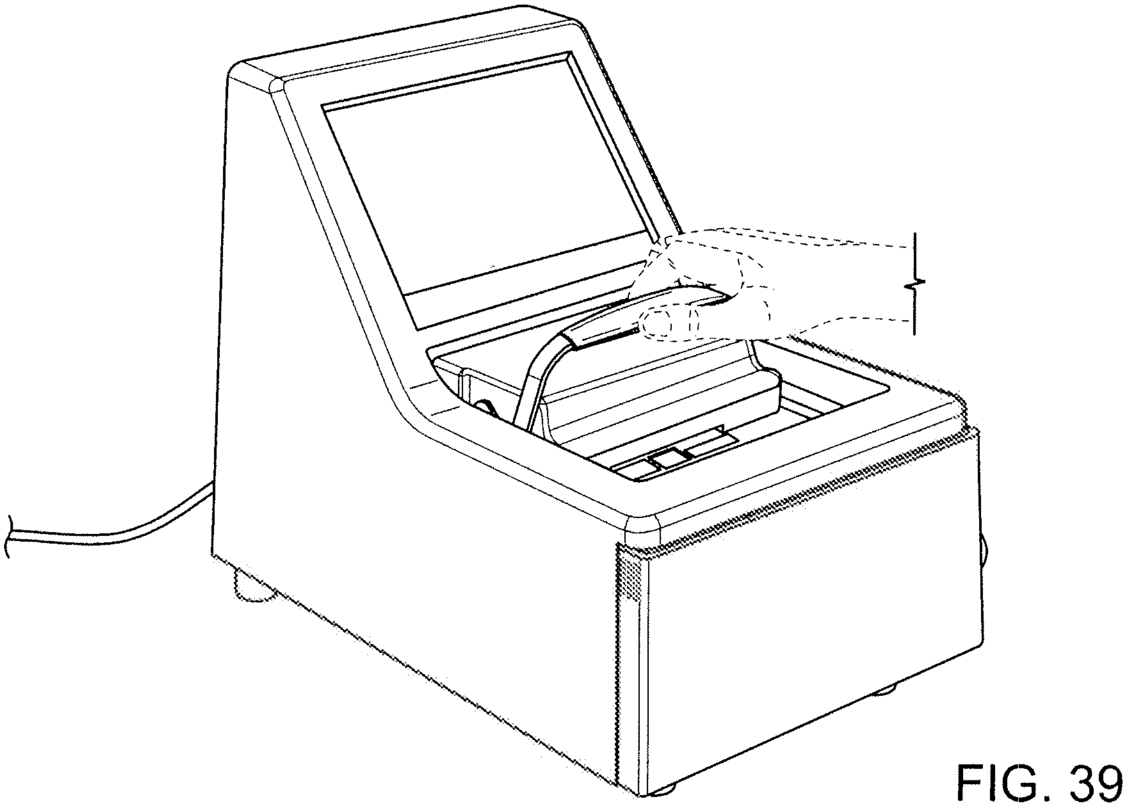

FIG. 37 shows an apparatus 1100 that includes a housing having a display output 1102, an openable lid 1104, and a bar code reader 1106. The cartridge is positioned in a single orientation in a receiving bay under the lid, FIG. 38. The lid of the apparatus can be closed to apply pressure to the cartridge, as shown in FIG. 39. The unit currently weighs about 20 lbs. and is approximately 10" wide by 16" deep by 13" high.

Figure 40:
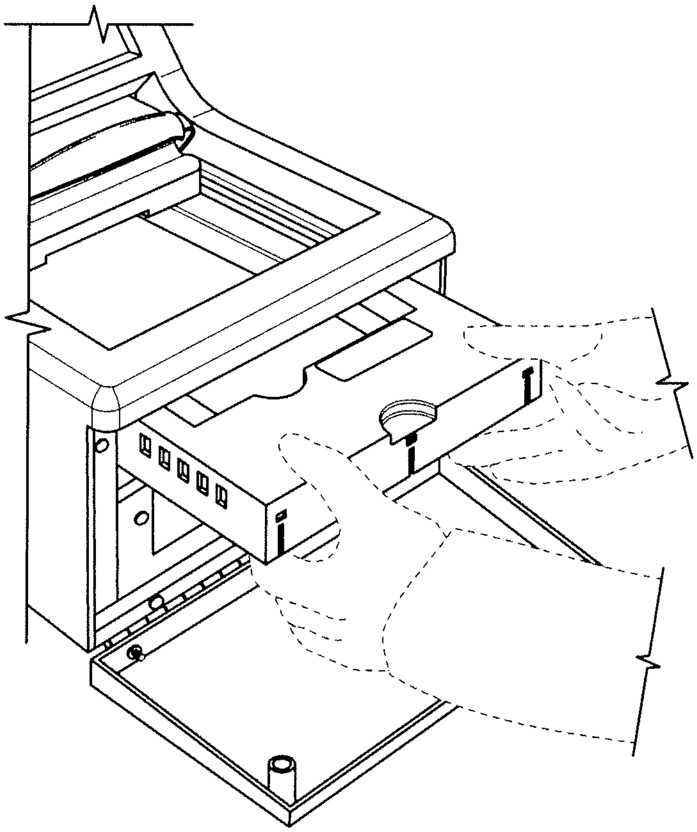
FIGS. 40 and 41 show removal of a heater unit from an exemplary apparatus.
Figure 41:
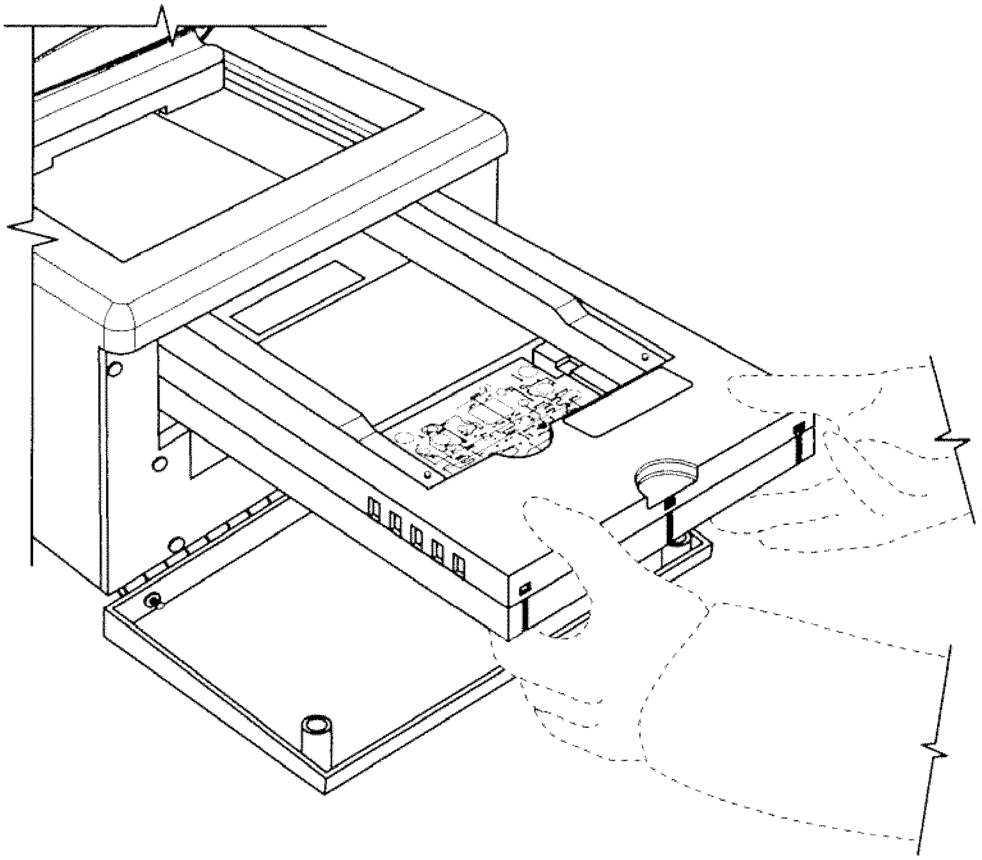

FIGS. 40 and 41: The heating stage of the apparatus can be removable for cleaning, maintenance, or to replace a custom heating stage for a particular microfluidic cartridge. FIGS. 40 and 41 also show how a heater unit is insertable and removable from a front access door to an analyzer apparatus.

Example 2: Assembly of an Exemplary Heater Unit

Figure 42B:
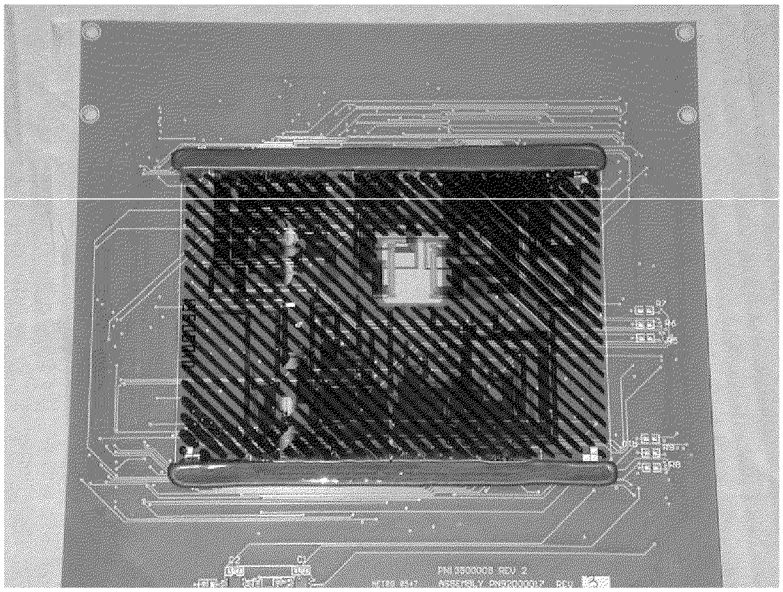
FIGS. 42A and 42B show an exemplary heater unit and heater substrate.
Figure 42A:
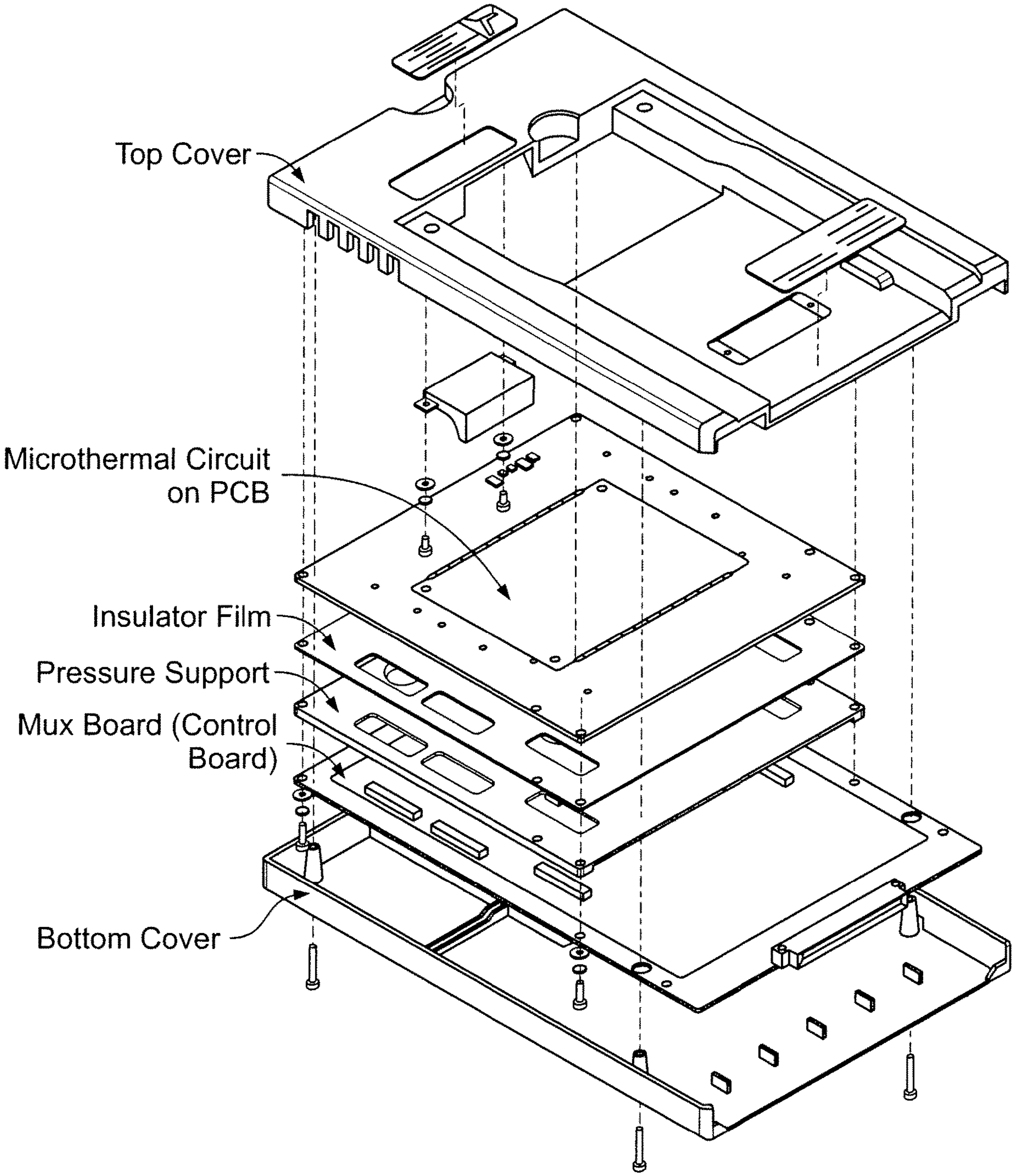

FIG. 42A shows an exploded view of an exemplary heater unit. The unit has a top cover and a bottom cover that together enclose a Mux board (control board), a pressure support layer, and insulator film, and a microthermal circuit on a PCB. The last of these is the heat source that selectively heats regions of a microfluidic substrate placed in contact therewith through the top cover.

An exemplary heater substrate, FIG. 42B, consists of a photo-lithographically processed glass wafer bonded to a standard 0.100" standard FR4 printed circuit board. The glass wafer is 0.5 mm thick and is cut into a rectangle the size of ~3.5×4.25 inches. The glass substrate has numerous metal heaters and resistive temperature sensors photo-lithographically etched on the surface of the glass wafer. The substrate is aligned and bonded to the PCBoard using a compliant epoxy, ensuring flatness to within 2-3 mils over the surface of the wafer. The cured epoxy should withstand up to 120° C. for two hours minimum. Approximately 300-400 bond pads of the size of approximately 1 mm×0.25 mm, with exposed gold surfaces, are located along the two long edges of the wafer. These pads are wirebonded (ball-bonding) to corresponding pads on the PCB using 1.5 mil gold wires. Wire bonding is a threading process, standard in semiconductor FAB. Alternatively, a flip-chip method may be used, though such methods are more complicated and may warp the wafer because of thermal mismatch. Wire bonds should have good integrity and pass defined pull strength. The substrate is baked at 120° C. for two hours and then the wire bonds are encapsulated by a compliant epoxy that will protect the wirebonds but not damage the bonds even at 120° C. Encapsulant should not spill over predefined area around the wirebonds and should not be taller than a defined height. For example, instead of laying epoxy all over the substrate, lines (e.g., a hash pattern) of it are made so that epoxy cures and air escapes through side. Alternatively, a laminate fill (adhesive on both sides) can be used. Standard connectors are soldered to the PCB and then the unit is tested using a test set-up to ensure all heaters and sensors read the right resistance values.

Figure 28:
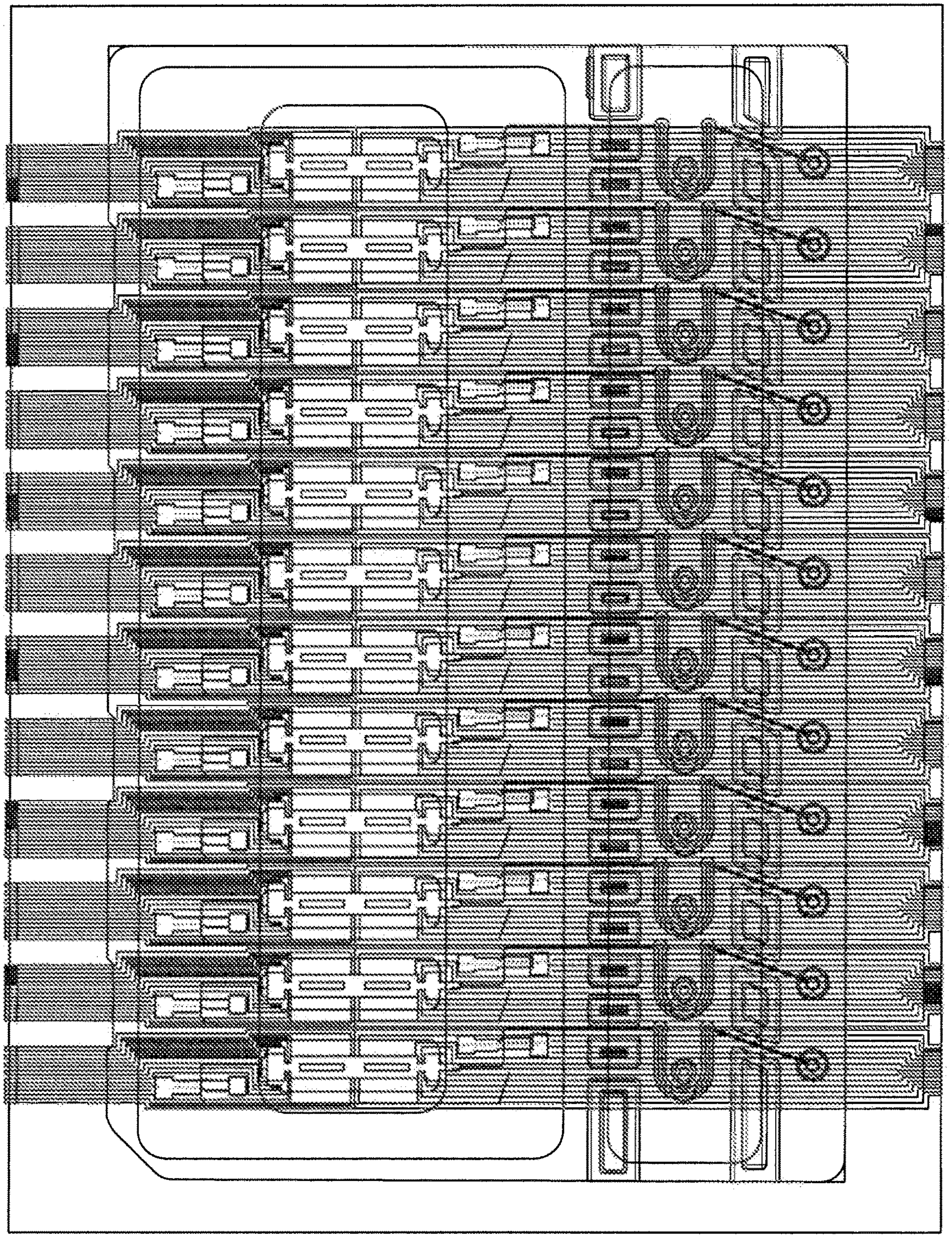
FIG. 28 shows an overlay of an array of heater elements on an exemplary multi-lane microfluidic cartridge, wherein various microfluidic networks are visible.
Figure 29:
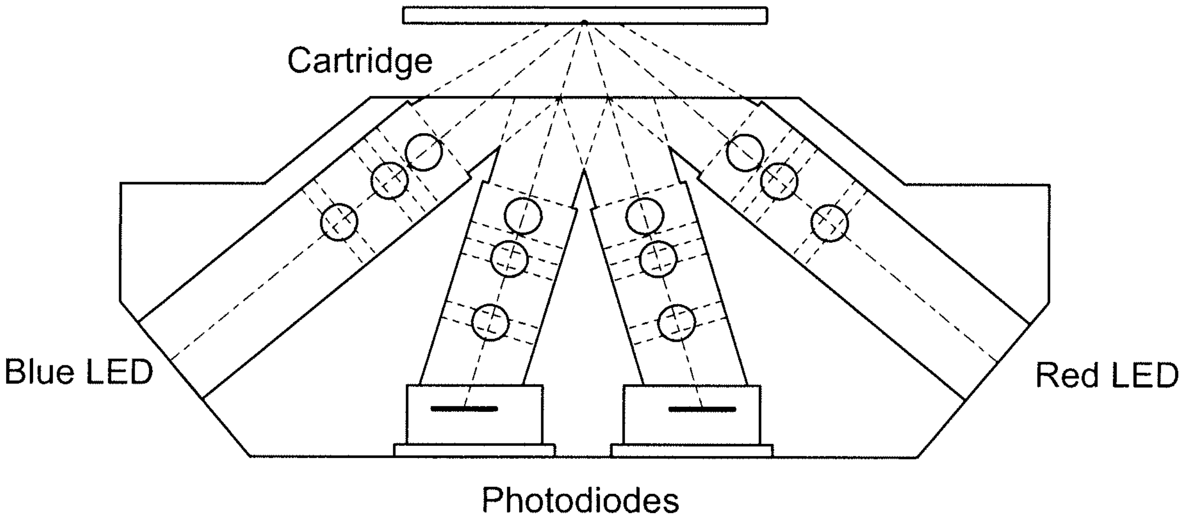
FIG. 29 shows a cross-sectional view of an exemplary detector.
Figure 30:
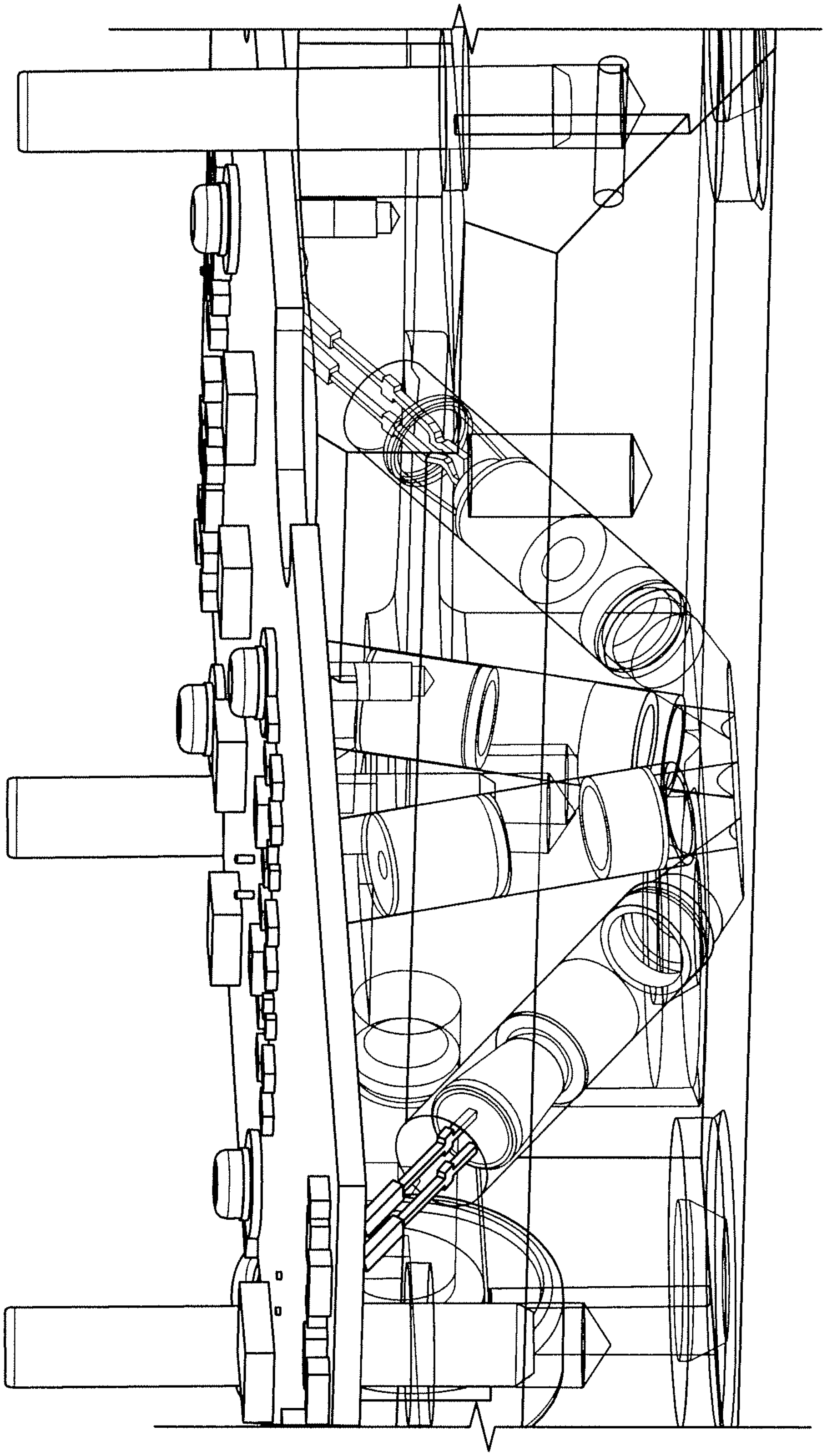
FIG. 30 shows a perspective view of a detector in a read-head.

Pictures of an exemplary Mux board and assembled heater unit are shown in FIGS. 27-29.

Example 3: Pulse Width Modulation for Heater Circuitry

In various embodiments, the operation of a PWM generator can also include a programmable start count in addition to the aforementioned end count and granularity. In such embodiments, multiple PWM generators can produce signals that can be selectively non-overlapping (e.g., by multiplexing the on-time of the various heaters) such that the current capacity of the high voltage power is not exceeded. Multiple heaters can be controlled by different PWM signal generators with varying start and end counts. The heaters can be divided into banks, whereby a bank defines a group of heaters of the same start count. For example, 36 PWM generators can be grouped into six different banks, each corresponding to a certain portion of the PWM cycle (500 ms for this example). The end count for each PWM generator can be selectively programmed such that not more than six heaters will be on at any given time. A portion of a PWM cycle can be selected as dead time (count 3000 to 4000 for this example) during which no heating takes place and sensitive temperature sensing circuits can use this time to sense the temperature. The table below represents a PWM cycle for the foregoing example:

| | Start Count | End Count | Max End count |
|---|---|---|---|
| Bank 1 | | | |
| PWM generator#1 | 0 | 150 | 500 |
| PWM generator#2 | 0 | 220 | 500 |
| . . . | . . . | . . . | |
| PWM generator#6 | 0 | 376 | 500 |
| Bank 2 | | | |
| PWM generator#7 | 500 | 704 | 1000 |
| PWM generator#8 | 500 | 676 | 1000 |
| . . . | . . . | . . . | . . . |
| PWM generator#12 | 500 | 780 | 1000 |

-continued

| | Start Count | End Count | Max End count |
|---|---|---|---|
| Bank 3 | | | |
| PWM generator#13 | 1000 | 1240 | 1500 |
| PWM generator#14 | 1000 | 1101 | 1500 |
| . . . | . . . | . . . | . . . |
| PWM generator#18 | 1000 | 1409 | 1500 |
| Bank 4 | | | |
| PWM generator#19 | 1500 | 1679 | 2000 |
| PWM generator#20 | 1500 | 1989 | 2000 |
| . . . | . . . | . . . | . . . |
| PWM generator#24 | 1500 | 1502 | 2000 |
| Bank 5 | | | |
| PWM generator#25 | 2000 | 2090 | 2500 |
| PWM generator#26 | 2000 | 2499 | 2500 |
| . . . | . . . | . . . | . . . |
| PWM generator#30 | 2000 | 2301 | 2500 |
| Bank 6 | | | |
| PWM generator#31 | 2500 | 2569 | 3000 |
| PWM generator#32 | 2500 | 2790 | 3000 |
| . . . | . . . | . . . | . . . |
| PWM generator#36 | 2500 | 2678 | 3000 |

Example 4: Detector Integrated in Force Member

This non-limiting example describes pictorially, various embodiments of a detection system integrated into a force member, in an apparatus for carrying out diagnostics on microfluidic samples.

Figure 43A:
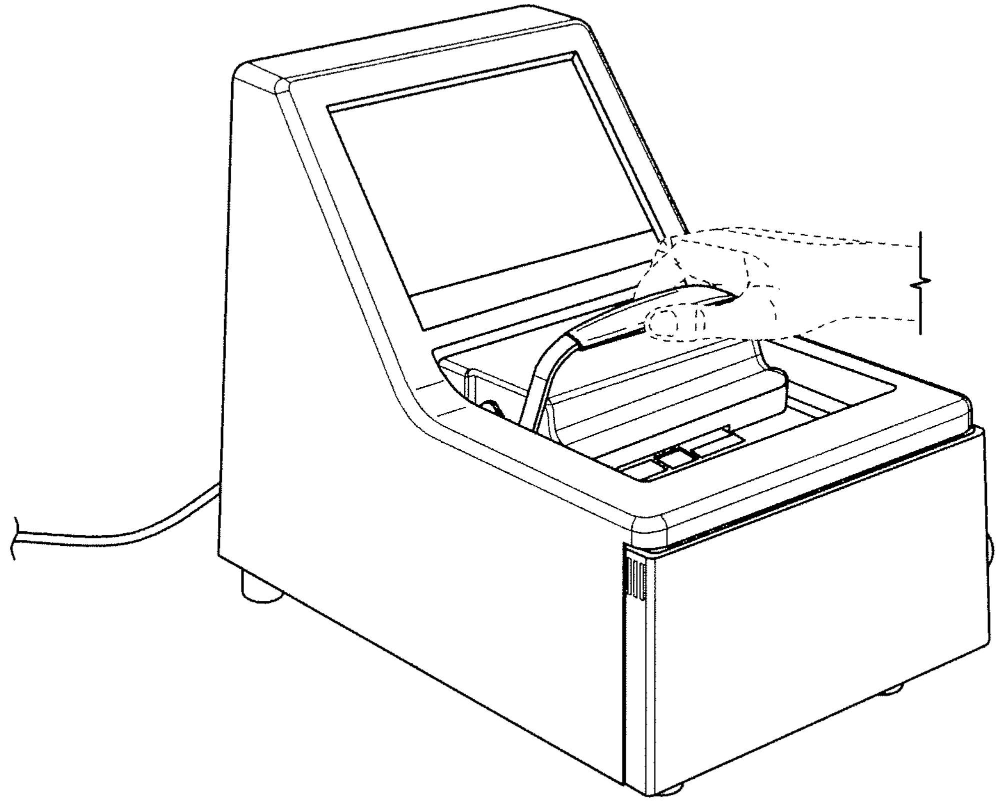
FIGS. 43A and 43B show an exemplary apparatus having a detector mounted in a sliding lid.

FIG. 43A: The lid of the apparatus can be closed, which can block ambient light from the sample bay, and place an optical detector contained in the lid into position with respect to the microfluidic cartridge.

Figure 43B:
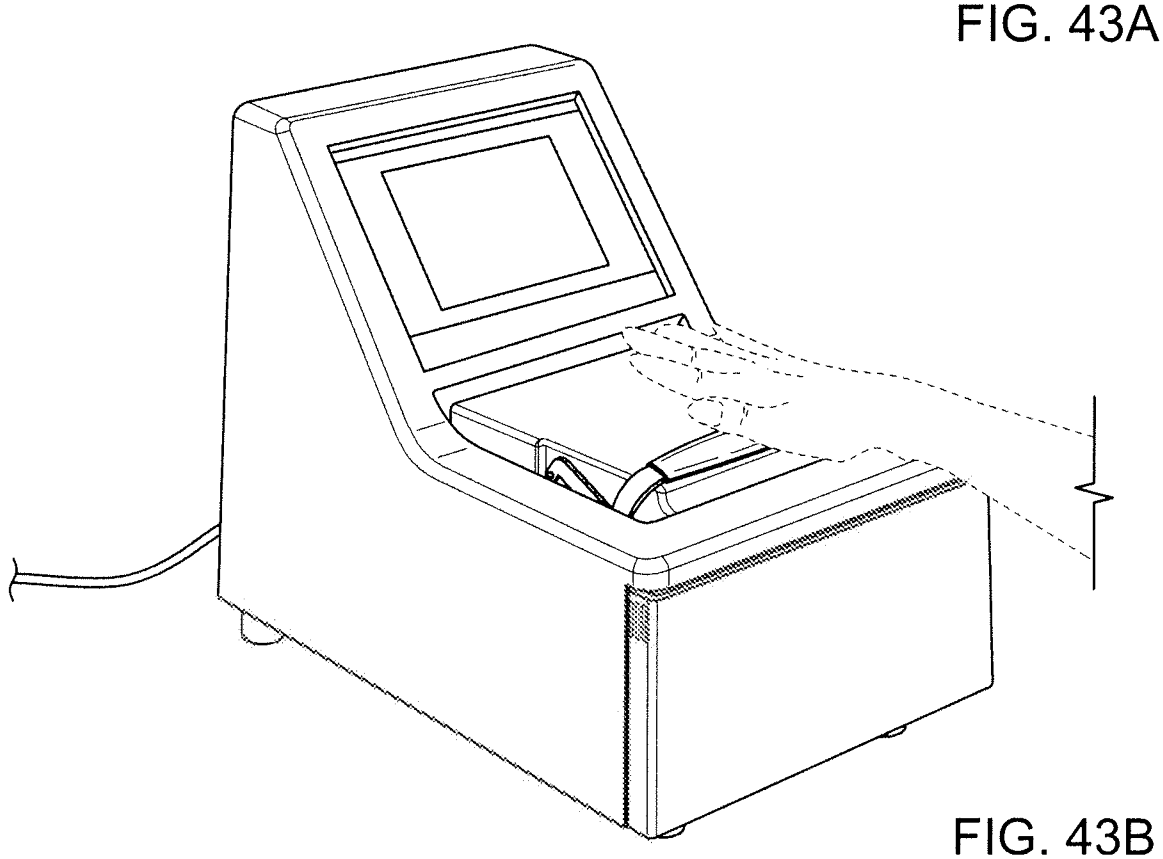

FIG. 43B: The lid of the apparatus can be closed to apply pressure to the cartridge. Application of minimal pressure on the cartridge: after the slider compresses the cartridge, the slider can compress the compliant label of the cartridge. This can cause the bottom of the cartridge to be pressed down against the surface of the heater unit present in the heater module. Springs present in the slider can deliver, for example approximately 50 lb of pressure to generate a minimum pressure, for example 2 psi over the entire cartridge bottom.

Thermal interface: the cartridge bottom can have a layer of mechanically compliant heat transfer laminate that can enable thermal contact between the microfluidic substrate and the microheater substrate of the heater module. A minimal pressure of 1 psi can be employed for reliable operation of the thermal valves, gate and pumps present in the microfluidic cartridge.

Mechanicals and assembly: the Analyzer can have a simple mechanical frame to hold the various modules in alignment. The optics module can be placed in rails for easy opening and placement of cartridges in the Analyzer and error-free alignment of the optics upon closing. The heater/sensor module can be also placed on rails or similar guiding members for easy removal and insertion of the assembly.

Figure 44A:
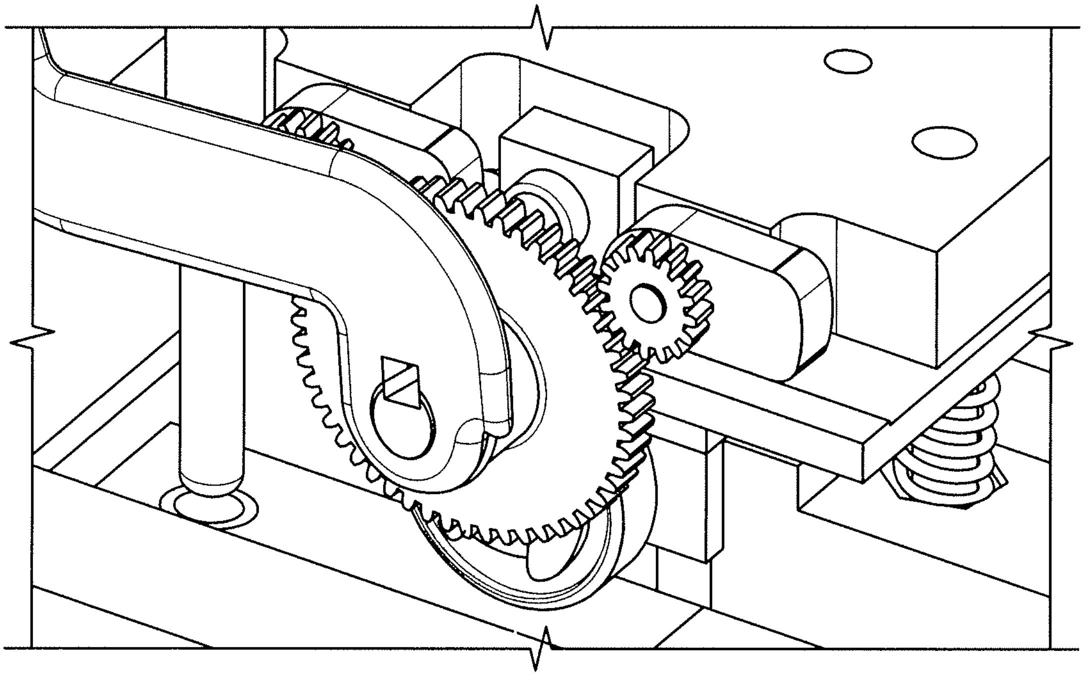
FIGS. 44A-44C show a force member.
Figure 44B:
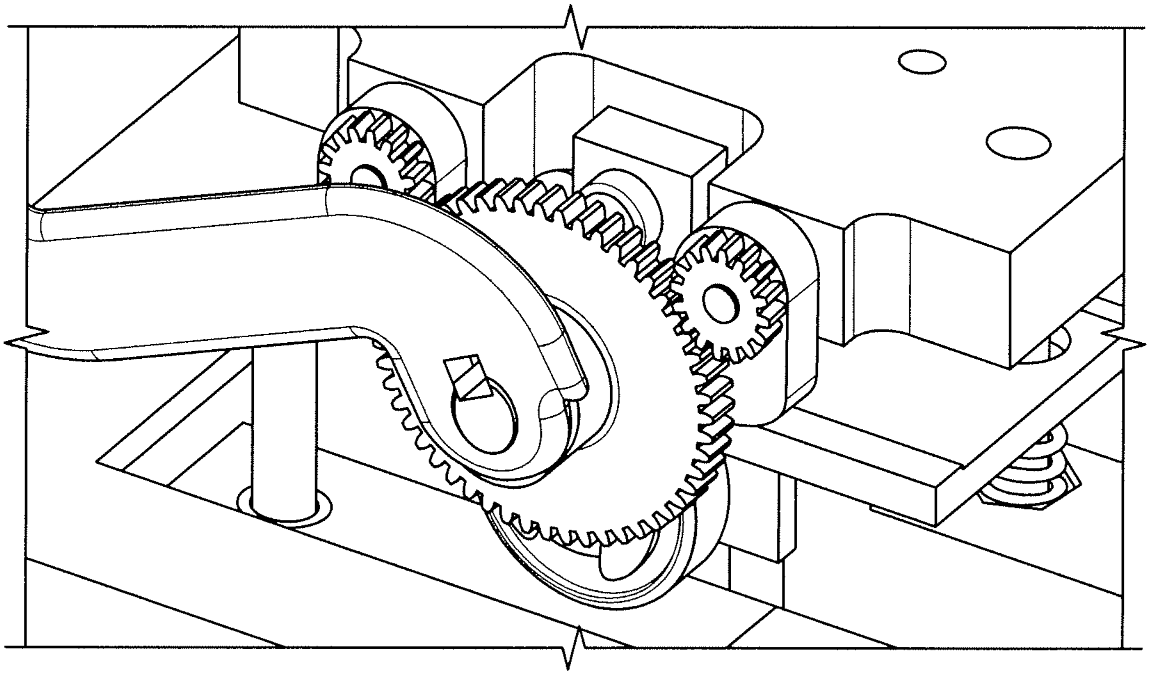
Figure 44C:
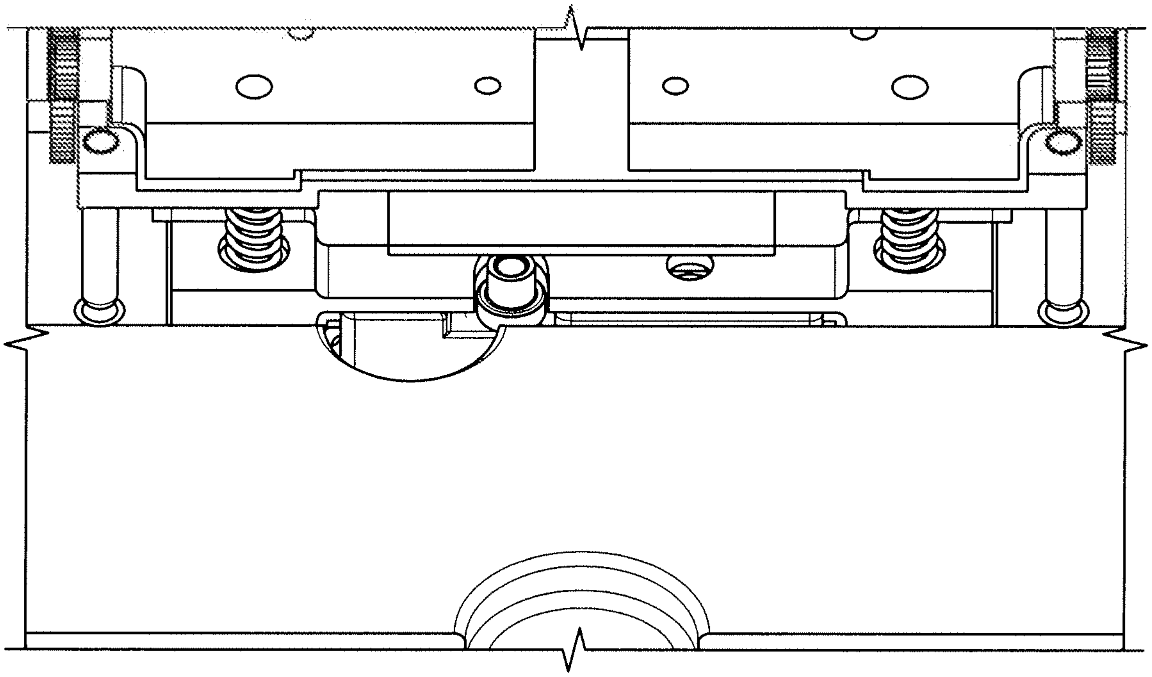

Slider: the slider of the Analyzer can house the optical detection system as well as the mechanical assembly that can enables the optics jig to press down on the cartridge when the handle of the slider is turned down onto the analyzer. The optics jig can be suspended from the case of the slider at 4 points. Upon closing the slider and turning the handle of the analyzer down, 4 cams can turn to push down a plate that presses on 4 springs. On compression, the springs can deliver approximately 50 lb on the optical block. See FIGS. 44A-44C.

The bottom surface of the optics block can be made flat to within 100 microns, typically within 25 microns, and this flat surface can press upon the compliant (shore hardness approximately 50-70) label (approximately 1.5 mm thick under no compression) of the cartridge making the pressure more or less uniform over the cartridge. An optional lock-in mechanism can also be incorporated to prevent the slider from being accidentally knocked-off while in use.

Figure 45A:
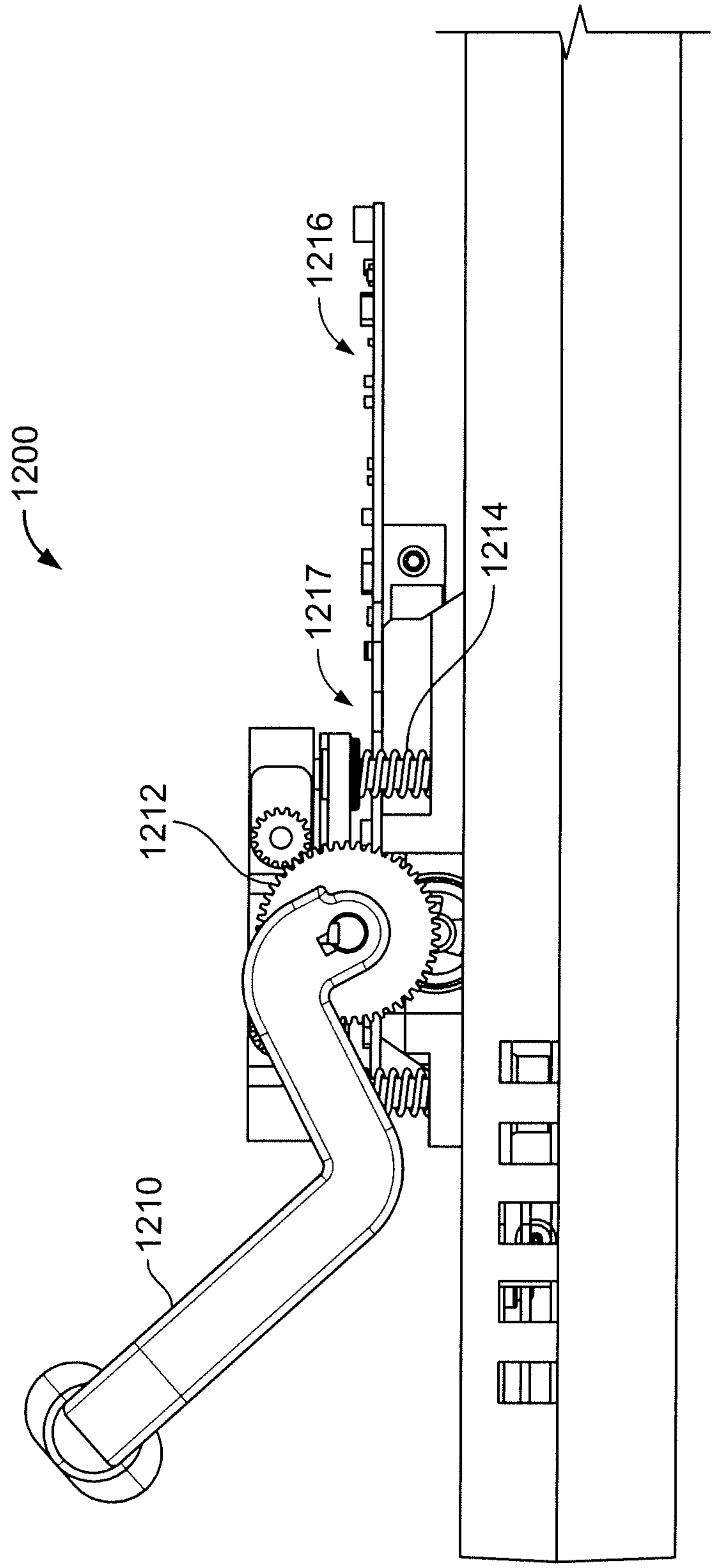
FIGS. 45A-45D show a force member associated with a detector.

FIG. 45A shows a side view of a lever assembly 1200, with lever 1210, gear unit 1212, and force member 1214. Assembly 1200 can be used to close the lid of the apparatus and (through force members 1214) apply force to a microfluidic cartridge 1216 in the receiving chamber 1217. One force member is visible in this cut away view, but any number, for example 4, can be used. The force members can be, for example, a manual spring loaded actuator as shown, an automatic mechanical actuator, a material with sufficient mechanical compliance and stiffness (e.g., a hard elastomeric plug), and the like. The force applied to the microfluidic cartridge 1216 can result in a pressure at the surface of the microfluidic cartridge 1216 of at least about 0.7 psi to about 7 psi (between about 5 and about 50 kilopascals), or in some embodiments about 2 psi (about 14 kilopascals.

Figure 45B:
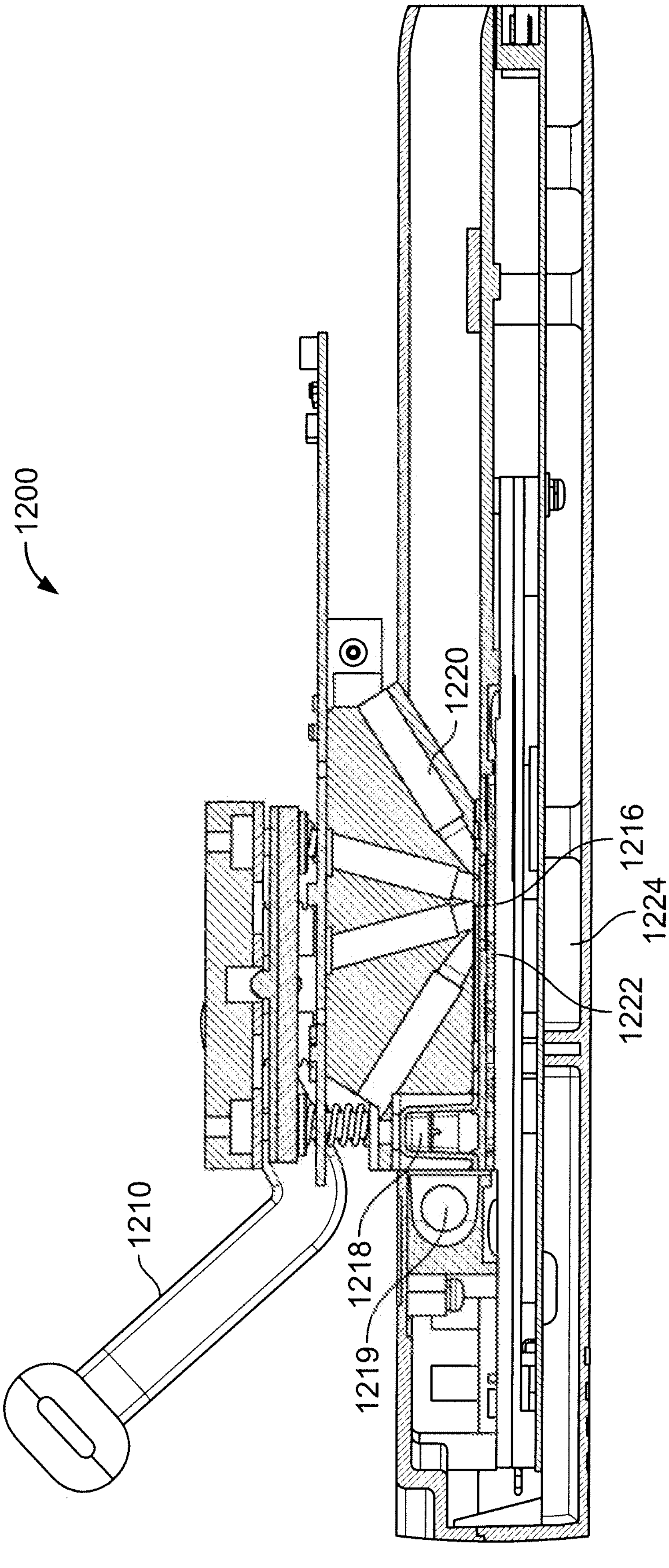

FIG. 45B shows a side view of lever assembly 1200, with microfluidic cartridge 1216 in the receiving chamber 1217. A heat source 1219 (for example, a xenon bulb as shown) can function as a radiant heat source directed at a sample inlet reservoir 1218, where the heat can lyse cells in reservoir 1218. A thermally conductive, mechanically compliant layer 1222 can lie at an interface between microfluidic cartridge 1216 and thermal stage 1224. Typically, microfluidic cartridge 1216 and thermal stage 1224 can be planar at their respective interface surfaces, e.g., planar within about 100 microns, or more typically within about 25 microns. Layer 1222 can improve thermal coupling between microfluidic cartridge 1216 and thermal stage 1224. Optical detector elements 1220 can be directed at the top surface of microfluidic cartridge 1216.

Figure 45C:
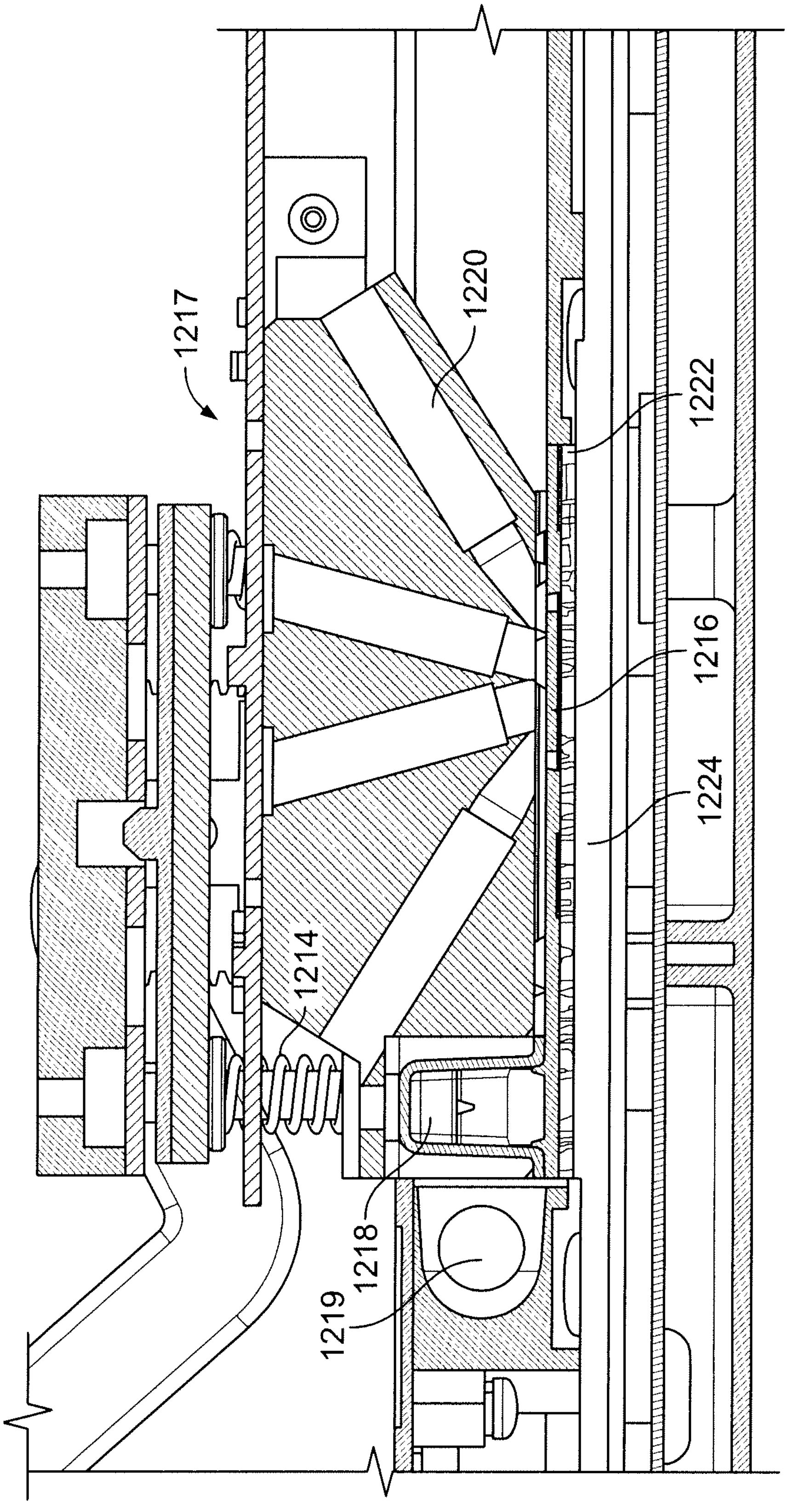
Figure 45D:
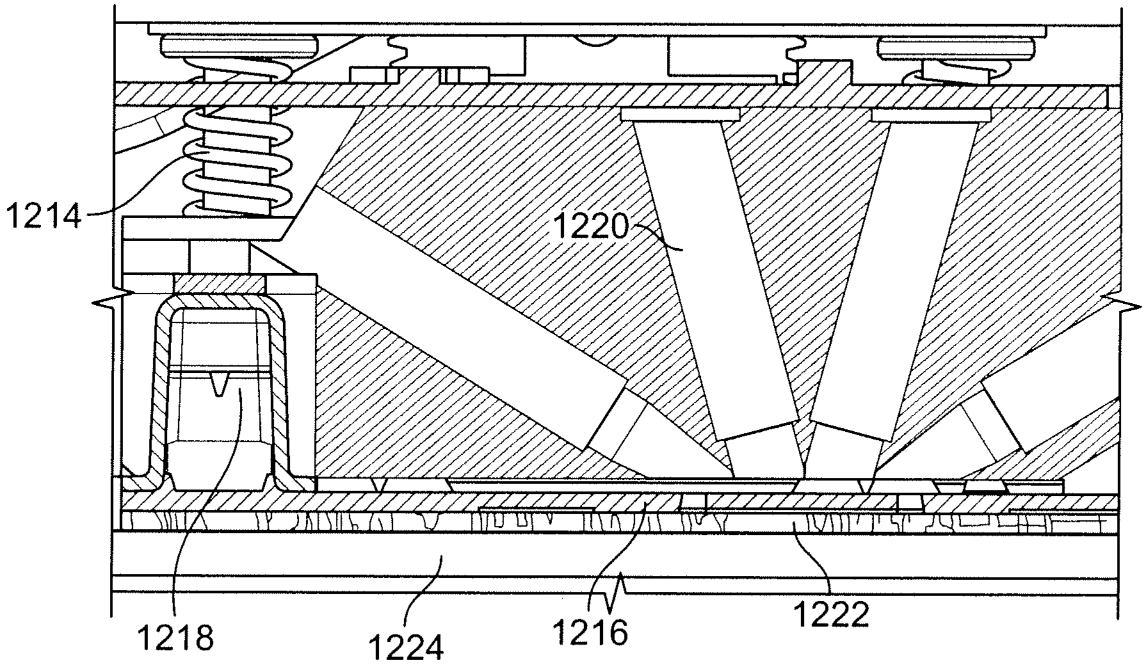

FIGS. 45C and 45D show further cross-sectional views.

Example 6: Exemplary Optics Board

Figure 46:
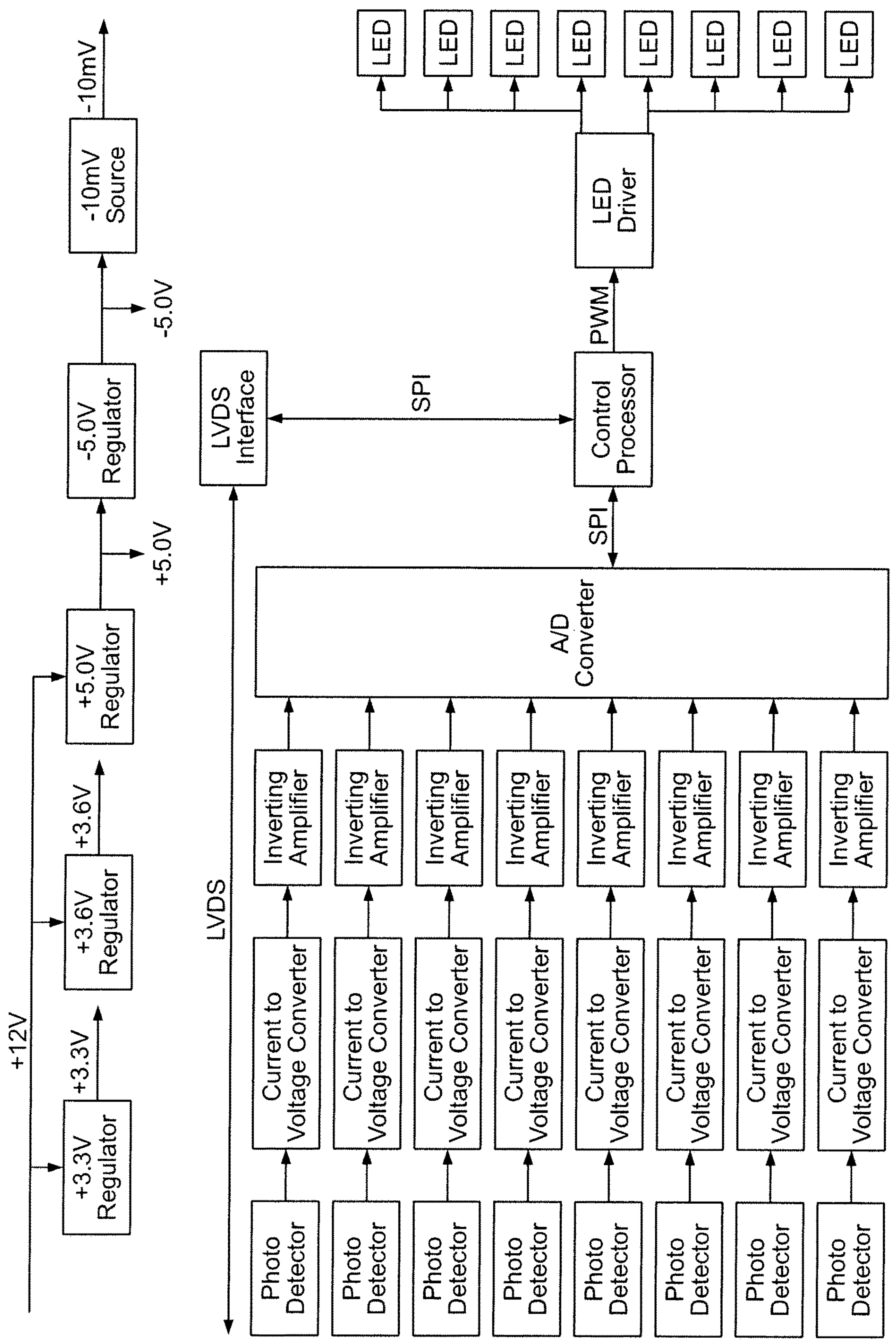
FIG. 46 shows a block diagram of exemplary electronic circuitry in conjunction with a detector as described herein.

An exemplary optics board is shown schematically in FIG. 46, and is used to collect and amplify the fluorescent signature of a successful chemical reaction on a microfluidic cartridge, and control the intensity of LED's using pulse-width modulation (PWM) to illuminate the cartridge sample over up to four channels, each with two color options. Additionally, it receives instructions and sends results data back over an LVDS (low-voltage differential signaling) SPI (serial peripheral interface). In some embodiments there is a separate instance of this circuitry for each PCR channel that is monitored.

The power board systems include: a +12V input; and +3.3V, +3.6V, +5V, and −5V outputs, configured as follows: the +3.3V output contains a linear regulator, is used to power the LVDS interface, should maintain a +/−5% accuracy, and supply an output current of 0.35 A; the +3.6V output contains a linear regulator, is used to power the MSP430, should maintain a +/−5% accuracy, and supply an output current of 0.35 A; the +5V output contains a linear regulator, is used to power the plus rail for op-amps, should maintain a +/−5% accuracy, and supply an output current of 0.35 A; the −5V output receives its power from the +5V supply, has a mV reference, is used to power the minus rail for op-amps and for the photo-detector bias, should maintain a +/−1% voltage accuracy, and supply an output current of 6.25 mA+/−10%. Additionally, the power board has an 80 ohm source resistance, and the main board software can enable/disable the regulator outputs.

The main board interface uses a single channel of the LVDS standard to communicate between boards. This takes place using SPI signaling over the LVDS interface which is connected to the main SPI port of the control processor. The interface also contains a serial port for in-system programming.

The optical detection system of FIG. 46 comprises a control processor, LED drivers, and a photo-detection system. In the exemplary embodiment, the control processor is a TI MSP430F1611 consisting of a dual SPI (one for main board interface, and one for ADC interface) and extended SRAM for data storage. It has the functions of power monitoring, PWM LED control, and SPI linking to the ADC and main board. The LED drivers contain NPN transistor switches, are connected to the PWM outputs of the control processor, can sink 10 mA @ 12V per LED (80 mA total), and are single channel with 2 LEDs (one of each color) connected to each. The photo-detection system has two channels and consists of a photo-detector, high-sensitivity photo-diode detector, high gain current to voltage converter, unity gain voltage inverting amplifier, and an ADC. Additionally it contains a 16 channel Sigma-delta (only utilizing the first 8 channels) which is connected to the second SPI port of the control processor.

During assembly of the various components on to the PC board, such as may occur on a production line, there are the following considerations. The extremely high impedance of the photo-detection circuit means that a rigorous cleaning procedure must be employed. Such a procedure may include, for example: After surface mount components are installed, the boards are washed on a Weskleen and blow dried upon exiting conveyor. The belt speed can be set at 20-30. The boards are soaked in an alcohol bath for approximately 3 minutes, then their entire top and bottom surfaces are scrubbed using a clean, soft bristle brush. The boards are baked in a 105° F. (40° C.) oven for 30 minutes to dry out all components.

After all the components are installed: the soldered areas of the boards can be hand wash using deionized water and a soft bristle brush. The same soldered areas can be hand washed using alcohol and a soft bristle brush. The boards are allowed to air dry. Once the board is cleaned, the optical circuitry must be conformal coated to keep contaminates out.

The foregoing description is intended to illustrate various aspects of the present technology. It is not intended that the examples presented herein limit the scope of the present technology. The technology now being fully described, it will be apparent to one of ordinary skill in the art that many changes and modifications can be made thereto without departing from the spirit or scope of the appended claims.

The invention claimed is:

1. An apparatus, comprising:

a multi-lane microfluidic cartridge, each lane comprising an amplification region within which amplification of polynucleotides is carried out;

an instrument, the instrument comprising:

a frame, a drawer configured to slide backward and forward relative to the frame, wherein the drawer comprises:

an area configured to receive the multi-lane microfluidic cartridge, a plurality of separately controllable heat sources configured to deliver localized heat to selected regions of the multi-lane microfluidic cartridge at specific times, and electrical connectors configured to transmit electrical signals to the plurality of separately controllable heat sources during analysis, a detector comprising a fluorescence detection module, wherein the detector is configured to detect the presence of one or more polynucleotides in samples, a display, wherein the display is configured to present information to a user and accept input from the user in response to various displayed prompts, and one or more processors configured to control various processing operations to be performed on the samples introduced into the multi-lane microfluidic cartridge;

wherein the instrument is configured to control the plurality of separately controllable heat sources to direct heat to the individual sample lanes separately, in all simultaneously, or in groups simultaneously to perform amplification of polynucleotides within the amplification region of each lane of the multi-lane microfluidic cartridge; and wherein the instrument is configured to analyze the products of amplification in each lane of the multi-lane microfluidic cartridge separately, in all simultaneously, or in groups simultaneously and transmitting results of the analysis of the samples processed in the multi-lane microfluidic cartridge to the display.

2. The apparatus of claim 1, wherein the detector is positioned on rails to facilitate placement of the multi-lane microfluidic cartridge in the drawer.

3. The apparatus of claim 1, wherein the detector is positioned on rails to facilitate alignment of optics.

4. The apparatus of claim 1, wherein the detector is configured to be positioned over the multi-lane microfluidic cartridge in use.

5. The apparatus of claim 1, wherein the plurality of separately controllable heat sources is configured to be positioned under the multi-lane microfluidic cartridge in use.

6. The apparatus of claim 1, wherein the display comprises a touch sensitive display.

7. The apparatus of claim 1, wherein the display is configured to present information in color.

8. The apparatus of claim 1, wherein the instrument is configured to apply pressure to the multi-lane microfluidic cartridge.

9. The apparatus of claim 1, wherein the instrument comprises a lid configured to slide from an open position to receive the multi-lane microfluidic cartridge to a closed position.

10. The apparatus of claim 1, wherein the instrument further comprises a sensor configured to sense whether the multi-lane microfluidic cartridge is present in the drawer.

11. The apparatus of claim 1, wherein the instrument further comprises a latch configured to prevent access to the multi-lane microfluidic cartridge when analysis is in progress.

12. The apparatus of claim 1, wherein the instrument comprises a connection to a computer network.

13. The apparatus of claim 1, wherein the instrument is configured to allow a user to remotely issue scheduling commands to start an analysis at a specific time in the future.

14. The apparatus of claim 1, wherein the detector is configured to detect a polynucleotide in the sample lanes separately.

15. The apparatus of claim 1, wherein the detector is configured to detect a polynucleotide in the sample lanes simultaneously.

16. The apparatus of claim 1, wherein the detector comprises a light source that selectively emits light in an absorption band of a fluorescent dye, and a light detector that selectively detects light in an emission band of the fluorescent dye, and wherein the fluorescent dye corresponds to a fluorescent polynucleotide probe or a fragment thereof.

17. The apparatus of claim 1, wherein the multi-lane microfluidic cartridge is disposable.

18. The apparatus of claim 1, wherein the display is configured to indicate progress of amplification.

19. The apparatus of claim 1, wherein the display is configured to indicate a warning message in the case of malfunction of the multi-lane microfluidic cartridge.

20. The apparatus of claim 1, wherein the display is configured to indicate one or more questions that prompt the user to provide input in response.

* * * * *